(12) United States Patent
Liu et al.

(10) Patent No.: US 12,054,787 B2
(45) Date of Patent: Aug. 6, 2024

(54) COMPOSITIONS AND METHODS COMPRISING DIGITAL SIGNATURES TO PREDICT RESPONSE AND RESISTANCE TO TARGETED THERAPY AND IMMUNOTHERAPY

(71) Applicant: DANA-FARBER CANCER INSTITUTE, INC., Boston, MA (US)

(72) Inventors: Xiaole Liu, Wayland, MA (US); Peng Jiang, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 18/047,910

(22) Filed: Oct. 19, 2022

(65) Prior Publication Data

US 2023/0295736 A1  Sep. 21, 2023

Related U.S. Application Data

(63) Continuation of application No. 16/223,470, filed on Dec. 18, 2018, now Pat. No. 11,505,831.

(60) Provisional application No. 62/608,110, filed on Dec. 20, 2017.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/158* (2013.01)

(58) Field of Classification Search
CPC ............ C12Q 1/6886; C12Q 2600/106; C12Q 2600/158
See application file for complete search history.

(56) References Cited

U.S. PATENT DOCUMENTS

2018/0357378 A1  12/2018  Bagaev et al.
2020/0157633 A1  5/2020  Regev et al.

OTHER PUBLICATIONS

Tang et al. (Cell Biosc. 8(30): 1-3, published Apr. 18, 2018).*
Zhao et al. (Cell Physiol. Biochem. 47: 721-734, published online May 28, 2018).*
Seidel et al. (Front. Oncol. 8(86): 1-14, published Mar. 28, 2018).*
Ascierto, Maria Libera, et al., "The Intratumoral Balance between Metabolic and Immunologic Gene Expression Is Associated with Anti-PD-1 Response in Patients with Renal Cell Carcinoma", Cancer Immunal Res; 4(9) Sep. 2016, p. 726.
Ayers, Mark, et al., "IFN-γ-Related mRNA Profile Predicts Clinical Response to PD-1 Blockade", The Journal of Clinical Investigation, 2017; 127(8):2930-2940.
Barrett, Tanya, et al., "NCBI GEO: Archive for Functional Genomics Data Sets—Update", Nucleic Acids Research, 2013, vol. 41, Database Issue, pp. D991-D995.
Benjamini, Yoav, et al., "Controlling the False Discovery Rate: a Practical and Powerful Approach to Multiple Testing", J.R. Statist. Soc. B (1995) 57, No. 1, pp. 289-300.
Beyer, Marc, et al., "High-Resolution Transcriptome of Human Macrophages", PLOS/ONE, Published: Sep. 21, 2012, pp. 1-16.
Bladergroen, Bellinda A., et al., "The Granzyme B Inhibitor, Protease Inhibitor 9, Is Mainly Expressed by Dendritic Cells and at Immune-Privileged Sites", The Journal of Immunology, Mar. 1, 2019, 166:3218-3225.
Bodin, Orjan, "Collaborative Environmental Governance: Achieving Collective Action in Social-Ecological Systems", Science 357, 659 (2017), Aug. 18, 2017.
Callahan, Margaret K., et al., "CTLA-4 and PD-1 Pathway Blockade: Combinations in the Clinic", Frontiers in Oncology, Jan. 2015, vol. 4, Article 385.
Calon, Alexandre, et al., "Dependency of Colorectal Cancer on a TGF-β-Driven Program in Stromal Cells for Metastasis Initiation", Cancer Cell 22, Nov. 13, 2012, pp. 571-584.
The Cancer Genome Atlas Research Network, et al., "The Cancer Genome Atlas Pan-Cancer Analysis Project", Nature Genetics, vol. 45, No. 10, Oct. 2013.
Charoentong, Pornpimol, et al., "Pan-Cancer Immunogenomic Analyses Reveal Genotype-Immunophenotype Relationships and Predictors of Response to Checkpoint Blockade", Cell Press, Cell Reports 18, Jan. 3, 2017, pp. 248-262.
Chen, Pei-Ling, et al., "Analysis of Immune Signatures in Longitudinal Tumor Samples Yields Insight into Biomarkers of Response and Mechanisms of Resistance to Immune Checkpoint Blockade", Cancer Discovery, Aug. 2016, p. 827.
Cogdill, Alexandria P., "Hallmarks of Response to Immune Checkpoint Blockade", British Journal of Cancer, May 18, 2017, 117, pp. 1-7.
Curtis, Christina, et al., "The Genomic and Transcriptomic Architecture of 2,000 Breast Tumours Reveals Novel Subgroups", Nature, vol. 486, Jun. 21, 2012.
Davoli, Teresa, et al., "Tumor Aneuploidy Correlates With Markers of Immune Evasion and With Reduced Response to Immunotherapy", Science 355, 261 (2017), Jan. 20, 2017.
Fernandez-Banet, Julio, et al., "OASIS: Web-Based Platform for Exploring Cancer Multi-Omics Data", Nature Methods, vol. 13, No. 1, Jan. 2016.
Gajewski, Thomas F., et al., "Innate and Adaptive Cells in the Tumor Microenvironment", NIH Public Access, Nat. Immunol. Oct. 2013; 14(10): pp. 1014-1022.
Gentles, Andrew J., et al., "The Prognostic Landscape of Genes and Infiltrating Immune Cells Across Human Cancers", Nature Medicine, vol. 21, No. 8, Aug. 2015.
Giordano, Marilyn, et al., "Molecular Profiling of CD8 T Cells in Autochthonous Melanoma Identifies Maf as Driver of Exhaustion", The EMBO Journal, vol. 34, No. 15, 2015.
Grosso, Joseph, F., et al., "CTLA-4 Blockade in Tumor Models: An Overview of Preclinical and Translational Research", Cancer Immunity, Jan. 22, 2013, vol. 13, p. 5.

(Continued)

*Primary Examiner* — Alana Harris Dent
(74) *Attorney, Agent, or Firm* — ArentFox Schiff, LLP; Daniel W. Clarke

(57) ABSTRACT

The present invention relates to gene expression signatures that predict response and resistance to targeted therapy and immunotherapy.

15 Claims, 50 Drawing Sheets

Specification includes a Sequence Listing.

(56) References Cited

OTHER PUBLICATIONS

Hanks, Brent Allen, et al., "Combinatorial TGF-β Signaling Blockade and Anti-CTLA-4 Antibody Immunotherapy in a Murine BRAFV600E-PTEN-/-Transgenic Model of Melanoma", Journal of Clinical Oncology 32, No. 15 suppl, May 20, 2014, p. 3011-3011.
Hirst, Claire E., et al., "Perforin-Independent Expression of Granzyme B and Proteinase Inhibitor 9 in Human Testis and Placenta Suggests a Role for Granzyme B-Mediated Proteolysis in Reproduction", Molecular Human Reproduction, vol. 7, pp. 1133-1142, 2001.
Hirst, Claire E., et al., "The Intracellular Granzyme B Inhibitor, Proteinase Inhibitor 9, Is Up-Regulated During Accessory Cell Maturation and Effector Cell Degranulation, and Its Overexpression Enhances CTL Potency", The Journal of Immunology 2003; 170:805-815.
Hugo, Willy, et al., "Genomic and Transcriptomic Features of Response to Anti-PD-1 Therapy in Metastatic Melanoma", Cell 165, Mar. 24, 2016, pp. 35-44.
Joyce, Johanna A., et al., "T Cell Exclusion, Immune Privilege, and the Tumor Microenvironment", Science, Apr. 3, 2015, vol. 348, Issue 6230.
Kaiserman, D., et al., "Control of Granzymes By Serpins", Cell Death and Differentiation (2010) 17, pp. 586-595.
Khong, Hung T., et al., "The Waardenburg Syndrome Type 4 Gene, SOX10, Is a Novel Tumor-Associated Antigen Identified in a Patient with a Dramatic Response to Immunotherapy", Cancer Research 62, Jun. 1, 2002, pp. 3020-3023.
Kleinbaum, D.G., "Book Review", Biometrical Journal 40, (1998)1 pp. 107-108.
Le, D.T., et al., "PD-1 Blockade in Tumors with Mismatch-Repair Deficiency", The New England Journal of Medicine, 372:26, Jun. 25, 2015.
Li, Bo, et al., "Comprehensive Analyses of Tumor Immunity: Implications for Cancer Immunotherapy", Genome Biology, DOI 10.1186/s 13059-016-1028-7, 2016.
Mahoney, Kathleen M., et al., "Combination Cancer Immunotherapy and New Immunomodulatory Targets", Nature Reviews, vol. 14, Aug. 2015, 561.
Masucci, Giuseppe V., et al. "Validation of Biomarkers to Predict Response to Immunotherapy in Cancer: vol. 1—Pre-Analytical and Analytical Validation", Journal for Immuno Therapy of Cancer, (2016) 4:67, DOI 10.1186/s40425-016-0178-1.
Miyan, M., et al., "Differential Tumor Infiltration by T-Cells Characterizes Intrinsic Molecular Subtypes in Breast Cancer", Journal of Translational Medicine, (2016) 14:227, DOI 10.1186/s12967-016-0983-9.
Murphy, Pat, "SJC Asked to Weigh in on Nursing Home Arbitration Clauses", Massachusetts Lawyers Weekly, Mar. 1, 2019.
Nathanson, Tavi, et al., "Somatic Mutations and Neoepitope Homology in Melanomas Treated with CTLA-4 Blockade", Cancer Immunology Research, Published Online First Dec. 12, 2016; DOI: 10.1158/2326-6066. CIR-16-0019.
Nishino, Mizuki, et al., "Monitoring Immune-Checkpoint Blockade: Response Evaluation and Biomarker Development", Nature Reviews/Clinical Oncology, vol. 14, Nov. 2017, 655.
Paik, Soonmyung, et al., "A Multigene Assay to Predict Recurrence of Tamoxifen-Treated, Node-Negative Breast Cancer", The New England Journal of Medicine, 351:27, Dec. 30, 2004.
Parker, Joel S., et al., "Supervised Risk Predictor of Breast Cancer Based on Intrinsic Subtypes", Journal of Clinical Oncology, vol. 27, No. 8, Mar. 10, 2009.
Patel, Shashank, J., et al., "Identification of Essential Genes for Cancer Immunotherapy", HHS Public Access, Nature, Aug. 31, 2017; 548(7669); pp. 537-542.
Philip, Mary, et al., "Chromatin States Define Tumor-Specific T Cell Dysfunction and Reprogramming", HHS Public Access, Nature. May 25, 2017; 545(7655).
Remark, Romain, et al., "Characteristics and Clinical Impacts of the Immune Environments in Colorectal and Renal Cell Carcinoma Lung Metastases: Influence of Tumor Origin", Human Cancer Biology, Published Jun. 19, 2013.
Rooney, Michael S., et al., "Molecular and Genetic Properties of Tumors Associated with Local Immune Cytolytic Activity", Cell 160, Jan. 15, 2015, pp. 48-61.
Schietinger, Andrea, et al., "Tumor-Specific T Cell Dysfunction Is a Dynamic Antigen-Driven Differentiation Program Initiated Early During Tumorigenesis", Cell Press, Immunity 45, pp. 389-401, Aug. 16, 2016.
Sharma, Padmanee, et al., "Primary, Adaptive, and Acquired Resistance to Cancer Immunotherapy", Cell 168, Feb. 9, 2017, p. 707.
Sharma, Padmanee, et al., "Immune Checkpoint Targeting in Cancer Therapy: Toward Combination Strategies with Curative Potential", Cell 161, Apr. 9, 2015, p. 205.
Shukla, Sachet A., et al., "Cancer-Germline Antigen Expression Discriminates Clinical Outcome to CTLA-4 Blockade", Cell 173, Apr. 19, 2018, pp. 624-633.
Sivan, Ayelet, et al., "Commensal Bifidobacterium Promotes Antitumor Immunity and Facilitates Anti-PD-L1 Efficacy", Science, Nov. 27, 2015, vol. 350, Issue 6264.
Snyder, Alexandra, M.D., et al., "Genetics Basis for Clinical Response to CTLA-4 Blockade in Melanoma", The New England Journal of Medicine 371; 23, Dec. 4, 2014.
Spranger, Stefani, et al., "Tumor-Intrinsic Oncogene Pathways Mediating Immune Avoidance", OncoImmunology, vol. 5, No. 3, 2016.
Cancer Genome Atlas Research, "Integrated genomic characterization of endometrial carcinoma", 2013, Nature, 497:67-73, doi:10.1038/nature 12113.
Cancer Genome Atlas, "Genomic Classification of Cutaneous Melanoma", 2015, Cell, 161(7):1681-1696, doi:10.1016/j.cell.2015.05.044.
Medema, J. P., et al., "Blockade of the granzyme B/perforin pathway through overexpression of the serine protease inhibitor PI-9/SPI-6 constitutes a mechanism for immune escape by tumors", 2001, Proceedings of the National Academy of Sciences of the United States of America 98, 11515-11520, doi:10.1073/pnas.201398198.
Metzeler, K. H. et al., "An 86-probe-set gene-expression signature predicts survival in cytogenetically normal acute myeloid leukemia", 2008, Blood 112:4193-4201, doi:10.1182/blood-2008-02-134411.
Oberthuer, A. et al., "Comparison of performance of one-color and two-color gene-expression analyses in predicting clinical endpoints of neuroblastoma patients", 2010, Pharmacogenomics Journal, 10:258-266, doi:10.1038/tpj.2010.53.
Storey, John D., et al., "Statistical Significance for Genomewide Studies", PNAS, Aug. 5, 2003, vol. 100, No. 16.
Schoenborn, J. R. & Wilson, C. B., "Regulation of interferon-gamma during innate and adaptive immune responses", Advances in immunology, 2007, 96:41-101, doi:10.1016/S0065-2776(07)96002-2
Thomas, Dori A., et al., "TGF-β Directly Targets Cytotoxic T Cell Functions During Tumor Evasion of Immune Surveillance", Cancer Cell, Nov. 2005, vol. 8, p. 369.
Thomas, Dori A., et al., "TGF-β Directly Targets Cytotoxic T Cell Functions During Tumor Evasion of Immune Surveillance", Cancer Cell, Nov. 2005, vol. 8, p. 369. Twyman, Christina, et al., "Radiation and Dual Checkpoint Blockade Activate Non-Redundant Immune Mechanisms in Cancer", Nature, Apr. 16, 2015, vol. 520.
Twyman, Christina, et al., "Radiation and Dual Checkpoint Blockade Activate Non-Redundant Immune Mechanisms in Cancer", Nature, Apr. 16, 2015, vol. 520.UHLEN, Mathias, et al., "A Pathology Atlas of the Human Cancer Transcriptome", Science 357, 660 (2017), Aug. 18, 2017.
Van Allen, Eliezer M., et al., "Genomic Correlates of Response to CTLA-4 Blockade in Metastatic Melanoma", Research/Reports, Oct. 9, 2015, vol. 350, Issue 6257.
Van't Veer, Laura J., et al., "Gene Expression Profiling Predicts Clinical Outcome of Breast Cancer", Nature, vol. 415, Jan. 2002.
Wakamatsu, El, et al., "Convergent and Divergent Effects of Constimulatory Molecules in Conventional and Regulatory CD4+ T Cells", PNAS, Jan. 15, 2013, vol. 110, No. 3, pp. 1023-1028.

(56) References Cited

OTHER PUBLICATIONS

Wherry, E. John, et al., "Molecular and Cellular Insights Into T Cell Exhaustion", Reviews, 486, Aug. 2015, vol. 15.

Woo, Edward Y., et al., "Regulatory CD4+CD25+ T Cells in Tumors from Patients with Early-Stage Non-Small Cell Lung Cancer and Late-Stage Ovarian Cancer", Cancer Research 61, Jun. 15, 2001, pp. 4766-4772.

Yaddanapudi, Kavitha, et al., "MIF is Necessary for Late-Stage Melanoma Patient MDSC Immune Suppression and Differentiation", AACR, Nov. 24, 2015.

Zhou, Penghui, et al., "In Vivo Discovery of Immunotherapy Targets in the Tumour Microenvironment", Nature, vol. 506, Feb. 6, 2014, p. 52.

Jiang, et al., "Signatures of T cell dysfunction and exclusion predict cancer immunotherapy response", Nature Medicine Oct. 2018, vol. 24, No. 10, pp. 1550-1558.

Iams, et al., "My Cancer Genome", Nov. 24, 2015, pp. 1-5.

Wang, et al., "Development of Inhibitors of the Programmed Cell Death-1/Programmed Cell Death-Ligand 1 Signaling Pathway", Journal of Medicinal Chemistry 2019, vol. 62, pp. 1715-1730.

Eisenhauer et al., "New response evaluation criteria in solid tumours: revised recist guideline", (version 1.1). European Journal of Cancer 2009, vol. 45, pp. 228-247.

Li, Bo, et al., "Comprehensive Analyses of Tumor Immunity: Implications for Cancer Immunotherapy", Genome Biology, Aug. 2016, 17(1):174, pp. 1-16, DOI 10.1186/s 13059-016-1028-7.

Schoenborn, J. R. & Wilson, C. B., "Regulation of interferon-gamma during innate and adaptive immune responses", Advances in immunology, 2007, 96:41-101, doi:10.1016/S0065-2776(07)96002-2.

Thomas, Dori A., et al., "TGF-$\beta$ Directly Targets Cytotoxic T Cell Functions During Tumor Evasion of Immune Surveillance", Cancer Cell, Nov. 2005, vol. 8, p. 369.

Twyman, Christina, et al., "Radiation and Dual Checkpoint Blockade Activate Non-Redundant Immune Mechanisms in Cancer", Nature, Apr. 16, 2015, vol. 520.

Uhlen, Mathias, et al., "A Pathology Atlas of the Human Cancer Transcriptome", Science 357, 660 (2017), Aug. 18, 2017.

Van't Veer, Laura J., et al., "Gene Expression Profiling Predicts Clinical Outcome of Breast Cancer", Nature, vol. 415, Jan. 2002.

Wakamatsu, El, et al., "Convergent and Divergent Effects of Constimulatory Molecules in Conventional and Regulatory CD4+ T Cells", PNAS, Jan. 15, 2013, vol. 110, No. 3, pp. 1023-1028.

\* cited by examiner

COMPOSITIONS AND METHODS COMPRISING DIGITAL SIGNATURES TO PREDICT RESPONSE AND RESISTANCE TO TARGETED THERAPY AND IMMUNOTHERAPY

RELATED APPLICATIONS

This application is a continuation of U.S. application Ser. No. 16/223,470, filed on Dec. 18, 2018, which claims the benefit of priority under 35 U.S.C. § 119(e) to U.S. Provisional Application No. 62/608,110, filed Dec. 20, 2017, each of which is incorporated herein by reference in its entirety.

GOVERNMENT LICENSE RIGHTS

This invention was made with government support under grant numbers CA224316 and HG008927 awarded by the National Institutes of Health. The government has certain rights in the invention.

INCORPORATION BY REFERENCE

The instant application contains a Sequence Listing which has been submitted electronically in XML format and is hereby incorporated by reference in its entirety. Said XML copy, created on Oct. 18, 2022, is named 52095_549C01US_ST26.xml and is 57 KB bytes in size.

BACKGROUND OF THE INVENTION

Cancer immunotherapies by immune checkpoint blockade (ICB) aim to help the immune system recognize and attack cancer cells. The primary targets of ICB treatment include programmed death-ligand 1 (PD-L1): programmed cell death protein 1 (PD1) and Cytotoxic T-lymphocyte-associated antigen-4 (CTLA4). Compared to conventional therapies, ICB can induce durable responses in patients with metastatic cancers. However, prior to the invention described herein, a significant limitation of ICB was that only small percentages of patients respond to ICB in most cancer types tested. As such, prior to the invention described herein, there was a pressing need to identify ICB response biomarkers and resistance regulators to predict response and resistance.

SUMMARY OF THE INVENTION

The invention is based upon the identification of a tumor immune dysfunction and exclusion (TIDE)-associated gene expression signature that predicts inhibition of CTLA4, PD1, or PD-L1 in a subject with neoplasia will result in clinical benefit (i.e., a TIDE prediction value). In some aspects, the invention relates to methods, arrays and kits for diagnosing and monitoring neoplasia.

Methods of determining whether inhibition of CTLA4, PD1, or PD-L1 in a subject with neoplasia will result in clinical benefit in the subject, e.g., a human subject, are carried out by obtaining a test sample from a subject having or at risk of developing neoplasia; determining the expression level of at least one TIDE-associated gene in the test sample; comparing the expression level of the TIDE-associated gene in the test sample with the expression level of the TIDE-associated gene in a reference sample; and determining whether CTLA4, PD1, or PD-L1 blockade (i.e., inhibition) will inhibit neoplasia in the subject if the expression level of the TIDE-associated gene in the test sample is differentially expressed as compared to the level of the TIDE-associated gene in the reference sample.

For example, the expression level of the TIDE-associated gene in the test sample is upregulated (i.e., increased) by at least 2 fold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, at least 30 fold, at least 35 fold, at least 40 fold, at least 45 fold, at least 50 fold, at least 60 fold, at least 70 fold, at least 80 fold, at least 90 fold, at least 100 fold, at least 125 fold, at least 150 fold, at least 175 fold, at least 200 fold, at least 250 fold, at least 300 fold, at least 350 fold, at least 400 fold, at least 500 fold, at least 600 fold, at least 700 fold, or at least 800 fold as compared to the level of the TIDE-associated gene in the reference sample, the threshold expression level, or the expression level of a housekeeping gene.

Alternatively, the expression level of the TIDE-associated gene in the test sample is downregulated (i.e., decreased) by at least 2 fold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, at least 30 fold, at least 35 fold, at least 40 fold, at least 45 fold, at least 50 fold, at least 60 fold, at least 70 fold, at least 80 fold, at least 90 fold, at least 100 fold, at least 125 fold, at least 150 fold, at least 175 fold, at least 200 fold, at least 250 fold, at least 300 fold, at least 350 fold, at least 400 fold, at least 500 fold, at least 600 fold, at least 700 fold, or at least 800 fold as compared to the level of the TIDE-associated gene in the reference sample, the threshold expression level, or the expression level of a housekeeping gene.

In some aspects, the number of predictive TIDE-associated genes comprises 100 genes. In other aspects, the number of predictive genes is at least 1 gene; e.g., at least 2 genes, at least 3 genes, at least 4 genes, at least 5 genes, at least 6 genes, at least 7 genes, at least 8 genes, at least 9 genes, at least 10 genes, at least 11 genes, at least 12 genes, at least 13 genes, at least 14 genes, at least 15 genes, at least 16 genes, at least 17 genes, at least 18 genes, at least 19 genes, at least 20 genes, at least 21 genes, at least 22 genes, at least 23 genes, at least 24 genes, at least 25 genes, at least 26 genes, at least 27 genes, at least 28 genes, at least 29 genes, at least 30 genes, at least 40 genes, at least 50 genes, at least 60 genes, at least 70 genes, at least 80 genes, at least 90 genes, or at least 100 genes.

In some cases, the at least one TIDE-associated gene comprises serine proteinase inhibitor (serpin) Family B Member 9 (SerpinB9), transforming growth factor beta-1 (TGFβ-1), prolyl endopeptidase (FAP), vascular endothelial growth factor A (VEGFA), and/or angiopoietin 2 (ANGPT2); and it is determined that inhibition of CTLA4, PD1, or PD-L1 in a subject with neoplasia will not result in clinical benefit in the subject if the expression level of SerpinB9, TGFβ-1, FAP, VEGFA, and/or ANGPT2 in the test sample is higher than the level of SerpinB9, TGFβ-1, FAP, VEGFA, and/or ANGPT2, respectively, in the reference sample.

In other cases, the at least one TIDE-associated gene comprises SerpinB9; and it is determined that inhibition of CTLA4, PD1, or PD-L1 in a subject with neoplasia will not result in clinical benefit in the subject if the expression level of SerpinB9 in the test sample is higher than the level of SerpinB9 in the reference sample.

Alternatively, the at least one TIDE-associated gene comprises SerpinB9 and/or TGFβ-1; and it is determined that inhibition of CTLA4, PD1, or PD-L1 in a subject with neoplasia will not result in clinical benefit in the subject if the expression level of SerpinB9 and/or TGFβ-1 in the test sample is higher than the level of SerpinB9 and/or TGFβ-1, respectively, in the reference sample.

In one aspect, the at least one TIDE-associated gene comprises FAP, VEGFA, and/or ANGPT2; and it is determined that inhibition of CTLA4, PD1, or PD-L1 in a subject with neoplasia will not result in clinical benefit in the subject if the expression level of FAP, VEGFA, and/or ANGPT2 in the test sample is higher than the level of FAP, VEGFA, and/or ANGPT2, respectively, in the reference sample.

In another aspect, the at least one TIDE-associated gene comprises alpha-mannosidase 2 (MAN2A1); and it is determined that inhibition of CTLA4, PD1, or PD-L1 in a subject with neoplasia will not result in clinical benefit in the subject if the expression level of MAN2A1 in the test sample is higher than the level of MAN2A1 in the reference sample.

In some cases, the at least one TIDE-associated gene comprises cluster of differentiation 274 (CD274) and/or interferon gamma (IFNγ); and it is determined that inhibition of CTLA4, PD1, or PD-L1 in a subject with neoplasia will result in clinical benefit in the subject if the expression level of CD274 and/or IFNγ in the test sample is higher than the level of the corresponding gene in the reference sample.

Alternatively, the at least one TIDE-associated gene comprises SerpinB9, TGFβ-1, FAP, VEGFA, ANGPT2, CD274, IFNγ; and it is determined that inhibition of CTLA4, PD1, or PD-L1 in a subject with neoplasia will not result in clinical benefit in the subject if i) the expression level of SerpinB9, TGFβ-1, FAP, VEGFA, and/or ANGPT2 in the test sample is higher than the level of SerpinB9, TGFβ-1, FAP, VEGFA, and/or ANGPT2, respectively, in the reference sample, and ii) the expression level of CD274 and/or IFNγ in the test sample is lower than the level of the corresponding gene in the reference sample.

In some cases, the methods include optimizing the negative predictive value for non-responding subjects, i.e., optimizing the probability that predicted non-responders will truly be non-responsive to therapy. For example, the methods further comprise determining the expression level of IFNγ in the test sample, comparing the expression level of IFNγ in the test sample with the expression level of IFNγ in a reference sample, and determining that inhibition of CTLA4, PD1, or PD-L1 in a subject with neoplasia will not result in clinical benefit in the subject if both the expression level of the TIDE-associated gene in the test sample is lower than the TIDE-associated gene in the reference sample and the expression level of IFNγ in the test sample is lower than the level of IFNγ in the reference sample. For example, if both the TIDE prediction value and the IFNγ expression level in the test sample are lower as compared to a control or a threshold level, inhibition of CTLA4, PD1, or PD-L1 in a subject with neoplasia will not result in clinical benefit.

In addition to predicting patient response with the gene set approaches described above, also described herein is a genome-scale signature approach to predict patient response to immunotherapy, i.e., a second version of a TIDE signature. For each patient tumor, a test sample is classified into two distinct categories of "T-cell inflamed tumor" or "non-inflamed tumor" according to the expression level of cytotoxic T-cell marker genes (cluster of differentiation 8A (CD8A), CD8B, granzyme A (GZMA), GZMB, perforin-1 (PRF1)) compared to a reference sample. For T-cell inflamed tumors, the patient response is predicted as the Pearson correlation between the tumor expression profile and a signature of T cell dysfunction. For non-inflamed tumors, the patient response is predicted as the Pearson correlation between the tumor expression profile and a signature of T cell exclusion. Patients with positive correlations are classified as "non-responders," while patients with negative correlations are classified as "responders."

Both T-cell dysfunction and T-cell exclusion signatures are genome-scale score vectors comprising one score per human gene. The score vector of T-cell dysfunction is computed through an interaction test in the Cox-PH survival regression, reflecting the gene expression feature of tumors with high infiltration of cytotoxic T-cells, but short overall survival. The score vector of T-cell exclusion is the average gene expression profile of three immunosuppressive cell types, including cancer-associated fibroblast, M2 tumor-associated macrophage, and myeloid-derived suppressor cell. As described herein, high levels of these cell types in the tumor could exclude cytotoxic T cells from infiltrating and eliminating the tumors.

Survival of the subject treated with a CTLA4 inhibitor, a PD1 inhibitor, or a PD-L1 inhibitor is shortened as compared to survival of the subject not treated with a CTLA4 inhibitor, a PD1 inhibitor, or a PD-L1 inhibitor.

For example, clinical benefit in the subject comprises complete or partial response as defined by response evaluation criteria in solid tumors (RECIST), stable disease as defined by RECIST, or long-term survival in spite of disease progression or response as defined by immune-related response criteria (irRC).

In some cases, the test sample is obtained from the neoplasia tissue or from tumor microenvironment or from tumor-infiltrating immune cells. For example, the sample comprises a biological sample, wherein the biological sample comprises a plasma sample or a blood sample. In one aspect, the sample comprises deoxyribonucleic acid (DNA) or ribonucleic acid (RNA).

For example, the reference sample is obtained from healthy normal tissue, a neoplasia that received a clinical benefit from CTLA4, PD1, or PD-L1 inhibition, or neoplasia that did not receive a clinical benefit from CTLA4, PD1, or PD-L1 inhibition.

In some cases, the expression level of the at least one TIDE-associated gene is detected via an Affymetrix Gene Array hybridization, next generation sequencing, ribonucleic acid sequencing (RNA-seq), a real time reverse transcriptase polymerase chain reaction (real time RT-PCR) assay, immunohistochemistry (IHC), immunofluorescence.

For example, the expression level of the at least one TIDE-associated gene is detected via RNA-seq and the reference sample is obtained from healthy normal tissue from the same individual as the test sample or one or more healthy normal tissues from different individuals. In another example, the expression level of the at least one TIDE-associated gene is detected via RT-PCR and wherein the reference sample is obtained from the same tissue as the test sample.

In some cases, the subject has not yet received treatment with a CTLA4 inhibitor, a PD1 inhibitor, or a PD-L1 inhibitor. Accordingly, in one aspect, the methods further comprise administering to the subject an effective amount of a CTLA4 inhibitor, a PD1 inhibitor, or a PD L1 inhibitor, thereby treating the neoplasia. For example, the inhibitor comprises a small molecule inhibitor, RNA interference (RNAi), an antibody, an antibody fragment, an antibody drug conjugate, an aptamer, a chimeric antigen receptor (CAR), or any combination thereof. Exemplary CTLA4 inhibitors include ipilimumab and tremelimumab. Suitable PD1 inhibitors include pembrolizumab and nivolumab. Exemplary PD-L1 inhibitors include atezolizumab, avelumab, and durvalumab.

In one aspect, the methods further comprise treating the subject with a chemotherapeutic agent, radiation therapy, cryotherapy, hormone therapy, or immunotherapy. For example, the chemotherapeutic agent comprises dacarbazine, temozolomide, nab-paclitaxel, paclitaxel, cisplatin, or carboplatin.

In other cases, the methods further comprise administering an inhibitor of the at least one TIDE-associated gene with a higher level of expression compared to the level of the TIDE-associated gene in the reference sample, wherein the TIDE-associated gene comprises SerpinB9, TGFβ-1, FAP, VEGFA, or ANGPT2, thereby treating the neoplasia. For example, the inhibitor comprises a small molecule inhibitor, RNAi, an antibody, an antibody fragment, an antibody drug conjugate, an aptamer, a CAR, or any combination thereof.

Exemplary neoplasias include melanoma, kidney cancer, urothelial carcinoma, lung cancer, bladder cancer, leukemia, endometrial cancer, neuroblastoma, and breast cancer. Other suitable neoplasias include kidney renal clear cell carcinoma, head neck squamous cell carcinoma, esophageal carcinoma, glioblastoma multiforme, breast invasive carcinoma, kidney renal papillary cell carcinoma, cholangiocarcinoma, uterine corpus endometrial carcinoma, stomach adenocarcinoma, kidney chromophobe, bladder urothelial carcinoma, prostate adenocarcinoma, liver hepatocellular carcinoma, lung adenocarcinoma, ovarian serous cystadenocarcinoma, thyroid carcinoma, and lung squamous cell carcinoma.

Also provided are kits comprising a package with at least one TIDE-associated gene, wherein the TIDE-associated gene comprises SerpinB9, TGFβ-1, FAP, VEGFA, ANGPT2, CD274, IFNγ, and/or MAN2A1 synthesized complementary DNA (cDNA), and instructions for use thereof in determining whether inhibition of CTLA4, PD1, or PD-L1 in a subject with neoplasia will result in clinical benefit in the subject. In some cases, the TIDE-associated gene is immobilized on a solid support. In one aspect, the TIDE-associated gene is linked to a detectable label. For example, the detectable label comprises a fluorescent label, a luminescent label, a chemiluminescent label, a radiolabel, a SYBR Green label, or a Cy3-label.

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term "about."

The phrase "aberrant expression" is used to refer to an expression level that deviates from (i.e., an increased or decreased expression level) the normal reference expression level of the gene.

The term "antineoplastic agent" is used herein to refer to agents that have the functional property of inhibiting a development or progression of a neoplasm in a human, e.g., melanoma. Inhibition of metastasis is frequently a property of antineoplastic agents.

By "agent" is meant any small compound, antibody, nucleic acid molecule, or polypeptide, or fragments thereof.

By "alteration" is meant a change (increase or decrease) in the expression levels or activity of a gene or polypeptide as detected by standard art-known methods such as those described herein. As used herein, an alteration includes at least a 1% change in expression levels, e.g., at least a 2%, 3%, 4%, 5%, 6%, 7%, 8%, 9%, 10%, 20%, 30%, 40%, 50%, 60%, 70%, 80%, 90%, or 100% change in expression levels. For example, an alteration includes at least a 5%-10% change in expression levels, preferably a 25% change, more preferably a 40% change, and most preferably a 50% or greater change in expression levels.

By "ameliorate" is meant decrease, suppress, attenuate, diminish, arrest, or stabilize the development or progression of a disease.

The term "antibody" (Ab) as used herein includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by sodium dodecyl sulfate-polyacrylamide gel electrophoresis (SDS-PAGE) under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

By "binding to" a molecule is meant having a physico-chemical affinity for that molecule.

By "control" or "reference" is meant a standard of comparison. As used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., an antibody, a protein) or a substance produced by a reporter construct (e.g, β-galactosidase or luciferase). Depending on the method used for detection, the amount and measurement of the change can vary. Determination of statistical significance is within the ability of those skilled in the art, e.g., the number of standard deviations from the mean that constitute a positive result.

"Detect" refers to identifying the presence, absence, or amount of the agent (e.g., a nucleic acid molecule, for example DNA or RNA) to be detected.

By "detectable label" is meant a composition that when linked (e.g., joined—directly or indirectly) to a molecule of interest renders the latter detectable, via, for example, spectroscopic, photochemical, biochemical, immunochemical, or chemical means. Direct labeling can occur through bonds or interactions that link the label to the molecule, and indirect labeling can occur through the use of a linker or bridging moiety which is either directly or indirectly labeled. Bridging moieties may amplify a detectable signal. For example, useful labels may include radioactive isotopes, magnetic beads, metallic beads, colloidal particles, fluorescent labeling compounds, electron-dense reagents, enzymes (for example, as commonly used in an enzyme-linked immunosorbent assay (ELISA)), biotin, digoxigenin, or haptens. When the fluorescently labeled molecule is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, p-phthalaldehyde and fluorescamine. The molecule can also be detectably labeled using fluorescence emitting metals such as 152 Eu, or others of the lanthanide series. These metals can be attached to the molecule using such metal chelating groups as diethylenetriaminepentacetic acid (DTPA) or ethylenediaminetetraacetic acid (EDTA). The molecule also can be detectably labeled by coupling it to a chemiluminescent compound. The presence of the chemiluminescent-tagged molecule is then determined by detecting the presence of luminescence that arises during the course of chemical reaction. Examples of particularly useful chemiluminescent labeling compounds are luminol, isoluminol, theromatic acridinium ester, imidazole, acridinium salt and oxalate ester.

A "detection step" may use any of a variety of known methods to detect the presence of nucleic acid. The types of detection methods in which probes can be used include Western blots, Southern blots, dot or slot blots, and Northern blots.

As used herein, the term "diagnosing" refers to classifying pathology or a symptom, determining a severity of the pathology (e.g., grade or stage), monitoring pathology progression, forecasting an outcome of pathology, and/or determining prospects of recovery.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to ameliorate the symptoms of a disease, e.g., melanoma, relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "expression profile" is used broadly to include a genomic expression profile. Profiles may be generated by any convenient means for determining a level of a nucleic acid sequence, e.g., quantitative hybridization of microRNA, labeled microRNA, amplified microRNA, complementary/synthetic DNA (cDNA), etc., quantitative polymerase chain reaction (qPCR), and ELISA for quantitation, and allow the analysis of differential gene expression between two samples. A subject or patient tumor sample is assayed. Samples are collected by any convenient method, as known in the art. In some cases, the term "expression profile" means measuring the relative abundance of the nucleic acid sequences in the measured samples.

By "FDR" is meant False Discovery Rate. When performing multiple statistical tests, for example, in comparing the signal of two groups in multiple data features, there is an increasingly high probability of obtaining false positive results, by random differences between the groups that can reach levels that would otherwise be considered statistically significant. In some cases, in order to limit the proportion of such false discoveries, statistical significance is defined only for data features in which the differences reached a p-value (by two-sided t-test) below a threshold, which is dependent on the number of tests performed and the distribution of p-values obtained in these tests.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. For example, a fragment may contain 10, 20, 30, 40, 50, 60, 70, 80, 90, or 100, 200, 300, 400, 500, 600, 700, 800, 900, or 1000 nucleotides or amino acids. However, the invention also comprises polypeptides and nucleic acid fragments, so long as they exhibit the desired biological activity of the full length polypeptides and nucleic acid, respectively. A nucleic acid fragment of almost any length is employed. For example, illustrative polynucleotide segments with total lengths of about 10,000, about 5000, about 3000, about 2,000, about 1,000, about 500, about 200, about 100, about 50 base pairs in length (including all intermediate lengths) are included in many implementations of this invention. Similarly, a polypeptide fragment of almost any length is employed. For example, illustrative polypeptide segments with total lengths of about 10,000, about 5,000, about 3,000, about 2,000, about 1,000, about 5,000, about 1,000, about 500, about 200, about 100, or about 50 amino acids in length (including all intermediate lengths) are included in many implementations of this invention.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

A "purified" or "biologically pure" gene or protein is sufficiently free of other materials such that any impurities do not materially affect the biological properties of the gene or protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a synthetic cDNA, a genomic fragment, a fragment produced by PCR, or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide. Isolated nucleic acid molecules also include messenger ribonucleic acid (mRNA) molecules.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by high performance liquid chromatography (HPLC) analysis.

The term "immobilized" or "attached" refers to a probe (e.g., nucleic acid or protein) and a solid support in which the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule to the support and the non-covalent binding of a biotinylated probe to the molecule. Immobilization may also involve a combination of covalent and non-covalent interactions.

"Laser capture microdissection" or "LCM" is a method for isolating specific cells from microscopic regions of tissues, cells or organisms. LCM is a method to procure subpopulations of tissue cells under direct microscopic visualization. LCM technology can harvest the cells of interest directly or it can isolate specific cells by cutting away unwanted cells to give histologically pure enriched cell populations.

By "marker" is meant any protein or polynucleotide having an alteration in expression level or activity that is associated with a disease or disorder, e.g., melanoma.

By "modulate" is meant alter (increase or decrease). Such alterations are detected by standard art-known methods such as those described herein.

The term, "normal amount" refers to a normal amount of a complex in an individual known not to be diagnosed with cancer. The amount of the molecule can be measured in a test sample and compared to the "normal control level," utilizing techniques such as reference limits, discrimination limits, or risk defining thresholds to define cutoff points and abnormal values (e.g., for cancer). The "normal control level" means the level of one or more proteins (or nucleic acids) or combined protein indices (or combined nucleic acid indices) typically found in a subject known not to be suffering from cancer. Such normal control levels and cutoff points may vary based on whether a molecule is used alone or in a formula combining other proteins into an index. Alternatively, the normal control level can be a database of protein patterns from previously tested subjects who did not convert to cancer over a clinically relevant time horizon.

The level that is determined may be the same as a control level or a cut off level or a threshold level, or may be increased or decreased relative to a control level or a cut off level or a threshold level. In some aspects, the control subject is a matched control of the same species, gender, ethnicity, age group, smoking status, body mass index (BMI), current therapeutic regimen status, medical history, or a combination thereof, but differs from the subject being diagnosed in that the control does not suffer from the disease in question or is not at risk for the disease.

Relative to a control level, the level that is determined may be an increased level. As used herein, the term "increased" with respect to level (e.g., expression level, biological activity level, etc.) refers to any % increase above a control level. The increased level may be at least or about a 1% increase, at least or about a 5% increase, at least or about a 10% increase, at least or about a 15% increase, at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, or at least or about a 95% increase, relative to a control level.

Relative to a control level, the level that is determined may be a decreased level. As used herein, the term "decreased" with respect to level (e.g., expression level, biological activity level, etc.) refers to any % decrease below a control level. The decreased level may be at least or about a 1% decrease, at least or about a 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, or at least or about a 95% decrease, relative to a control level.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule.

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "neoplasia" is meant a disease or disorder characterized by excess proliferation or reduced apoptosis. Illustrative neoplasms for which the invention can be used include, but are not limited to pancreatic cancer, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

As used herein, in one aspect, "next-generation sequencing" (NGS), also known as high-throughput sequencing, is the catch-all term used to describe a number of different sequencing methodologies including, but not limited to, Illumina® sequencing, Roche 454 Sequencing™, Ion Torrent™: Proton/personal genome machine (PGM) sequencing, and SOLiD sequencing. These recent technologies allow for sequencing DNA and RNA much more quickly and cheaply than the previously used Sanger sequencing. See, LeBlanc et al., 2015 Cancers, 7: 1925-1958, incorporated herein by reference; and Goodwin et al., 2016 Nature Reviews Genetics, 17: 333-351, incorporated herein by reference.

As used herein, "obtaining" as in "obtaining an agent" includes synthesizing, purchasing, or otherwise acquiring the agent.

Unless specifically stated or obvious from context, as used herein, the term "or" is understood to be inclusive. Unless specifically stated or obvious from context, as used herein, the terms "a", "an", and "the" are understood to be singular or plural.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

By "protein" or "polypeptide" or "peptide" is meant any chain of more than two natural or unnatural amino acids, regardless of post-translational modification (e.g., glycosylation or phosphorylation), constituting all or part of a naturally-occurring or non-naturally occurring polypeptide or peptide, as is described herein.

"Primer set" means a set of oligonucleotides that may be used, for example, for PCR. A primer set would consist of at least 2, 4, 6, 8, 10, 12, 14, 16, 18, 20, 30, 40, 50, 60, 80, 100, 200, 250, 300, 400, 500, 600, or more primers.

The terms "preventing" and "prevention" refer to the administration of an agent or composition to a clinically asymptomatic individual who is at risk of developing, susceptible, or predisposed to a particular adverse condition, disorder, or disease, and thus relates to the prevention of the occurrence of symptoms and/or their underlying cause.

The term "prognosis," "staging," and "determination of aggressiveness" are defined herein as the prediction of the degree of severity of the neoplasia, e.g., melanoma, and of its evolution as well as the prospect of recovery as anticipated from usual course of the disease. Once the aggressiveness has been determined, appropriate methods of treatments are chosen.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 10%, 25%, 50%, 75%, or 100%.

A "reference sequence" is a defined sequence used as a basis for sequence comparison or a gene expression comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 40 nucleotides, preferably at least about 60 nucleotides, more preferably at least about 75 nucleotides, and even more preferably about 100 nucleotides or about 300 or about 500 nucleotides or any integer thereabout or there between.

The term "sample" as used herein refers to a biological sample obtained for the purpose of evaluation in vitro. Exemplary tissue samples for the methods described herein include tissue samples from tumors or the surrounding microenvironment (i.e., the stroma). With regard to the methods disclosed herein, the sample or patient sample preferably may comprise any body fluid or tissue. In some embodiments, the bodily fluid includes, but is not limited to, blood, plasma, serum, lymph, breast milk, saliva, mucous, semen, vaginal secretions, cellular extracts, inflammatory fluids, cerebrospinal fluid, feces, vitreous humor, or urine obtained from the subject. In some aspects, the sample is a composite panel of at least two of a blood sample, a plasma sample, a serum sample, and a urine sample. In exemplary aspects, the sample comprises blood or a fraction thereof (e.g., plasma, serum, fraction obtained via leukopheresis). Preferred samples are whole blood, serum, plasma, or urine. A sample can also be a partially purified fraction of a tissue or bodily fluid.

A reference sample can be a "normal" sample, from a donor not having the disease or condition fluid, or from a normal tissue in a subject having the disease or condition. A reference sample can also be from an untreated donor or cell culture not treated with an active agent (e.g., no treatment or administration of vehicle only). A reference sample can also be taken at a "zero time point" prior to contacting the cell or subject with the agent or therapeutic intervention to be tested or at the start of a prospective study.

A "solid support" describes a strip, a polymer, a bead, or a nanoparticle. The strip may be a nucleic acid-probe (or protein) coated porous or non-porous solid support strip comprising linking a nucleic acid probe to a carrier to prepare a conjugate and immobilizing the conjugate on a porous solid support. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to a binding agent (e.g., an antibody or nucleic acid molecule). Thus, the support configuration may be spherical, as in a bead, or cylindrical, as in the inside surface of a test tube, or the external surface of a rod. Alternatively, the surface may be flat such as a sheet, or test strip, etc. For example, the supports include polystyrene beads. Those skilled in the art will know many other suitable carriers for binding antibody or antigen, or will be able to ascertain the same by use of routine experimentation. In other aspects, the solid support comprises a polymer, to which an agent is chemically bound, immobilized, dispersed, or associated. A polymer support may be a network of polymers, and may be prepared in bead form (e.g., by suspension polymerization). The location of active sites introduced into a polymer support depends on the type of polymer support. For example, in a swollen-gel-bead polymer support the active sites are distributed uniformly throughout the beads, whereas in a macroporous-bead polymer support they are predominantly on the internal surfaces of the macropores. The solid support, e.g., a device contains a binding agent alone or together with a binding agent for at least one, two, three or more other molecules.

By "specifically binds" is meant a compound or antibody that recognizes and binds a polypeptide of the invention, but which does not substantially recognize and bind other molecules in a sample, for example, a biological sample, which naturally includes a polypeptide of the invention.

A "specific binding agent" describes agents having greater than 10-fold, preferably greater than 100-fold, and most preferably, greater than 1000-fold affinity for the target molecule as compared to another molecule. As the skilled artisan will appreciate the term specific is used to indicate that other biomolecules present in the sample do not significantly bind to the binding agent specific for the target molecule. Preferably, the level of binding to a biomolecule other than the target molecule results in a binding affinity which is at most only 10% or less, only 5% or less only 2% or less or only 1% or less of the affinity to the target molecule, respectively. A preferred specific binding agent will fulfill both the above minimum criteria for affinity as well as for specificity. For example, an antibody has a binding affinity in the low micromolar ($10^{-6}$), nanomolar ($10^{-7}$-$10^{-9}$), with high affinity antibodies in the low nanomolar ($10^{-9}$), or pico molar ($10^{-12}$) range for its specific target molecule.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95%, or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

The term "subject" as used herein includes all members of the animal kingdom prone to suffering from the indicated disorder. In some aspects, the subject is a mammal, and in some aspects, the subject is a human. The methods are also applicable to companion animals such as dogs and cats as well as livestock such as cows, horses, sheep, goats, pigs, and other domesticated and wild animals.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from conditions associated with cancer (e.g., prostate cancer) is within the ability of those in the art. Subjects suffering from, and suspected of suffering from, a specific disease, condition, or syndrome are not necessarily two distinct groups.

As used herein, "susceptible to" or "prone to" or "predisposed to" or "at risk of developing" a specific disease or condition refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. It will be appreciated that, although not precluded, treating a disorder or condition does not require that the disorder, condition or symptoms associated therewith be completely eliminated.

As used herein, in one aspect, the "tumor microenvironment" (TME) is the cellular environment in which a tumor exists, including surrounding blood vessels, immune cells, fibroblasts, bone marrow-derived inflammatory cells, lymphocytes, signaling molecules and the extracellular matrix (ECM). The tumor and the surrounding microenvironment are closely related and interact constantly. Tumors can influence the microenvironment by releasing extracellular signals, promoting tumor angiogenesis and inducing peripheral immune tolerance, while the immune cells in the microenvironment can affect the growth and evolution of cancerous cells, such as in immuno-editing.

In some cases, a composition of the invention is administered orally or systemically. Other modes of administration include rectal, topical, intraocular, buccal, intravaginal, intracisternal, intracerebroventricular, intratracheal, nasal, transdermal, within/on implants, or parenteral routes. The term "parenteral" includes subcutaneous, intrathecal, intravenous, intramuscular, intraperitoneal, or infusion. Intravenous or intramuscular routes are not particularly suitable for long-term therapy and prophylaxis. They could, however, be preferred in emergency situations. Compositions comprising a composition of the invention can be added to a physiological fluid, such as blood. Oral administration can be preferred for prophylactic treatment because of the convenience to the patient as well as the dosing schedule. Parenteral modalities (subcutaneous or intravenous) may be preferable for more acute illness, or for therapy in patients that are unable to tolerate enteral administration due to gastrointestinal intolerance, ileus, or other concomitants of critical illness. Inhaled therapy may be most appropriate for pulmonary vascular diseases (e.g., pulmonary hypertension).

Pharmaceutical compositions may be assembled into kits or pharmaceutical systems for use in arresting cell cycle in rapidly dividing cells, e.g., cancer cells. Kits or pharmaceutical systems according to this aspect of the invention comprise a carrier means, such as a box, carton, tube, having in close confinement therein one or more container means, such as vials, tubes, ampoules, bottles, syringes, or bags. The kits or pharmaceutical systems of the invention may also comprise associated instructions for using the kit.

Any compositions or methods provided herein can be combined with one or more of any of the other compositions and methods provided herein.

Any compositions or methods provided herein can be combined with one or more of any of the other compositions and methods provided herein.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference.

Genbank and National Center for Biotechnology Information (NCBI) submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 1A is a graph showing the association between the cytotoxic T lymphocyte level (CTL) and survival outcome based on TGFB1 expression for patients with metastatic melanoma tumors profiled in The Cancer Genome Atlast (TCGA). For each tumor, the CTL level was estimated by the expression sum of CD8A, CD8B, GZMA, GZMB, and PRF1. Samples were divided into 2 groups for each Kaplan Meier plot: "High CTL" (red) have above-average CTL values among all samples, while "Low CTL" samples (blue) are below average. Left panel shows melanomas with High TGFB1 expression (>1 standard deviation above the average); Low TGFβ1 (the remaining samples) are plotted in the right panel. FIG. 1B is a graph showing the interaction test in a Cox-PH regression to identify genes associated with the T-cell dysfunction. The variable CTL represents the level of cytotoxic T lymphocytes in each tumor. The variable P represents the expression status of a candidate gene in the test. The coefficient "d" reflects the interaction between the CTL and P on death hazard outcome, estimated from the survival data. Graphs represent the association slopes between CTL and death hazard. The black and gold arrows represent the association slopes before and after increasing the level of P. FIG. 1C is a graph showing the distribution of test p-values computed using TCGA melanoma and glioblastoma datasets. p-values deemed significant are shown in red. The melanoma samples met the criteria for more than 1% genes passing a false discover rate (FDR) of 0.1. Glioblastoma did not meet the threshold. FIG. 1D is a schematic showing hierarchical clustering of T-cell dysfunction scores among the top five datasets with more than 1% of genes passing the FDR threshold 0.1. The genome-wide Pearson correlation between profiles is the similarity metric. UCEC: uterine corpus endometrial carcinoma, TNBC: triple negative breast cancer, AML: acute myeloid leukemia, SKCM: skin cutaneous melanoma, NB: neuroblastoma.

FIG. 2 is a colorimetric display of the T-cell dysfunction score for genes that had a p-value corresponding to an FDR less than 0.1 in at least two cancer types among the five cancer types that passed the statistical threshold described in FIG. 1C. Orange stars indicate genes of special interest.

FIG. 3A is a graph showing the dysfunction scores averaged across five cancer types (FIG. 2) for the positive (red) and negative (blue) hits of each of the gene signatures defined in Table 3. The bottom and top of the boxes are the 25th and 75th percentiles (interquartile range). Whiskers encompass 1.5 times the inter-quartile range. : p-value<1e-2; *: p-value<1e-3 (two-sided Wilcoxon rank-sum test).

FIG. 3B is a graph showing the receiver operating characteristic (ROC) curves measuring the performance of the average T-cell dysfunction scores (bottom row in FIG. 2) in predicting the positive and negative gene hits in each signature in panel A. FIG. 3C is a graph showing the area under ROC curve (AUC) of the average profile of all the tested cancer types (black squares; ROC curve in FIG. 1B), and each of the individual cancer types SKCM, AML, NB, UCEC, TNBC with different dot colors. FIG. 3D is a graph showing a colorimetric representation of the Pearson correlations between the T-cell dysfunction scores for five human cancer types and the gene expression profile of exhausted T cells at different time points in a mouse model of T-cell exhaustion states ("T exh Fixed" in Table 3).

FIG. 4A is a series of dot plots, wherein for each metastatic tumor in the TCGA melanoma dataset (blue dots, n=317), the Pearson correlation was computed between each sample's expression profile and expression signature of either myeloid-derived suppressor cells, M2 tumor-associated macrophages, cancer-associated fibroblasts (described in Table 3) or the average of those three expression signatures (right). In each graph, those values are plotted along the x-axis. The y-axis shows the CTL level for each sample (expression sum of CD8A, CD8B, GZMA, GZMB, PRF1). The Pearson correlation between the plotted values is shown in the upper right corner of each plot. FIG. 4B is a histogram across 43 datasets of solid tumors, representing the correlations between the CTL level and the "T-cell exclusion signature", which is defined for as the Pearson correlation between the tumor expression value in each dataset and the average expression profile among the three cell types shown in the right part of panel A. Gliomas are excluded because of low T-cell infiltration levels in most gliomas. FIG. 4C is a dot plot, wherein for each metastatic melanoma tumor (color dots, n=317), the Pearson correlation was computed between the sample's expression profile and the TIDE signature of T-cell dysfunction. This value is called the "dysfunction correlation" and was plotted on the Y-axis. The same computation was made for the patient's cancer expression profile and the TIDE signature of T-cell exclusion. This value is called the "exclusion correlation" and was plotted on the X-axis. The Pearson correlation between the plotted values is shown in the upper right. Dot color indicates the level of CTL infiltration in each tumor sample. FIG. 4D is a dot plot, wherein for each TCGA cancer type with normal control samples (n=17), the average expression difference was calculated between tumor versus normal samples. Next, the Pearson correlation was computed between that value and the TIDE signatures of T-cell dysfunction. This Pearson correlation is called the "dysfunction correlation" and plotted on the Y-axis. The same calculation was made but for TIDE signature of T-cell exclusion, and those Pearson Correlation values were plotted on the X-axis. The Pearson correlation between the plotted values is shown in the upper right. The CTL level difference between tumor and normal samples is shown by the dot color. KIRC: kidney renal cell carcinoma, LUSC: lung squamous carcinoma.

FIG. 5A is a histogram wherein 25 tumors subjected to anti-PD1 immunotherapy were divided into T-cell inflamed (high T-cell infiltration) or non-inflamed (low T-cell infiltration) categories based on the expression level of CTL marker genes (FIG. 12A). Red indicates a tumor that responded to therapy. Blue indicates a non-responder. Next, the tumors in each category were sorted in descending order according to their TIDE score, defined as follows: for the inflamed class, TIDE scores are the scaled correlations between tumor expression profiles and T-cell dysfunction scores; for the non-inflamed class, TIDE scores are the scaled correlations between tumor expression profiles and T-cell exclusion scores (FIG. 12B). FIG. 5B is a histogram showing the same results as FIG. 5A, but for the 35 tumors subjected to anti-CTLA4 treatment. FIG. 5C is a line graph showing the ability of TIDE score (black), the total mutation load (purple), and PD-L1 expression (green) to predict response to anti-PD1 therapy, using ROC curves. There are 25 tumors for anti-PDJ treatment. FIG. 5D is a line graph showing the same results presented in FIG. 5C, but for the 35 tumors for anti-CTLA4 treatment. FIG. 5E is a graph showing the area under receiver operating characteristic curve (ROC) curve area under the curve (AUC) for TIDE and other response biomarkers of anti-PD1. FIG. 5F is a bar graph showing the same results presented in FIG. 5E, but for the anti CTLA-4 treatment. FIG. 5G is a graph showing Kaplan-Meier plots for patients with positive (>0) and negative (<0) TIDE scores under anti-PD1 treatment. The p-values shown were calculated by testing the association between TIDE scores and overall survival with the two-sided Ward test in a Cox-PH regression. FIG. 5H is a graph showing the same results presented in FIG. 5G, but for anti-CTLA4 treatment.

FIG. 6A is a graph, wherein for genes with significant T-cell dysfunction scores in FIG. 2, the log-fold change (log FC) of expression between anti-CTLA4 resistant and parental B16 murine tumors is shown in increasing order. The top gene is labeled by name. FIG. 6B is a graph showing the expression value of Serpinb9 between anti-CTLA4 resistant and parental B16 tumors. The p-value was calculated with the two-sided Wilcoxon rank-sum test. FIG. 6C is a line graph showing Kaplan-Meier plots of Serpinb9 positive (higher than average of all samples) and negative (lower than average) patients using the data from an anti-CTLA4 clinical study with 35 patients profiled (Van Allen et al., 2015 Science, 350: 207-211). Both progression-free survival and overall survival are shown. The association between Serpinb9 expression and patient survival was computed by the two-sided Wald test in a Cox-PH regression (Table 6A and Table 6B). FIG. 6D is a bar chart, wherein B16F10 tumor cells were co-cultured for three days with cytotoxic T cells at three different B16F10 to T cell ratios (3:1, 2:1, or 1:1). Each clustered regularly interspaced short palindromic repeats (CRISPR) guide ribonucleic acid (gRNA)-transduced green fluorescent protein (GFP) positive cell line (Control gray; Guide 1 pink; Guide 2 orange) was mixed with the parental GFP negative cell line at a 1:1 ratio. After co-culture, and the ratio of edited GFP+ cells to parental cells (GFP−) was determined by flow cytometry. The p-values of comparison between control and knockout conditions are all 0.0495 by two-sided Wilcoxon rank-sum test, showing an increased sensitivity of Serpinb9 knockout B16F10 tumor cells to T cell-mediated killing.

FIG. 7A is a graph, wherein for TCGA metastatic melanoma tumors, all samples were divided at CTL value zero (the average level of all samples) for comparison of survival fractions in the Kaplan Meier plot. The association between the CTL level and patient overall survival was computed through the two-sided Wald test in the Cox-PH regression. FIG. 7B is a graph showing the association between the CTL level and survival outcome based on the sex determining region Y (SRY)-Box 10 (SOX10) expression for patients with metastatic melanoma tumors profiled in TCGA. Melanoma tumors with 1 standard deviation above the average SOX10 expression value were selected for the analysis in the left panel. All of the remaining samples were plotted in the right panel.

FIG. 12A is a schematic wherein all cancer samples are classified into T cell inflamed or non-inflamed subtypes through the bulk tumor expression values of cytotoxic T lymphocyte (CTL) markers, including CD8A, CD8B, GZMA, GZMB, and PRF1. Tumors with all positive values are classified as T cell inflamed and other tumors are classified as non-inflamed. The TIDE scores of inflamed tumors are computed as the Pearson correlation between tumor expression profiles and TIDE signature of T cell dysfunction. The TIDE scores of non-inflamed tumors are computed as the Pearson correlation between tumor expression profiles and TIDE signature of T cell exclusion. FIG. 12B is a graph showing that each part of TIDE signature (e.g., dysfunction or exclusion) is a vector of scores across all human genes. The TIDE score for each tumor is a genome-wide scaled correlation between TIDE signatures and tumor gene expression profiles. The scaled correlation was computed as the Pearson correlation divided by the standard deviation of all correlations pre-computed using TCGA data of the same cancer type.

FIG. 13A is a graph, wherein 25 tumors subjected to anti-PD1 immunotherapy (Hugo et al., 2016 Cell, 165: 35-44) were divided into T-cell inflamed (high T-cell infiltration) or non-inflamed (low T-cell infiltration) categories based on the expression level of CTL marker genes (FIG. 12A). Red indicates a tumor that responded to therapy. Blue indicates a non-responder. Next, the tumors in each category were sorted in descending order according to their TIDE score, defined as follows. For the inflamed class, TIDE scores are the scaled correlations between tumor expression profiles and T-cell dysfunction scores. For the non-inflamed class, TIDE scores are the scaled correlations between tumor expression profiles and T-cell exclusion scores (FIG. 12B). FIG. 13B is the same results presented in FIG. 13A, but for the 35 tumors subjected to anti-CTLA4 treatment (Van Allen et al., 2015 Science, 350: 207-211). FIG. 13C is a dot plot showing TIDE scores for responders and nonresponders in clinical studies of anti-PD1 (Hugo et al., 2016 Cell, 165: 35-44) and anti-CTLA4 (Van Allen et al., 2015 Science, 350: 207-211). The difference between two groups was tested by the two-sided Wilcoxon rank-sum test. FIG. 13D is a bar chart wherein the area under ROC curve (AUC) is compared among several gene signatures of T-cell dysfunction and immunotherapy resistance in FIG. 3 (Table 3). FIG. 13E is a bar chart wherein the area under ROC curve (AUC) for each part of TIDE signatures (Dysfunction, Exclusion) in predicting ICB outcome of T-cell inflamed and non-inflamed tumors. For both anti-PD1 and anti-CTLA4 therapies, the T-cell dysfunction signature cannot achieve reliable response prediction for the non-inflamed tumors, and the T-cell exclusion signature cannot achieve reliable prediction for the T-cell inflamed tumors.

FIG. 14A is a dot plot wherein the Serpinb9 expression level in pre-treatment tumors is shown for responders and nonresponders of anti-CTLA4 therapy from a previous study of 9 patients (Nathanson et al., 2017 Cancer Immunol Res, 5: 84-91). FIG. 14B is a graph showing the overall survival for Serpinb9 positive (higher than average of all samples) and negative (lower than average) patients from an anti-CTLA4 study of 9 patients (Nathanson et al., 2017 Cancer Immunol Res, 5: 84-91). The association between the Serpinb9 expression in pre-treatment tumors and patient overall survival under anti-CTLA4 treatment was evaluated through the two-sided Wald test in a Cox-PH regression.

FIG. 15A is a graph, wherein for each cancer type, the fraction of samples with protein expression level high, medium, low, or not detected are provided by the blue color scales. The length of the bar represents the number of patient samples. FIG. 15B is a series of photographs showing the staining data for all melanoma tumors with two representative regions amplified for details. The cell nuclei are labeled by blue color and the Serpinb9 protein is stained with brown color. According to the Protein Atlas annotation, the Serpinb9 protein is highly expressed at cancer cell cytoplasm, membrane, and nucleus.

DETAILED DESCRIPTION OF THE INVENTION

Figure 1A:
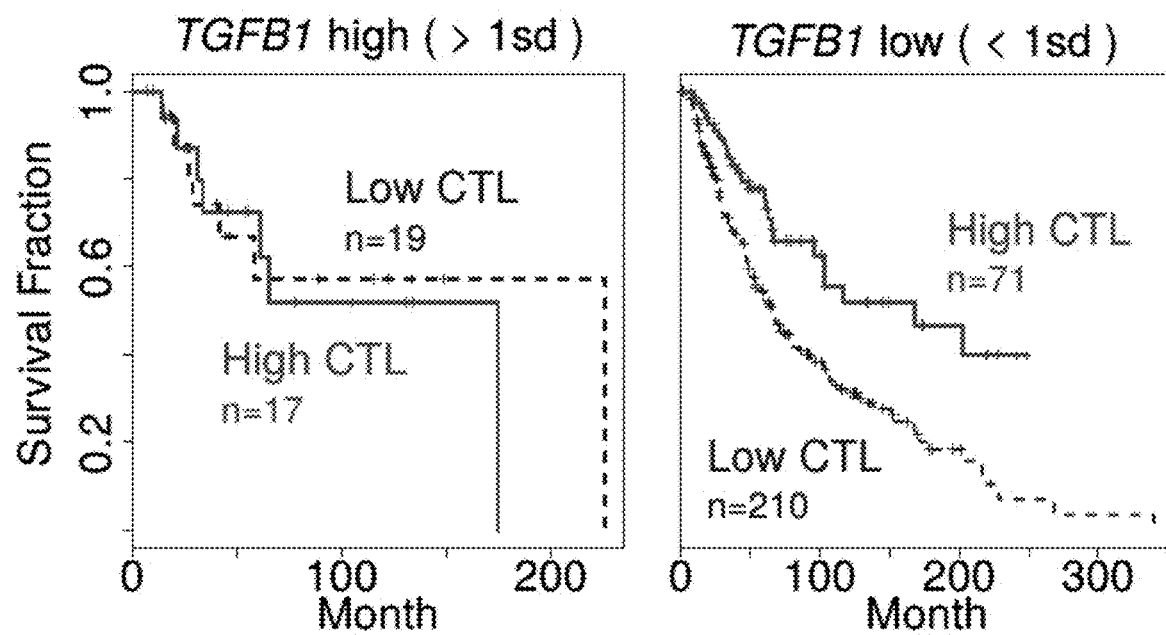
FIG. 1A-1D is a series of line graphs, histograms, and a schematic showing that an interaction test identifies gene signatures of T-cell dysfunction.

The present invention is based, at least in part, upon the surprising identification that gene signatures of T-cell dysfunction and exclusion predict cancer immunotherapy response. Specifically, described herein is a computational framework, Tumor Immune Dysfunction and Exclusion (TIDE), which utilizes the vast amount of public clinical datasets to predict biomarkers of immunotherapy response. As described in detail below, TIDE utilized the interaction test in a multivariate model to identify the molecular features of tumors where high CD8 T cell infiltration does not associate with survival benefits. As describe in the examples below, the top scored genes are enriched with drivers of T cell dysfunction identified by short hairpin ribonucleic acid (shRNA) screen in mouse models, markers of T cell exhaustion in irreversible state, and reversely correlated with transcriptome profiles of cell types that drives T cell exclusion in tumors. The TIDE signatures described herein, computed from clinical data without immunotherapies, reliably predict the clinical response of melanoma patients for both anti-programmed cell death protein 1 (anti-PD1) and anti-cytotoxic T-lymphocyte associated antigen 4 (anti-CTLA4) therapies, with higher accuracy than mutation load and other biomarkers for both targeted therapy and immunotherapy.

Prior to the invention described herein, despite success in treating several cancer types, immunotherapy only showed response in a subset of patients. Accordingly, prior to the invention described herein, there was a pressing need to identify methods of predicting therapy response, as well as to understand the related resistance mechanisms. The TIDE signature described herein achieved a higher prediction accuracy of clinical response than previous biomarkers for immunotherapy.

Cancer immunotherapies by immune checkpoint blockade (ICB) aim to help the immune system recognize and attack cancer cells (Sharma, P. & Allison, J. P. 2015 Cell, 161: 205-214). The primary targets of ICB treatment are programmed death-ligand 1 (PD-L1): programmed cell death protein 1 (PD1) and Cytotoxic T-lymphocyte-associated antigen-4 (CTLA4) (Mahoney et al., 2015 Nature Reviews. Drug discovery, 14: 561-584). Compared to conventional therapies, ICB can induce durable responses in patients with metastatic cancers. However, prior to the invention described herein, a significant limitation of ICB was that only small percentages of patients respond to ICB in most cancer types tested (Sharma et al., 2017 Cell 168, 707-723). Combination ICB therapies have shown improved outcomes but also result in more severe side effects than single-agent therapy (Callahan et al., 2014 Frontiers in Oncology, 4: 385). Multiple factors have been associated with ICB effectiveness, including the degree of cytotoxic T-cell infiltration, mutation or neo-antigen load, checkpoint molecule expression, antigen presentation defects, interferon signaling, tumor aneuploidy, some oncogenic signatures, and intestinal microbiota (Sharma et al., 2017 Cell 168, 707-723; Masucci et al. 2016 Journal for Immunotherapy of Cancer, 4: 76; Davoli et al., 2017 Science, 355(6322): 8399; Cogdill et al., 2017 British Journal of Cancer, 117: 1-7; Snyder et al., 2014 The New England Journal of Medicine, 371: 2189-2199; Le et al., 2015 The New England Journal of Medicine, 372: 2509-2520; Sivan et al., 2015 Science, 350: 1084-1089). However, none of these factors are sufficiently robust to achieve accurate outcome prediction (Nishino et al., 2017 Nature Reviews. Clinical Oncology, 14(11): 655-668). Prior to the invention described herein, identification of ICB response biomarkers and resistance regulators were critical challenges in the field.

Gene expression biomarkers, such as Oncotype DX (Paik et al., 2004 The New England Journal of Medicine, 351: 2817-2826), MammaPrint (van 't Veer et al., 2002 Nature, 415: 530-536), and Prosigna (Parker et al., 2009 Journal of Clinical Oncology: Official Journal of the American Society of Clinical Oncology, 27: 1160-1167), have demonstrated clinical utility in predicting therapy benefits in breast cancer. As described herein, it is hypothesized that transcriptome signatures also serve as reliable ICB biomarkers. Ideally, a large number of tumor molecular profiles together with the patient clinical outcome could be used to train a reliable multi-gene biomarker. However, prior to the invention described herein, ICB clinical trials only had gene expression profiles on a small number of pre-treatment samples, which are insufficient to train robust prognostic biomarkers (Van Allen et al., 2015 Science, 350: 207-211; Hugo et al., 2016 Cell, 165: 35-44; Chen et al., 2016 Cancer Discovery, 6: 827-837; Nathanson et al., 2017 Cancer Immunol Res, 5: 84-91; Ascierto et al., 2016 Cancer Immunol Res, 4: 726-733).

Alternatively, there are many public tumor profiling datasets from human and mouse models without immunotherapy treatment, but which are informative regarding tumor immune escape. For example, analyses of the The Cancer Genome Atlas (TCGA) and Prediction of Clinical Outcomes from Genomics (PRECOG) data uncovered that the tumor-infiltrating levels of different immune cell types have significant effects on patient overall survival (Rooney et al., 2015 Cell, 160: 48-61; Gentles et al., 2015 Nature Medicine, 21: 938-945; Li et al., 2016 Genome Biology, 17: 174). Predicting tumor response to ICB requires an understanding of how tumors escape the immune system. Therefore, as described herein, the public tumor molecular profiles, even without ICB treatment, are still be valuable resources to model immune evasion and derive surrogate biomarkers of ICB response.

Recent work has revealed two distinct mechanisms (Gajewski et al., 2013 Nat Immunol, 14: 1014-1022; Joyce et al., 2015 Science 348, 74-80). In some resistant tumors, a high level of infiltration by cytotoxic T cells is observed, but these T cells tend to be in a dysfunctional state. In other resistant tumors, T cells are excluded from tumors (Spranger, S. & Gajewski, T. F. 2016 Oncoimmunology, 5(3): 1086862). As described in detail below, based on these two mechanisms, a computational framework, Tumor Immune Dysfunction and Exclusion (TIDE), was developed to identify factors that underlie tumor immune escape. The framework integrated and modeled the data from hundreds of human and murine cancer studies. As described herein, it was validated that an accurate gene signature to model the tumor immune escape could serve as a reliable surrogate biomarker to predict ICB response.

Tumor Immune Dysfunction and Exclusion (TIDE)

Cancer treatment by Immune Checkpoint Blockade (ICB) can bring long-lasting clinical benefits, but only a fraction of patients responds to treatment and side effects can be severe. Tumors evade the immune system by two primary mechanisms: inducing T-cell dysfunction or preventing T-cell infiltration. As described in detail below, to predict the ICB clinical response, a computational model called TIDE was developed. As described herein, transcriptome signatures of T-cell dysfunction were identified by testing how the expression of each gene in tumors interacts with the degree of cytotoxic T cell infiltration to influence patient survival. Next, factors that exclude T-cell infiltration into tumors were modeled using the gene signatures of immune-suppressive cells. As described in the examples below, gene expression profiling of sensitive versus resistant tumors from clinical trials was performed. With this framework and using pre-treatment tumor expression profiles, TIDE could predict the outcome of melanoma patients treated with anti-PD1 and anti-CTLA4 with a higher accuracy than other biomarkers such as PD-L1 level and mutation load. TIDE also revealed new ICB resistance regulators, such as Serpinb9, which demonstrated its utility for immunotherapy research.

The computational method described herein, TIDE, integrates expression signatures of T-cell dysfunction and T-cell exclusion to model the potential of tumor immune escape. As described in the examples below, the TIDE signatures, trained from treatment-naïve tumor data, predict ICB clinical response based on pre-treatment tumor profiles. The results presented herein suggest that the transcriptome of primary tumors can inform immunotherapy decisions. Furthermore, TIDE predicted regulators of ICB resistance whose inhibition might improve patient response to ICB treatment. Also, as described herein, the role of Serpinb9, an inhibitor of the cytotoxic lymphocyte protease GZMB, was experimentally validated in tumor immune evasion. Prior to the invention described herein, a small molecule inhibitor of Serpinb9 had not yet been developed; however, the Pfizer OASIS database indicates that this gene is druggable (Fernandez-Banet et al., 2016 Nat Methods, 13: 9-10).

When using the TIDE model to predict ICB response, a cutoff for classifying the T-cell inflamed versus non-inflamed tumors was determined. The cutoff to call inflamed tumors could be based on the average expression of CTL markers (CD8A, CD8B, GZMA, GZMB, PRF1) across all tumors, or comparing the CTL marker expression in tumors with matched normal tissues. However, for clinical trials that use different analysis platforms, such as NanoString, or qPCR, the CTL cutoff for calling inflamed tumors will need platform-specific calibration. The TIDE signature consists of genome-wide scores of T-cell dysfunction and exclusion. While a genome-wide transcriptome biomarker might be more robust for ICB response prediction, RNA-seq has not been a clinically adopted assay for biomarker analysis. A smaller gene panel for qPCR or NanoString assays could be implemented clinically, although the robust selection of gene panels would require additional tumor profiling data from ICB clinical trials. Also, the results presented herein validated the performance of TIDE in 60 melanoma patients treated with ICB from two cohorts. Going forward, the performance of TIDE as prognostic biomarkers is further examined in larger clinical datasets and other cancer types. As described herein, TIDE predicts the response and resistance to initial ICB treatment. However, tumors initially responding to ICB may later acquire mutations in β2 microglobulin (B2M), interferon gamma receptor 1/2 (IFNGR1/2), and janus kinase 1 (JAK1/2) genes to become resistant (Sharma et al., 2017 Cell 168, 707-723). Accordingly, going forward, computational methods are utilized to examine ICB-acquired resistance.

Figure 1B:
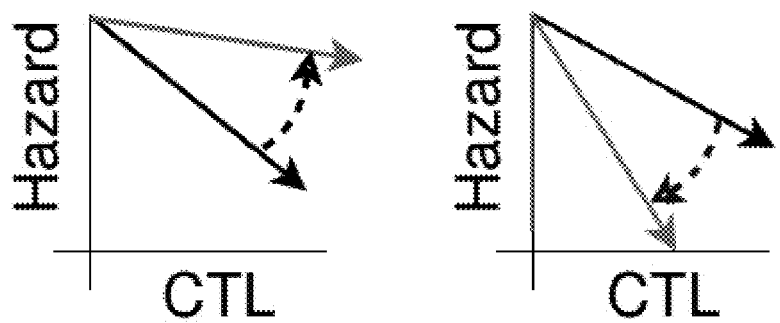
Figure 1C:
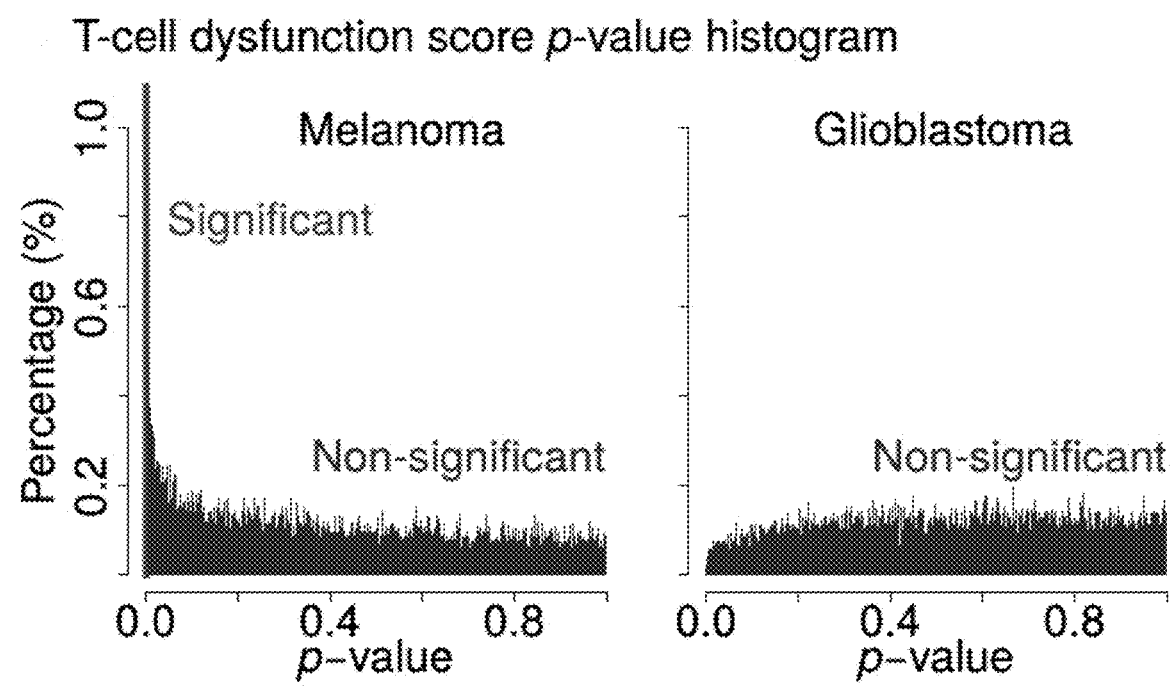
Figure 1D:
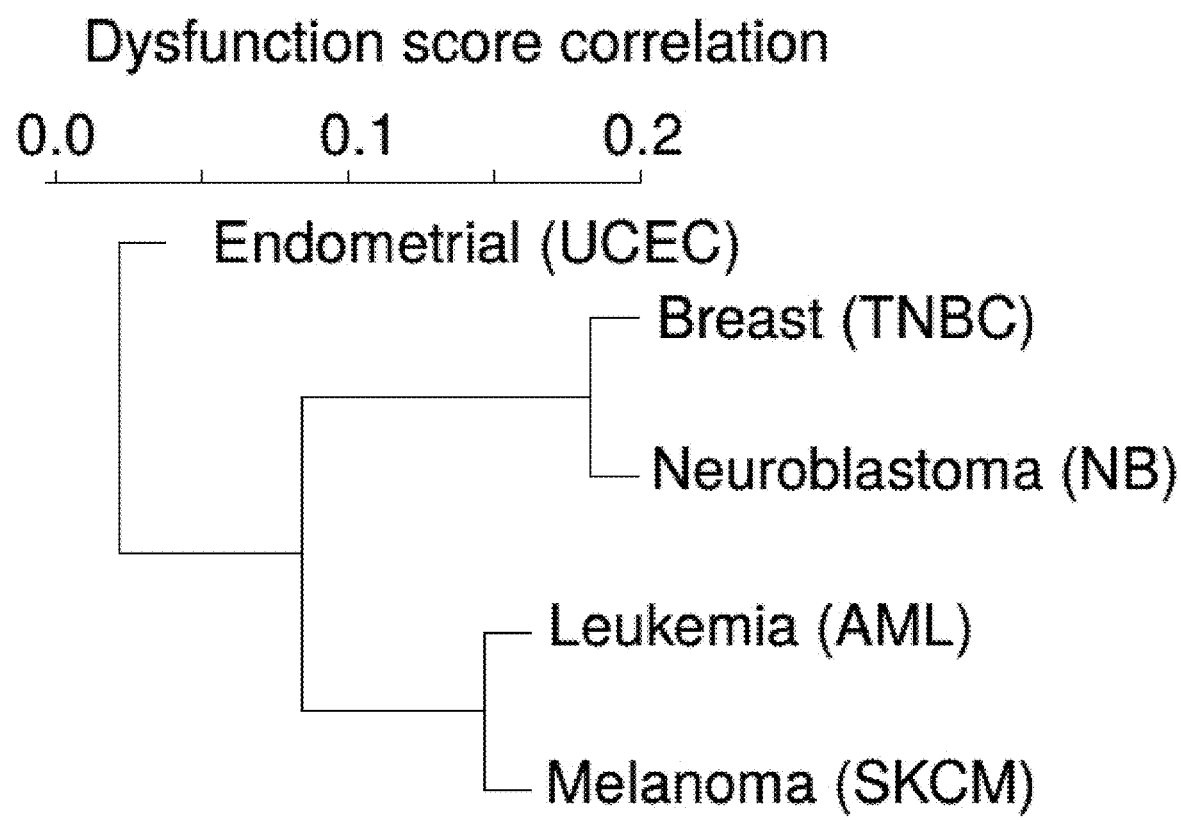
Figure 3A:
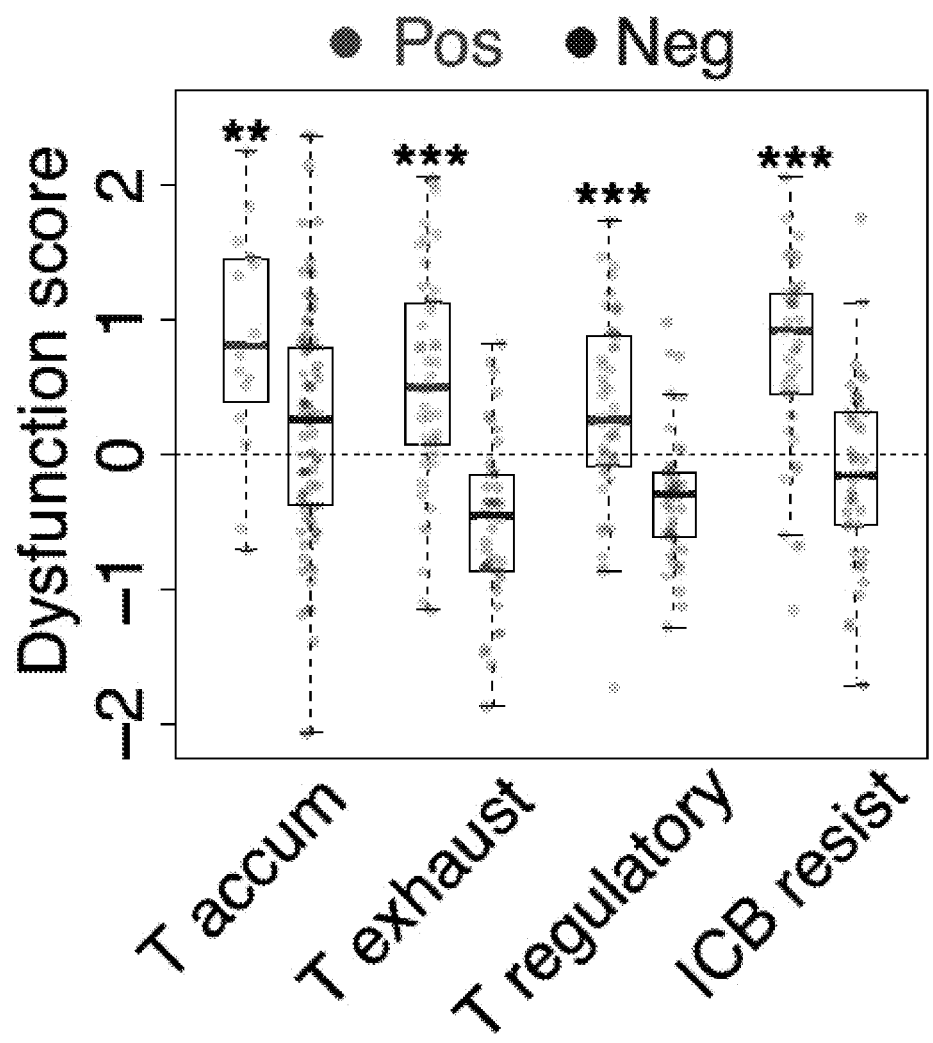
FIG. 3A-FIG. 3D is a series of graphs showing that predicted T-cell dysfunction scores are consistent with gene signatures of T-cell dysfunction in tumors. To evaluate the reliability of the dysfunction scores, four published gene signatures related to T-cell dysfunction and immunotherapy resistance were collected (Table 3): T accum—short hairpin (shRNA) screens for regulators of T-cell accumulation in tumors; T exhaust—transcriptome of exhausted T cells; T regulatory—transcriptome of regulatory T cells. ICB resist—transcriptome of murine tumors that resist anti-CTLA4 immune checkpoint blockade.
Figure 3B:
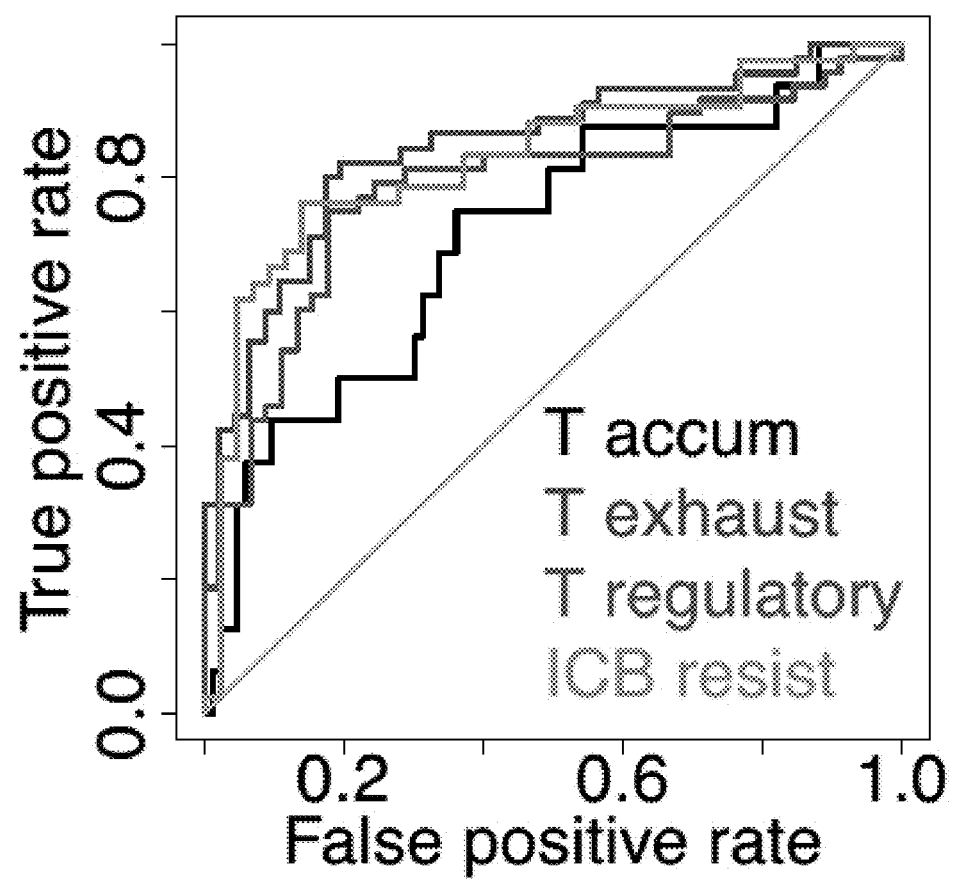
Figure 3C:
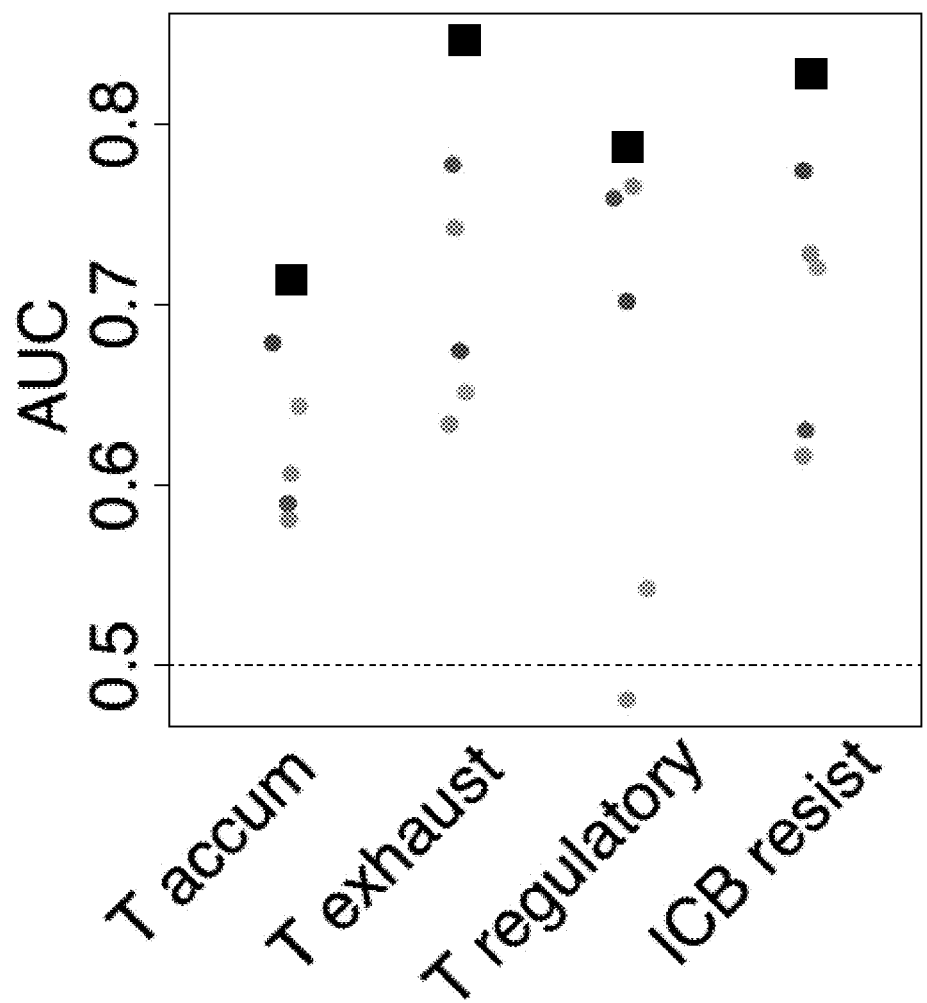

Of the 71 datasets analyzed in this study, five gave statistically significant T-cell dysfunction signatures from the interaction test (FIG. 1D). This observation is partly because only datasets where a higher level of tumor-infiltrating cytotoxic T cells correlated with better survival outcome were considered. In some cancer types or datasets, such as renal cell carcinoma which has a substantial level of CD8 T-cell infiltration, higher CTL may not correlate with survival benefits (Remark et al., 2013 Clinical Cancer Research: an Official Journal of the American Association for Cancer Research, 19: 4079-4091). Also, depending on the sample size or characteristics of specific datasets, there might not be statistically significant genes interacting with CTL to influence survival (FIG. 1C). This prospect is supported by consistent results derived from the five significant datasets described herein (FIG. 1D), and the observation that averaging the signatures from the five datasets yields a more robust signature (FIG. 3C).

As described herein, TIDE demonstrates the value of transcriptome profiling of treatment-naïve samples for informing tumor immune evasion and ICB treatment outcome. For example, as described in detail below, TIDE informs oncologists in immuno-oncology trials to select those patients who are more likely to benefit from ICB. Accordingly, the clinical utility of TIDE in ICB decision-making is examined in a clinical trial. It is also valuable to compare TIDE to PD-L1 immunohistochemistry tests that are currently used to inform treatment decisions in several cancers. With fast-growing data on immunotherapy trials, it is envisioned that computational modeling and data integration play an increasingly significant role in refining the ICB response biomarkers and identifying new immunotherapy targets.

Melanoma

Cancer starts when cells in the body begin to grow out of control. Cells in nearly any part of the body can become cancer, and can then spread to other areas of the body. Melanoma is a cancer that usually starts in a certain type of skin cell, i.e., melanocytes. Melanocytes make a brown pigment called melanin, which gives the skin its tan or brown color. Melanin protects the deeper layers of the skin from some of the harmful effects of the sun. For most people, when skin is exposed to the sun, melanocytes make more melanin, causing the skin to tan or darken.

Other names for "melanoma" include malignant melanoma and cutaneous melanoma. Most melanoma cells still make melanin, so melanoma tumors are usually brown or black. However, some melanomas do not make melanin and can appear pink, tan, or even white. Melanomas can develop anywhere on the skin, but they are more likely to start on the trunk (chest and back) in men and on the legs in women. The neck and face are other common sites. Having darkly pigmented skin lowers the risk of melanoma at these more common sites, but anyone can get melanoma on the palms of the hands, soles of the feet, and under the nails. Melanomas can also form in other parts of the body such as the eyes, mouth, genitals, and anal area, but these are much less common than melanoma of the skin. Melanoma is much less common than basal cell and squamous cell skin cancers. However, melanoma is more dangerous because it is much more likely to spread to other parts of the body if not caught early.

The primary cause of melanoma is ultraviolet light (UV) exposure in those with low levels of skin pigment. The UV light may be from either the sun or from other sources, such as tanning devices. About 25% develop from moles. Those with many moles, a history of affected family members, and who have poor immune function are at greater risk. A number of rare genetic defects such as xeroderma pigmentosum also increase risk. Avoiding UV light and the use of sunscreen may prevent melanoma.

Melanoma may spread to other sites in the body by metastasis. Metastatic melanoma may cause nonspecific paraneoplastic symptoms, including loss of appetite, nausea, vomiting and fatigue. Metastasis of early melanoma is possible, but relatively rare: less than a fifth of melanomas diagnosed early become metastatic. Brain metastases are particularly common in patients with metastatic melanoma. Melanoma may also spread to the liver, bones, abdomen or distant lymph nodes.

Melanoma Diagnosis

Visual inspection is the most common diagnostic technique. Moles that are irregular in color or shape are typically treated as candidates. To detect melanomas (and increase survival rates), it is recommended to regularly examine moles for changes (shape, size, color, itching or bleeding) and to consult a qualified physician when a candidate appears.

Early signs of melanoma are changes to the shape or color of existing moles or, in the case of nodular melanoma, the appearance of a new lump anywhere on the skin. At later stages, the mole may itch, ulcerate or bleed. Early signs of melanoma are summarized by the mnemonic "ABCDE":

Asymmetry
Borders (irregular with edges and corners)
Color (variegated)
Diameter (greater than 6 mm (0.24 in), about the size of a pencil eraser)
Evolving over time These classifications do not, however, apply to the most dangerous form of melanoma, nodular melanoma, which has its own classifications:

Elevated above the skin surface
Firm to the touch
Growing

Following a visual examination and a dermatoscopic exam, or in vivo diagnostic tools such as a confocal microscope, the doctor may biopsy the suspicious mole. A skin biopsy performed under local anesthesia is often required to assist in making or confirming the diagnosis and in defining severity. Elliptical excisional biopsies may remove the tumor, followed by histological analysis and Breslow scoring. Punch biopsies are contraindicated in suspected melanomas, for fear of seeding tumor cells and hastening the spread of malignant cells.

Lactate dehydrogenase (LDH) tests are often used to screen for metastases, although many patients with metastases (even end-stage) have a normal LDH; extraordinarily high LDH often indicates metastatic spread of the disease to the liver.

It is common for patients diagnosed with melanoma to have chest X-rays and an LDH test, and in some cases computerized tomography (CT), magnetic resonance imaging (MRI), positron emission tomography (PET) and/or PET/CT scans. Although controversial, sentinel lymph node biopsies and examination of the lymph nodes are also performed in patients to assess spread to the lymph nodes.

A diagnosis of melanoma is supported by the presence of the S-100 protein marker. Additionally, human melanoma black 45 (HMB-45) is a monoclonal antibody that reacts against an antigen present in melanocytic tumors such as melanomas. It is used in anatomic pathology as a marker for such tumors. The antibody was generated to an extract of melanoma. It reacts positively against melanocytic tumors, but not other tumors, thus demonstrating specificity and sensitivity.

The following are melanoma stages with 5 year survival rates. Stage 0: melanoma in situ (99.9% survival); Stage I/II: invasive melanoma (89-95% survival); Stage II: high risk melanoma (45-79% survival); Stage III: regional metastasis (24-70% survival); Stage IV: distant metastasis (7-19% survival).

Recent evidence suggests that the prognosis of melanoma patients with regional metastases is influenced by tumor stroma immunobiology (Akbani et al., 2015 Cell (161), 1681-1696, incorporated herein by reference).

Melanoma Treatment

Treatment is typically removal by surgery. In those with slightly larger cancers, nearby lymph nodes may be tested for spread. Most people are cured after tumor excision if spread has not occurred. Excisional biopsies may remove the tumor, but further surgery is often necessary to reduce the risk of recurrence. Complete surgical excision with adequate surgical margins and assessment for the presence of detectable metastatic disease along with short- and long-term follow-up is standard. Often this is done by a wide local excision (WLE) with 1 to 2 cm margins.

For those in whom melanoma has spread, immunotherapy, biologic therapy, radiation therapy, or chemotherapy may improve survival. With treatment, the five-year survival rates in the United States is 98% among those with localized disease and 17% among those in whom spread has occurred. The likelihood that it will come back or spread depends on the melanoma thickness, how fast the cells are dividing, and whether or not the overlying skin has broken down.

Various chemotherapy agents, including temozolomide, dacarbazine (also termed DTIC), immunotherapy (with interleukin-2 (IL-2) or interferon (IFN)), as well as local perfusion, are used for treatment of melanoma. The overall success in metastatic melanoma is quite limited. Therapies for metastatic melanoma include biologic immunotherapy agents ipilimumab, pembrolizumab, and nivolumab; BRAF inhibitors, such as vemurafenib and dabrafenib; and a MEK inhibitor, trametinib.

Radiation therapy is often used after surgical resection for patients with locally or regionally advanced melanoma or for patients with unresectable distant metastases. Kilovoltage x-ray beams are often used for these treatments and have the property of the maximum radiation dose occurring close to the skin surface.

PD-L1 Blockade

Programmed death-ligand 1 (PD-L1) also known as cluster of differentiation 274 (CD274) or B7 homolog 1 (B7-H1) is a protein that is encoded by the CD274 gene in humans. PD-L1 is a 40 kDa type 1 transmembrane protein that plays a major role in suppressing the immune system. Normally, the immune system reacts to foreign antigens that are associated with exogenous or endogenous "danger" signals, which triggers a proliferation of antigen-specific CD8+ T cells and/or CD4+ helper cells. The binding of PD-L1 to PD-1 or B7.1 transmits an inhibitory signal that reduces the proliferation of these T cells and can also induce apoptosis. Upregulation of PD-L1 may allow cancers to evade the host immune system. For example, an analysis of 196 tumor specimens from patients with renal cell carcinoma found that high tumor expression of PD-L1 was associated with increased tumor aggressiveness and a 4.5-fold increased risk of death. Many PD-L1 inhibitors are in development as immuno-oncology therapies and are showing good results in clinical trials. Clinically available examples include durvalumab, atezolizumab and avelumab.

CTLA-4 Blockade

CTLA4 or CTLA-4 (cytotoxic T-lymphocyte-associated protein 4), also known as CD152 (cluster of differentiation 152), is a protein receptor that, functioning as an immune checkpoint, downregulates immune responses. CTLA4 is constitutively expressed in regulatory T cells (Tregs), but only upregulated in conventional T cells after activation. CTLA4 acts as an "off" switch when bound to CD80 or CD86 on the surface of antigen-presenting cells. Recent reports suggest that blocking CTLA4 (using antagonistic antibodies against CTLA such as ipilimumab (FDA approved for melanoma in 2011)) results in therapeutic benefit. CTLA4 blockade inhibits immune system tolerance to tumors and provides a useful immunotherapy strategy for patients with cancer. See, Grosso J. and Jure-Kunkel M. 2013, Cancer Immun., 13: 5, incorporated herein by reference.

World Health Organization (WHO) Criteria

The WHO Criteria for evaluating the effectiveness of anti-cancer agents on tumor shrinkage, developed in the 1970s by the International Union Against Cancer and the World Health Organization, represented the first generally agreed specific criteria for the codification of tumor response evaluation. These criteria were first published in 1981 (Miller et al., 1981 Clin Cancer Res., 47(1): 207-14, incorporated herein by reference). WHO Criteria proposed >50% tumor shrinkage for a Partial Response and >25% tumor increase for Progressive Disease.

Response Evaluation Criteria in Solid Tumors (RECIST)

RECIST is a set of published rules that define when tumors in cancer patients improve ("respond"), stay the same ("stabilize"), or worsen ("progress") during treatment (Eisenhauer et al., 2009 European Journal of Cancer, 45: 228-247, incorporated herein by reference). Only patients with measurably disease at baseline should be included in protocols where objective tumor response is the primary endpoint.

The response criteria for evaluation of target lesions are as follows:
Complete Response (CR): Disappearance of all target lesions.
Partial Response (PR): At least a 30% decrease in the sum of the longest diameter (LD) of target lesions, taking as reference the baseline sum LD.
Stable Disease (SD): Neither sufficient shrinkage to qualify for PR nor sufficient increase to qualify for PD, taking as reference the smallest sum LD since the treatment started.
Progressive Disease (PD): At least a 20% increase in the sum of the LD of target lesions, taking as reference the smallest sum LD recorded since the treatment started or the appearance of one or more new lesions.

The response criteria for evaluation of non-target lesions are as follows:
Complete Response (CR): Disappearance of all non-target lesions and normalization of tumor marker level.
Incomplete Response/Stable Disease (SD): Persistence of one or more non-target lesion(s) or/and maintenance of tumor marker level above the normal limits.
Progressive Disease (PD): Appearance of one or more new lesions and/or unequivocal progression of existing non-target lesions.

The response criteria for evaluation of best overall response are as follows. The best overall response is the best response recorded from the start of the treatment until disease progression/recurrence (taking as reference for PD the smallest measurements recorded since the treatment started). In general, the patient's best response assignment will depend on the achievement of both measurement and confirmation criteria.
Patients with a global deterioration of health status requiring discontinuation of treatment without objective evidence of disease progression at that time should be classified as having "symptomatic deterioration". Every effort should be made to document the objective progression even after discontinuation of treatment.
In some circumstances, it may be difficult to distinguish residual disease from normal tissue. When the evaluation of complete response depends on this determination, it is recommended that the residual lesion be investigated (fine needle aspirate/biopsy) to confirm the complete response status.

Immune-Related Response Criteria (irRC)

The irRC is a set of published rules that define when tumors in cancer patients improve ("respond"), stay the same ("stabilize"), or worsen ("progress") during treatment, where the compound being evaluated is an immuno-oncology drug. The Immune-Related Response Criteria, first published in 2009 (Wolchok et al., 2009 Clin Cancer Res, 15(23):7412, incorporated herein by reference), arose out of observations that immuno-oncology drugs would fail in clinical trials that measured responses using the WHO or RECIST Criteria, because these criteria could not account for the time gap in many patients between initial treatment and the apparent action of the immune system to reduce the tumor burden. The key driver in the development of the irRC was the observation that, in studies of various cancer therapies derived from the immune system such as cytokines and monoclonal antibodies, the looked-for Complete and Partial Responses as well as Stable Disease only occurred after an increase in tumor burden that the conventional RECIST Criteria would have dubbed "Progressive Disease". RECIST failed to take account of the delay between dosing and an observed anti-tumor T cell response, so that otherwise 'successful' drugs—that is, drugs which ultimately prolonged life—failed in clinical trials.

The irRC are based on the WHO Criteria; however, the measurement of tumor burden and the assessment of immune-related response have been modified as set forth below.

Measurement of Tumor Burden

In the irRC, tumor burden is measured by combining 'index' lesions with new lesions. Ordinarily, tumor burden would be measured with a limited number of 'index' lesions (that is, the largest identifiable lesions) at baseline, with new lesions identified at subsequent timepoints counting as 'Progressive Disease'. In the irRC, by contrast, new lesions are a change in tumor burden. The irRC retained the bidirectional measurement of lesions that had originally been laid down in the WHO Criteria.

Assessment of Immune-Related Response

In the irRC, an immune-related Complete Response (irCR) is the disappearance of all lesions, measured or unmeasured, and no new lesions; an immune-related Partial Response (irPR) is a 50% drop in tumor burden from baseline as defined by the irRC; and immune-related Progressive Disease (irPD) is a 25% increase in tumor burden from the lowest level recorded. Everything else is considered immune-related Stable Disease (irSD). Even if tumor burden is rising, the immune system is likely to "kick in" some months after first dosing and lead to an eventual decline in tumor burden for many patients. The 25% threshold accounts for this apparent delay.

The Cancer Genome Atlas (TCGA)

The Cancer Genome Atlas (TCGA) is a project to catalogue genetic mutations responsible for cancer, using genome sequencing and bioinformatics (Cancer Genome Atlas N. Genomic Classification of Cutaneous Melanoma. 2015 Cell, 161(7):1681-96, incorporated herein by reference). TCGA applies high-throughput genome analysis techniques to improve the ability to diagnose, treat, and prevent cancer through a better understanding of the genetic basis of this disease.

The project scheduled 500 patient samples, more than most genomics studies, and used different techniques to analyze the patient samples. Techniques include gene expression profiling, copy number variation profiling, SNP genotyping, genome wide DNA methylation profiling, microRNA profiling, and exon sequencing of at least 1,200 genes. TCGA is sequencing the entire genomes of some tumors, including at least 6,000 candidate genes and microRNA sequences. This targeted sequencing is being performed by all three sequencing centers using hybrid-capture technology. In phase II, TCGA is performing whole exon sequencing on 80% of the cases and whole genome sequencing on 80% of the cases used in the project.

Gene Expression Profiling

In general, methods of gene expression profiling can be divided into two large groups: methods based on hybridization analysis of polynucleotides, and methods based on sequencing of polynucleotides. Methods known in the art for the quantification of messenger ribonucleic acid (mRNA) expression in a sample include northern blotting and in situ hybridization, RNAse protection assays, and reverse transcription polymerase chain reaction (RT-PCR). Alternatively, antibodies are employed that recognize specific duplexes, including deoxyribonucleic acid (DNA) duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). For example, RT-PCR is used to compare mRNA levels in different sample populations, in normal and tumor tissues, with or without drug treatment, to characterize patterns of gene expression, to discriminate between closely related mRNAs, and/or to analyze RNA structure.

In some cases, a first step in gene expression profiling by RT-PCR is the reverse transcription of the RNA template into complementary deoxyribonucleic acid (cDNA), followed by amplification in a PCR reaction. For example, extracted RNA is reverse-transcribed using a GeneAmp RNA PCR kit (Perkin Elmer, Calif., USA), following the manufacturer's instructions. The cDNA is then used as template in a subsequent PCR amplification and quantitative analysis using, for example, a TaqMan® (Life Technologies, Inc., Grand Island, N.Y.) assay.

Microarrays

Differential gene expression can also be identified, or confirmed using a microarray technique. In these methods, polynucleotide sequences of interest (including cDNAs and oligonucleotides) are plated, or arrayed, on a microchip substrate. The arrayed sequences are then hybridized with specific DNA probes from cells or tissues of interest. Just as in the RT-PCR method, the source of mRNA typically is total RNA isolated from human tumors or tumor cell lines and corresponding normal tissues or cell lines. Thus, RNA is isolated from a variety of primary tumors or tumor cell lines. If the source of mRNA is a primary tumor, mRNA is extracted from frozen or archived tissue samples.

In the microarray technique, PCR-amplified inserts of cDNA clones are applied to a substrate in a dense array. The microarrayed genes, immobilized on the microchip, are suitable for hybridization under stringent conditions.

In some cases, fluorescently labeled cDNA probes are generated through incorporation of fluorescent nucleotides by reverse transcription of RNA extracted from tissues of interest (e.g., cancer tissue). Labeled cDNA probes applied to the chip hybridize with specificity to loci of DNA on the array. After washing to remove non-specifically bound probes, the chip is scanned by confocal laser microscopy or by another detection method, such as a charge-coupled device (CCD) camera. Quantification of hybridization of each arrayed element allows for assessment of corresponding mRNA abundance.

In some configurations, dual color fluorescence is used. With dual color fluorescence, separately labeled cDNA probes generated from two sources of RNA are hybridized pairwise to the array. The relative abundance of the transcripts from the two sources corresponding to each specified gene is thus determined simultaneously. In various configurations, the miniaturized scale of the hybridization can afford a convenient and rapid evaluation of the expression pattern for large numbers of genes. In various configurations, such methods can have sensitivity required to detect rare transcripts, which are expressed at fewer than 1000, fewer than 100, or fewer than 10 copies per cell. In various configurations, such methods can detect at least approximately two-fold differences in expression levels (Schena et al., Proc.

Natl. Acad. Sci. USA 93(2): 106-149 (1996)). In various configurations, microarray analysis is performed by commercially available equipment, following manufacturer's protocols, such as by using the Affymetrix GenChip technology, or Incyte's microarray technology.

RNA-Seq

RNA sequencing (RNA-seq), also called whole transcriptome shotgun sequencing (WTSS), uses next-generation sequencing (NGS) to reveal the presence and quantity of RNA in a biological sample at a given moment in time.

RNA-Seq is used to analyze the continually changing cellular transcriptome. See, e.g., Wang et al., 2009 Nat Rev Genet, 10(1): 57-63, incorporated herein by reference. Specifically, RNA-Seq facilitates the ability to look at alternative gene spliced transcripts, post-transcriptional modifications, gene fusion, mutations/SNPs and changes in gene expression. In addition to mRNA transcripts, RNA-Seq can look at different populations of RNA to include total RNA, small RNA, such as miRNA, tRNA, and ribosomal profiling. RNA-Seq can also be used to determine exon/intron boundaries and verify or amend previously annotated 5' and 3' gene boundaries.

Prior to RNA-Seq, gene expression studies were done with hybridization-based microarrays. Issues with microarrays include cross-hybridization artifacts, poor quantification of lowly and highly expressed genes, and needing to know the sequence of interest. Because of these technical issues, transcriptomics transitioned to sequencing-based methods. These progressed from Sanger sequencing of Expressed Sequence Tag libraries, to chemical tag-based methods (e.g., serial analysis of gene expression), and finally to the current technology, NGS of cDNA (notably RNA-Seq).

Gene Set Enrichment Analysis

By "ssGSEA" is meant single-sample Gene Set Enrichment Analysis. When analyzing genome-wide transcription profiles from microarray data, a typical goal is to find genes significantly differentially correlated with distinct sample classes defined by a particular phenotype (e.g., tumor vs. normal). These findings can be used to provide insights into the underlying biological mechanisms or to classify (predict the phenotype of) a new sample. Gene Set Enrichment Analysis (GSEA) evaluates whether a priori defined sets of genes, associated with particular biological processes (such as pathways), chromosomal locations, or experimental results are enriched at either the top or bottom of a list of differentially expressed genes ranked by some measure of differences in a gene's expression across sample classes. Examples of ranking metrics are fold change for categorical phenotypes (e.g., tumor vs. normal) and Pearson correlation for continuous phenotypes (e.g., age). Enrichment provides evidence for the coordinate up- or down-regulation of a gene set's members and the activation or repression of some corresponding biological process.

Where GSEA generates a gene set's enrichment score with respect to phenotypic differences across a collection of samples within a dataset, ssGSEA calculates a separate enrichment score for each pairing of sample and gene set, independent of phenotype labeling. In this manner, ssGSEA transforms a single sample's gene expression profile to a gene set enrichment profile. A gene set's enrichment score represents the activity level of the biological process in which the gene set's members are coordinately up- or down-regulated. This transformation allows researchers to characterize cell state in terms of the activity levels of biological processes and pathways rather than through the expression levels of individual genes.

In working with the transformed data, the goal is to find biological processes that are differentially active across the phenotype of interest and to use these measures of process activity to characterize the phenotype. Thus, the benefit here is that the ssGSEA projection transforms the data to a higher-level (pathways instead of genes) space representing a more biologically interpretable set of features on which analytic methods can be applied.

Tumor Immune Dysfunction and Exclusion (TIDE) Gene Signature

Described herein is a gene signature, "TIDE," that predicts response and resistance to immune checkpoint blockade in melanoma. In some cases, the gene signature comprises a 7-gene signature. In other cases, the gene signature comprises 1, 2, 3, 4, 5, 6 or more genes. Exemplary distinguishing genes include: serine proteinase inhibitor (serpin) Family B Member 9 (SERPINB9), transforming growth factor beta-1 (TGFβ-1), prolyl endopeptidase (FAP), vascular endothelial growth factor A (VEGFA), angiopoietin 2 (ANGPT2), cluster of differentiation 274 (CD274; also known as programmed death-ligand 1 (PD-L1)), and interferon gamma (IFNγ or INFγ). Another exemplary distinguishing gene includes alpha-mannosidase 2 (MAN2A1).

As described herein, it was identified that SERPINB9 and TGFβ-1 are T-cell dysfunction/exhaustion predictive genes. FAP, VEGFA, and ANGPT2 are T-cell exclusion predictive genes. CD274 and IFNγ are T-cell activation predictive genes.

An exemplary human SERPINB9 amino acid sequence is set forth below (SEQ ID NO: 1; GenBank Accession No: NP_004146, Version NP_004146.1, incorporated herein by reference):

```
  1 metlsnasgt fairllkilc qdnpshnvfc spvsissala mvllgakgnt atqmaqalsl 61 nteedihraf qslltevnka gtqyllrtan rlfgektcqf lstfkesclq fyhaelkels 121 firaaeesrk hintwvskkt egkieellpg ssidaetrlv lvnaiyfkgk wnepfdetyt 181 rempfkinqe eqrpvqmmyq eatfklahvg evraqllelp yarkelsllv llpddgvels 241 tveksltfek ltawtkpdcm kstevevllp kfklqedydm esvlrhlgiv dafqqgkadl 301 samsaerdlc lskfvhksfv evneegteaa aasscfvvae ccmesgprfc adhpflffir 361 hnransilfc grfssp
```

An exemplary human SerpinB9 nucleic acid sequence is set forth below (SEQ ID NO: 2; GenBank Accession No: NM_004155, Version NM_004155.5, incorporated herein by reference):

```
   1 agcgggagtc cgcggcgagc gcagcagcag ggccgggtcc tgcgcctcgg gggtcggcgt
  61 ccaggctcgg agcgcggcac ggagacggcg gcagcgctgg actaggtggc aggccctgca
 121 tcatggaaac tctttctaat gcaagtggta cttttgccat acgccttttta aagatactgt
 181 gtcaagataa cccttcgcac aacgtgttct gttctcctgt gagcatctcc tctgccctgg
 241 ccatggttct cctaggggca aagggaaaca ccgcaaccca gatggcccag gcactgtctt
 301 taaacacaga ggaagacatt catcgggctt ccagtcgct ctcactgaa gtgaacaagg
 361 ctggcacaca gtacctgctg agaacggcca acaggctctt tggagagaaa acttgtcagt
 421 tcctctcaac gtttaaggaa tcctgtcttc aattctacca tgctgagctg aaggagcttt
 481 cctttatcag agctgcagaa gagtccagga acacatcaa cacctgggtc tcaaaaaaga
 541 ccgaaggtaa aattgaagag ttgttgccgg gtagctcaat tgatgcagaa accaggctgg
 601 ttcttgtcaa tgccatctac ttcaaaggaa agtggaatga accgtttgac gaaacataca
 661 caagggaaat gcccttttaaa ataaaccagg aggagcaaag gccagtgcag atgatgtatc
 721 aggaggccac gtttaagctc gcccacgtgg gcgaggtgcg cgcgcagctg ctggagctgc
 781 cctacgccag gaaggagctg agcctgctgg tgctgctgcc tgacgacggc gtggagctca
 841 gcacggtgga aaaaagtctc acttttgaga aactcacagc ctggaccaag ccagactgta
 901 tgaagagtac tgaggttgaa gttctccttc caaaatttaa actacaagag gattatgaca
 961 tggaatctgt gcttcggcat ttgggaattg ttgatgcctt caacagggc aaggctgact
1021 tgtcggcaat gtcagcggag agagacctgt gtctgtccaa gttcgtgcac aagagttttg
1081 tggaggtgaa tgaagaaggc accgaggcag cggcagcgtc gagctgcttt gtagttgcag
1141 agtgctgcat ggaatctggc cccaggttct gtgctgacca cccttctt ttcttcatca
1201 ggcacaacag agccaacagc attctgttct gtggcaggtt ctcatcgcca taagggtgc
1261 acttaccgtg cactcggcca tttccctctt cctgtgtccc cagatcccca ctacagctcc
1321 aagaggatgg gcctagaaag ccaagtgcaa agatgagggc agattctta cctgtctgcc
1381 ctcatgattt gccagcatga attcatgatg ctccacactc gcttatgcta cttaatcaga
1441 atcttgagaa aatagaccat aatgattccc tgttgtatta aaattgcagt ccaaatccca
1501 taggatggca agcaaagttc ttctagaatt ccacatgcaa ttcactctgg cgaccctgtg
1561 ctttcctgac actgcgaata cattccttaa cccgctgcct cagtggtaat aaatggtgct
1621 agatattgct actattttat agatttcctg gtgcttagcc ttataaaaaa ggttgtaaaa
1681 tgtacattta tattttatct ttttttttt tttttttctg agacgcagtc tggctctctg
1741 tcgcccaggc tggagtgcag tggctcgatc tcggctcact gcaagctccg cctcccgggt
1801 tcacgccatt ctcctgcctc agcctcccga gtagctggga ctacaggcgc ccgccaccac
1861 gcccggctaa ttttttgtat tttagtagagacggggttt caccgtgtta gccaggatgg
1921 tgtcgatctc ctgacctcgt gatccacccg cctcggcctc ccaaagtgct gggattacag
1981 gcttgagcca ccgcgcccgg ctatatttta tcttttatct ttttctttga catttaccaa
2041 tcaccaagca tgcaccaaac actgctttag gcactgggga cacaaagggg acagagccat
2101 cctcctttga cacctggtct tcagttctgt gcccaacgta tatagttttg acaatgacca
2161 ggttggactg tttaatgtct ttcaacttac cacgtaatcc tcttgtaggg atcacatctt
2221 tctttatgat attgtatttc tctacctcta acagtaaaaa ttccattcaa cccttaaagc
```

-continued

```
2281 tcacttcaaa ttcttctttg agaagttttt cctttctccg caaccagatg tacatatttg
2341 aactctcttt gtacttggag ggcacttctt tcgtggtagt tcttttattt ttattaatct
2401 ctgtatcctt agatagtcct ccaacaacca aaggttggga ctctgtctta catatctggg
2461 tgcccctcat agtgcagtaa taagtaagtt gattatatac gagctatgta acttatattt
2521 tttaatggtt ggatatcact gagttttttt ttttaagaat tttttttattg aggtaaactt
2581 cacataacat aaaattaact attttaaagt gagaagttca gtgccactta gtattgttaa
2641 caatgttgca taaccaccac ctttatttaa agttccaaaa aaaatgttct cctctaaaag
2701 gaaaccccat cccattaagc agatactctc cattccttcc ttcctccagc ccccagcaac
2761 caccaatctg ctttctgtct ctatggattt atctattctt gctatttat ataaattgaa
2821 ttgtatgaga cctttgtgt ctggcttctt tcacttagta caagttttg agatttattt
2881 acatagtagc atgtatcaac acttcatttt tatggccaaa taaaattgta ttatgtgttt
2941 atagcacaat ttatttatcc actcattcat tgatggactt tggttgttt ctgactttg
3001 gctattggga atagtgctgc tatgaatgtt tgtgtacctg tatttgtttg aatgcctatt
3061 ttgcattctc ttgggtatat atctaggagt ggaactgctg ggtcatatgt taattctatg
3121 tttagctttt tgaggaacag acaaactgtt ttccacagca gttgaaccat tccacattcc
3181 caccagcaat gtatgagaat tccaatttct gtccacttcc tcaccaacac ttattatttt
3241 ccttttcctt tttttaaaaa aaataagtta tggccatctt agtgggtgtg aagtggtatc
3301 tcattgtgtt ttttatttgc atttcctatg taatgagcta gaaactaaag tacaaactag
3361 atgggacatc cagtcccttt gatagataat gctgagtaaa aaatgagatg aaagacattt
3421 gtttgttttt agaacacgag tgacagtttg ttaaaaagct ttagaggagg aatgaaaaca
3481 aagtgaagta cacttagaaa agggccaagt ggacatcttg gatgtcaagt gcctagttca
3541 gtatcttttt tttttttttt tttttttttg agacagtgcc tcactctgtc acccaggctg
3601 gagtgtagtg gcatgatctg ggctcactgc aacctcctcc tcctggattc aagcaattct
3661 cttgcttcag cctcccaagt agctgagact acaagcaccc accatcacac ccagctaatt
3721 ttgtattttt cagtagagac ggggtttcgc cacattggcc gtgttggtct tgaactcctg
3781 gcctcaagcg atccgcctac ctcagcctcc caaagtgcta ggattacagg cataagccac
3841 tgagcccagc cctagttcag tatctttat gtaaattaca aacatctgca acattatgta
3901 tcatatgcag atacttattg catttctttt attagtggtg aaagtgttct atgcatttat
3961 tggctcttga atttcctcat ctatgaattg tcattcatac acctacttt ctgcttcgtt
4021 tttacatatg tctttgccta ttaaagatat tatccctctg ttttatattt tctctcattc
4081 ttgtattgcc tttaaattt tgttatgatg tttcattaat aaacagtgtt ttgttttcct
4141 ctataatcaa aaaaaaaaa aaaaaaa
```

An exemplary human TGFβ3-1 amino acid sequence is set forth below (SEQ ID NO: 3; GenBank Accession No: P01137, Version P01137.2, incorporated herein by reference):

```
  1 mppsglrlll lllpllwllv ltpgrpaagl stcktidmel vkrkrieair gqilsklrla
 61 sppsqgevpp gplpeavlal ynstrdrvag esaepepepe adyyakevtr vlmvethnei
121 ydkfkqsths iymffntsel reavpepvll sraelrllrl klkveqhvel yqkysnnswr
181 ylsnrllaps dspewlsfdv tgvvrqwlsr ggeiegfrls ahcscdsrdn tlqvdingft
```

-continued

```
241 tgrrgdlati hgmnrpflll matpleraqh lqssrhrral dtnycfsste knccvrqlyi 301 dfrkdlgwkw ihepkgyhan fclgpcpyiw sldtqyskvl alynqhnpga saapccvpqa 361 leplpivyyv grkpkveqls nmivrsckcs
```

An exemplary human TGFβ-1 nucleic acid sequence is set forth below (SEQ ID NO: 4; GenBank Accession No: NM_000660, Version NM_000660.6, incorporated herein by reference):

```
   1 acctccctcc gcggagcagc cagacagcga gggccccggc cggggggcagg ggggacgccc 61 cgtccggggc accccccgg ctctgagccg cccgcggggc cggcctcggc ccggagcgga 121 ggaaggagtc gccgaggagc agcctgaggc cccagagtct gagacgagcc gccgccgccc 181 ccgccactgc ggggaggagg gggaggagga gcgggaggag ggacgagctg gtcgggagaa 241 gaggaaaaaa acttttgaga cttttccgtt gccgctggga gccggaggcg cggggacctc 301 ttggcgcgac gctgccccgc gaggaggcag gacttgggga ccccagaccg cctcccttg 361 ccgccgggga cgcttgctcc ctccctgccc cctacacggc gtccctcagg cgccccatt 421 ccggaccagc cctcgggagt cgccgacccg gcctcccgca aagactttc cccagacctc 481 gggcgcaccc cctgcacgcc gccttcatcc ccggcctgtc tcctgagccc ccgcgcatcc 541 tagacccttt ctcctccagg agacggatct ctctccgacc tgccacagat cccctattca 601 agaccaccca ccttctggta ccagatcgcg cccatctagg ttatttccgt gggatactga 661 gacacccccg gtccaagcct cccctccacc actgcgccct tctccctgag gacctcagct 721 ttccctcgag gccctcctac cttttgccgg gagaccccca gccctgcag gggcggggcc 781 tccccaccac accagccctg ttcgcgctct cggcagtgcc gggggcgcc gcctccccca 841 tgccgccctc cgggctgcgg ctgctgccgc tgctgctacc gctgctgtgg ctactggtgc 901 tgacgcctgg ccggccggcc gcgggactat ccacctgcaa gactatcgac atggagctgg 961 tgaagcggaa gcgcatcgag gccatccgcg gccagatcct gtccaagctg cggctcgcca 1021 gccccccgag ccaggggag gtgccgcccg gcccgctgcc cgaggccgtg ctcgccctgt 1081 acaacagcac ccgcgaccgg gtggccgggg agagtgcaga accggagccc gagcctgagg 1141 ccgactacta cgccaaggag gtcacccgcg tgctaatggt ggaaaccac aacgaaatct 1201 atgacaagtt caagcagagt acacacagca tatatatgtt cttcaacaca tcagagctcc 1261 gagaagcggt acctgaaccc gtgttgctct cccgggcaga gctgcgtctg ctgaggctca 1321 agttaaaagt ggagcagcac gtggagctgt accagaaata cagcaacaat tcctggcgat 1381 acctcagcaa ccggctgctg cacccagcg actcgccaga gtggttatct tttgatgtca 1441 ccggagttgt gcggcagtgg ttgagccgtg aggggaaat tgagggcttt cgccttagcg 1501 cccactgctc ctgtgacagc agggataaca cactgcaagt ggacatcaac gggttcacta 1561 ccggccgccg aggtgacctg gccaccattc atggcatgaa ccggcctttc tgcttctca 1621 tggccacccc gctggagagg gcccagcatc tgcaaagctc ccggcaccgc cgagccctgg 1681 acaccaacta ttgcttcagc tccacggaga agaactgctg cgtgcggcag ctgtacattg 1741 acttccgcaa ggacctcggc tggaagtgga tccacgagcc caagggctac catgccaact 1801 tctgcctcgg gccctgcccc tacatttgga gcctggacac gcagtacagc aaggtcctgg 1861 ccctgtacaa ccagcataac ccgggcgcct cggcggcgcc gtgctgcgtg ccgcaggcgc 1921 tggagccgct gcccatcgtg tactacgtgg gccgcaagcc caaggtggag cagctgtcca 1981 acatgatcgt gcgctcctgc aagtgcagct gaggtcccgc cccgccccgc cccgccccgg
```

-continued

```
2041 caggcccggc cccaccccgc cccgccccg ctgccttgcc catgggggct gtatttaagg 2101 acacccgtgc cccaagccca cctggggccc cattaaagat ggagagagga ctgcggatct 2161 ctgtgtcatt gggcgcctgc ctggggtctc catccctgac gttcccccac tcccactccc 2221 tctctctccc tctctgcctc ctcctgcctg tctgcactat tcctttgccc ggcatcaagg 2281 cacaggggac cagtggggaa cactactgta gttagatcta tttattgagc accttgggca 2341 ctgttgaagt gccttacatt aatgaactca ttcagtcacc atagcaacac tctgagatgc 2401 agggactctg ataacaccca ttttaaaggt gaggaaacaa gcccagagag gttaagggag 2461 gagttcctgc ccaccaggaa cctgctttag tgggggatag tgaagaagac aataaaagat 2521 agtagttcag gccaggcggg gtggctcacg cctgtaatcc tagcactttt gggaggcaga 2581 gatgggagga ttacttgaat ccaggcattt gagaccagcc tggtaacat agtgagaccc 2641 tatctctaca aaacactttt aaaaaatgta cacctgtggt cccagctact ctggaggcta 2701 aggtgggagg atcacttgat cctgggaggt caaggctgca g
```

An exemplary human FAP amino acid sequence is set forth below (SEQ ID NO: 5; GenBank Accession No: Q12884, Version Q12884.5, incorporated herein by reference):

```
  1 mktwvkivfg vatsavlall vmcivlrpsr vhnseentmr altlkdilng tfsyktffpn 61 wisgqeylhq sadnnivlyn ietgqsytil snrtmksvna snyglspdrq fvylesdysk 121 lwrysytaty yiydlsngef vrgnelprpi qylcwspvgs klayvyqnni ylkqrpgdpp 181 fqitfngren kifngipdwv yeeemlatky alwwspngkf layaefndtd ipviaysyyg 241 deqyprtini pypkagaknp vvrifiidtt ypayvgpqev pvpamiassd yyfswltwvt 301 dervclqwlk rvqnsvlsi cdfredwqtw dcpktqehie esrtgwaggf fvstpvfsyd 361 aisyykifsd kdgykhihyi kdtvenaiqi tsgkweaini frvtqdslfy ssnefeeypg 421 rrniyrisig syppskkcvt chlrkercqy ytasfsdyak yyalvcygpg ipistlhdgr 481 tdqeikilee nkelenalkn iqlpkeeikk levdeitlwy kmilppqfdr skkyplliqv 541 yggpcsqsvr svfavnwisy laskegmvia lvdgrgtafq gdkllyavyr klgvyevedq 601 itavrkfiem gfidekriai wgwsyggyvs slalasgtgl fkcgiavapv ssweyyasvy 661 terfmglptk ddnlehykns tvmaraeyfr nvdyllihgt addnvhfqns aqiakalvna 721 qvdfqamwys dqnhglsgls tnhlythmth flkqcfslsd
```

An exemplary human FAP nucleic acid variant 1 sequence is set forth below (SEQ ID NO: 6; GenBank Accession No: NM_004460, Version NM_004460.4, incorporated herein by reference):

```
  1 actcacagtt catttgaggg ccaagaacgc ccccaaaatc tgtttctaat tttacagaaa 61 tcttttgaaa cttggcacgg tattcaaaag tccgtggaaa gaaaaaaacc ttgtcctggc 121 ttcagcttcc aactacaaag acagactggg tccttttcaa cggttttcac agatccagtg 181 acccacgctc tgaagacaga attagctaac tttcaaaaac atctggaaaa atgaagactt 241 gggtaaaaat cgtatttgga gttgccacct ctgctgtgct tgccttattg gtgatgtgca 301 ttgtcttacg cccttcaaga gttcataact ctgaagaaaa tacaatgaga gcactcacac 361 tgaaggatat tttaaatgga acatttctt ataaacatt ttttccaaac tggatttcag
```

-continued

```
 421 gacaagaata tcttcatcaa tctgcagata acaatatagt actttataat attgaaacag
 481 gacaatcata taccattttg agtaatagaa ccatgaaaag tgtgaatgct tcaaattacg
 541 gcttatcacc tgatcggcaa tttgtatatc tagaaagtga ttattcaaag ctttggagat
 601 actcttacac agcaacatat tacatctatg accttagcaa tggagaattt gtaagaggaa
 661 atgagcttcc tcgtccaatt cagtatttat gctggtcgcc tgttgggagt aaattagcat
 721 atgtctatca aaacaatatc tatttgaaac aaagaccagg agatccacct tttcaaataa
 781 catttaatgg aagagaaaat aaaatattta atggaatccc agactgggtt tatgaagagg
 841 aaatgcttgc tacaaaatat gctctctggt ggtctcctaa tggaaaattt ttggcatatg
 901 cggaatttaa tgatacggat ataccagtta ttgcctattc ctattatggc gatgaacaat
 961 atcctagaac aataaatatt ccatacccaa aggctggagc taagaatccc gttgttcgga
1021 tatttattat cgataccact taccctgcgt atgtaggtcc ccaggaagtg cctgttccag
1081 caatgatagc ctcaagtgat tattatttca gttggctcac gtgggttact gatgaacgag
1141 tatgtttgca gtggctaaaa agagtccaga atgtttcggt cctgtctata tgtgacttca
1201 gggaagactg gcagacatgg gattgtccaa agacccagga gcatatagaa gaaagcagaa
1261 ctggatgggc tggtggattc tttgtttcaa caccagtttt cagctatgat gccatttcgt
1321 actacaaaat atttagtgac aaggatggct acaaacatat tcactatatc aaagacactg
1381 tggaaaatgc tattcaaatt acaagtgcaa gtgggaggc cataaatata ttcagagtaa
1441 cacaggattc actgttttat tctagcaatg aatttgaaga ataccctgga agaagaaaca
1501 tctacagaat tagcattgga agctatcctc caagcaagaa gtgtgttact tgccatctaa
1561 ggaaagaaag gtgccaatat tacacagcaa gtttcagcga ctacgccaag tactatgcac
1621 ttgtctgcta cggcccaggc atccccattt ccacccttca tgatggacgc actgatcaag
1681 aaattaaaat cctggaagaa aacaaggaat tggaaaatgc tttgaaaaat atccagctgc
1741 ctaaagagga aattaagaaa cttgaagtag atgaaattac tttatggtac aagatgattc
1801 ttcctcctca atttgacaga tcaaagaagt atcccttgct aattcaagtg tatggtggtc
1861 cctgcagtca gagtgtaagg tctgtatttg ctgttaattg gatatcttat cttgcaagta
1921 aggaagggat ggtcattgcc ttggtggatg gtcgaggaac agctttccaa ggtgacaaac
1981 tcctctatgc agtgtatcga aagctgggtg tttatgaagt tgaagaccag attacagctg
2041 tcagaaaatt catagaaatg ggtttcattg atgaaaaaag aatagccata tggggctggt
2101 cctatggagg atacgtttca tcactggccc ttgcatctgg aactggtctt ttcaaatgtg
2161 gtatagcagt ggctccagtc tccagctggg aatattacgc gtctgtctac acagagagat
2221 tcatgggtct cccaacaaag gatgataatc ttgagcacta taagaattca actgtgatgg
2281 caagagcaga atatttcaga aatgtagact atcttctcat ccacggaaca gcagatgata
2341 atgtgcactt tcaaaactca gcacagattg ctaaagctct ggttaatgca caagtggatt
2401 tccaggcaat gtggtactct gaccagaacc acggcttatc cggcctgtcc acgaaccact
2461 tatacaccca catgacccac ttcctaaagc agtgtttctc tttgtcagac taaaaacgat
2521 gcagatgcaa gcctgtatca gaatctgaaa accttatata aaccccctcag acagtttgct
2581 tattttattt tttatgttgt aaaatgctag tataaacaaa caattaatg ttgttctaaa
2641 ggctgttaaa aaaagatga ggactcagaa gttcaagcta atattgttt acattttctg
2701 gtactctgtg aaagaagaga aaagggagtc atgcattttg ctttggacac agtgttttat
2761 cacctgttca tttgaagaaa aataataaag tcagaagttc aagtgctaaa aaaaaaaaa
2821 aaaaaaaaaa aaaaaaa
```

An exemplary human VEGFA isoform A amino acid sequence is set forth below (SEQ ID NO: 7; GenBank Accession No: NP_001020537, Version NP_001020537.2, incorporated herein by reference):

```
  1 mtdrqtdtap spsyhllpgr rrtvdaaasr gqgpepapgg gvegvgargv alklfvqllg
 61 csrfggavvr ageaepsgaa rsassgreep qpeegeeeee keeergpqwr lgarkpgswt
121 geaavcadsa paarapqala rasgrggrva rrgaeesgpp hspsrrgsas ragpgraset
181 mnfllswvhw slalllylhh akwsqaapma egggqnhhev vkfmdvyqrs ychpietlvd
241 ifqeypdeie yifkpscvpl mrcggccnde glecvptees nitmqimrik phqgqhigem
301 sflqhnkcec rpkkdrarqe kksvrgkgkg qkrkrkksry kswsvyvgar cclmpwslpg
361 phpcgpcser rkhlfvqdpq tckcscknta srckarqlel nertcrcdkp rr
```

An exemplary human VEGFA nucleic acid variant 1 sequence is set forth below (SEQ ID NO: 8; GenBank Accession No: NM_001171623, Version NM_001171623.1, incorporated herein by reference):

```
   1 tcgcggaggc ttggggcagc cgggtagctc ggaggtcgtg gcgctggggg ctagcaccag
  61 cgctctgtcg ggaggcgcag cggttaggtg gaccggtcag cggactcacc ggccagggcg
 121 ctcggtgctg gaatttgata ttcattgatc cgggttttat ccctcttctt ttttcttaaa
 181 cattttttt taaaactgta ttgtttctcg ttttaattta ttttgcttg ccattcccca
 241 cttgaatcgg gccgacggct tggggagatt gctctacttc cccaaatcac tgtggatttt
 301 ggaaaccagc agaaagagga aagagtagc aagagctcca gagagaagtc gaggaagaga
 361 gagacggggt cagagagagc gcgcgggcgt gcgcgcagcg aaagcgacag gggcaaagtg
 421 agtgacctgc ttttgggggt gaccgccgga gcgcggcgtg agccctcccc cttgggatcc
 481 cgcagctgac cagtcgcgct gacggacaga cagacagaca ccgcccccag ccccagctac
 541 cacctcctcc ccggccggcg gcggacagtg gacgcggcgg cgagccgcgg gcaggggccg
 601 gagcccgcgc ccggaggcgg ggtggagggg gtcgggctc gcggcgtcgc actgaaactt
 661 ttcgtccaac ttctgggctg ttctcgcttc ggaggagccg tggtccgcgc ggggaagcc
 721 gagccgagcg gagccgcgag aagtgctagc tcgggccggg aggagccgca gccggaggag
 781 ggggaggagg aagaagagaa ggaagaggag aggggccgc agtggcgact cggcgctcgg
 841 aagccgggct catggacggg tgaggcggcg gtgtgcgcag acagtgctcc agccgcgcgc
 901 gctccccagg ccctggcccg ggcctcgggc cggggaggaa gagtagctcg ccgaggcgcc
 961 gaggagagcg ggccgcccca gcccgagc cggagaggga gcgcgagccg cgccggcccc
1021 ggtcgggcct ccgaaaccat gaactttctg ctgtcttggg tgcattggag ccttgccttg
1081 ctgctctacc tccaccatgc caagtggtcc caggctgcac ccatggcaga aggaggaggg
1141 cagaatcatc acgaagtggt gaagttcatg gatgtctatc agcgcagcta ctgccatcca
1201 atcgagaccc tggtggacat cttccaggag taccctgatg agatcgagta catcttcaag
1261 ccatcctgtg tgcccctgat gcgatgcggg ggctgctgca atgacgaggg cctggagtgt
1321 gtgcccactg aggagtccaa catcaccatg cagattatgc ggatcaaacc tcaccaaggc
1381 cagcacatag gagagatgag cttcctacag cacaacaaat gtgaatgcag accaaagaaa
1441 gatagagcaa gacaagaaaa aaaatcagtt cgaggaaagg gaaaggggca aaacgaaag
1501 cgcaagaaat cccggtataa gtcctggagc gtgtacgttg gtgcccgctg ctgtctaatg
1561 ccctggagcc tccctggccc ccatccctgt gggccttgct cagagcggag aaagcatttg
```

-continued

```
1621 tttgtacaag atccgcagac gtgtaaatgt tcctgcaaaa acacagactc gcgttgcaag 1681 gcgaggcagc ttgagttaaa cgaacgtact tgcagatgtg acaagccgag gcggtgagcc 1741 gggcaggagg aaggagcctc cctcagggtt tcgggaacca gatctctcac caggaaagac 1801 tgatacagaa cgatcgatac agaaaccacg ctgccgccac cacaccatca ccatcgacag 1861 aacagtcctt aatccagaaa cctgaaatga aggaagagga gactctgcgc agagcacttt 1921 gggtccggag ggcgagactc cggcggaagc attcccgggc gggtgaccca gcacggtccc 1981 tcttggaatt ggattcgcca tttattttt cttgctgcta aatcaccgag cccggaagat 2041 tagagagttt tatttctggg attcctgtag acacacccac ccacatacat acatttatat 2101 atatatatat tatatatata taaaaataaa tatctctatt ttatatatat aaaatatata 2161 tattctttt ttaaattaac agtgctaatg ttattggtgt cttcactgga tgtatttgac 2221 tgctgtggac ttgagttggg aggggaatgt tcccactcag atcctgacag gaagaggag 2281 gagatgagag actctggcat gatcttttt ttgtcccact tggtggggcc agggtcctct 2341 cccctgccca ggaatgtgca aggccagggc atggggcaa atatgaccca gttttgggaa 2401 caccgacaaa cccagccctg gcgctgagcc tctctacccc aggtcagacg gacagaaaga 2461 cagatcacag gtacagggat gaggacaccg gctctgacca ggagtttggg gagcttcagg 2521 acattgctgt gctttgggga ttccctccac atgctgcacg cgcatctcgc ccccaggggc 2581 actgcctgga agattcagga gcctgggcgg ccttcgctta ctctcacctg cttctgagtt 2641 gcccaggaga ccactggcag atgtcccggc gaagagaaga gacacattgt tggaagaagc 2701 agcccatgac agctcccctt cctgggactc gccctcatcc tcttcctgct cccttcctg 2761 gggtgcagcc taaaaggacc tatgtcctca caccattgaa accactagtt ctgtcccccc 2821 aggagacctg gttgtgtgtg tgtgagtggt tgaccttcct ccatccctg gtccttccct 2881 tcccttcccg aggcacagag agacagggca ggatccacgt gcccattgtg gaggcagaga 2941 aaagagaaag tgttttatat acggtactta tttaatatcc cttttaatt agaaattaaa 3001 acagttaatt taattaaaga gtagggtttt ttttcagtat tcttggttaa tatttaattt 3061 caactattta tgagatgtat cttttgctct ctcttgctct cttatttgta ccggttttttg 3121 tatataaaat tcatgtttcc aatctctctc tccctgatcg gtgacagtca ctagcttatc 3181 ttgaacagat atttaatttt gctaacactc agctctgccc tccccgatcc cctggctccc 3241 cagcacacat tcctttgaaa taaggtttca atatacatct acatactata tatatatttg 3301 gcaacttgta tttgtgtgta tatatatata tatgtttta tgtatatatg tgattctgat 3361 aaaatagaca ttgctattct gttttttata tgtaaaaaca aaacaagaaa aaatagagaa 3421 ttctacatac taaatctctc tccttttta attttaatat ttgttatcat ttatttattg 3481 gtgctactgt ttatccgtaa taattgtggg gaaaagatat taacatcacg tctttgtctc 3541 tagtgcagtt tttcgagata ttccgtagta catatttatt tttaaacaac gacaaagaaa 3601 tacagatata tcttaaaaaa aaaaaagcat tttgtattaa agaatttaat tctgatctca 3661 aaaaaaaaaa aaaaaa
```

An exemplary human ANGPT2 amino acid sequence is set forth below (SEQ ID NO: 9; GenBank Accession No: AAI26201, Version AAI26201.1, incorporated herein by reference).

```
  1 mwqivfftls cdlvlaaayn nfrksmdsig kkqyqvqhgs csytfllpem dncrsssspy
 61 vsnavqrdap leyddsvqrl qvlenimenn tqwlmkleny iqdnmkkemv eiqqnavqnq
121 tavmieigtn llnqtaeqtr kltdveaqvl nqttrlelql lehslstnkl ekqildqtse
181 inklqdknsf lekkvlamed khiiqlqsik eekdqlqvlv skqnsiieel ekkivtatvn
241 nsvlqkqqhd lmetvnnllt mmstsnsakd ptvakeeqis frdcaevfks ghttngiytl
301 tfpnsteeik aycdmeaggg gwtiiqrred gsvdfqrtwk eykvgfgnps geywlgnefv
361 sqltnqqryv lkihlkdweg neayslyehf ylsseelnyr ihlkgltgta gkissisqpg
421 ndfstkdgdn dkcickcsqm ltggwwfdac gpsnlngmyy pqrqntnkfn gikwyywkgs
481 gyslkattmm irpadf
```

An exemplary human ANGPT2 nucleic acid variant 1 sequence is set forth below (SEQ ID NO: 10; GenBank Accession No: NM_001147, Version NM_001147.2, incorporated herein by reference):

```
   1 aaagtgattg attcggatac tgacactgta ggatctgggg agagaggaac aaaggaccgt
  61 gaaagctgct ctgtaaaagc tgacacagcc ctcccaagtg agcaggactg ttcttcccac
 121 tgcaatctga cagtttactg catgcctgga gagaacacag cagtaaaaac caggtttgct
 181 actggaaaaa gaggaaagag aagactttca ttgacggacc cagccatggc agcgtagcag
 241 ccctgcgttt tagacggcag cagctcggga ctctggacgt gtgtttgccc tcaagtttgc
 301 taagctgctg gtttattact gaagaaagaa tgtggcagat tgttttcttt actctgagct
 361 gtgatcttgt cttggccgca gcctataaca actttcggaa gagcatggac agcataggaa
 421 agaagcaata tcaggtccag catgggtcct gcagctacac tttcctcctg ccagagatgg
 481 acaactgccg ctcttcctcc agcccctacg tgtccaatgc tgtgcagagg gacgcgccgc
 541 tcgaatacga tgactcggtg cagaggctgc aagtgctgga aacatcatg aaaacaaca
 601 ctcagtggct aatgaagctt gagaattata tccaggacaa catgaagaaa gaaatggtag
 661 agatacagca gaatgcagta cagaaccaga cggctgtgat gatagaaata gggacaaacc
 721 tgttgaacca acagcggag caaacgcgga gttaactga tgtggaagcc caagtattaa
 781 atcagaccac gagacttgaa cttcagctct tggaacactc cctctcgaca aacaaattgg
 841 aaaaacagat tttggaccag accagtgaaa taaacaaatt gcaagataag aacagtttcc
 901 tagaaaagaa ggtgctagct atggaagaca agcacatcat ccaactacag tcaataaaag
 961 aagagaaaga tcagctacag gtgttagtat ccaagcaaaa ttccatcatt gaagaactag
1021 aaaaaaaaat agtgactgcc acggtgaata ttcagttct tcagaagcag caacatgatc
1081 tcatggagac agttaataac ttactgacta tgatgtccac atcaaactca gctaaggacc
1141 ccactgttgc taaagaagaa caaatcagct tcagagactg tgctgaagta ttcaaatcag
1201 gacacaccac gaatggcatc tacacgttaa cattccctaa ttctacagaa gagatcaagg
1261 cctactgtga catggaagct ggaggaggcg ggtggacaat tattcagcga cgtgaggatg
1321 gcagcgttga ttttcagagg acttggaaag aatataaagt gggatttggt aacccttcag
1381 gagaatattg gctgggaaat gagtttgttt cgcaactgac taatcagcaa cgctatgtgc
1441 ttaaaataca ccttaaagac tgggaaggga atgaggctta ctcattgtat gaacatttct
```

```
1501 atctctcaag tgaagaactc aattatagga ttcaccttaa aggacttaca gggacagccg
1561 gcaaaataag cagcatcagc caaccaggaa atgattttag cacaaaggat ggagacaacg
1621 acaaatgtat ttgcaaatgt tcacaaatgc taacaggagg ctggtggttt gatgcatgtg
1681 gtccttccaa cttgaacgga atgtactatc cacagaggca gaacacaaat aagttcaacg
1741 gcattaaatg gtactactgg aaaggctcag gctattcgct caaggccaca accatgatga
1801 tccgaccagc agatttctaa acatcccagt ccacctgagg aactgtctcg aactattttc
1861 aaagacttaa gcccagtgca ctgaaagtca cggctgcgca ctgtgtcctc ttccaccaca
1921 gagggcgtgt gctcggtgct gacgggaccc acatgctcca gattagagcc tgtaaacttt
1981 atcacttaaa cttgcatcac ttaacggacc aaagcaagac cctaaacatc cataattgtg
2041 attagacaga acacctatgc aaagatgaac ccgaggctga gaatcagact gacagtttac
2101 agacgctgct gtcacaacca agaatgttat gtgcaagttt atcagtaaat aactggaaaa
2161 cagaacactt atgttataca atacagatca tcttggaact gcattcttct gagcactgtt
2221 tatacactgt gtaaataccc atatgtcctg aattcaccat cactatcaca attaaaagga
2281 agaaaaaaac tctctaagcc ataaaaagac atattcaggg atattctgag aaggggttac
2341 tagaagttta atatttggaa aaacagttag tgcatttta ctccatctct taggtgcttt
2401 aaatttttat ttcaaaaaca gcgtatttac atttatgttg acagcttagt tataagttaa
2461 tgctcaaata cgtatttcaa atttatatgg tagaaacttc cagaatctct gaaattatca
2521 acagaaacgt gccattttag tttatatgca gaccgtacta ttttttttctg cctgattgtt
2581 aaatatgaag gtatttttag taattaaata taacttatta ggggatatgc ctatgtttaa
2641 cttttatgat aatatttaca atttataat ttgtttccaa aagacctaat tgtgccttgt
2701 gataaggaaa cttcttactt ttaatgatga ggaaaattat acatttcatt ctatgacaaa
2761 gaaactttac tatcttctca ctattctaaa acagaggtct gttttctttc ctagtaagat
2821 atattttat agaactagac tacaatttaa tttctggttg agaaaagcct tctatttaag
2881 aaatttacaa agctatatgt ctcaagattc acccttaaat ttacttaagg aaaaaaataa
2941 ttgacactag taagttttt tatgtcaatc agcaaactga aaaaaaaaaa agggtttcaa
3001 agtgcaaaaa caaaatctga tgttcataat atatttaaat atttaccaaa aatttgagaa
3061 cacagggctg ggcgcagtgg ctcacaccta aatcccagt acattggtag gcaaggtggg
3121 cagatcacct gaggtcagga gttcaagacc agcctggaca acatggtgaa accctgtctc
3181 tactaaataa tacaaaaatt agccaggcgt gctggcgggc acctgtaatc ccagctactc
3241 gggaggctga ggcagggaga attgcttgca ccagggaggg agaggttgca gtgagccaag
3301 atcgcaccac tgcactccag ccggggcaac agagcaagac tccatctcaa aaaaaaaaaa
3361 aaaaaaagaa agaaaagaaa atttgagaac acagctttat actcgggact acaaaaccat
3421 aaactcctgg agttttaact ccttttgaaa tttcatagt acaattaata ctaatgaaca
3481 tttgtgtaaa gctttataat ttaaaggcaa tttctcatat attcttttct gaatcatttg
3541 caaggaagtt cagagtccag tctgtaacta gcatctacta tatgtctgtc ttcaccttac
3601 agtgttctac cattattttt tctttattcc atttcaaaat ctaatttatt ttaccccaac
3661 ttctccccac cacttgacgt agttttagaa cacacaggtg ttgctacata tttggagtca
3721 atgatggact ctggcaaagt caaggctctg tttattcc accaaggtgc acttttccaa
3781 caactattta actagttaag aacctcccta tcttagaact gtatctactt tatatttaag
3841 aaggttttat gaattcaaca acggtatcat ggccttgtat caagttgaaa acaactgaa
3901 aataagaaaa tttcacagcc tcgaaagaca acaacaagtt tctaggatat ctcaatgaca
```

-continued

```
3961 agagtgatgg atacttaggt agggaaacgc taatgcagga aaaactggca acaacacaat
4021 ttatatcaat tctctttgta ggcaggtgat aaaaaattca aggacaaatc tcattatgtc
4081 attgtgcatc atatataatc tcttatgagc gagaatgggg ggaatttgtg tttttacttt
4141 acacttcaat tccttacacg gtatttcaaa caaacagttt tgctgagagg agcttttgtc
4201 tctccttaag aaaatgttta taaagctgaa aggaaatcaa acagtaatct taaaaatgaa
4261 aacaaaacaa cccaacaacc tagataacta cagtgatcag ggagcacagt tcaactcctt
4321 gttatgtttt agtcatatgg cctactcaaa cagctaaata acaacaccag tggcagataa
4381 aaatcaccat ttatctttca gctattaatc ttttgaatga ataaactgtg acaaacaaat
4441 taacatttt gaacatgaaa ggcaacttct gcacaatcct gtatccaagc aaactttaaa
4501 ttatccactt aattattact taatcttaaa aaaaattaga acccagaact tttcaatgaa
4561 gcatttgaaa gttgaagtgg aatttaggaa agccataaaa atataaatac tgttatcaca
4621 gcaccagcaa gccataatct ttatacctat cagttctatt tctattaaca gtaaaaacat
4681 taagcaagat ataagactac ctgcccaaga attcagtctt tttcatttt tgtttttctc
4741 agttctgagg atgttaatcg tcaaattttc tttggactgc attcctcact acttttttgca
4801 caatggtctc acgttctcac atttgttctc gcgaataaat tgataaaagg tgttaagttc
4861 tgtgaatgtc ttttttaatta tgggcataat tgtgcttgac tggataaaaa cttaagtcca
4921 cccttatgtt tataataatt tcttgagaac agcaaactgc atttaccatc gtaaaacaac
4981 atctgactta cgggagctgc agggaagtgg tgagacagtt cgaacggctc ctcagaaatc
5041 cagtgaccca attctaaaga ccatagcacc tgcaagtgac acaacaagca gatttattat
5101 acatttatta gccttagcag gcaataaacc aagaatcact ttgaagacac agcaaaaagt
5161 gatacactcc gcagatctga aatagatgtg ttctcagaca acaaagtccc ttcagaatct
5221 tcatgttgca taaatgttat gaatattaat aaaaagttga ttgagaaaaa
```

An exemplary human CD274 (also known as PD-L1) amino acid sequence is set forth below (SEQ ID NO: 11; GenBank Accession No: AAI13735, Version AAI13735.1, incorporated herein by reference):

```
  1 mrifavfifm tywhllnaft vtvpkdlyvv eygsnmtiec kfpvekqldl aalivyweme
 61 dkniiqfvhg eedlkvqhss yrqrarllkd qlslgnaalq itdvklqdag vyrcmisygg
121 adykritvkv napynkinqr ilvvdpvtse heltcqaegy pkaeviwtss dhqvlsgktt
181 ttnskreekl fnvtstlrin tttneifyct frrldpeenh taelvipelp lahppnerth
241 lvilgaillc lgvaltfifr lrkgrmmdvk kcgiqdtnsk kqsdthleet
```

An exemplary human CD274 (also known as PD-L1) nucleic acid sequence is set forth below (SEQ ID NO: 12; GenBank Accession No: NM_014143, Version NM_014143.3, incorporated herein by reference):

```
  1 ggcgcaacgc tgagcagctg gcgcgtcccg cgcggcccca gttctgcgca gcttcccgag
 61 gctccgcacc agccgcgctt ctgtccgcct gcagggcatt ccagaaagat gaggatattt
121 gctgtcttta tattcatgac ctactggcat ttgctgaacg catttactgt cacggttccc
181 aaggacctat atgtggtaga gtatggtagc aatatgacaa ttgaatgcaa attcccagta
241 gaaaaacaat tagacctggc tgcactaatt gtctattggg aaatggagga taagaacatt
```

-continued

```
 301 attcaatttg tgcatggaga ggaagacctg aaggttcagc atagtagcta cagacagagg
 361 gcccggctgt tgaaggacca gctctccctg ggaaatgctg cacttcagat cacagatgtg
 421 aaattgcagg atgcaggggt gtaccgctgc atgatcagct atggtggtgc cgactacaag
 481 cgaattactg tgaaagtcaa tgccccatac aacaaaatca accaaagaat tttggttgtg
 541 gatccagtca cctctgaaca tgaactgaca tgtcaggctg agggctaccc caaggccgaa
 601 gtcatctgga caagcagtga ccatcaagtc ctgagtggta agaccaccac caccaattcc
 661 aagagagagg agaagctttt caatgtgacc agcacactga gaatcaacac aacaactaat
 721 gagattttct actgcacttt taggagatta gatcctgagg aaaaccatac agctgaattg
 781 gtcatcccag aactacctct ggcacatcct ccaaatgaaa ggactcactt ggtaattctg
 841 ggagccatct tattatgcct tggtgtagca ctgacattca tcttccgttt aagaaaaggg
 901 agaatgatgg atgtgaaaaa atgtggcatc caagatacaa actcaaagaa gcaaagtgat
 961 acacatttgg aggagacgta atccagcatt ggaacttctg atcttcaagc agggattctc
1021 aacctgtggt ttaggggttc atcggggctg agcgtgacaa gaggaaggaa tgggcccgtg
1081 ggatgcaggc aatgtgggac ttaaaaggcc caagcactga aaatggaacc tggcgaaagc
1141 agaggaggag aatgaagaaa gatggagtca acaggagc ctggagggag accttgatac
1201 tttcaaatgc ctgaggggct catcgacgcc tgtgacaggg agaaaggata cttctgaaca
1261 aggagcctcc aagcaaatca tccattgctc atcctaggaa gacgggttga gaatccctaa
1321 tttgagggtc agttcctgca gaagtgccct ttgcctccac tcaatgcctc aatttgtttt
1381 ctgcatgact gagagtctca gtgttggaac gggacagtat ttatgtatga gttttttccta
1441 tttatttga gtctgtgagg tcttcttgtc atgtgagtgt ggttgtgaat gatttctttt
1501 gaagatatat tgtagtagat gttacaattt tgtcgccaaa ctaaacttgc tgcttaatga
1561 tttgctcaca tctagtaaaa catggagtat ttgtaaggtg cttggtctcc tctataacta
1621 caagtataca ttggaagcat aaagatcaaa ccgttggttg cataggatgt caccttttatt
1681 taacccatta atactctggt tgacctaatc ttattctcag acctcaagtg tctgtgcagt
1741 atctgttcca tttaaatatc agctttacaa ttatgtggta gcctacacac ataatctcat
1801 ttcatcgctg taaccaccct gttgtgataa ccactattat tttacccatc gtacagctga
1861 ggaagcaaac agattaagta acttgcccaa accagtaaat agcagacctc agactgccac
1921 ccactgtcct tttataatac aatttacagc tatattttac tttaagcaat tcttttattc
1981 aaaaaccatt tattaagtgc ccttgcaata tcaatcgctg tgccaggcat tgaatctaca
2041 gatgtgagca agacaaagta cctgtcctca aggagctcat agtataatga ggagattaac
2101 aagaaaatgt attattacaa tttagtccag tgtcatagca taaggatgat gcgaggggaa
2161 aacccgagca gtgttgccaa gaggaggaaa taggccaatg tggtctggga cggttggata
2221 tacttaaaca tcttaataat cagagtaatt ttcatttaca aagagaggtc ggtacttaaa
2281 ataaccctga aaaataacac tggaattcct tttctagcat tatatttatt cctgatttgc
2341 ctttgccata taatctaatg cttgtttata tagtgtctgg tattgtttaa cagttctgtc
2401 ttttctattt aaatgccact aaattttaaa ttcataccct tccatgattc aaaattcaaa
2461 agatcccatg ggagatggtt ggaaaatctc cacttcatcc tccaagccat tcaagtttcc
2521 tttccagaag caactgctac tgcctttcat tcatatgttc ttctaaagat agtctacatt
2581 tggaaatgta tgttaaaagc acgtattttt aaaattttt tcctaaatag taacacattg
2641 tatgtctgct gtgtactttg ctatttttat ttatttagt gtttcttata tagcagatgg
2701 aatgaatttg aagttcccag ggctgaggat ccatgccttc tttgtttcta agttatcttt
```

-continued

```
2761 cccatagctt ttcattatct ttcatatgat ccagtatatg ttaaatatgt cctacatata
2821 catttagaca accaccattt gttaagtatt tgctctagga cagagtttgg atttgtttat
2881 gtttgctcaa aaggagaccc atgggctctc cagggtgcac tgagtcaatc tagtcctaaa
2941 aagcaatctt attattaact ctgtatgaca gaatcatgtc tggaactttt gttttctgct
3001 ttctgtcaag tataaacttc actttgatgc tgtacttgca aaatcacatt ttctttctgg
3061 aaattccggc agtgtacctt gactgctagc taccctgtgc cagaaaagcc tcattcgttg
3121 tgcttgaacc cttgaatgcc accagctgtc atcactacac agccctccta agaggcttcc
3181 tggaggtttc gagattcaga tgccctggga gatcccagag tttcctttcc ctcttggcca
3241 tattctggtg tcaatgacaa ggagtacctt ggctttgcca catgtcaagg ctgaagaaac
3301 agtgtctcca acagagctcc ttgtgttatc tgtttgtaca tgtgcatttg tacagtaatt
3361 ggtgtgacag tgttctttgt gtgaattaca ggcaagaatt gtggctgagc aaggcacata
3421 gtctactcag tctattccta agtcctaact cctccttgtg gtgttggatt tgtaaggcac
3481 tttatccctt ttgtctcatg tttcatcgta aatggcatag gcagagatga tacctaattc
3541 tgcatttgat tgtcactttt tgtacctgca ttaatttaat aaaatattct tatttatttt
3601 gttacttggt acaccagcat gtccattttc ttgtttattt tgtgtttaat aaaatgttca
3661 gtttaacatc ccagtggaga aagttaaaaa a
```

An exemplary human IFN-γ amino acid sequence is set forth below (SEQ ID NO: 13; GenBank Accession No: AAA53230, Version AAA53230.1, incorporated herein by reference):

```
  1 mamlrvqpea qakvdvfred lctktenllg syfpkkisel daflkepaln eanlsnlkap
 61 ldipvpdpvk ekekeerkkq qekedkdekk kgededkgpp cgpvncneki vvllqrlkpe
121 ikdvieqlnl vttwlqlqip riedgnnfgv avqekvfelm tslhtklegf htqiskyfse
181 rgdavtkaak qphvgdyrql vheldeaeyr dirlmvmeir nayavlydii lknfeklkkp
241 rgetkgmiy
```

An exemplary human IFN-γ nucleic acid sequence is set forth below (SEQ ID NO: 14; GenBank Accession No: NM_000619, Version NM_000619.2, incorporated herein by reference):

```
  1 cacattgttc tgatcatctg aagatcagct attagaagag aaagatcagt taagtccttt
 61 ggacctgatc agcttgatac aagaactact gatttcaact tctttggctt aattctctcg
121 gaaacgatga atatacaag ttatatcttg gcttttcagc tctgcatcgt tttgggttct
181 cttggctgtt actgccagga cccatatgta aagaagcag aaaaccttaa gaaatatttt
241 aatgcaggtc attcagatgt agcggataat ggaactcttt tcttaggcat tttgaagaat
301 tggaaagagg agagtgacag aaaaataatg cagagccaaa ttgtctcctt ttacttcaaa
361 cttttaaaa actttaaaga tgaccagagc atccaaaaga gtgtggagac catcaaggaa
421 gacatgaatg tcaagttttt caatagcaac aaaaagaaac gagatgactt cgaaaagctg
481 actaattatt cggtaactga cttgaatgtc aacgcaaag caatacatga actcatccaa
541 gtgatggctg aactgtcgcc agcagctaaa acagggaagc gaaaaggag tcagatgctg
601 tttcgaggtc gaagagcatc ccagtaatgg ttgtcctgcc tgcaatattt gaattttaaa
```

```
 661 tctaaatcta tttattaata tttaacatta tttatatggg gaatatattt ttagactcat 721 caatcaaata agtatttata atagcaactt ttgtgtaatg aaaatgaata tctattaata 781 tatgtattat ttataattcc tatatcctgt gactgtctca cttaatcctt tgttttctga 841 ctaattaggc aaggctatgt gattacaagg ctttatctca ggggccaact aggcagccaa 901 cctaagcaag atcccatggg ttgtgtgttt atttcacttg atgatacaat gaacacttat 961 aagtgaagtg atactatcca gttactgccg gtttgaaaat atgcctgcaa tctgagccag 1021 tgctttaatg gcatgtcaga cagaacttga atgtgtcagg tgaccctgat gaaaacatag 1081 catctcagga gatttcatgc ctggtgcttc caaatattgt tgacaactgt gactgtaccc 1141 aaatggaaag taactcattt gttaaaatta tcaatatcta atatatatga ataaagtgta 1201 agttcacaac aaaaaaaaaa aaaaaaaaaa aaaaaaaaaa
```

An exemplary human MAN2A1 amino acid sequence is set forth below (SEQ ID NO: 15; GenBank Accession No: AAI42697, Version AAI42697.1, incorporated herein by reference):

```
   1 mklsrqftvf gsaifcvvif slylmldrgh ldyprnprre gsfpqgqlsm lqekidhler 61 llaenneiis nirdsvinls esvedgpkss qsnfsqgags hllpsqlsls vdtadclfas 121 qsgshnsdvq mldvyslisf dnpdggvwkq gfdityesne wdteplqvfv vphshndpgw 181 lktfndyfrd ktqyifnnmv lklkedsrrk fiwseisyls kwwdiidiqk kdavkslien 241 gqleivtggw vmpdeatphy falidqlieg hqwlennigv kprsgwaidp fghsptmayl 301 lnraglshml iqrvhyavkk hfalhktlef fwrqnwdlgs vtdilchmmp fysydiphtc 361 gpdpkiccqf dfkrlpggrf gcpwgvppet ihpgnvqsra rmlldqyrkk sklfrtkvll 421 aplgddfryc eytewdlqfk nyqqlfdymn sqskfkvkiq fgtlsdffda ldkadetqrd 481 kgqsmfpvls gdfftyadrd dhywsgyfts rpfykrmdri meshlraaei lyyfalrqah 541 kykinkflss slytaltear rnlglfqhhd aitgtakdwv vvdygtrpfh slmvlekiig 601 nsafllilkd kltydsyspd tflemdlkqk sqdslpqkni irlsaepryl vvynpleqdr 661 islvsvyvss ptvqvfsasg kpvevqvsav wdtantiset ayeisfrahi pplglkvyki 721 lesassnshl adyvlyknkv edsgiftikn minteegitl ensfvllrfd qtglmkqmmt 781 kedgkhhevn vqfswygtti krdksgaylf lpdgnakpyv yttppfvrvt hgriysevtc 841 ffdhvthrvr lyhiqgiegq svevsnivdi rkvynreiam kissdiksqn rfytdlngyq 901 iqprmtlskl plqanvypmt tmayiqdakh rltllsaqsl gvsslnsgqi evimdrrlmq 961 ddnrgleqgi qdnkitanlf rillekrsav nteeekksvs ypsllshits slmnhpvipm 1021 ankfsptlel qgefsplqss lpcdihlvnl rtiqskvgng hsneaalilh rkgfdcrfss 1081 kgtglfcstt qgkilvqkll nkfivesltp sslslmhspp gtqniseinl spmeistfri 1141 qlr
```

An exemplary human MAN2A1 nucleic acid sequence is set forth below (SEQ ID NO: 16; GenBank Accession No: NM_002372, Version NM_002372.3, incorporated herein by reference):

```
   1 ggcggggcca gccgcccgct cggctcaggc gctgcgggcg cctattgacc cagcggctgc 61 tgcgccgccg ctgtctcctc ctgctcgtgg cgggcggtgc tggagcgcca agtggcgctg 121 gagaaccggc gcttcctttc gccgcttccg ccgccatctc cgcgtttgtg gggcgggaaa
```

-continued

```
 181 gagggagggg gctagcggct gcagctggag cgggcttctc tccggggacg gtcctttcct
 241 ccctgctctc cttttccttc tttccgcgtt gccgccgccc gcccctgcg cctcccgcg
 301 gagcctgggt ccgggagggg gaaggtaggg gcggcggggg gcgggagagt ctggcgagcg
 361 gacgctagct ctgaggaaac tcatcaatcc gtgagcccg gagtccgggg tgcacatcgg
 421 cccagccgca gcgtcggcgg cggcggcggc agcagcacga aggggctcag tcggggtagg
 481 cgggggcggt gccggtgccg cggggggcggg cccgaccgtc ccgcccagaa gttgtagggc
 541 ttggctcctc gcgatcttgt tcctttcccc tccgcttctc tgacctagct gcgcggcccc
 601 ggcccgggag ctgccgaacc cgcgcctccc ctgggtgagg aggacacgcc tgccctcgtc
 661 gagaaaactt ttcctgccga ctcagttggg gcggcggtgg caggaagtgc gggcagcgac
 721 ctctcctccg cctgccccgc gcgccctgcc ggaggtcggc gctgagcttg cgatcaagtt
 781 tgtgggggcc cccttccca gttgccggcg agtctcgcct cgagaggggc gcccgacccc
 841 ggggagggc gcaggccagg gcgaaggcca agggcgtgtg gtggcgccgg agactaggtg
 901 cggagcaagg cggggactcg cacccgcatc cgagagcgcg gaggtcgcgc agcccgggag
 961 aagggagcct ccggcggctg cttcctagag tccacagtgc gctgtctcct ttggctgagg
1021 agagtgtcct ggccccgagt ctatcgagga aaatgaagtt aagccgccag ttcaccgtgt
1081 tcggcagtgc gatcttctgt gtggtgattt tctcgctcta cctgatgctg gaccggggtc
1141 acttagacta ccccaggaac ccgcgccgcg agggctcctt ccctcagggc cagctctcaa
1201 tgttgcaaga aaaatagac catttggagc gtttgctagc tgagaataat gagatcatct
1261 caaatattag agactcagtc atcaatttga gtgagtctgt ggaggatggt ccgaaaagtt
1321 cacaaagcaa tttcagccaa ggtgctggct cacatcttct gccctcacaa ttatccctct
1381 cagttgacac tgcagactgt ctgtttgctt cacaaagtgg aagtcacaat tcagatgtgc
1441 agatgttgga tgtttacagt ctaatttctt ttgacaatcc agatggtgga gtttggaagc
1501 aaggatttga cattacttat gaatctaatg aatgggacac tgaaccctt caagtctttg
1561 tggtgcctca ttcccataac gacccaggtt ggttgaagac tttcaatgac tactttagag
1621 acaagactca gtatattttt aataacatgg tcctaaagct gaaagaagac tcacggagga
1681 agtttatttg gtctgagatc tcttaccttt caaagtggtg ggatattata gatattcaga
1741 agaaggatgc tgttaaaagt ttaatagaaa atggtcagct tgaaattgtg acaggtggct
1801 gggttatgcc tgatgaagct actccacatt attttgcctt aattgatcaa ctaattgaag
1861 gacatcagtg gctggaaaat aatataggag tgaaacctcg gtccggctgg gctattgatc
1921 cctttggaca ctcaccaaca atggcttatc ttctaaaccg tgctggactt tctcacatgc
1981 ttatccagag agttcattat gcagttaaaa aacactttgc actgcataaa acattggagt
2041 ttttttggag acagaattgg gatctgggat ctgtcacaga tattttatgc cacatgatgc
2101 ccttctacag ctatgacatc cctcacactt gtggacctga tcctaaaata tgctgccagt
2161 ttgattttaa acgtcttcct ggaggcagat ttggttgtcc ctggggagtc ccccagaaa
2221 caatacatcc tggaaatgtc caaagcaggg ctcggatgct actagatcag taccgaaaga
2281 agtcaaagct ttttcgtacc aaagttctcc tggctccact aggagatgat ttccgctact
2341 gtgaatacac ggaatgggat ttacagttta agaattatca gcagcttttt gattatatga
2401 attctcagtc caagtttaaa gttaagatac agtttggaac tttatcagat tttttttgatg
2461 cgctggataa agcagatgaa actcagagag acaagggcca atcgatgttc cctgttttaa
2521 gtggagattt tttcacttat gccgatcgag atgatcatta ctggagtggc tattttacat
```

-continued

```
2581 ccagacccett ttacaaacga atggacagaa tcatggaatc tcatttaagg gctgctgaaa
2641 ttctttacta tttcgccctg agacaagctc acaaatacaa gataaataaa tttctctcat
2701 catcacttta cacggcactg acagaagcca gaaggaattt gggactgttt caacatcatg
2761 atgctatcac aggaactgca aaagactggg tggttgtgga ttatggtacc agacttttc
2821 attcgttaat ggttttggag aagataattg gaaattctgc atttcttctt attttgaagg
2881 acaaactcac atacgactct tactctcctg ataccttcct ggagatggat ttgaaacaaa
2941 aatcacaaga ttctctgcca caaaaaaata taataaggct gagtgcggag ccaaggtacc
3001 ttgtggtcta taatccttta gaacaagacc gaatctcgtt ggtctcagtc tatgtgagtt
3061 ccccgacagt gcaagtgttc tctgcttcag gaaaacctgt ggaagttcaa gtcagcgcag
3121 tttgggatac agcaaatact atttcagaaa cagcctatga gatctctttt cgagcacata
3181 taccgccatt gggactgaaa gtgtataaga ttttggaatc agcaagttca aattcacatt
3241 tagctgatta tgtcttgtat aagaataaag tagaagatag cggaattttc accataaaga
3301 atatgataaa tactgaagaa ggtataacac tagagaactc ctttgtttta cttcggtttg
3361 atcaaactgg acttatgaag caaatgatga ctaaagaaga tggtaaacac catgaagtaa
3421 atgtgcaatt ttcatggtat ggaaccacaa ttaaaagaga caaaagtggt gcctacctct
3481 tcttacctga tggtaatgcc aagccttatg tttacacaac accgcccttt gtcagagtga
3541 cacatggaag gattattcg gaagtgactt gcttttttga ccatgttact catagagtcc
3601 gactatacca catacaggga atagaaggac agtctgtgga agtttccaat attgtggaca
3661 tccgaaaagt atataaccgt gagattgcaa tgaaaatttc ttctgatata aaagccaaa
3721 atagatttta tactgaccta aatgggtacc agattcaacc tagaatgaca ctgagcaaat
3781 tgcctcttca agcaaatgtc tatcccatga ccacaatggc ctatatccag gatgccaaac
3841 atcgtttgac actgctctct gctcagtcat tagggggttc gagtttgaat agtggtcaga
3901 ttgaagttat catggatcga agactcatgc aagatgataa tcgtggcctt gagcaaggta
3961 tccaggataa caagattaca gctaatctat ttcgaatact actagaaaaa agaagtgctg
4021 ttaatacgga agaagaaaag aagtcggtca gttatccttc tctccttagc cacataactt
4081 cttctctcat gaatcatcca gtcattccaa tggcaaataa gttctcctca cctacccttg
4141 agctgcaagg tgaattctct ccattacagt catctttgcc ttgtgacatt catctggtta
4201 atttgagaac aatacagtca aaggtgggca atgggcactc caatgaggca gccttgatcc
4261 tccacagaaa agggttttgat tgtcggttct ctagcaaagg cacagggctg ttttgttcta
4321 ctactcaggg aaagatattg gtacagaaac ttttaaacaa gtttattgtc gaaagtctca
4381 caccttcatc actatccttg atgcattcac ctcccggcac tcagaatata agtgagatca
4441 acttgagtcc aatggaaatc agcacattcc gaatccagtt gaggtgaacc tgactttcac
4501 atttggattg agaatcattg gcttttatac cttcttggt ttgacgtgca ataagaagc
4561 acattatttt agcttctggc tactgtgaga acatgaattc tgtgattctg tgggttttt
4621 ctttttctt ttaccagtac agtaagaaaa aaaaaaaaa aaaaaagcc atgctatcaa
4681 tcaagattct ttttttttaa actttctccc atgaactacc accatcagta tgaattgatg
4741 caacaaatga agaaatattt aaagacagcc tctcaacaga ttgtatctca ggttaaatgc
4801 taactaatta tgtctgtgtt ggggggttgcg aagagattct taaaagtatc tgtgtgttga
4861 tcatcagttt tacaaaaaca cctatttggc tgaaatggaa taaatgtttt gtgggtaaaa
4921 gctaatggcc aaaatggttg caatcattca tactagttag aaaaattatg tgttgaaata
4981 agtggaaaag tgcaatccat ccacccttat gattaacgta gatgattttt atacctttt
```

-continued

```
5041 ctgatgtacc tcttgacctt ctccttccct tcctacccct tctaagtatt tccagaaata 5101 cctgattttg aatcattcaa cagtagaaaa agaggcatat tttcattact tgacaatgtg 5161 ggatgggtgc aatttattcc atcttcacta aaatagaagc aattccatag gtaccataaa 5221 cctattttag gtaccacaag gtgtcttttt acacagctca tttgaataca ggtgttctga 5281 gaagggtttt ctattttaaa attaccatat caaaataaat gtgccttatt tttttataag 5341 tcttgttaaa tcagtgtcca tattactgtt tggggaaggg ggaatgttgt ggggtctggg 5401 agagggtggg tactttctat gacacataaa ttgtgtaatt tttgcctgac aatgctggcc 5461 acattctgat ctgtttcatt aaatttgtgg tgatgttact ctaaacattt tgactatttg 5521 aatgtactga gatgtcagaa acaaaacaa ggaaggaaaa tattgttaat taaaatgtgc 5581 tgctgccaag gaaactgcaa cttgaagcaa ggattttgta aaatgcaaaa tccagctact 5641 gtttccattt cacagtagtt aactatatta agagagaat gctttaaaat tgatcttgtt 5701 ttgaacccca cttttatgta gctcatcatg gtttatctta ctaaggaata tgtttgttca 5761 ttcagttctc aacttttgta tgtgctaacc ttaaagtgaa gttctgagcc cgtgtgccat 5821 tacagtgctt ttaataaaat ttatttggga ttattgtttc cttaacatta aaataatagc 5881 gacatttaga ctatgcaatt ttagcataga aaggagtctt tgagtatgta cagttttgaa 5941 aattctcttt gagataattg atttcatatt ctgtggcttt caacctccat ttacctcttg 6001 tcattccaac atctttatag agaaataaaa acccaatttc tctttcacca tttagtttga 6061 ttatcatctg gattttcact caagatgcag ctcctaagat tattgttatg ttaaattcat 6121 aaactccttc acctttaata attaaggaaa caataccagt gttgataaag atattacaag 6181 gggtaatttc atgcaataaa catgtaccgt aagttttctt ccacatattt tgggaaaaaa 6241 ctaaaaaaag aaaaaggact tccttttgt ggacatctac agatgttagg gttgccagaa 6301 gcaaatccca ggaatgagat cagtattttc attgcatctt aaatgtataa ccttcctgtg 6361 ggagttcagt tgtctgtgg ttaagtgggt gtgcttaatc attctcgaaa ttgtgatcag 6421 atgaaataaa aaaaaaatct tgatgcaata acagtggttt tgccacttct ggttgtttgc 6481 gatggatctg tcccatgtca gtctggggtt ttattcagct tgtgttgcta ccagcagttc 6541 acaggtaaag cagaaattct ctttaaccag caagtttctg cttttttaagg ttacttttag 6601 aataaatcat cagggaaaca gagaggatgc tttgctttgg gttgtagtca aaaactgatt 6661 aaataattta atgtctctgg cacacactaa aaaccataca cttcagttgt gatctcagtg 6721 gcatatttat ttggttaggt ttcgttacat ttattattac agatgttcag ttgaccaagt 6781 agttcagtgt tttctttcct ttttttggaa attttagttt gagtttgtga ctgcagtgtt 6841 caagaactca gcatccttgt tttctacaaa tactgattaa aataaaatgc tgtaaaatgt 6901 gatgtaaaac attatcatga tcttcccatg cctttgttgt acttgtgccg aagtgttttg 6961 atattccttt gtctggaaga aaatgtttgc tttcattttg atcattttgt tcaccttgga 7021 atcaacaggt tttgatattt tctcttggaa gatttttat cttttgggga atatgtaata 7081 taagatctct aataaaagat aatcttatca tgta
```

An exemplary human programmed cell death protein 1 (PD1) amino acid sequence is set forth below (SEQ ID NO: 17; GenBank Accession No: AAH74740, Version AAH74740.1, incorporated herein by reference):

```
  1 mqipqapwpv vwavlqlgwr pgwfldspdr pwnpptfspa llvvtegdna tftcsfsnts
 61 esfvlnwyrm spsnqtdkla afpedrsqpg qdcrfrvtql pngrdfhmsv vrarrndsgt
121 ylcgaislap kaqikeslra elrvterrae vptahpspsp rpagqfqtlv vgvvggllgs
181 lvllvwvlav icsraargti garrtgqplk edpsavpvfs vdygeldfqw rektpeppvp
241 cvpeqteyat ivfpsgmgts sparrgsadg prsaqplrpe dghcswpl
```

An exemplary human PDJ nucleic acid sequence is set forth below (SEQ ID NO: 18; GenBank Accession No: NM_005018, Version NM_005018.2, incorporated herein by reference):

```
   1 agtttccctt ccgctcacct ccgcctgagc agtggagaag gcggcactct ggtggggctg
  61 ctccaggcat gcagatccca caggcgccct ggccagtcgt ctgggcggtg ctacaactgg
 121 gctggcggcc aggatggttc ttagactccc cagacaggcc ctggaacccc ccacccttct
 181 ccccagccct gctcgtggtg accgaagggg acaacgccac cttcacctgc agcttctcca
 241 acacatcgga gagcttcgtg ctaaactggt accgcatgag ccccagcaac cagacggaca
 301 agctggccgc cttccccgag gaccgcagcc agcccggcca ggactgccgc ttccgtgtca
 361 cacaactgcc caacgggcgt gacttccaca tgagcgtggt cagggcccgg cgcaatgaca
 421 gcggcaccta cctctgtggg gccatctccc tggcccccaa ggcgcagatc aaagagagcc
 481 tgcgggcaga gctcagggtg acagagagaa gggcagaagt gcccacagcc accccagcc
 541 cctcacccag gccagccggc cagttccaaa ccctggtggt tggtgtcgtg ggcggcctgc
 601 tgggcagcct ggtgctgcta gtctgggtcc tggccgtcat ctgctcccgg gccgcacgag
 661 ggacaatagg agccaggcgc accggccagc ccctgaagga ggacccctca gccgtgcctg
 721 tgttctctgt ggactatggg gagctggatt tccagtggcg agagaagacc ccggagcccc
 781 ccgtgccctg tgtccctgag cagacggagt atgccaccat tgtctttcct agcggaatgg
 841 gcacctcatc cccgcccgc aggggctcag ctgacggccc tcggagtgcc cagccactga
 901 ggcctgagga tggacactgc tcttggcccc tctgaccggc ttccttggcc accagtgttc
 961 tgcagaccct ccaccatgag cccgggtcag cgcatttcct caggagaagc aggcagggtg
1021 caggccattg caggccgtcc aggggctgag ctgcctgggg cgaccggggg ctccagcctg
1081 cacctgcacc aggcacagcc ccaccacagg actcatgtct caatgcccac agtgagccca
1141 ggcagcaggt gtcaccgtcc cctacaggga gggccagatg cagtcactgc ttcaggtcct
1201 gccagcacag agctgcctgc gtccagctcc ctgaatctct gctgctgctg ctgctgctgc
1261 tgctgctgcc tgcggcccgg ggctgaaggc gccgtggccc tgcctgacgc cccggagcct
1321 cctgcctgaa cttgggggct ggttggagat ggccttggag cagccaaggt gcccctggca
1381 gtggcatccc gaaacgccct ggacgcaggg cccaagactg gcacaggag tgggaggtac
1441 atggggctgg ggactcccca ggagttatct gctccctgca ggcctagaga agtttcaggg
1501 aaggtcagaa gagctcctgg ctgtggtggg cagggcagga aaccctcca cctttacaca
1561 tgcccaggca gcacctcagg ccctttgtgg ggcagggaag ctgaggcagt aagcgggcag
1621 gcagagctgg aggcctttca ggcccagcca gcactctggc ctcctgccgc cgcattccac
1681 cccagcccct cacaccactc gggagaggga catcctacgg tcccaaggtc aggagggcag
```

-continued

```
1741 ggctggggtt gactcaggcc cctcccagct gtggccacct gggtgttggg agggcagaag 1801 tgcaggcacc tagggccccc catgtgccca ccctgggagc tctccttgga acccattcct 1861 gaaattattt aaagggggttg gccgggctcc caccagggcc tgggtgggaa ggtacaggcg 1921 ttcccccggg gcctagtacc cccgccgtgg cctatccact cctcacatcc acacactgca 1981 cccccactcc tggggcaggg ccaccagcat ccaggcggcc agcaggcacc tgagtggctg 2041 ggacaaggga tcccccttcc ctgtggttct attatattat aattataatt aaatatgaga 2101 gcatgctaag gaaaa
```

An exemplary human CTLA4 amino acid sequence is set forth below (SEQ ID NO: 19-GenBank Accession No: AAL07473, Version AAL07473.1, incorporated herein by reference):

```
  1 maclgfqrhk aqlnlatrtw pctllffllf ipvfckamhv aqpavvlass rgiasfvcey 61 aspgkatevr vtvlrqadsq vtevcaatym mgneltfldd sictgtssgn qvnltiqglr 121 amdtglyick velmypppyy lgigngtqiy vidpepcpds dfllwilaav ssglffysfl 181 ltavslskml kkrsplttgv yvkmpptepe cekqfqpyfi pin
```

An exemplary human CTLA4 nucleic acid sequence is set forth below (SEQ ID NO: 20; GenBank Accession No: AF414120, Version AF414120.1, incorporated herein by reference):

```
   1 cttctgtgtg tgcacatgtg taatacatat ctgggatcaa agctatctat ataaagtcct 61 tgattctgtg tgggttcaaa cacatttcaa agcttcagga tcctgaaagg ttttgctcta 121 cttcctgaag acctgaacac cgctcccata aagccatggc ttgccttgga tttcagcggc 181 acaaggctca gctgaacctg ctaccagga cctggccctg cactctcctg ttttttcttc 241 tcttcatccc tgtcttctgc aaagcaatgc acgtggccca gcctgctgtg gtactggcca 301 gcagccgagg catcgccagc tttgtgtgtg agtatgcatc tccaggcaaa gccactgagg 361 tccgggtgac agtgcttcgg caggctgaca gccaggtgac tgaagtctgt gcggcaacct 421 acatgatggg gaatgagttg accttcctag atgattccat ctgcacgggc acctccagtg 481 gaaatcaagt gaacctcact atccaaggac tgagggccat ggacacggga ctctacatct 541 gcaaggtgga gctcatgtac ccaccgccat actacctggg cataggcaac ggaacccaga 601 tttatgtaat tgatccagaa ccgtgcccag attctgactt cctcctctgg atccttgcag 661 cagttagttc ggggttgttt ttttatagct ttctcctcac agctgtttct ttgagcaaaa 721 tgctaaagaa aagaagccct cttacaacag gggtctatgt gaaaatgccc caacagagc 781 cagaatgtga aaagcaattt cagccttatt ttattcccat caattgagaa accattatga 841 agaagagagt ccatatttca atttccaaga gctgaggcaa ttctaacttt tttgctatcc 901 agctattttt atttgtttgt gcatttgggg ggaattcatc tctctttaat ataaagttgg 961 atgcggaacc caaattacgt gtactacaat ttaaagcaaa ggagtagaaa gacagagctg 1021 ggatgttttct gtcacatcag ctccactttc agtgaaagca tcacttggga ttaatatggg 1081 gatgcagcat tatgatgtgg gtcaaggaat taagttaggg aatggcacag cccaaagaag 1141 gaaaaggcag ggagcgaggg agaagactat attgtacaca ccttatattt acgtatgaga 1201 cgtttatagc cgaaatgatc ttttcaagtt aaatttatg cctttatttt cttaaacaaa 1261 tgtatgatta catcaaggct tcaaaaatac tcacatggct atgttttagc cagtgatgct
```

-continued

```
1321 aaaggttgta ttgcatatat acatatatat atatatatat atatatatat atatatatat 1381 atatatatat tttaatttga tagtattgtg catagagcca cgtatgtttt tgtgtatttg 1441 ttaatggttt gaatataaac actatatggc agtgtctttc caccttgggt cccagggaag 1501 ttttgtggag gagctcagga cactaataca ccaggtagaa cacaaggtca tttgctaact 1561 agcttggaaa ctggatgagg tcatagcagt gcttgattgc gtggaattgt gctgagttgg 1621 tgttgacatg tgctttgggg cttttacacc agttcctttc aatggtttgc aaggaagcca 1681 cagctggtgg tatctgagtt gacttgacag aacactgtct tgaagacaat ggcttactcc 1741 aggagaccca caggtatgac cttctaggaa gctccagttc gatgggccca attcttacaa 1801 acatgtggtt aatgccatgg acagaagaag gcagcaggtg gcagaatggg gtgcatgaag 1861 gtttctgaaa attaacactg cttgtgtttt taactcaata ttttccatga aaatgcaaca 1921 acatgtataa tatttttaat taaataaaaa tctgtggtgg tcgttttaaa aaaaaaaaa 1981 aaaaaaaaaa aaaaaaaaaa aaaaaaaaaa aaaaaaaaaa aaaaa
```

Pharmaceutical Therapeutics

For therapeutic uses, the compositions or agents described herein may be administered systemically, for example, formulated in a pharmaceutically-acceptable buffer such as physiological saline. Preferable routes of administration include, for example, subcutaneous, intravenous, intraperitoneally, intramuscular, or intradermal injections that provide continuous, sustained levels of the drug in the patient. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia. Generally, amounts will be in the range of those used for other agents used in the treatment of other diseases associated with neoplasia, although in certain instances lower amounts will be needed because of the increased specificity of the compound. For example, a therapeutic compound is administered at a dosage that is cytotoxic to a neoplastic cell.

Formulation of Pharmaceutical Compositions

The administration of a compound or a combination of compounds for the treatment of a neoplasia, e.g., melanoma, may be by any suitable means that results in a concentration of the therapeutic that, combined with other components, is effective in ameliorating, reducing, or stabilizing a neoplasia. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 µg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other cases, this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/Kg body weight. In other aspects, it is envisaged that doses may be in the range of about 5 mg compound/Kg body to about 20 mg compound/Kg body. In other embodiments, the doses may be about 8, 10, 12, 14, 16, or 18 mg/Kg body weight. Of course, this dosage amount may be adjusted upward or downward, as is routinely done in such treatment protocols, depending on the results of the initial clinical trials and the needs of a particular patient.

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the thymus; (v) formulations that allow for convenient dosing, such that doses are administered, for example, once every one or two weeks; and (vi) formulations that target a neoplasia by using carriers or chemical derivatives to deliver the therapeutic agent to a particular cell type (e.g., neoplastic cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner.

Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a neoplasia, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active antineoplastic therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug may be incorporated in biocompatible carriers, liposomes, nanoparticles, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutam-nine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly (glycolic acid) or poly(ortho esters), or combinations thereof).

Kits or Pharmaceutical Systems

The present compositions may be assembled into kits or pharmaceutical systems for use in ameliorating a neoplasia (e.g., melanoma). Kits or pharmaceutical systems according to this aspect of the invention comprise a carrier means, such as a box, carton, tube or the like, having in close confinement therein one or more container means, such as vials, tubes, ampoules, or bottles. The kits or pharmaceutical systems of the invention may also comprise associated instructions for using the agents of the invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Materials and Methods

The following materials and methods were used.

Data Collection of Clinical Genomics Studies

Cancer datasets were collected with both patient survival durations and tumor gene expression profiles from the TCGA (Cancer Genome Atlas Research, N. et al. 2013 Nature Genetics, 45: 1113-1120), PRECOG (Gentles et al., 2015 Nature Medicine, 21: 938-945), and the Molecular Taxonomy of Breast Cancer International Consortium (METABRIC) (Curtis et al., 2012 Nature, 486: 346-352) databases. If the clinical information is available, the breast cancer datasets were separated into subtypes of luminal A, luminal B, Her2 positive, Basal, and triple negative (partially overlap with Basal), since each subtype has a distinct degree of cytotoxic T-cell infiltration (Miyan et al., 2016 J Transl Med, 14: 227). To ensure the robustness of this analysis, the datasets were excluded from microarray platforms with less than 15,000 genes or without probes for cytotoxicity T-cell markers (CD8A, CD8B, GZMA, GZMB, PRF1). Also, only datasets with more than 50 patients and 10% death rate were included because low event number may undermine the reliability of Cox-PH survival regression (Kleinbaum, D. G. 1998 Biometrical Journal, 40: 107-108). Finally, 71 datasets from three databases passed the selection criteria (Table 2A and Table 2B). The expression values of all genes are normalized by subtracting the mean values across all samples in a dataset.

Table 2A and Table 2B. Cancer Gene Expression Datasets

| Database | Total | 10% death | 15K genes | 50 patients | CTL profiled |
|---|---|---|---|---|---|
| A. all datasets | | | | | |
| TCGA | 50 | 32 | 31 | 27 | 22 |
| PRECOG | 122 | 122 | 51 | 44 | 44 |
| METABRIC | 5 | 5 | 5 | 5 | 5 |

| Name | Database | Count | Description |
|---|---|---|---|
| B. significant datasets | | | |
| SKCM | TCGA | 317 | Metastatic tumors of skin cutaneous melanoma (Cancer Genome Atlas, N. et al., 2015 Cell, 161: 1681-1696). |
| UCEC | | 541 | All tumors of uterine corpus endometrial carcinoma (Cancer Genome Atlas Research, N. et al. 2013 Nature, 497: 67-73). |
| TNBC | METABRIC | 233 | Triple negative breast tumors (Curtis et al., 2012 Nature, 486: 346-352). |
| AML | PRECOG | 79 | Acute myeloid leukemia profiled by U133 + 2.0 array (Metzeler et al., 2008 Blood, 112: 4193-4201)[60]. |
| NB | | 389 | All neuroblastoma tumors (Oberthuer et al., 2010 Pharmacogenomics J, 10: 258-266). |

In Table 2A, each column indicates the number of datasets that passed each filtering criterion. (Total: total number of datasets collected from the TCGA (Cancer Genome Atlas Research, N. et al. 2013 Nature Genetics, 45: 1113-1120), PRECOG (Gentles et al., 2015 Nature Medicine, 21: 938-945), and METABRIC (Curtis et al., 2012 Nature, 486: 346-352) databases; 10% death: the dataset should have more than 10% death rate of patients for robust analysis in the Cox-PH survival regression; 15K genes: The transcriptome profiling platform should include more than 15,000 genes; 50 patients: the dataset should have more than 50 patients for robust analysis in the Cox-PH regression; CTL profiled: all cytotoxic T lymphocyte (CTL) markers, including CD8A, CD8B, GZMA, GZMB, and PRF1, should be included by the transcriptome profiling platform.) Table 2B shows that the top five datasets that can predict sufficient number of genes (>1% of all genes) with statistically significant p-values (FDR<0.1) in the interaction test. (Count: number of patients profiled).

Interaction Test in Multivariate Cox-PH Regression

In statistics, two variables interact if the effect of one variable depends on the status of the other, and a multiplication term in a multivariate linear model can test the interaction effect between two variables (Freedman, D. Statistical Models: Theory and Practice. (Cambridge University Press, 2009)). The Cox-PH survival regression to test was applied to determine how the level of cytotoxic T lymphocyte (CTL) interacts with other genes in the tumor to affect survival outcome. A linear model, "Hazard=a*CTL+b*P+d*CTL*P+Intercept", was solved using the Cox-PH regression (Kleinbaum, D. G. 1998 Biometrical Journal, 40: 107-108). The CTL level is estimated through the bulk-tumor expression sum of CD8A, CD8B, GZMA, GZMB, and PRF1. In the Cox-PH model, the death hazard was estimated through the patient survival information. The variable P represents the expression level of a candidate gene in the test. Since datasets where CTL correlates with favorable survival outcome were selected, the coefficient "a" is always negative. The association slope between CTL and Hazard is "a+d*P" (FIG. 1B). If the coefficient "d" is positive, a higher P level will flatten the slope between CTL and Hazard, indicating a reduced association between cytotoxic T-cell level and better survival outcome. If "d" is negative, a higher P level will sharpen the slope between CTL and Hazard, indicating an increased association between cytotoxic T-cell level and better survival outcome. The T-cell dysfunction score for each gene is defined as the Ward test z-score, which is the coefficient "d" divided by its standard deviation (Kleinbaum, D. G. 1998 Biometrical Journal, 40: 107-108) (Table 1A and Table 1B).

TABLE 1A and TABLE 1B

The interactions between the cytotoxic T-cell level and candidate genes

| | Coef | Stderr | Z | Pr(>|z|) |
|---|---|---|---|---|
| A. Antagonistic interaction | | | | |
| Age | 0.02 | 0.01 | 3.55 | 3.78E-04 |
| Gender | 0.02 | 0.17 | 0.12 | 9.07E-01 |
| Stage | 0.29 | 0.09 | 3.31 | 9.34E-04 |
| CTL | −0.50 | 0.15 | −3.32 | 9.05E-04 |
| TGFB1 | −0.10 | 0.10 | −1.04 | 3.00E-01 |
| CTL * TGFB1 | 0.11 | 0.03 | 3.47 | 5.18E-04 |
| B. Synergistic interaction | | | | |
| Age | 0.02 | 0.01 | 3.26 | 1.11E-03 |
| Gender | 0.03 | 0.17 | 0.15 | 8.80E-01 |
| Stage | 0.29 | 0.09 | 3.33 | 8.63E-04 |
| CTL | −0.79 | 0.21 | −3.79 | 1.51E-04 |
| SOX10 | −0.01 | 0.10 | −0.11 | 9.10E-01 |
| CTL * SOX10 | −0.59 | 0.16 | −3.69 | 2.23E-04 |

The Cox-PH regression was used to test how the expression level of a candidate gene interacts with the cytotoxic T lymphocyte (CTL) level to affect the patient survival outcome using TCGA metastatic melanoma data. Clinical factors (e.g., age, gender and stage) were included as the background in regression. The statistical significance of coefficients was estimated by the two-sided Ward test. Table 1A shows the antagonistic interaction between TGFB1 and CTL, while Table 1B shows the synergistic interaction between SOX10 and CTL.

To identify significant genes in the interaction test, the Benjamini-Hochberg method was applied to convert the test p-values to false discovery rates (FDR) (Benjamini, Y. & Hochberg, Y. 1995 J Roy Stat Soc B Met, 57: 289-300), and clinical data sets with more than 1% genes having FDR smaller than 0.1 were selected. This procedure is equal to selecting datasets where the distribution of p-values has a significant peak near zero (Storey, J. D. & Tibshirani, R. 2003 Proceedings of the National Academy of Sciences of the United States of America, 100: 9440-9445). For example, the p-value histogram computed using TCGA melanoma data has a spike near zero, indicating that a set of genes significantly interact with CTL to affect survival outcome (FIG. 1C). In contrast, the result computed from glioblastoma data does not contain any genes with significant interactions (FIG. 1C).

Performance Comparison on Predicting ICB Response

The published data in melanoma for anti-CTLA4 (Van Allen et al., 2015 Science, 350: 207-211) and anti-PD1 (Hugo et al., 2016 Cell, 165: 35-44) therapies with gene expression profiles for 25 and 35 pretreatment tumors, respectively, were utilized. For each dataset, the expression values of each gene were normalized by subtracting the average among all samples. Therefore, a zero value indicates the average expression.

Figure 5A:
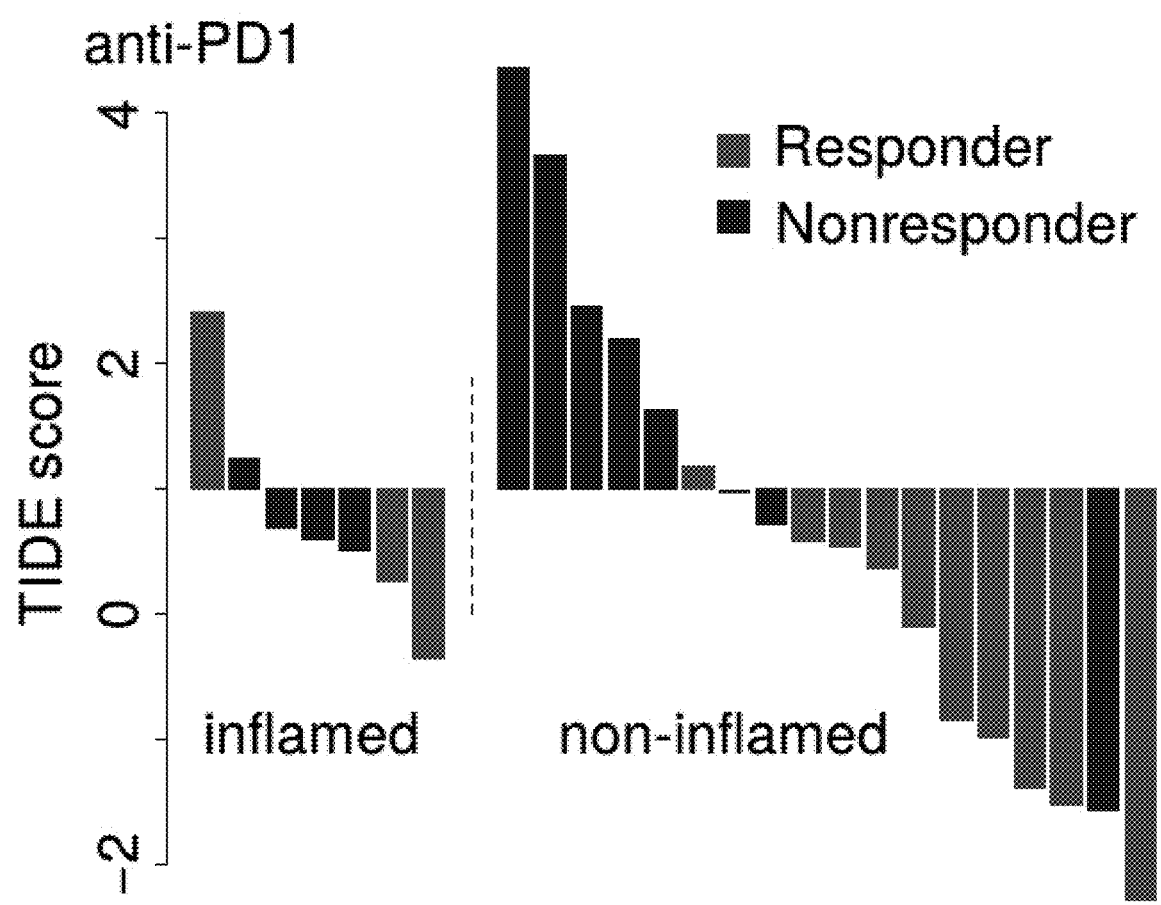
FIG. 5A-FIG. 5H is a series of histograms and line graphs showing the prediction of immunotherapy response through TIDE signatures.
Figure 5B:
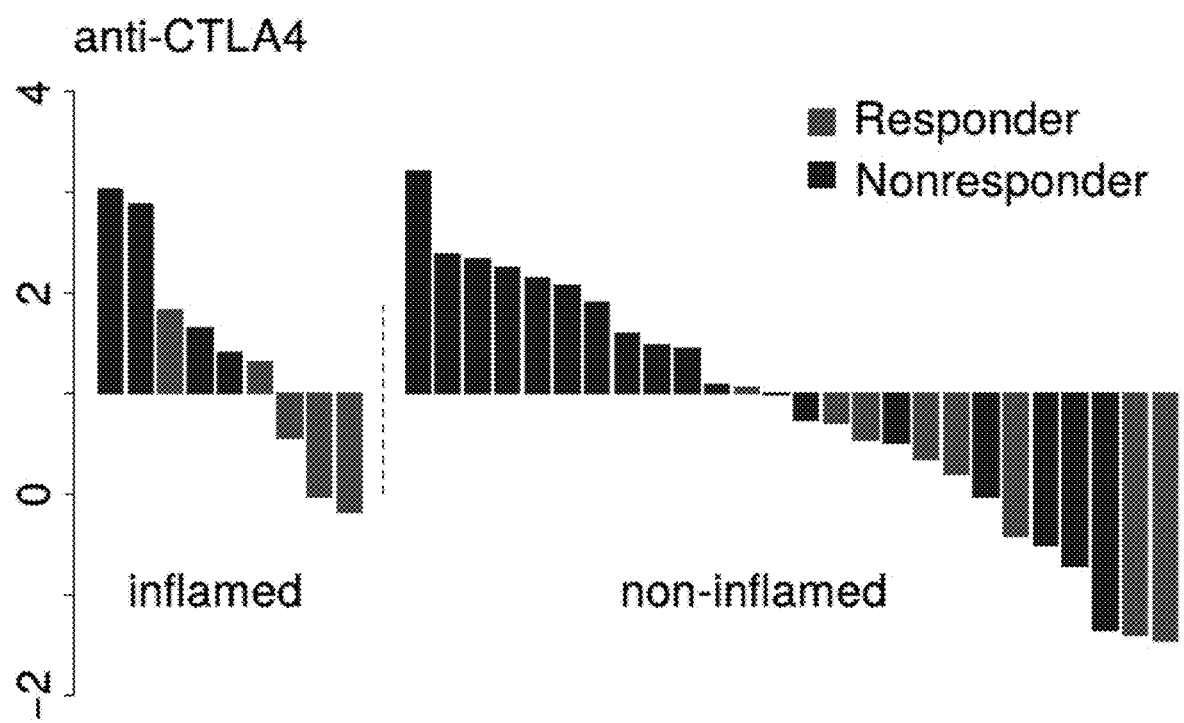
Figure 12A:
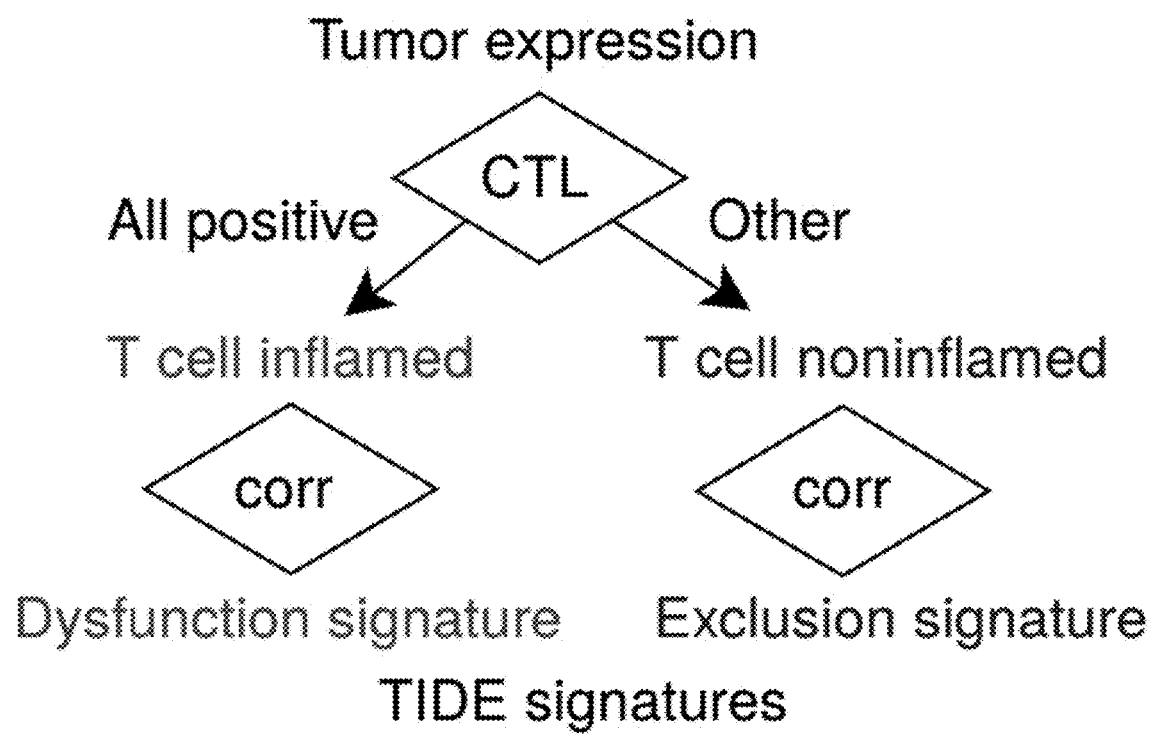
FIG. 12A-FIG. 12B is a schematic and a graph showing prediction of immunotherapy response.

To predict each tumor's potential to escape T cell-mediated killing, each tumor was first classified into T-cell inflamed or non-inflamed through the CTL marker expression levels (CD8A, CD8B, GZMA, GZMB, and PRF1). Tumors with all positive values (higher than average) are classified as the T-cell inflamed, while the rest as non-inflamed (FIG. 12A). For the inflamed tumors, the Pearson correlation between tumor gene expression profiles and the T-cell dysfunction signature (FIG. 12B) was computed. For the non-inflamed tumors, the Pearson correlation between tumor gene expression profiles and the T-cell exclusion signature (FIG. 12B) was computed. To make the scale of Pearson correlations comparable between T-cell inflamed and non-inflamed tumors, the correlation values within each sub-category were normalized through the standard deviation of correlation values pre-computed using the TCGA melanoma data. The scaled correlations were defined as the TIDE scores, representing the potential of tumor immune escape (FIG. 5A and FIG. 5B).

The response prediction from other biomarkers published in the literature was also computed. The predicted values of gene expression biomarkers (e.g., IFNG, CD8, PDL1, CRMA (cytokine response modifier A) were the average values among all members defined by the original publications (Table 5). The predicted values of Immunophenoscore (IPS) were computed using the source codes provided by the authors (Charoentong et al., 2017 Cell Reports, 18: 248-262). The predicted value of tumor SCNA biomarker was downloaded from the original publication for the anti-CTLA4 dataset (Davoli et al., 2017 Science, 355(6322): 8399) and provided by Dr. Willy Hugo for the anti-PD1 dataset (Hugo et al., 2016 Cell, 165: 35-44).

Figure 5C:
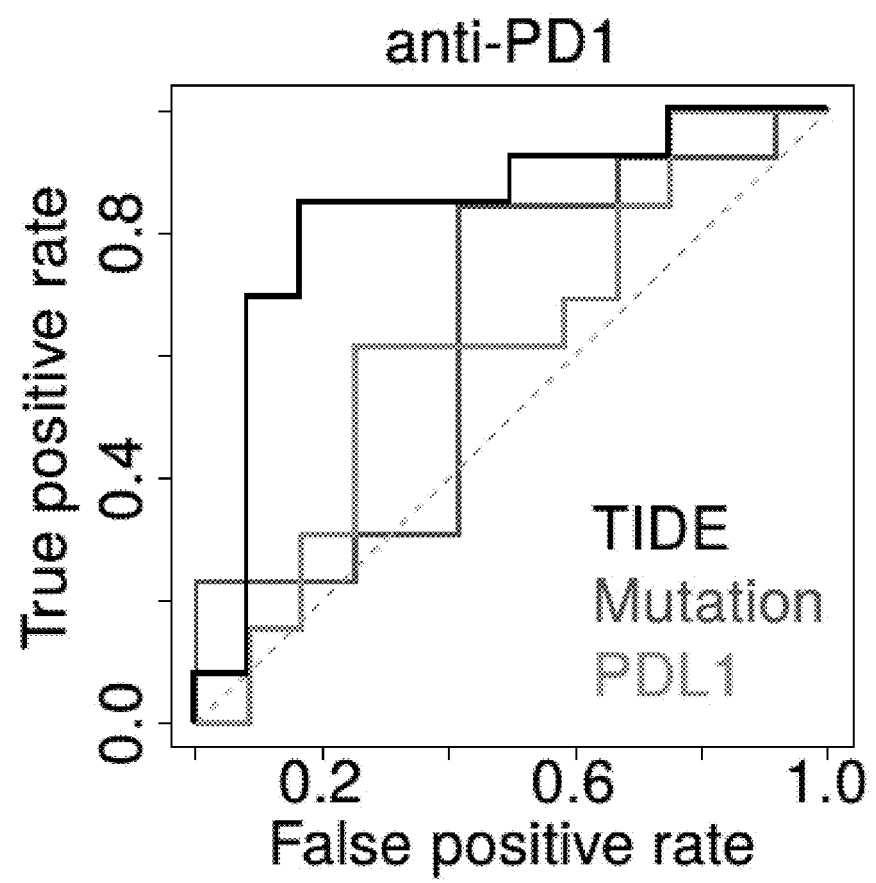
Figure 5D:
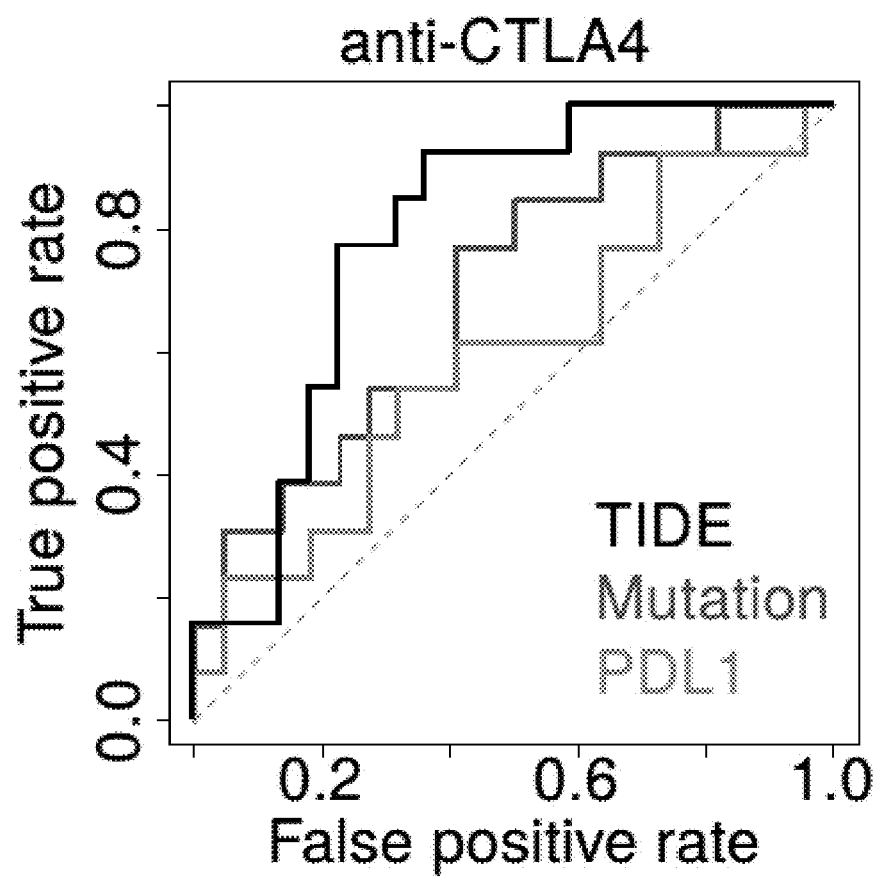
Figure 5E:
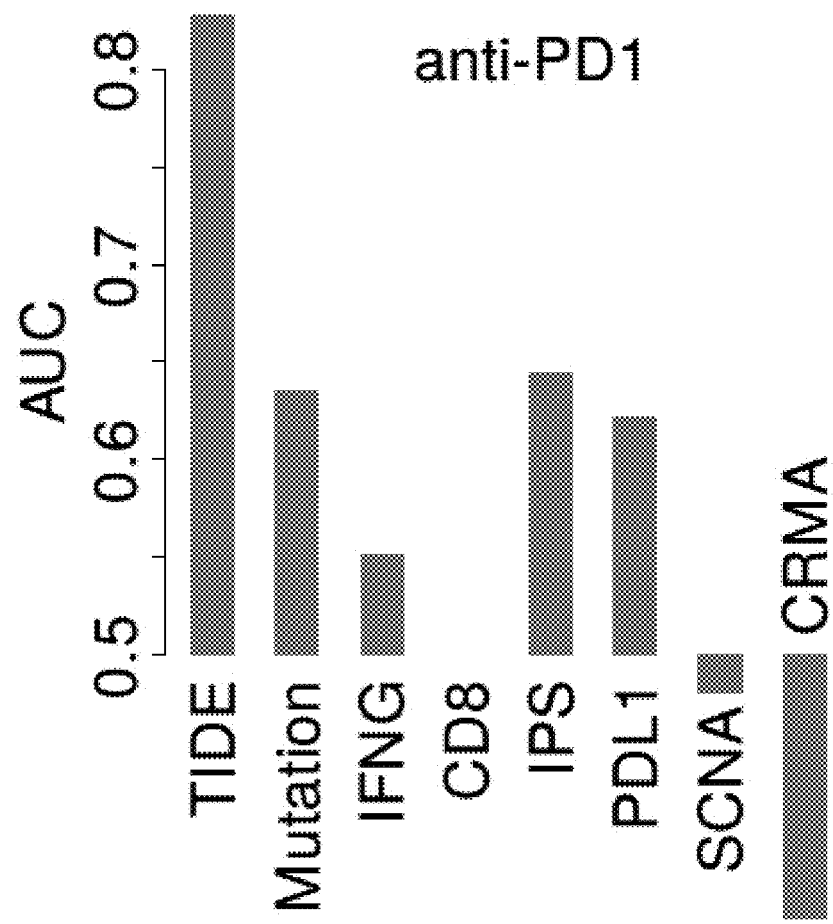
Figure 5F:
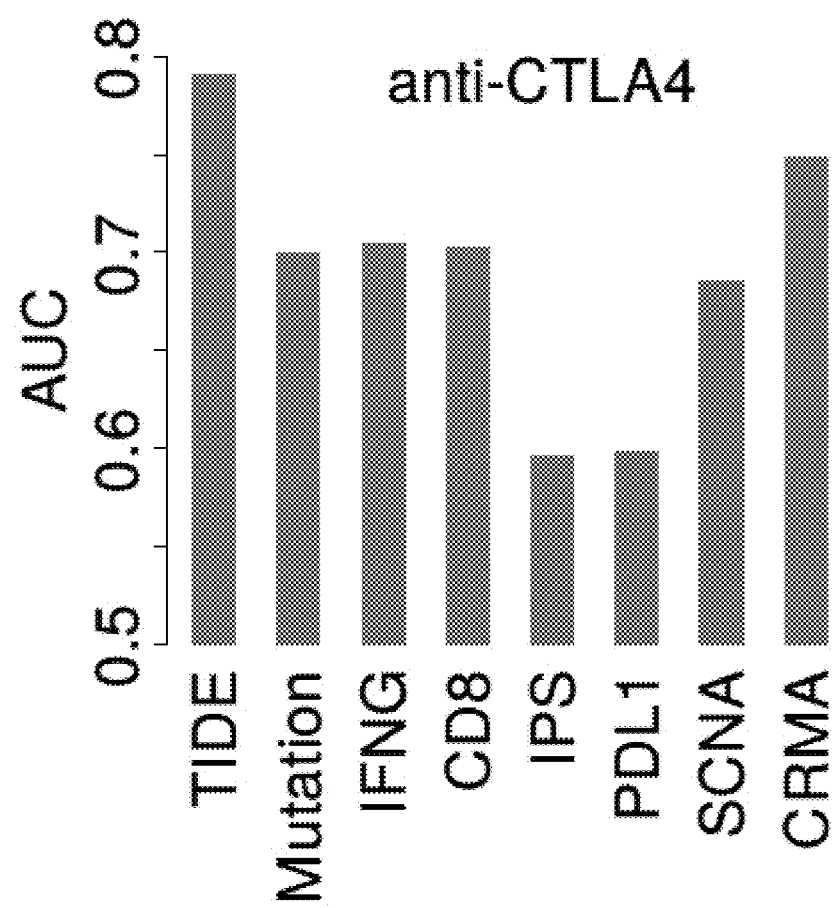

The outcome predicted by all biomarkers are a range of values, instead of a binary outcome. For example, total mutation load, CD8 expression level, and TIDE all give one value for each patient tumor instead of a response classification. Therefore, the receiver operating characteristic (ROC) curves, which plots the true positive rates versus false positives rates at various thresholds of biomarker values were utilized (FIG. 5C and FIG. 5D). The area under ROC curve (AUC) was used as the quality metric of prediction (FIG. 5E and FIG. 5F).

T-Cell Killing Assay Based on Co-Culture Between B16 and T Cells

B16F10 cells were maintained in complete Dulbecco's Modified Eagle Medium (DMEM) media (10% FBS and 50 U/ml of Penicillin-Streptomycin). B16F10-Cas9 cells were maintained in complete DMEM media with 2.5-5 ug/ml of blasticidin. CD8 T cells isolated from mice were cultured in complete Roswell Park Memorial Institute (RPMI) 1640 media (10% fetal bovine serum (FBS), 20 mM HEPES (N-2-hydroxyethylpiperazine-N-2-ethane sulfonic acid), 1 mM sodium pyruvate, 0.05 mM 2-mercaptoethanol, 2 mM L-glutamine and 50 U/ml streptomycin and penicillin). All cell lines are tested for mycoplasma contamination.

Pmel-1 TCR transgenic mice were purchased from Jackson Laboratory (stock #005023). CD8 T cells were isolated from spleen and lymph nodes from Pmel-1 TCR transgenic mice using the EasySep mouse CD8+ T-cell isolation kit (STEMCELL #19753) according to the manufacturer's protocol. Freshly isolated CD8 T cells were stimulated with anti-CD3/CD28 beads (ThermoFisher #11452D) at a bead to cell ratio of 1:2 to induce differentiation into an effector state. On day 3, recombinant mouse IL-2 (Biolegend, #575406) was added to the culture at 20 ng/ml. T cells were used for co-culture with B16F10 cells at least 6 days of in vitro activation.

Guide RNA sequences targeting Serpinb9 or non-targeting control were cloned into a PLKO3G-GFP vector and confirmed by sequencing. gRNA constructs were co-transfected with pCMV-dR8.91 and pCMV-VSV-G (Addgene #8454) into HEK293T cells to generate lentiviral vectors. Transfection was performed using TransIT-293 (Mirus, MIR2700) following the manufacturer's protocol. Lentivirus was harvested 48 hours later and stored at −80° C. B16F10-Cas9 cells were infected with a lentivirus driving expression of a single gRNA overnight to inactivate Serpinb9 genes individually. Infected cells were sorted based on GFP expression by BD FACS Aria II. Control (non-targeting gRNA) B16F10 or Serpinb9 deficient B16F10 cells were lysed and subjected to Western blot analysis with the following antibodies: anti-Serpinb9 clone F-6 (Santa Cruz Biotechnology #sc-390501), clone PI9-17 (#sc-57531), and anti-VCL (Sigma Aldrich #V9264).

Figure 17:
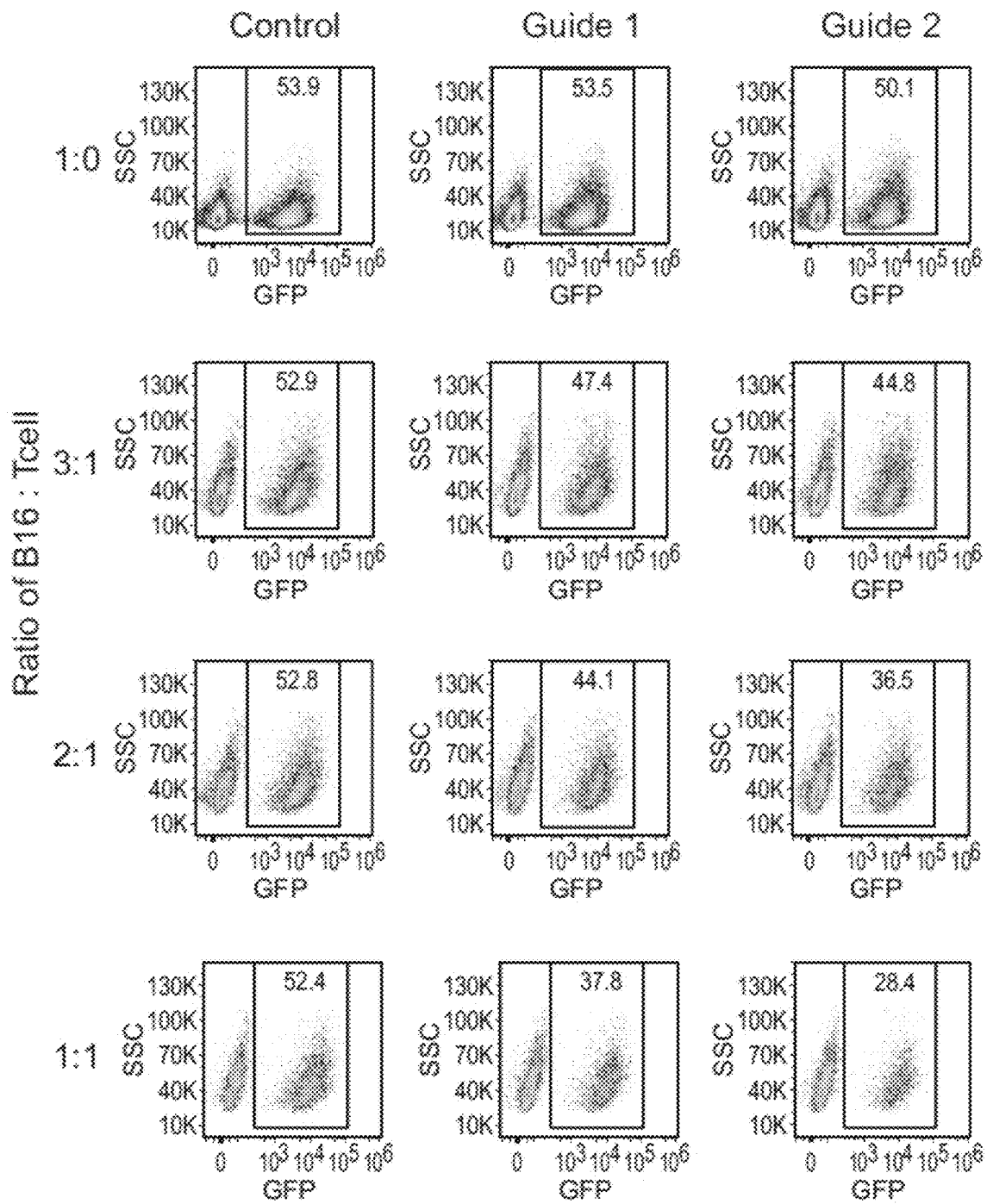
FIG. 17 is a series of flow cytometry graphs showing that knocking out Serpinb9 facilitates CD8+ T-cell cytotoxicity. B16F10-Cas9 cells were transduced with lentivirus co-expressing GFP and guide RNAs (gRNA) targeting Serpinb9 or non-targeting gRNA. Each gRNA-transduced GFP positive cell line was mixed with the parental GFP negative cell line at a 1:1 ratio. Each group of mixed cells were cultured in the absence (B16: T cell=1:0 as in the figure) or presence (B16: T cell=3:1, 2:1, or 1:1) of Pmel-1 T cells targeting the gp100 antigen on B16 cells. After 3 days in culture, the percentage of GFP positive B16F10 cells was assessed by flow cytometry. T cells present in these cultured were gated out based using CD45 antibodies. One representative FACS plot with the median percentage value is shown for each group.
Figure 18A:
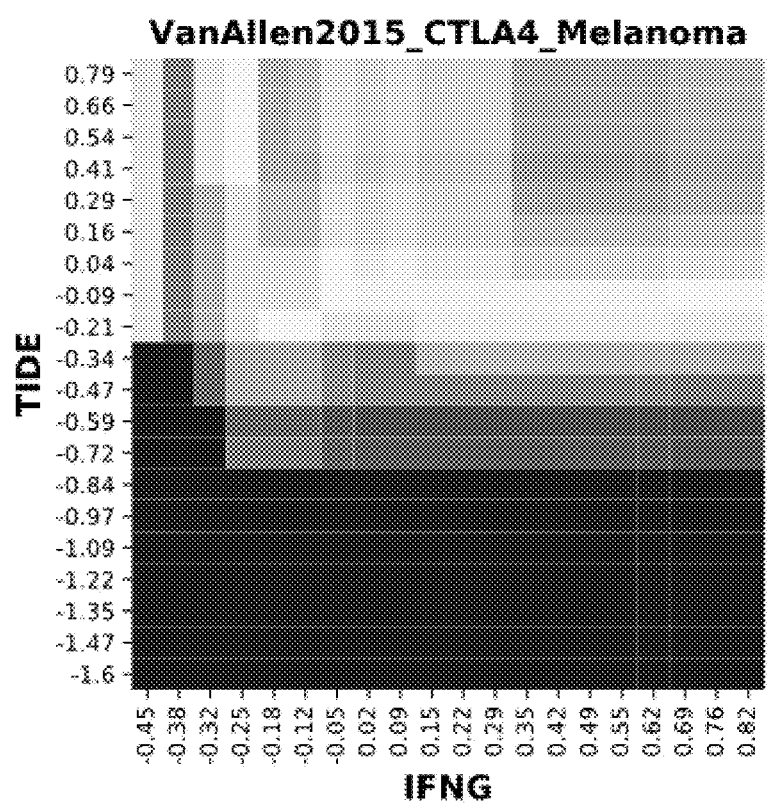
FIG. 18A, FIG. 18B, FIG. 18C, FIG. 18D, and FIG. 18E is a series of 2-D heatmaps showing the negative predictive value for non-responders through combination metrics. The X-axis represents the cutoffs for TIDE prediction values, and the Y-axis represents the cutoffs for Interferon gamma (IFNG) expression levels. At each threshold combination, it is predicated that a patient is a non-responder if both measured values are lower than the respective cutoff values. The negative predictive values, defined by the fractions of predicted non-responders who truly will not benefit from the treatment, are plotted in 2-D heatmaps.
Figure 18B:
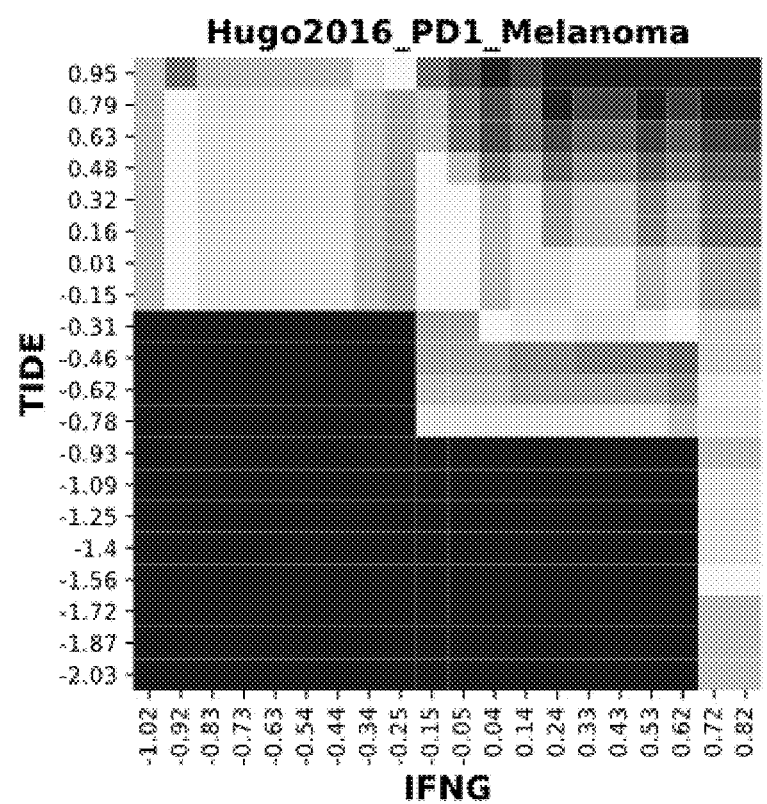
Figure 18C:
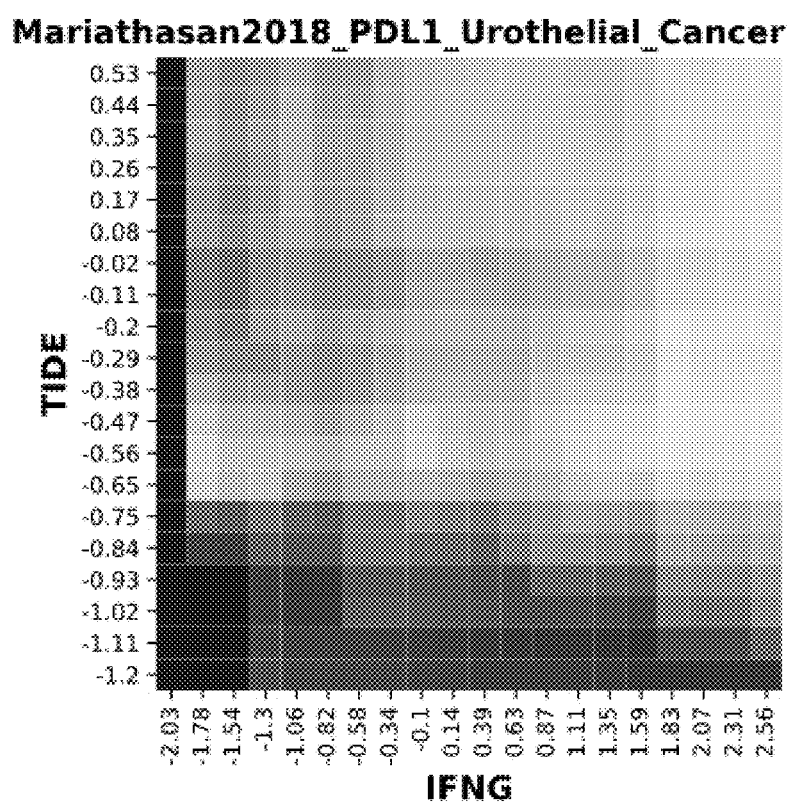
Figure 18D:
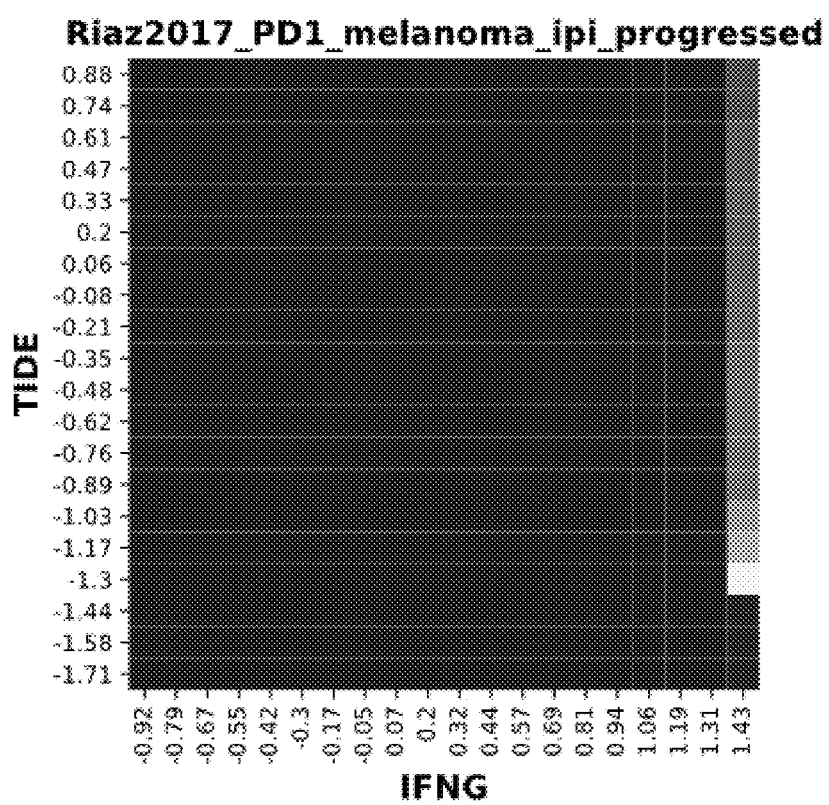
Figure 18E:
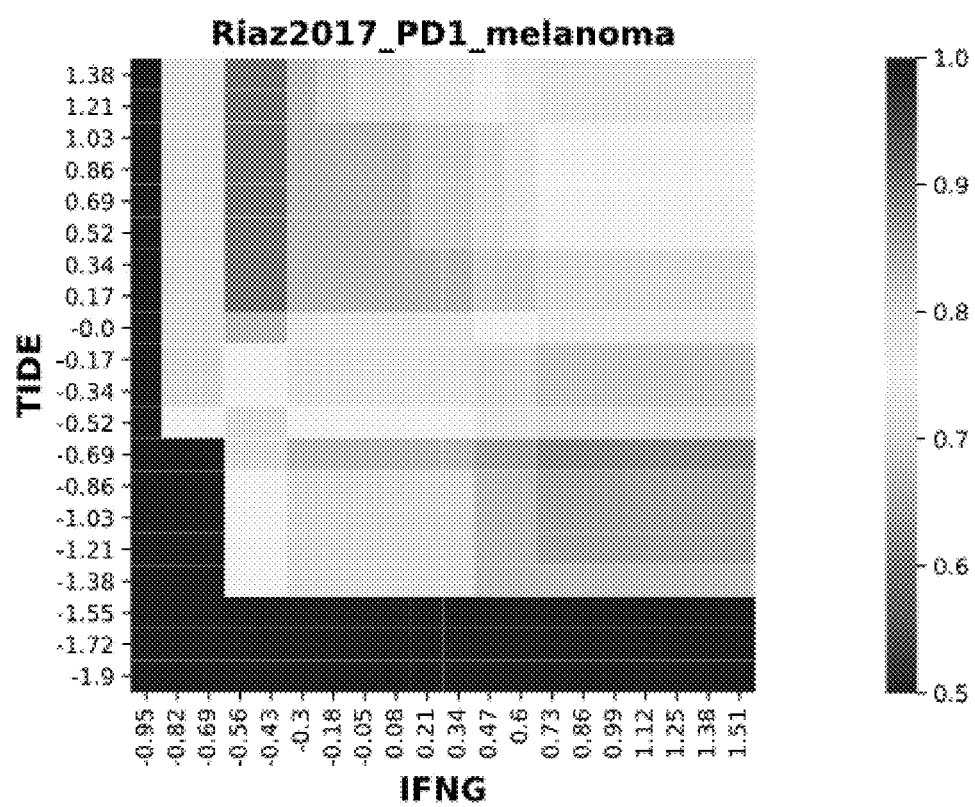

Serpinb9 edited or non-targeting guide control B16F10-Cas9 cells (GFP positive) were mixed with control B16F10-Cas9 cells (GFP negative) at a 1:1 ratio and stimulated with 10 ng/ml of interferon gamma for 24 hours to enhance MHC class I expression. These tumor cells were then co-cultured with in vitro activated Pmel-1 T cells at different effector to target ratios in a 6-well plate (triplicate conditions for each gRNA). After a three-day co-culture with T cells, fold depletion of Serpinb9 edited B16F10 cells was determined by fluorescence-activated cell sorting (FACS), comparing the percentage of Serpinb9 edited B16F10 cells (GFP+) to control B16F10 cell (GFP−). T cells present in these cultured were gated out based using antibodies specific for CD45 (APC-Cy7) (Biolegend, 103115) (FIG. 17).

Figure 7A:
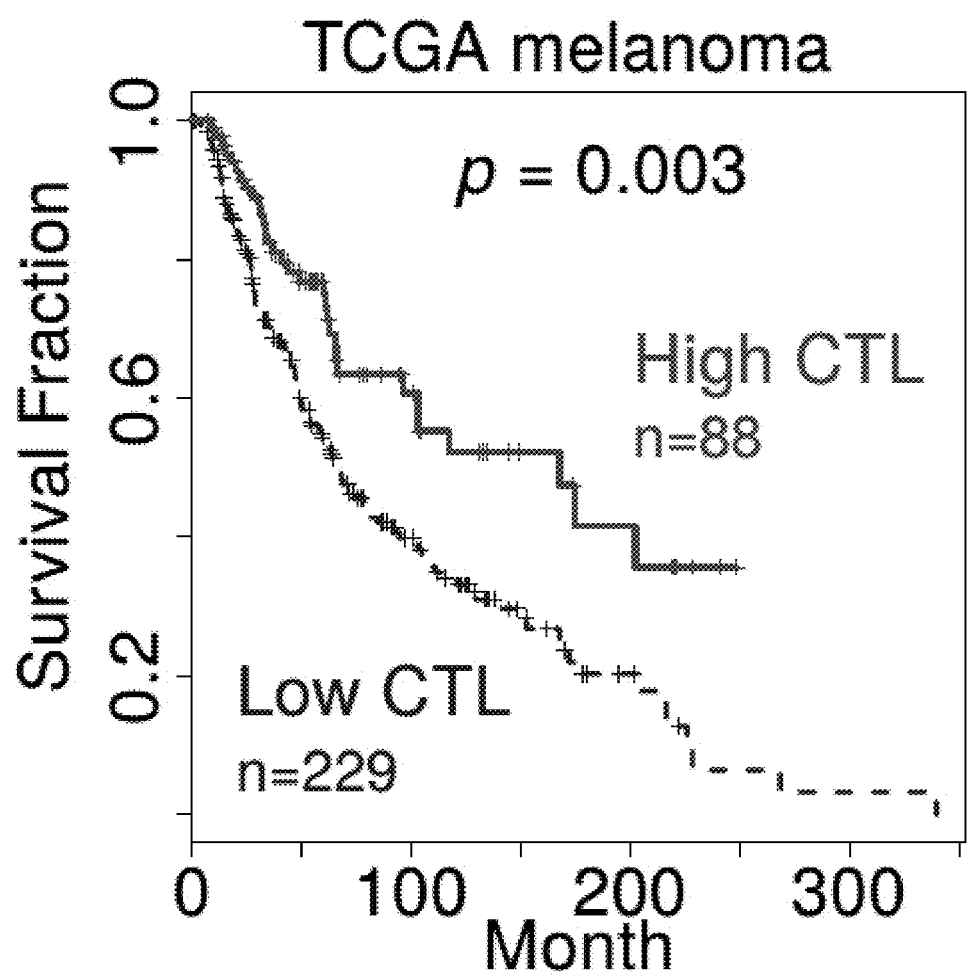
FIG. 7A-FIG. 7B is a series of line graphs showing the association between the cytotoxic T-cell level and overall survival. For each tumor, the infiltration level of cytotoxic T lymphocyte (CTL) was estimated as the expression sum of CD8A, CD8B, GZMA, GZMB, and PRF1.
Figure 7B:
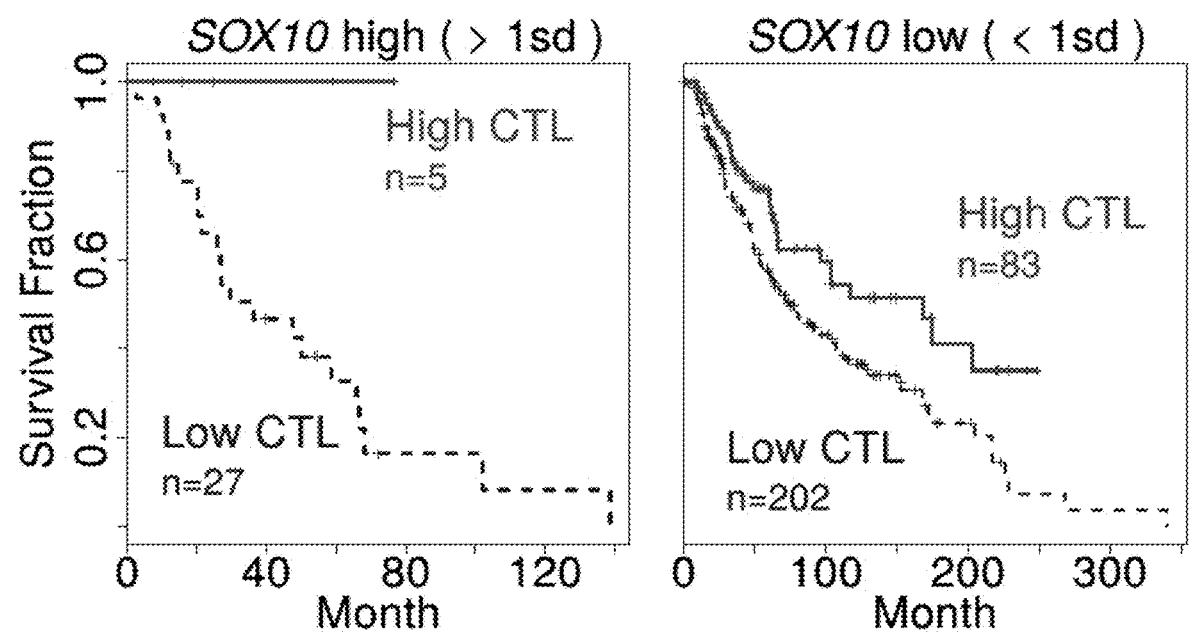

Example 2: A Statistical Interaction Test Identifies Gene Signatures of T-Cell Dysfunction Previous analysis showed that a subset of tumors is infiltrated by cytotoxic T cells, although in a dysfunctional state that fails to control tumor growth (Wherry, E. J. & Kurachi, M. 2015 Nat Rev Immunol, 15: 486-499). As described herein, it was reasoned that by combining transcriptome profiles of treatment-naïve tumors with patient survival outcome, known regulators of T-cell dysfunction could be identified. For example, in the TCGA melanoma study, the expression level of CD8A, CD8B, GZMA, GZMB, and PRF1 were used to estimate the cytotoxic T lymphocyte (CTL) level in a tumor (Rooney et al., 2015 Cell, 160: 48-61) (FIG. 7A). Among metastatic melanoma tumors, a higher CTL level indicates a better patient survival, but only when TGFB1 has a low expression level (FIG. 1A). This observation corroborates the known role of TGFβ cytokine (encoded by TGFB1) in promoting tumor immune escape and resistance to immunotherapy (Sharma et al., 2017 Cell 168, 707-723; Hanks et al., 2014 Journal of Clinical Oncology, 32: 3011-3011). In contrast, a higher expression level of SOX10 correlates with a stronger association between the CTL level and melanoma patient survival (FIG. 7B). The activity of SOX10 in cancer cells is known to promote the T cell-mediated tumor killing (Patel et al., 2017 Nature, 548(7699): 537-542; Khong, H. T. & Rosenberg, S. A., 2002 Cancer Research, 62: 3020-3023).

In statistics, two variables interact if the effect of one variable depends on the other variable (Freedman, D. Statistical Models: Theory and Practice. (Cambridge University Press, 2009). In the previous examples, the effect of CTL on survival outcome depends on the TGFB1 (or SOX10) level. This is a typical case of interaction between variables. The interaction of any two variables on survival outcome can be tested by a multiplication term in the Cox proportional hazard (Cox-PH) model (Kleinbaum, D. G. 1998 Biometrical Journal, 40: 107-108) (FIG. 1B). The coefficient "d" of the multiplication term indicates the level of the interaction effect, whose statistical significance can be evaluated by the Wald test (Kleinbaum, D. G. 1998 Biometrical Journal, 40: 107-108) (Table 1A and Table 1B). The examples of TGFB1 and SOX10 illustrate how this strategy could be systematically applied to human clinical studies with both tumor genomics profiles and patient survival outcome, to identify genes associated with cytotoxic T-cell function in tumors. Using the Cox-PH model, TIDE tests how the interaction between a candidate gene P and the CTL affects death hazard (estimated from survival) (FIG. 1B). The TIDE output is a T-cell dysfunction score for each gene, defined as the interaction coefficient "d" divided by its standard deviation (Table 1A and Table 1B).

The example of TGFB1 illustrates an important conceptual point of this approach (Table 1A). The method is not restricted to genes expressed by T cells that cause dysfunction in a cell-intrinsic manner, but instead tests the impact of gene expression in all cell populations in the tumor, including cancer cells and immunosuppressive cells such as T regulatory cells (Treg). In the case of TGFB1, both cancer cells (Thomas, D. A. & Massague, J. 2005 Cancer Cell, 8: 369-380) and CD4+ FoxP3+ Treg cells (Woo et al., Cancer Research, 61: 4766-4772) can express the cytokine TGFβ to inhibit T-cell proliferation and function.

Figure 2:
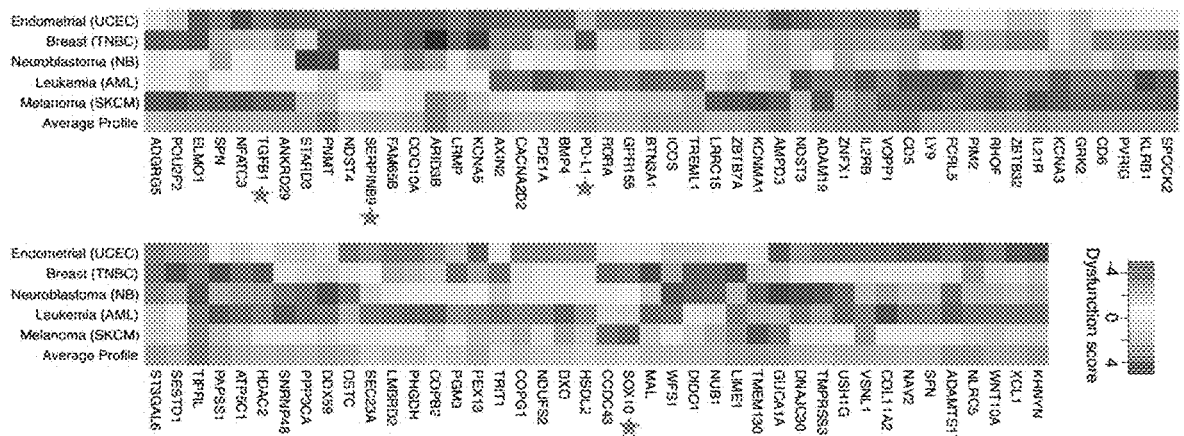
FIG. 2 is a graph showing genes with significant T-cell dysfunction scores in multiple cancer types. Specifically.

To compute the T-cell dysfunction scores in different cancer datasets, 71 datasets that had a minimum of 50 samples with both tumor expression profiles and patient survival data from TCGA (Cancer Genome Atlas Research, N. et al. 2013 Nature Genetics, 45: 1113-1120), PRECOG (Gentles et al., 2015 Nature Medicine, 21: 938-945), and METABRIC (Curtis et al., 2012 Nature, 486: 346-352) databases were collected (Table 2A). Different numbers of genes were observed to interact with CTL with statistical significance among the datasets. For example, the p-value distribution for genes in TCGA melanoma was skewed to the left and harbored many significant genes, but that was not the case in TCGA glioblastoma (FIG. 1C). This is likely due to differences in T-cell infiltration (nearly absent in glioblastoma), and in other cases differences in data quality or sample size. In five datasets, over 1% of genes have significant interaction with CTL to affect survival at a false discovery rate (FDR) cutoff of 0.1: melanoma, neuroblastoma, triple negative breast cancer, endometrial cancer, and acute myeloid leukemia (Table 2B). The dysfunction scores of the genes from those 5 datasets are correlated (FIG. 1D), suggesting that these cancers might adopt similar mechanisms to cause T-cell dysfunction. Genes with significant dysfunction scores (FDR<0.1) in at least two cancer types are shown in FIG. 2. Although some of the genes are known to inhibit T cell-mediated tumor immunity, such as PD-L1, others are likely to be co-regulated with immune-suppressive genes.

Example 3: The TIDE Dysfunction Scores are Consistent with T-Cell Dysfunction Signatures Previous studies in human and mouse models identified genes associated with T-cell dysfunction in tumors (Table 3). For example, a short hairpin RNA (shRNA) screen identified positive hit genes whose knockdown in T cells enhances T-cell accumulation in mouse tumors, while negative hits as genes whose knockdown decreased the T-cell accumulation (Zhou et al. 2014 Nature, 506: 52-57).

Figure 8:
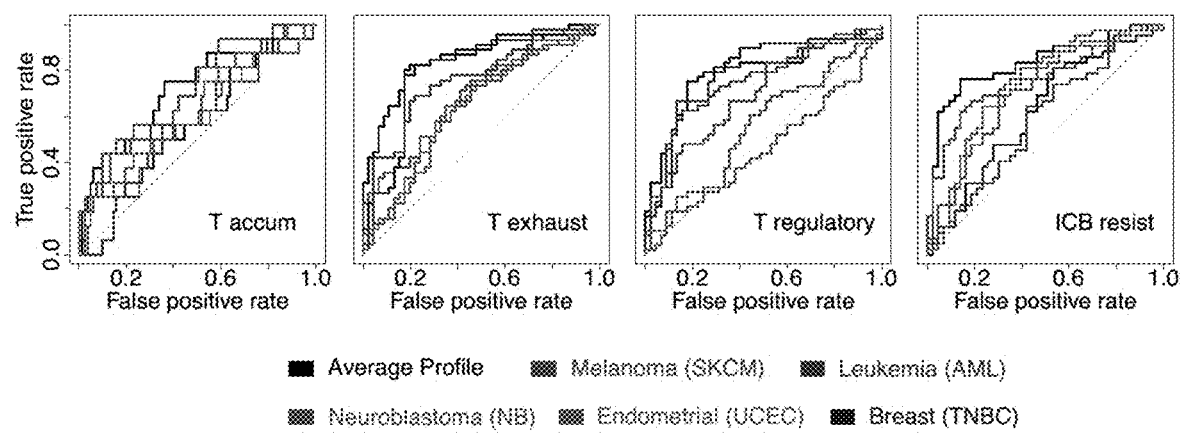
FIG. 8 is a series of graphs showing the prediction performance of T-cell dysfunction scores on previous gene signatures of T-cell dysfunction and immunotherapy resistance. The receiver operating characteristic (ROC) curves measure the performance of dysfunction scores in predicting top gene hits in each signature listed in Table 3.

Gene expression profiles to study T-cell dysfunction are also publicly available, including the transcriptome of exhausted CD8 T cells (Giordano et al. 2015 The EMBO Journal, 34: 2042-2058), activated regulatory T cells (Wakamatsu et al., 2013 Proceedings of the National Academy of Sciences of the United States of America, 110: 1023-1028), and tumors with acquired ICB resistance (Twyman-Saint Victor et al., 2015 Nature, 520: 373-377). The positive hits are defined as genes up-regulated in the process of T-cell dysfunction or acquisition of ICB resistance, while negative hits as genes down-regulated in the process (Table 3). Using these published studies of T-cell dysfunction or ICB resistance, the quality of TIDE T-cell dysfunction scores were evaluated. The positive gene hits from all studies have significantly higher dysfunction scores (averaged across cancer types) than the negative gene hits (FIG. 3A). The receiver operating characteristic (ROC) curves were used to evaluate the performance of TIDE dysfunction scores in predicting genes identified in published studies (FIG. 3B). The dysfunction scores derived from each cancer type have predictive power, with the average score across the cancers having the best performance (FIG. 3C and FIG. 8).

TABLE 3

Gene signatures of tumor immune escape

| Name | Description |
|---|---|
| T accum | In-vivo shRNA screen in mouse T cells to identify genes whose knock down can increase the efficiency of T-cell accumulation in tumor (Zhou et al. 2014 Nature, 506: 52-57). The top hits are defined as genes with median log fold change (logFC) larger than 2 in the primary screen and larger than one in the validation screen. The negative hits are defined as genes with median logFC smaller than one in the primary screen. In totally, there are 17 and 88 positive and negative hits, respectively. |
| T exhaust | Gene expression difference between exhausted CD8 T cells and activated CD8 T cells in mouse model (Giordano et al. 2015 The EMBO Journal, 34: 2042-2058). The top and negative hits are defined as the top and bottom 50 genes ranked by the logFC of differential gene expression. |
| T regulatory | Gene expression change of CD4 regulatory T cells before and after activation (Wakamatsu et al., 2013 Proceedings of the National Academy of Sciences of the United States of America, 110: 1023-1028). The top and negative hits are defined as the top and bottom 50 genes ranked by the logFC of differential gene expression. |
| ICB resist | Gene expression difference between anti-CTLA4 resistant mouse tumors and parental sensitive B16 tumors (Twyman-Saint Victor et al., 2015 Nature, |

TABLE 3-continued

Gene signatures of tumor immune escape

| Name | Description |
|---|---|
| | 520: 373-377). The top and negative hits are defined as the top and bottom 50 genes ranked by the logFC of differential gene expression. |
| T exh Fixed | Gene expression difference of exhausted CD8 T cells between late stage (after day 14) and early stage (day 5) (Philip et al., 2017 Nature, 545: 452-456). |
| MDSC | Gene expression profiles of myeloid derived suppressor cells that can inhibit T-cell activation compared to monocytes sorted from peripheral blood mononuclear cells (Yaddanapudi et al., 2016 Cancer Immunol Res, 4: 101-112). |
| M2 TAM | Gene expression profile of M2 macrophage compared to M1 macrophage (Beyer et al., 2012 PloS One, 7: e45466). |
| CAF | Gene expression profile of FAP+ cancer associated fibroblast compared to other cell types sorted from the same patients (Calon et al., 2012 Cancer Cell, 22: 571-584). |

Figure 3D:
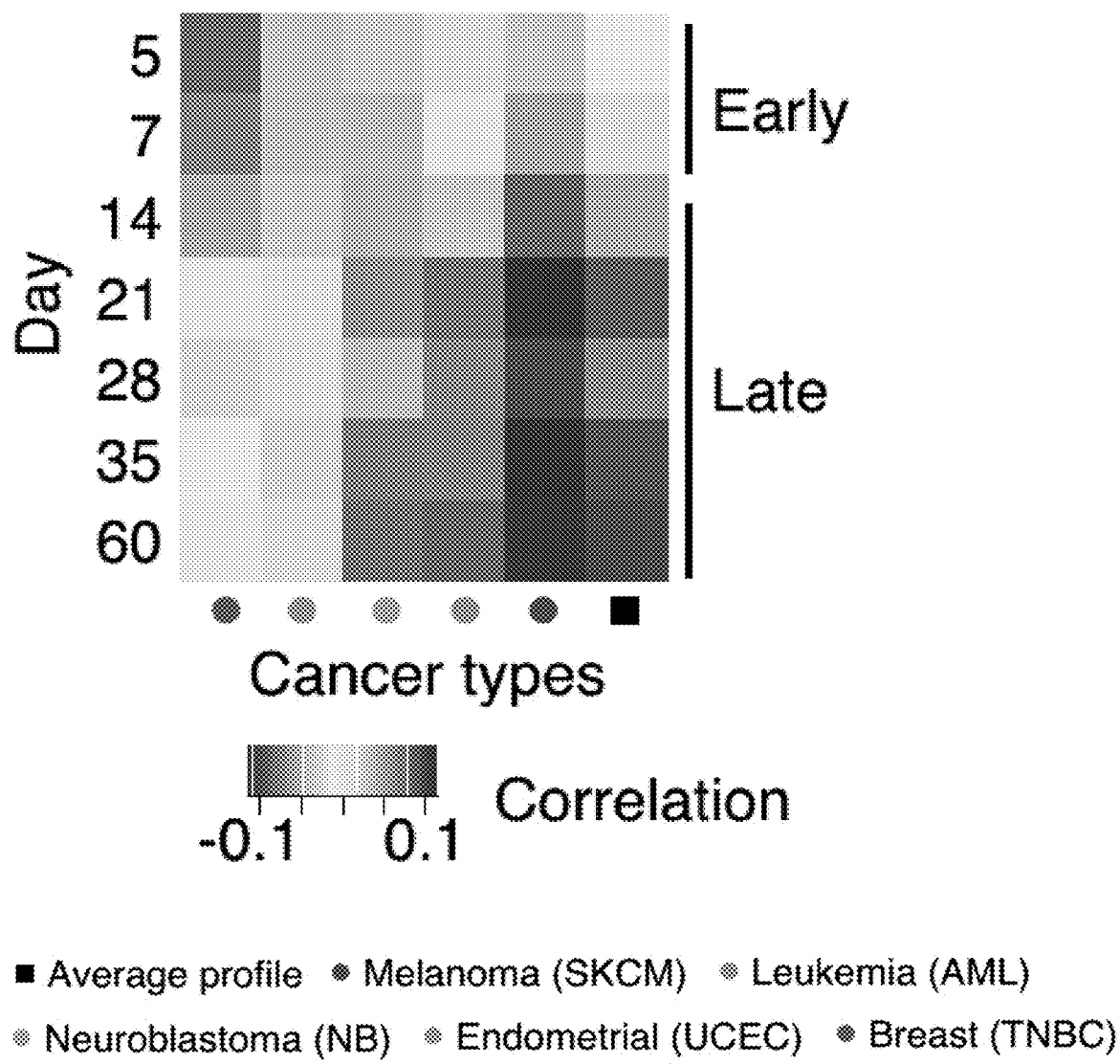

Studies in mouse models of cancer revealed two stages of T-cell dysfunction (Schietinger et al., 2016 Immunity, 45: 389-401; Philip et al., 2017 Nature, 545: 452-456). While the early-stage dysfunctional T cells can be revived by anti-PD1 treatment, late-stage dysfunctional T cells are resistant to reprogramming by ICB. The TIDE dysfunction scores derived from different cancer types show increasing correlation with the gene expression profiles of dysfunctional T cells in later stages (Philip et al., 2017 Nature, 545: 452-456) (FIG. 3D). This suggests that the genome-wide TIDE dysfunction scores reflect the expression profile at late-stage of T-cell dysfunction.

Figure 4A:
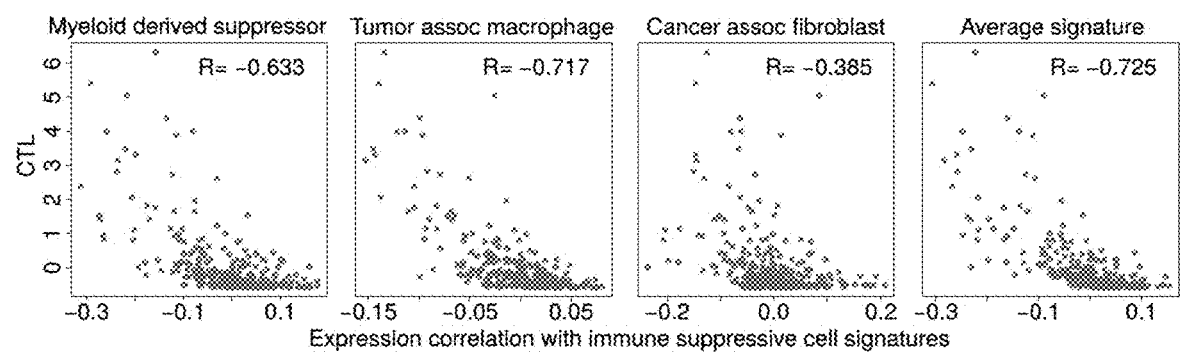
FIG. 4A-FIG. 4D is a series of dot plots and a histogram showing gene signatures of T-cell exclusion in tumors.
Figure 4B:
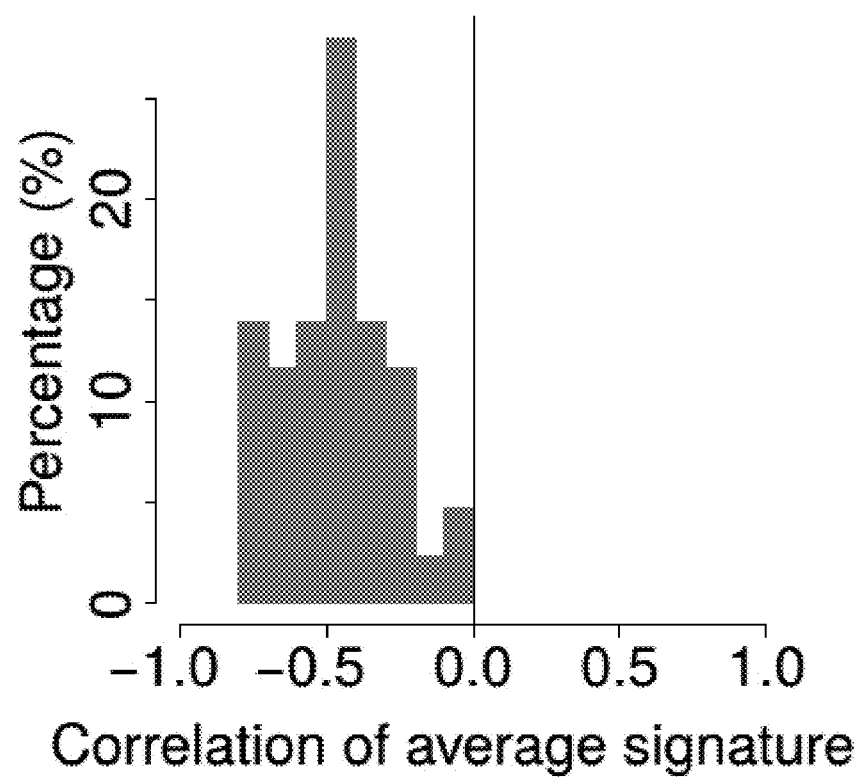
Figure 9:
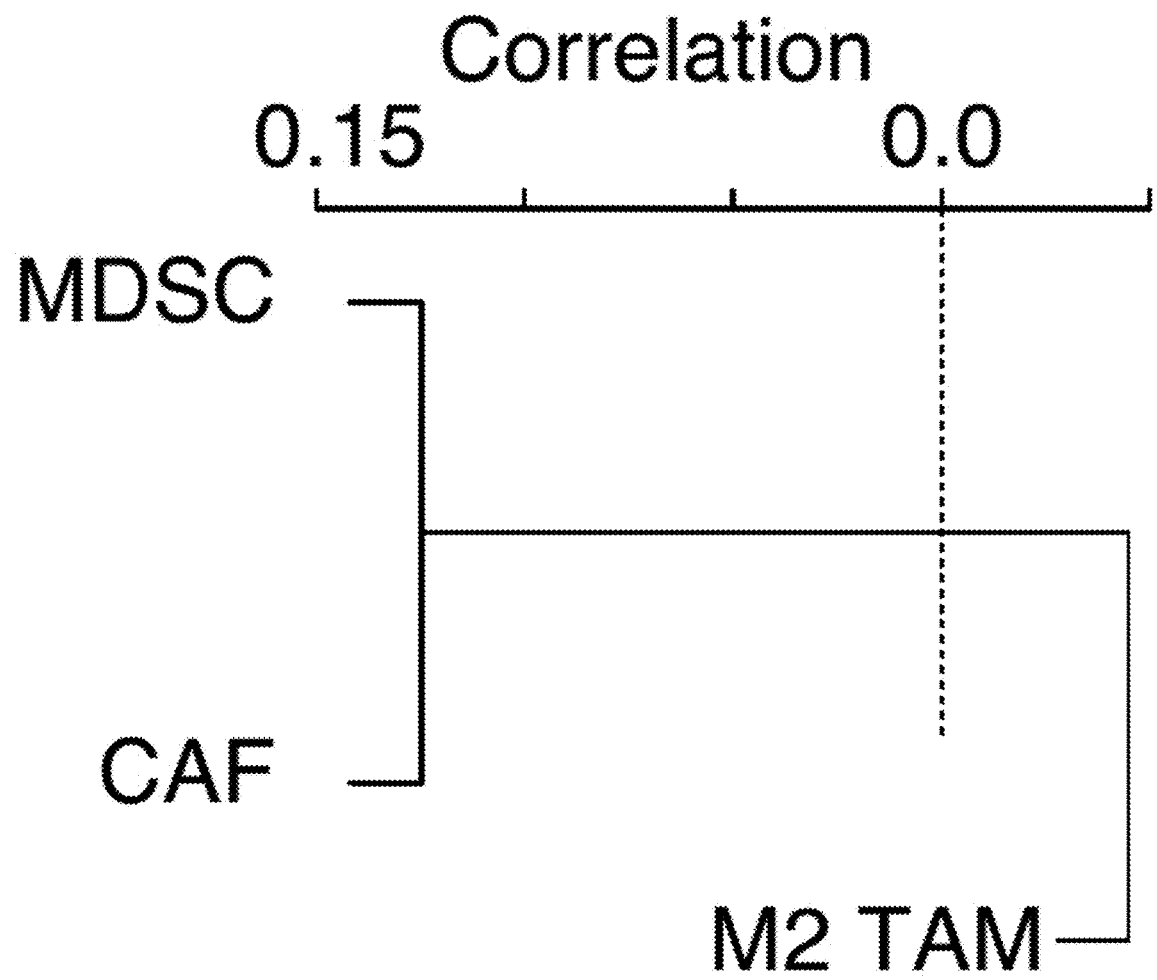
FIG. 9 is a schematic showing the hierarchical clustering among T-cell exclusion signatures. The genome-wide Pearson correlation between the gene expression profiles of each cell type is the similarity metric. MDSC: myeloid derived suppressor cell, CAF: cancer associated fibroblast, M2 TAM: M2 subtype of tumor associated macrophage.

Example 4: Immunosuppressive Cell Signatures Predict Immune Escape by T-Cell Exclusion In the previous section, gene signatures were developed to model the T-cell dysfunction in tumors with high T-cell infiltration. However, many tumors have low or no T-cell infiltration, resisting immune attack through T-cell exclusion (Gajewski et al., 2013 Nat Immunol, 14: 1014-1022; Joyce et al., 2015 Science 348, 74-80). Therefore, gene signatures of escape through T-cell exclusion were also explored. The absence of T-cell infiltration in the tumor may be caused by more than one molecular mechanism, such as impaired priming of tumor-specific T cells or suppressive cells prohibiting T-cell infiltration into the tumor (Gajewski et al., 2013 Nat Immunol, 14: 1014-1022; Joyce et al., 2015 Science 348, 74-80). Previous studies implicated several cell types, namely cancer-associated fibroblasts (CAF), myeloid-derived suppressor cells (MDSC), and the M2 subtype of tumor-associated macrophages (TAM) (Joyce et al., 2015 Science 348, 74-80), as being responsible for restricting the T-cell accumulation in the tumor. For each cell type, public expression profiles in the GEO database were found (Barrett et al., 2013 Nucleic Acids Research, 41: D991-995; FIG. 9 and Table 3). In TCGA melanoma data, tumors whose expression profile have higher correlation with the MDSC, TAM, or CAF signatures show a significantly lower level of cytotoxic T lymphocyte (CTL) level (FIG. 4A). Moreover, using the average expression profile of MDSC, TAM, and CAF to model T-cell exclusion, an even stronger negative correlation was observed between the T-cell exclusion signature and the CTL level (FIG. 4A). Additionally, using the average profile of T-cell exclusion signatures, the CTL and T-cell exclusion signature was negatively correlated in all solid tumor types (FIG. 4B).

Figure 4C:
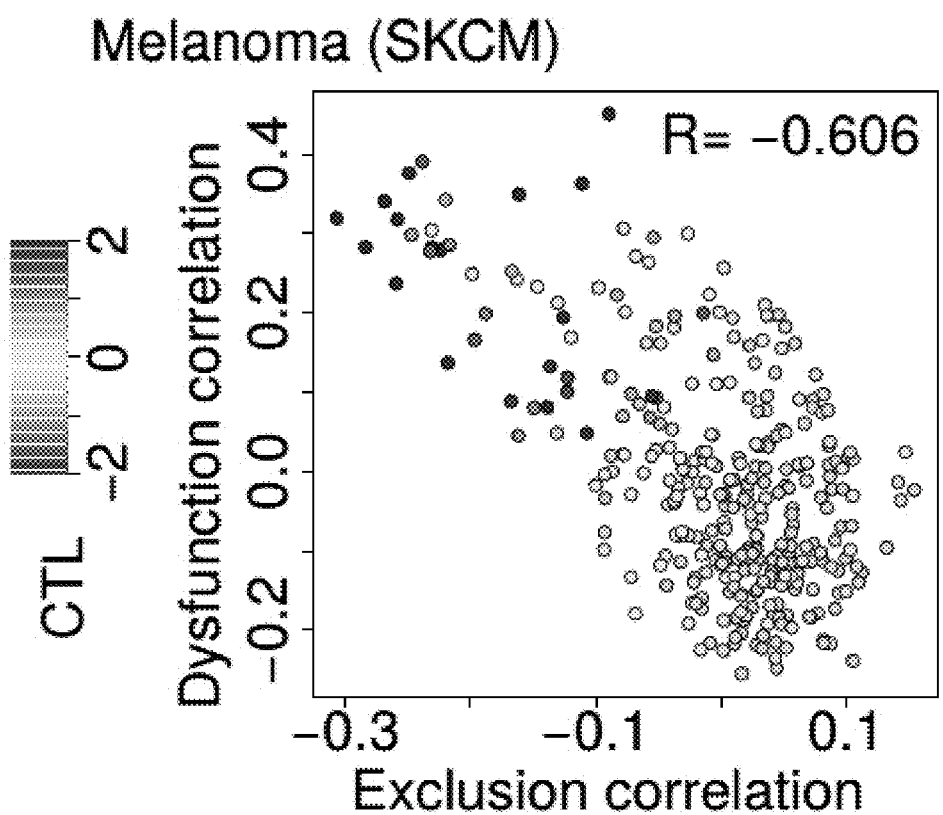
Figure 4D:
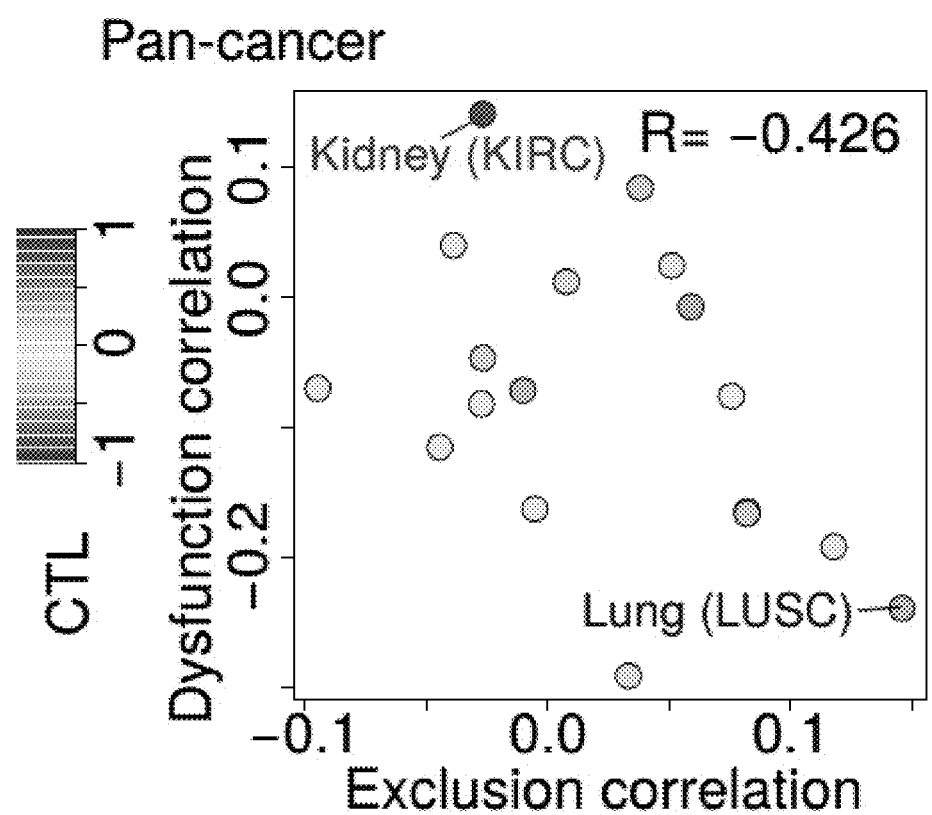
Figure 10:
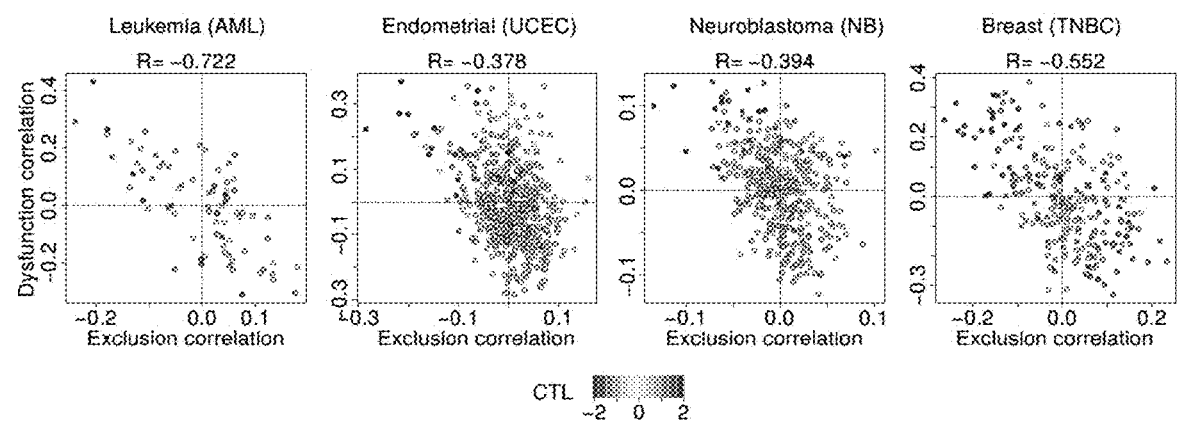
FIG. 10 is a series of plots showing that T-cell dysfunction signatures anti-correlate with T-cell exclusion signatures. The figure is a supplement of FIG. 4C, the plot for melanoma. For each cancer type, the T-cell dysfunction and exclusion signatures are computed as the Pearson correlations between the patient expression profiles and TIDE signatures of T-cell dysfunction and exclusion. The association between dysfunction and exclusion signature correlations are shown with 2D plot with CTL level of each patient as the color of dots. The Pearson correlation between X and Y axis are shown after each cancer name. (TNBC: triple negative breast cancer, AML: acute myeloid leukemia, UCEC: uterine corpus endometrial carcinoma, NB: neuroblastoma).

Next, the associations between the gene signatures of T-cell exclusion and T-cell dysfunction were examined. For each tumor, the enrichment of a signature is computed as the Pearson correlation between tumor gene expression profile and the genome-wide scores of T-cell exclusion and dysfunction signatures. In the five cancer types where reliable T-cell dysfunction scores were identified, the level of T-cell exclusion in a tumor inversely correlates with the level of T-cell dysfunction (FIG. 4C and FIG. 10). Meanwhile, for TCGA cancer types with normal-tissue controls, the enrichment of immune-escape signatures were analyzed for the average differential expression between tumor and normal controls. Similar to the observation across tumors in a cancer type, the level of T-cell exclusion in each cancer type inversely correlates with the level of T-cell dysfunction (FIG. 4D and Table 4).

TABLE 4

Correlation with gene signatures of T-cell dysfunction and exclusion in tumors

| | Name | CTL | Dysfunction | Exclusion |
|---|---|---|---|---|
| KIRC | Kidney Renal Clear Cell Carcinoma | 0.84 | 0.14 | −0.03 |
| HNSC | Head Neck Squamous Cell Carcinoma | 0.41 | −0.01 | 0.06 |
| ESCA | Esophageal Carcinoma | 0.37 | −0.07 | −0.01 |
| GBM | Glioblastoma Multiforme | 0.27 | −0.17 | 0.08 |
| BRCA | Breast Invasive Carcinoma | 0.23 | −0.05 | −0.03 |
| KIRP | Kidney Renal Papillary Cell Carcinoma | 0.18 | 0.01 | 0.01 |
| CHOL | Cholangiocarcinoma | 0.09 | 0.02 | 0.05 |
| UCEC | Uterine Corpus Endometrial Carcinoma | 0.06 | −0.07 | −0.09 |
| STAD | Stomach Adenocarcinoma | 0.05 | −0.16 | −0.01 |
| KICH | Kidney Chromophobe | 0.04 | 0.04 | −0.04 |
| BLCA | Bladder Urothelial Carcinoma | 0.03 | −0.12 | −0.04 |
| PRAD | Prostate Adenocarcinoma | 0.01 | −0.08 | −0.03 |
| LIHC | Liver Hepatocellular Carcinoma | −0.08 | −0.08 | 0.08 |
| LUAD | Lung Adenocarcinoma | −0.16 | −0.19 | 0.12 |
| OV | Ovarian Serous Cystadenocarcinoma | −0.22 | −0.29 | 0.03 |
| THCA | Thyroid Carcinoma | −0.34 | 0.08 | 0.04 |
| LUSC | Lung Squamous Cell Carcinoma | −0.43 | −0.24 | 0.15 |

In Table 4, for each TCGA cancer type with normal control samples, the average expression difference between tumor and normal samples was calculated. Next, the Pearson correlation between that value and the TIDE signatures of T-cell dysfunction and T-cell exclusion was calculated. The CTL level difference between tumor and normal samples is shown as the first column.

Figure 11A:
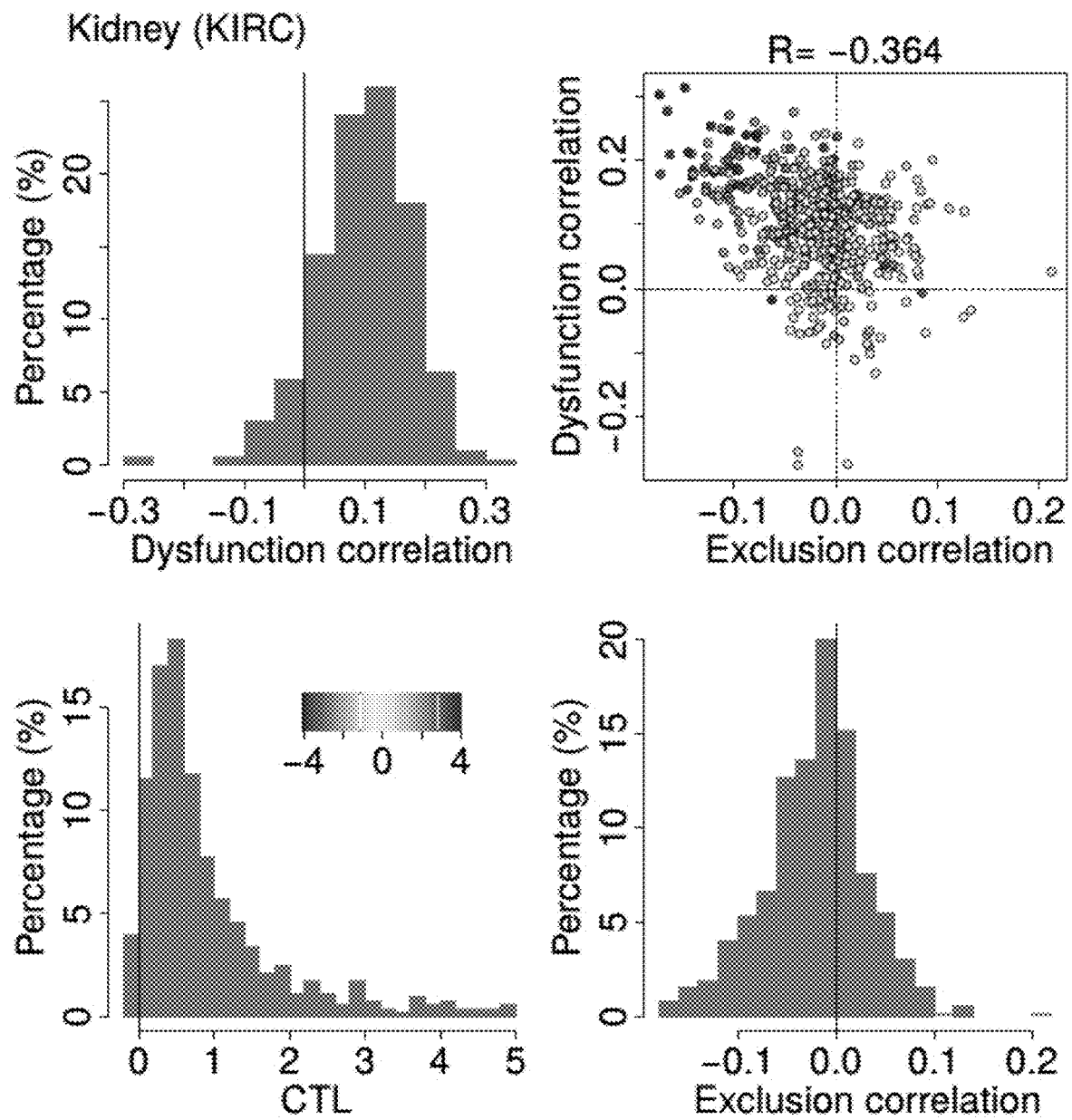
FIG. 11A-FIG. 11B is a series of graphs showing the TIDE signatures for kidney renal cell and lung squamous cell carcinoma. Among all TCGA cancer types with normal samples profiled, the kidney renal cell carcinoma (KIRC) has the highest enrichment of T-cell dysfunction signature and the lung squamous cell carcinoma (LUSC) has the highest enrichment of T-cell exclusion signature. The signature enrichment is shown as 2D plot on the level of individual tumors with the CTL level as the dot color. The histograms of signature enrichment and CTL levels are also shown together for KIRC (FIG. 11A) and LUSC (FIG. 11B).
Figure 11B:
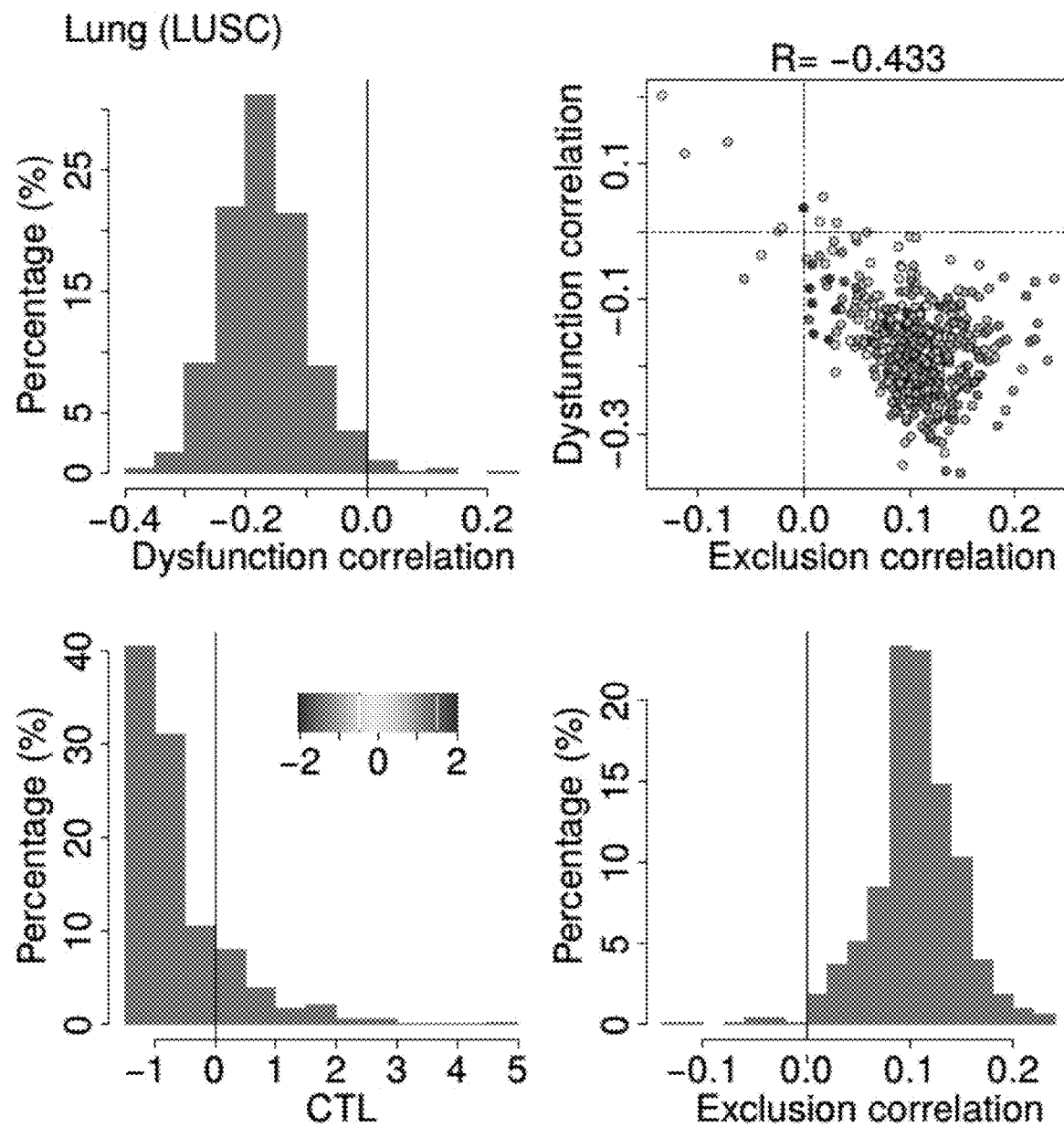

Among all cancer types, kidney renal cell carcinoma (KIRC) has the highest CTL level, and the highest enrichment of T-cell dysfunction signature (FIG. 4D and FIG. 11A). In contrast, lung squamous carcinoma (LUSC) has the highest correlation to T-cell exclusion signature (FIG. 4D and FIG. 11B). Consistent with the results, previous studies reported that the cytotoxic T-cell level is high in KIRC and lower in LUSC (Rooney et al., 2015 Cell, 160: 48-61). The results presented herein suggest that the KIRC and LUSC tumors utilize distinct strategies for immune evasion, with KIRC operating through T-cell dysfunction and LUSC through T-cell exclusion. Paradoxically, in KIRC, there is a substantial degree of CD8 cytotoxic T-cell infiltration, but the degree of T-cell infiltration is anti-correlated with survival benefits (Remark et al., 2013 Clinical Cancer Research: an Official Journal of the American Association for Cancer Research, 19: 4079-4091). The analysis revealed that KIRC tumors with the highest CTL levels tend to have a strong T-cell dysfunction signature, which might impair the ability of cytotoxic T cells to kill KIRC cancer cells (FIG. 11A).

Example 5: TIDE Signature Predicts ICB Response

In previous sections, gene signatures were developed to measure the level of T-cell dysfunction in T-cell inflamed tumors and the level of T-cell exclusion in non-inflamed tumors. Next, it was examined whether integration of these two signatures could predict ICB clinical response. Among the five cancer types for which TIDE signatures were computed (FIG. 1D), only melanoma has publicly available tumor expression and clinical outcome datasets of ICB therapies for both anti-PD1 (Hugo et al., 2016 Cell, 165: 35-44) and anti-CTLA4 (Van Allen et al., 2015 Science, 350: 207-211) treatments. Therefore, the evaluation was focused on melanoma.

Figure 12B:
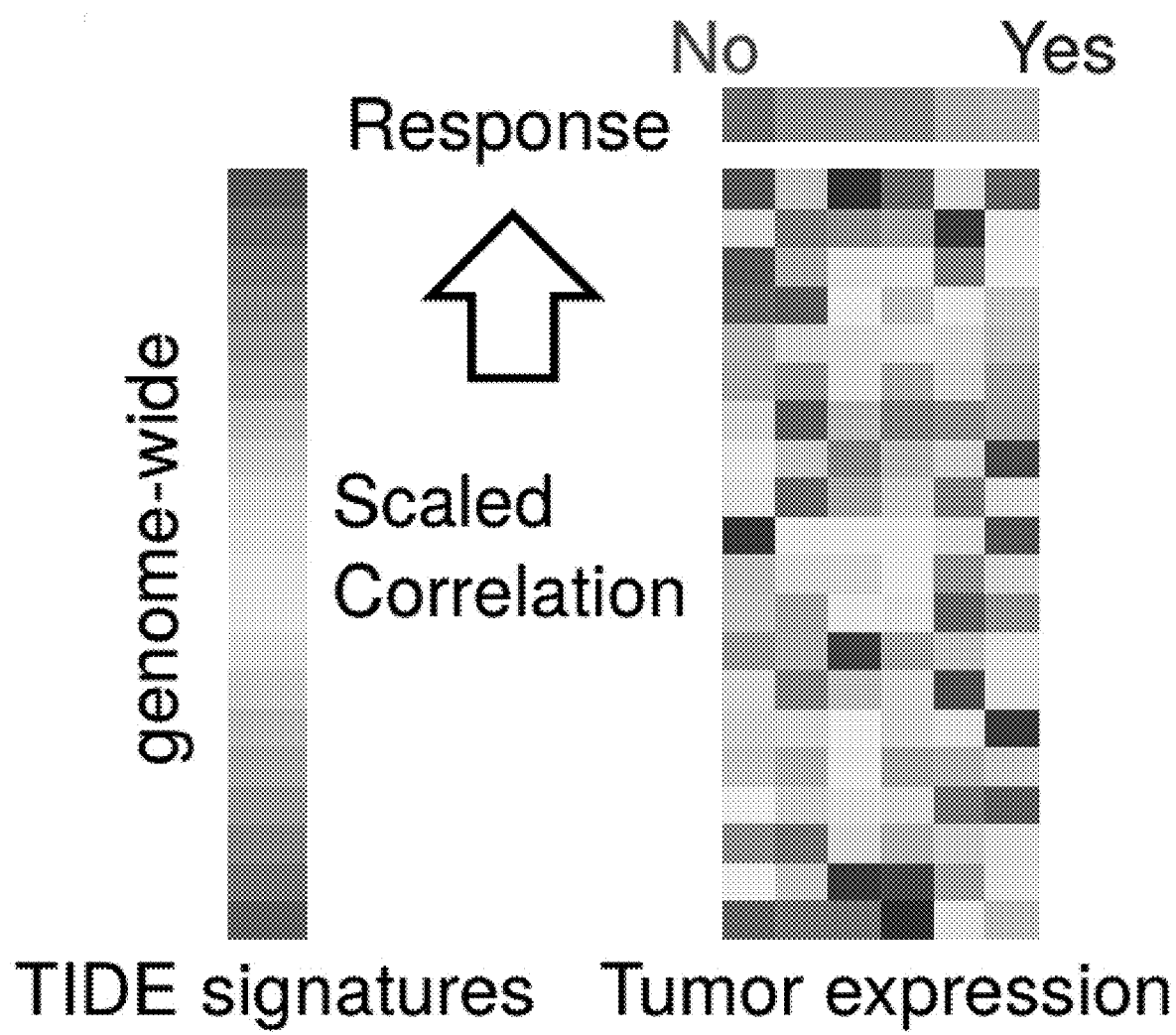

The tumors were classified as T-cell inflamed if the expression levels of all CTL genes (CD8A, CD8B, GZMA, GZMB, PRF1) were higher than their average values in each dataset, while the remaining tumors were classified as non-inflamed. To predict the degree of immune escape and clinical outcome, the expression data of each tumor was correlated either with the T-cell dysfunction signature for inflamed tumors or with the T-cell exclusion signature for non-inflamed tumors (FIG. 12A). Notably, the correlation between tumor expression profiles and the genome-scale TIDE signatures is a single value computed across all human genes, and therefore not subject to multiple hypotheses testing and insensitive to the noise from individual gene expression value or TIDE signature value (FIG. 12B). The correlation value computed for each tumor, depending on the T-cell infiltration category, was defined as the TIDE score (FIG. 5A, FIG. 5B, and FIG. 13A-FIG. 13C). All tumors were ranked by their TIDE scores as a potential predictor of their response to ICB treatment (FIG. 5A and FIG. 5B).

Figure 5G:
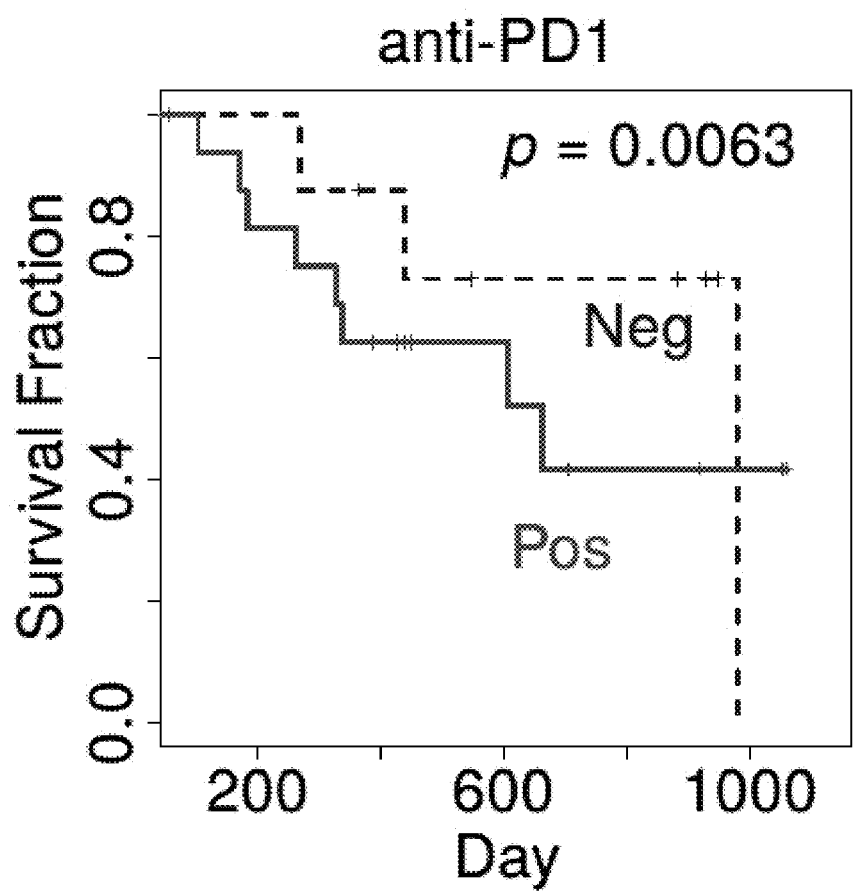
Figure 5H:
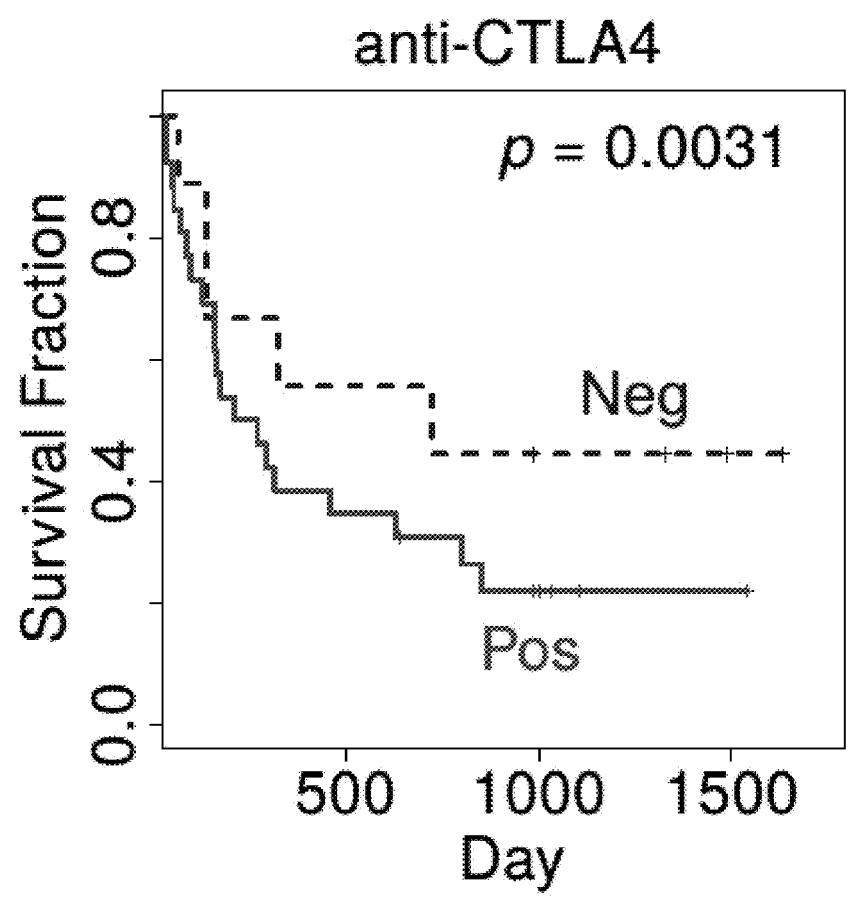
Figure 13A:
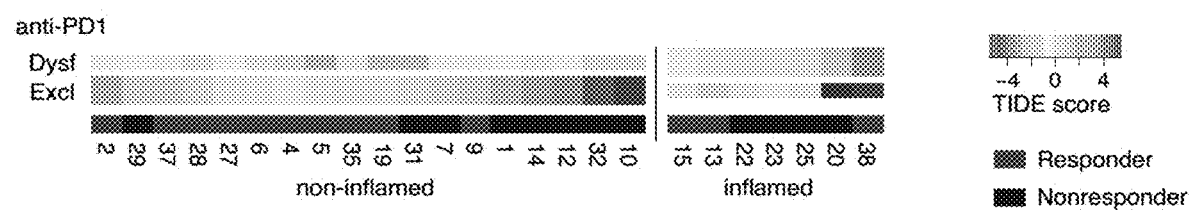
FIG. 13A-FIG. 13E is a series of graphs showing the performance of different biomarkers and gene signatures on predicting ICB response.
Figure 13B:
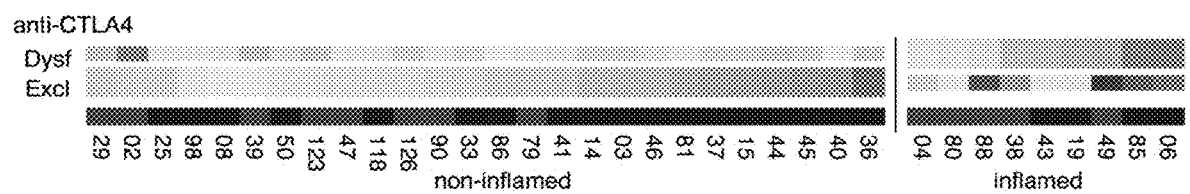
Figure 13C:
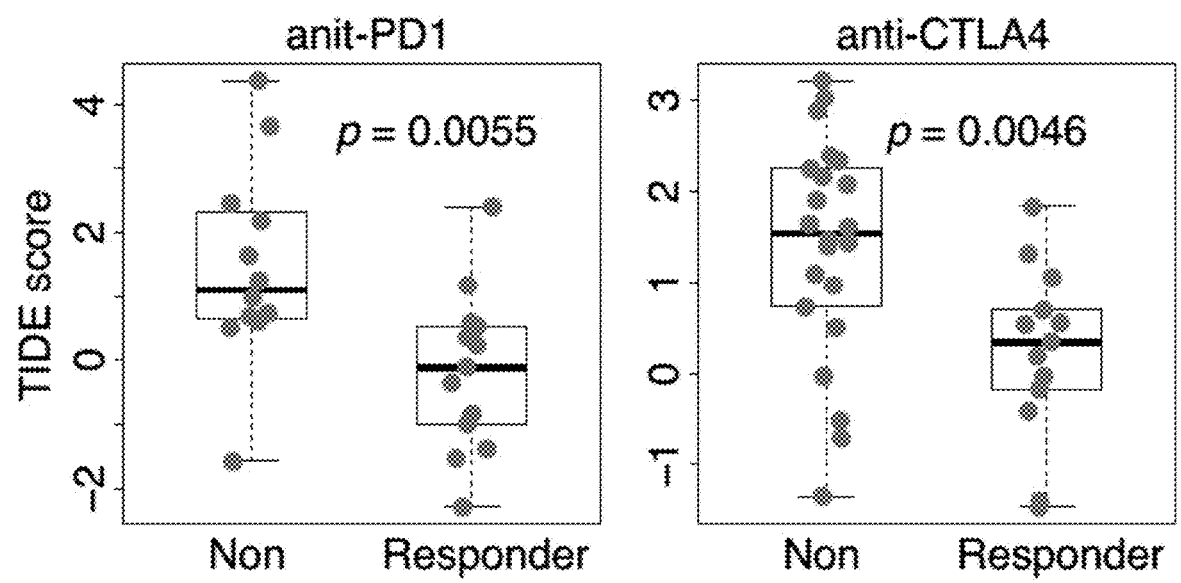
Figure 13D:
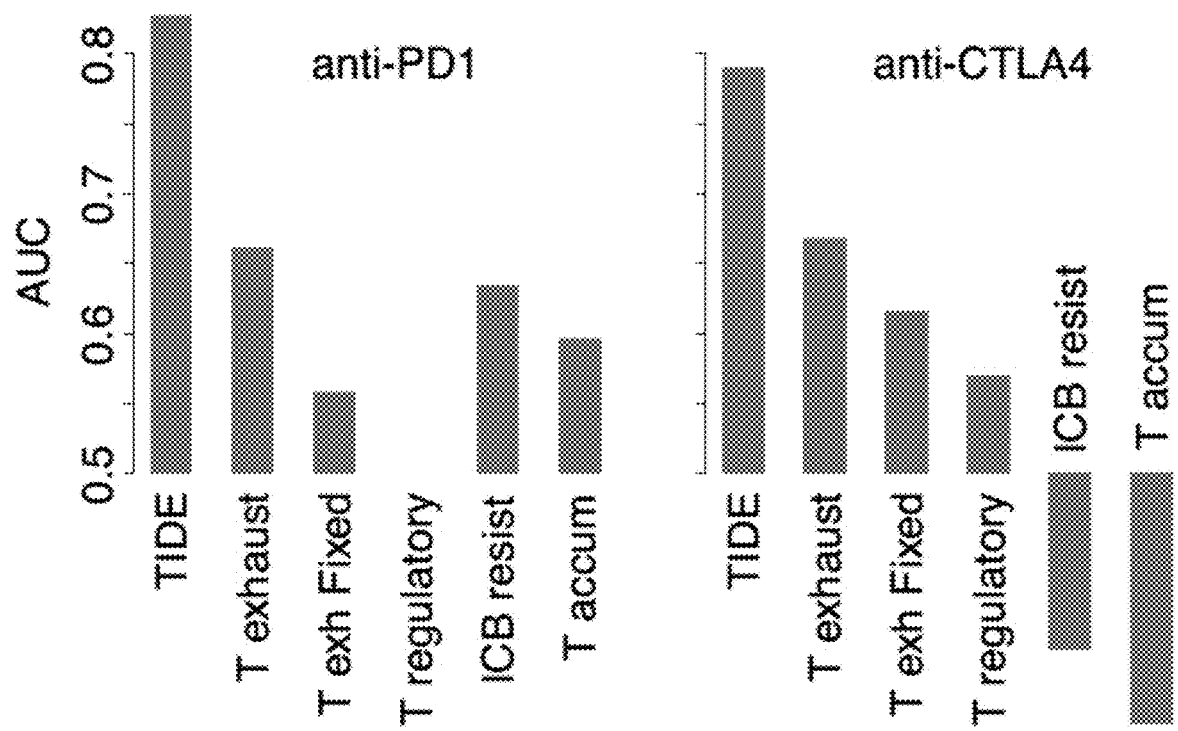
Figure 13E:
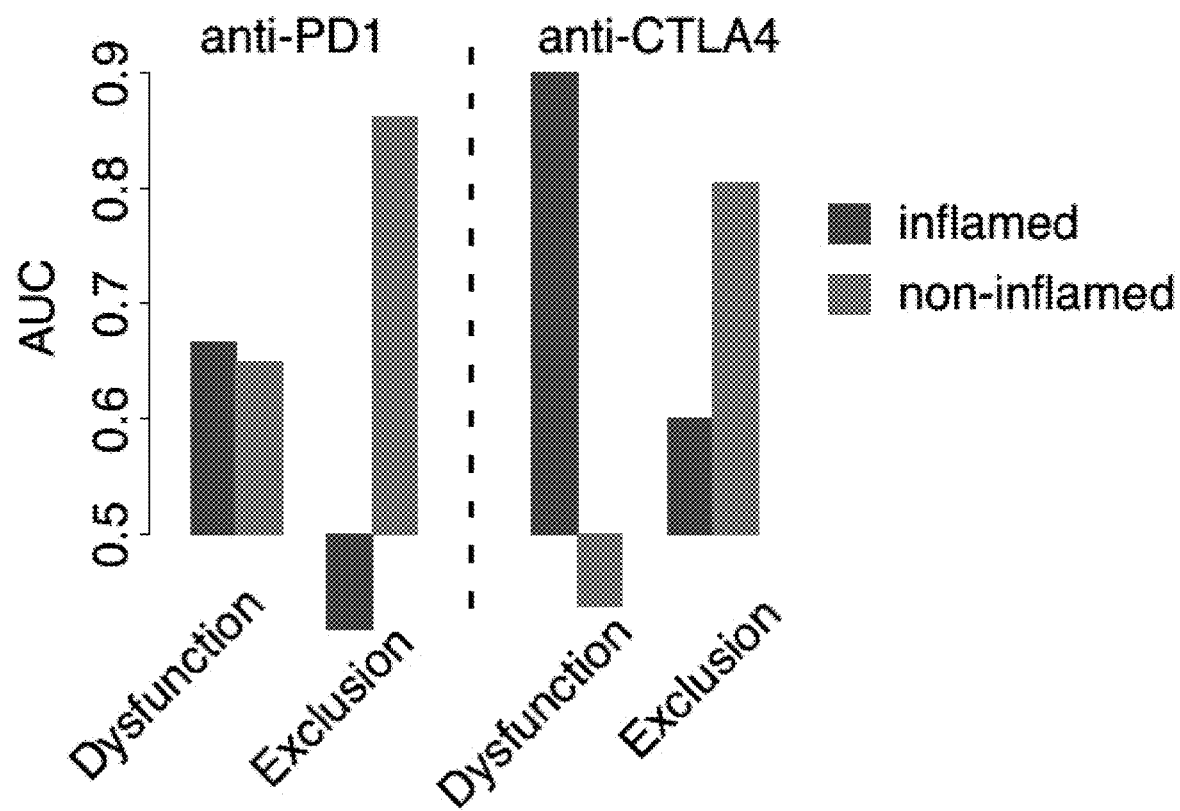

To evaluate the prediction performance for ICB response, the receiver operating characteristic (ROC) curves, which scores the true-positive rates against the false-positive rates at various thresholds, were utilized (FIG. 5C and FIG. 5D). Tumor mutation load and PD-L1 level are the most widely used biomarkers of ICB response (Nishino et al., 2017 Nature Reviews. Clinical Oncology, 14(11): 655-668). Compared to mutation load and PD-L1 expression level, TIDE signature achieved consistently better performance for both anti-PD1 and anti-CTLA4 therapies (FIG. 5C and FIG. 5D). TIDE was also compared with other ICB response biomarkers (Davoli et al., 2017 Science, 355(6322): 8399; Shukla et al., 2017 Abstract PR10: Cancer-germline antigens discriminate clinical outcome to CTLA4 blockade. AACR special conference on Tumor Immunology and Immunotherapy; Charoentong et al., 2017 Cell Reports, 18: 248-262; Ayers et al., 2017 The Journal of Clinical Investigation, 127: 2930-2940) (Table 5). Among all candidate biomarkers, it was identified that the TIDE signature was the best predictor for both anti-PD1 and anti-CTLA4 therapies (FIG. 5E and FIG. 5F). The prediction performance of TIDE is also higher than the gene signatures of T-cell dysfunction and immunotherapy resistance discussed in FIG. 3 (FIG. 13D). Finally, a higher tumor TIDE score is not only associated with worse ICB response, but also with worse patient overall survival under anti-PD-1 and anti-CTLA4 therapies (FIG. 5G and FIG. 5H). One explanation for the better performance of TIDE relative to other signatures is that TIDE considers tumor immune escape in terms of both T-cell dysfunction and exclusion (Gajewski et al., 2013 Nat Immunol, 14: 1014-1022; Joyce et al., 2015 Science 348, 74-80). Both are necessary to predict ICB response (FIG. 13E), but other biomarkers consider only one aspect.

TABLE 5

Biomarkers for response to immune checkpoint blockade

| Gene | Description |
| --- | --- |
| Mutation | Total count of non-synonymous mutations in cancer cell. |
| IFNG | Interferon gamma (IFNγ) response biomarkers of 6 genes including IFNG, STAT1, IDO1, CXCL10, CXCL9, and HLA-DRA (Ayers et al., 2017 The Journal of Clinical Investigation, 127: 2930-2940). |
| CD8 | Gene expression level of CD8A + CD8B. |
| IPS | Computational method Immunophenoscore to predict immunotherapy response from pre-treatment tumor expression profiles (Charoentong et al., 2017 Cell Reports, 18: 248-262). |
| PDL1 | An immunohistochemistry (IHC) biomarker approved by FDA (Nishino et al., 2017 Nature Reviews. Clinical Oncology, 14(11): 655-668). In this study, the PDL1 gene expression was used as the IHC surrogate. |
| SCNA | Tumor somatic copy number alterations as biomarkers of immunotherapy response (Davoli et al., 2017 Science, 355(6322): 8399). |
| CRMA | Anti-CTLA4 resistance MAGE genes, including MAGEA2, MAGEA2B, MAGEA3, MAGEA6, and MAGEA12 (Shukla et al., 2017 Abstract PR10: Cancer-germline antigens discriminate clinical outcome to CTLA4 blockade. AACR special conference on Tumor Immunology and Immunotherapy). |

Example 6: The TIDE Dysfunction Score Predicts Regulators of ICB Resistance

Figure 6A:
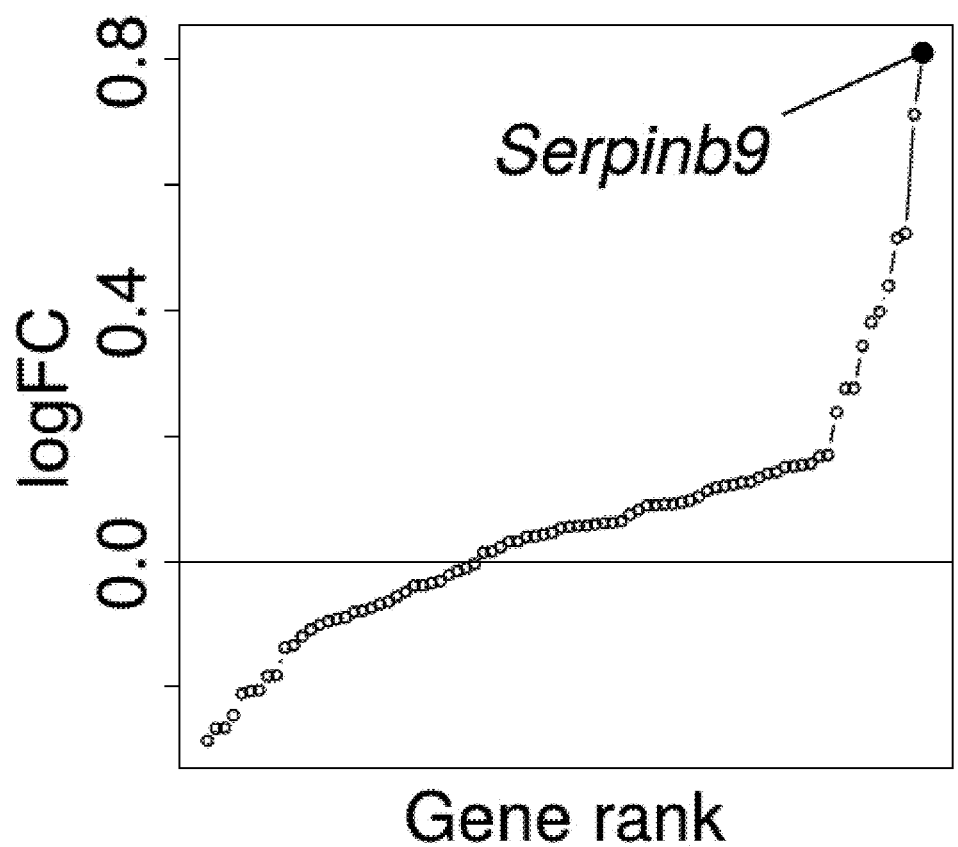
FIG. 6A-FIG. 6D is a series of graphs showing validation of serine proteinase inhibitor (serpin) Family B Member 9 (Serpinb9) as a regulator of tumor immune escape.
Figure 6B:
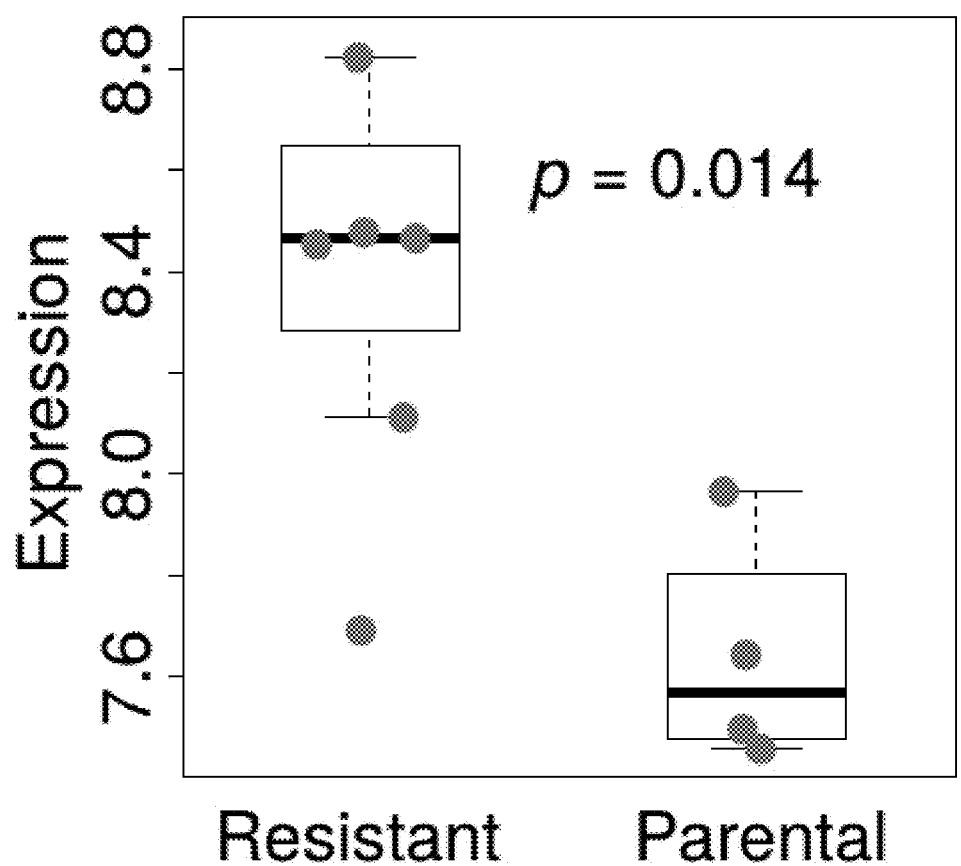
Figure 6C:
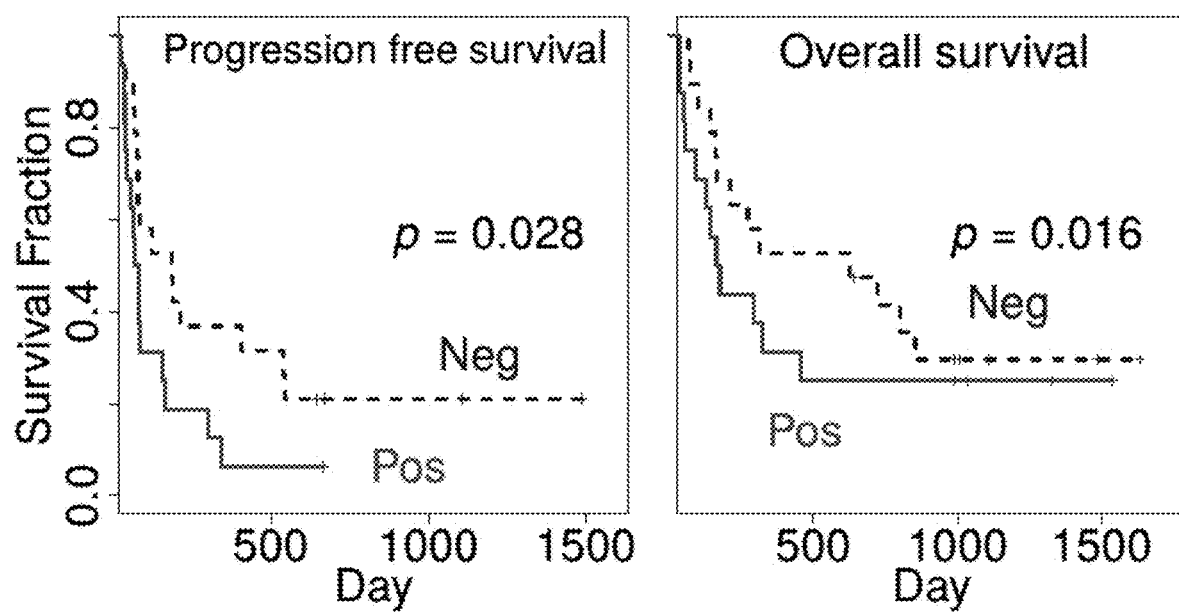
Figure 14A:
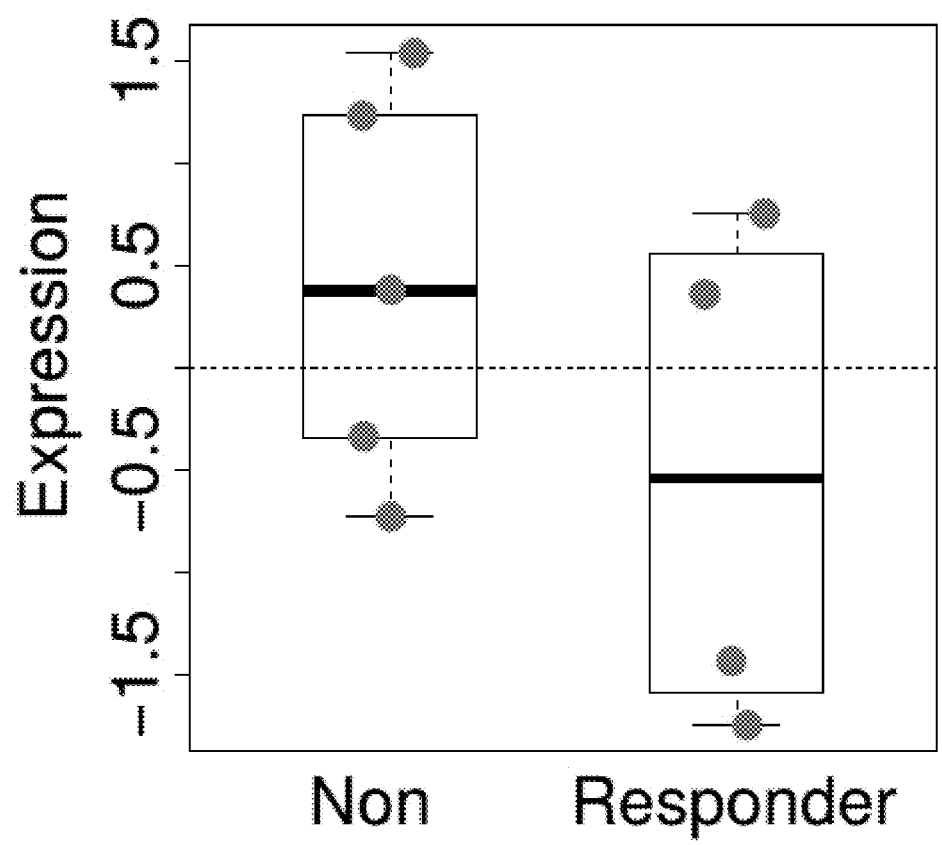
FIG. 14A-FIG. 14B is a series of graphs showing that Serpinb9 expression was associated with ICB response.
Figure 14B:
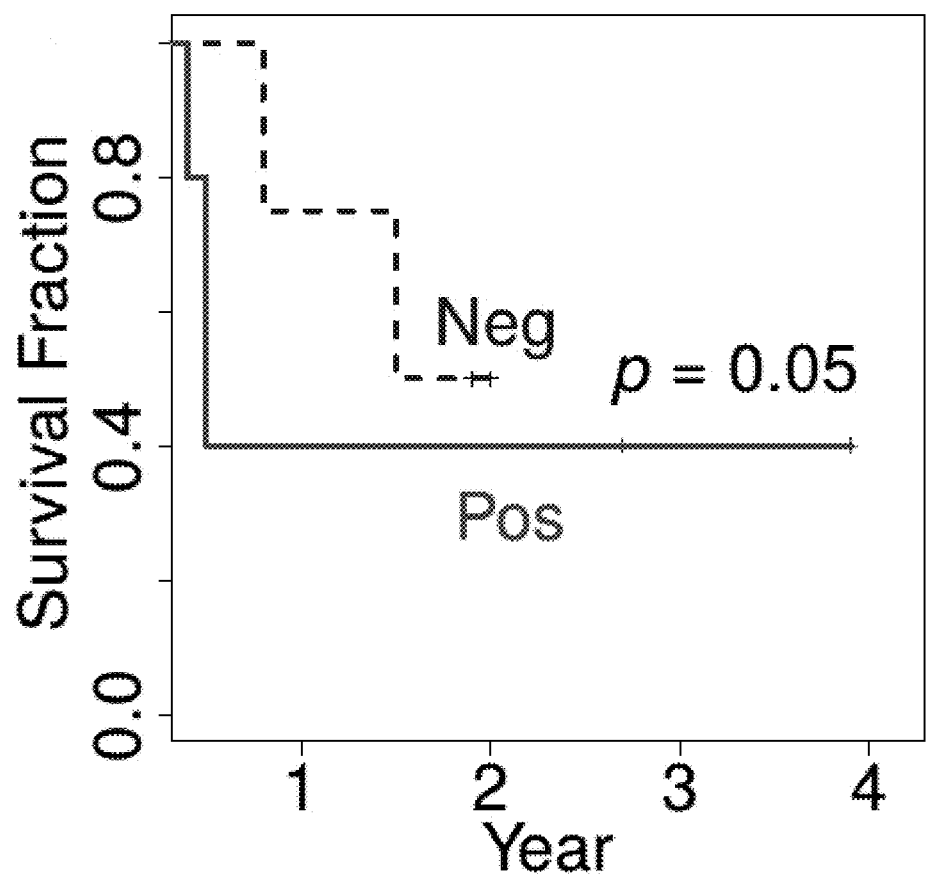

It was next determined whether some of the genes with high scores in TIDE signature might serve not only as biomarkers, but also as ICB resistance regulators. The T-cell dysfunction signature, which indicates potential factors of T-cell dysfunction in the tumor microenvironment, was analyzed. Because the T-cell dysfunction scores were computed using the data from treatment naïve tumors, orthogonal data from a mouse model of acquired anti-CTLA4 resistance was utilized to identify genes that are directly associated with ICB resistance (Twyman-Saint Victor et al., 2015 Nature, 520: 373-377). In this study, the up-regulated genes in anti-CTLA4 resistant tumors have significantly higher T-cell dysfunction scores than the down-regulated genes (FIG. 3A). All genes with significant T-cell dysfunction scores were ranked (FIG. 2) by the gene expression change after the acquisition of ICB resistance (Twyman-Saint Victor et al., 2015 Nature, 520: 373-377), and Serpinb9 was identified as the most up-regulated gene in resistant tumors (FIG. 6A and FIG. 6B). Serpinb9 expression level alone is significantly associated with worse survival outcome in two independent clinical studies of anti-CTLA4 therapy (Van Allen et al., 2015 Science, 350: 207-211; Nathanson et al., 2017 Cancer Immunol Res, 5: 84-91) (FIG. 6C, FIG. 14A, FIG. 14B, Table 6A and Table 6B). Accordingly, as described herein, high Serpinb9 levels in tumor is associated with ICB resistance.

TABLE 6A and TABLE 6B

High Serpinb9 level correlates with short patient survival during ICB treatment

|  | Coef | Stderr | Z | Pr(>|z|) |
|---|---|---|---|---|
| A. progress free survival |  |  |  |  |
| Age | −0.03 | 0.02 | −1.68 | 9.26E−02 |
| Gender | 0.04 | 0.43 | 0.10 | 9.19E−01 |
| Stage | 0.19 | 0.33 | 0.59 | 5.55E−01 |
| PreTherapy | −0.02 | 0.14 | −0.15 | 8.80E−01 |
| Neoantigen | 0.00 | 0.00 | −0.19 | 8.52E−01 |
| CTL | −0.57 | 0.22 | −2.56 | 1.04E−02 |
| Serpinb9 | 0.41 | 0.19 | 2.20 | 2.77E−02 |
| B. overall survival |  |  |  |  |
| Age | −0.02 | 0.02 | −0.90 | 3.68E−01 |
| Gender | 0.36 | 0.51 | 0.72 | 4.74E−01 |
| Stage | 0.33 | 0.35 | 0.95 | 3.43E−01 |
| PreTherapy | 0.15 | 0.14 | 1.09 | 2.76E−01 |
| Neoantigen | 0.00 | 0.00 | −0.89 | 3.74E−01 |
| CTL | −0.61 | 0.23 | −2.64 | 8.41E−03 |
| Serpinb9 | 0.48 | 0.20 | 2.41 | 1.60E−02 |

The association between the Serpinb9 expression level and patient survival outcome in anti-CTLA4 treatment are tested by the Cox-PH regression using a public dataset with 35 patients (Van Allen et al., 2015 Science, 350: 207-211). Several clinical and tumor factors are included as background in the regression. (PreTherapy: whether the patients were treated with other therapies before. Neoantigen: total load of neo-antigens. CTL: the cytotoxic T-cell level). Table 6A shows the results with the progress free survival as end points. Table 6B shows the results with the overall survival as end points.

Figure 15A:
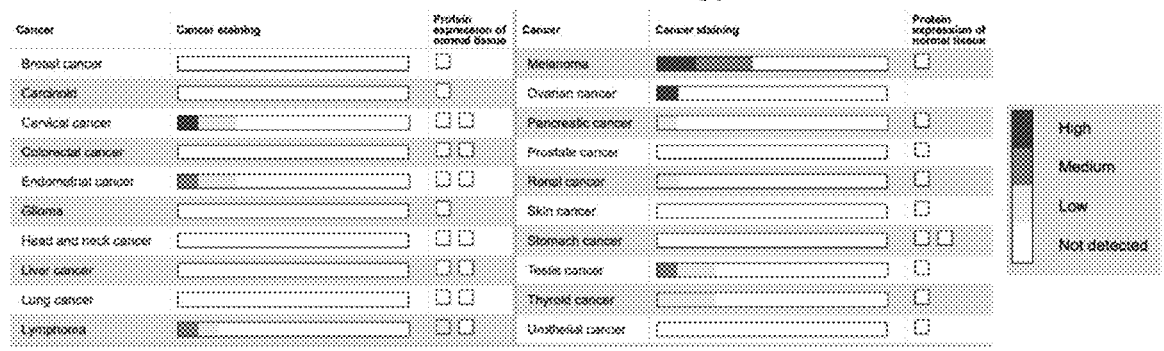
FIG. 15A-FIG. 15B is a series of graphs showing Serpinb9 protein staining in cancer. The Protein Atlas database provided the immunohistochemistry (IHC) protein staining for 15287 genes in 20 cancer types (Uhlen et al., 2017 Science, 357(6352): eaan2507).
Figure 15B:
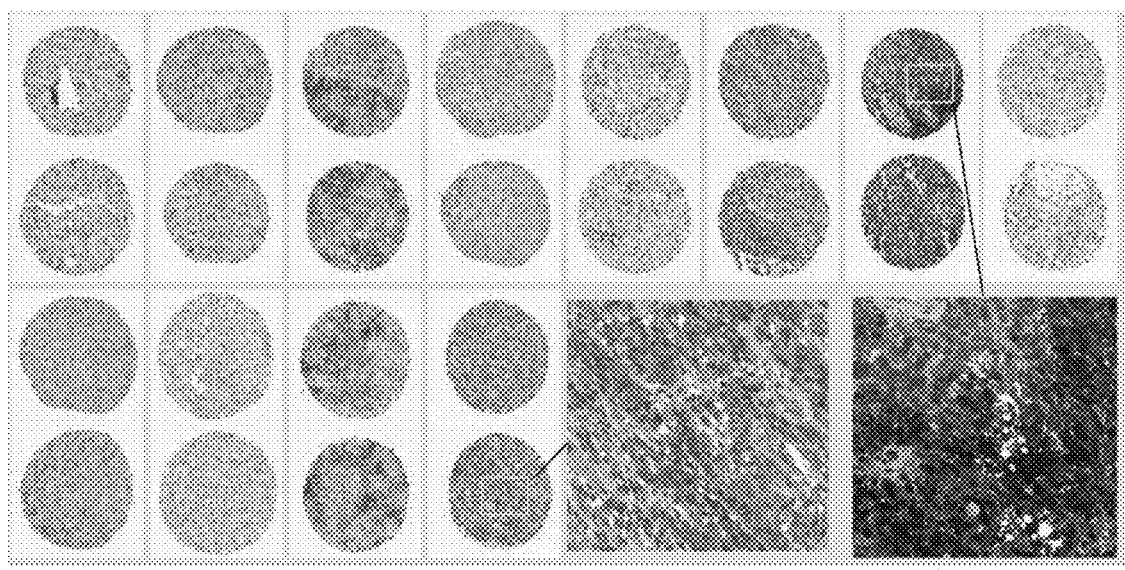

Serpinb9 is a member of the serine protease inhibitor (serpin) family. The encoded protein can inactivate Granzyme B to protect lymphocytes (e.g., T cell, natural killer cell) from Granzyme that may leak from the granules (Kaiserman, D. & Bird, P. I. 2010 Cell Death Differ, 17: 586-595). It is highly expressed in cytotoxic lymphocytes, antigen presenting cells, and immune-privileged sites (Hirst et al., 2003 J Immunol, 170: 805-815; Bladergroen et al., 2001 J Immunol, 166: 3218-3225; Hirst et al., Mol Hum Reprod, 7: 1133-1142). Also, a study using in-vitro cell culture models reported that high Serpinb9 level in cancer cells resulted in the resistance to T cell-mediated killing (Medema et al., 2001 Proceedings of the National Academy of Sciences of the United States of America, 98: 11515-11520). To infer which cell type in the tumor microenvironment is the potential source of high Serpinb9 level, the Protein Atlas database of immunohistochemistry results for 15 thousand genes in 20 cancer types was examined (Uhlen et al., 2017 Science, 357(6352): eaan2507). Serpinb9 protein level is very high in cancer cells in melanoma and several other cancer types as compared to normal tissues (FIG. 15A-FIG. 15B). Thus, it was next determined whether Serpinb9 could promote the resistance to T cell-mediated killing and ICB through its high expression in cancer cells.

Figure 6D:
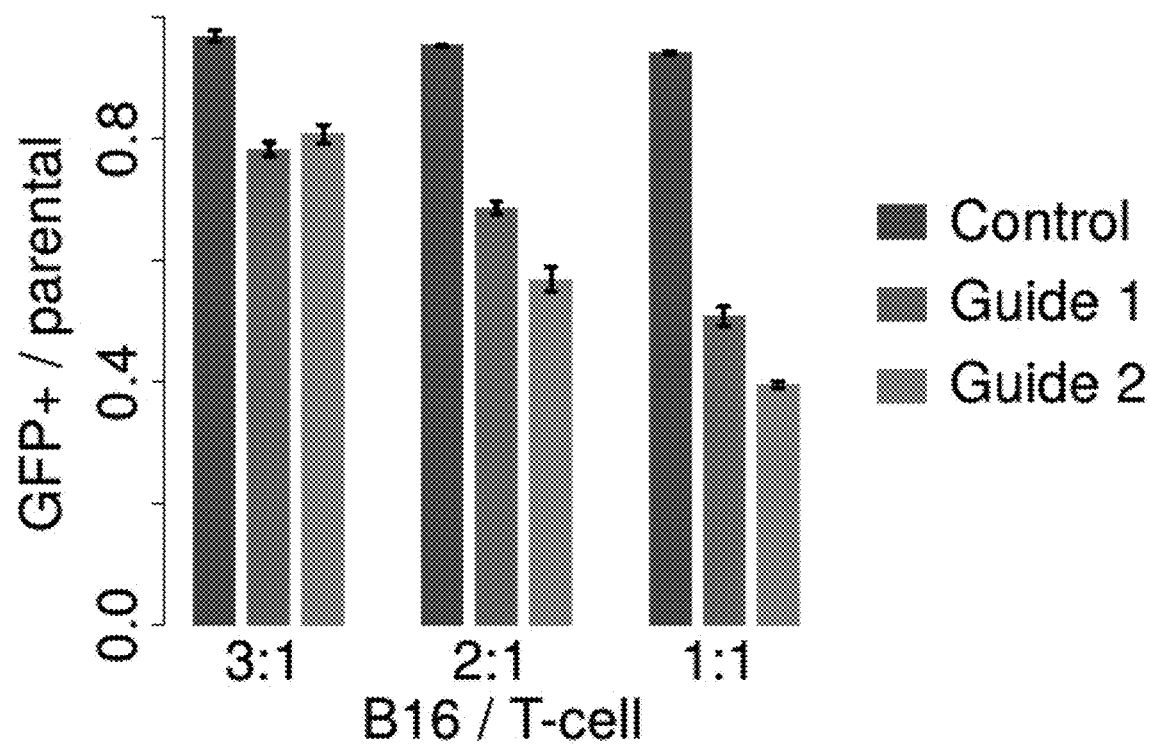
Figure 16:
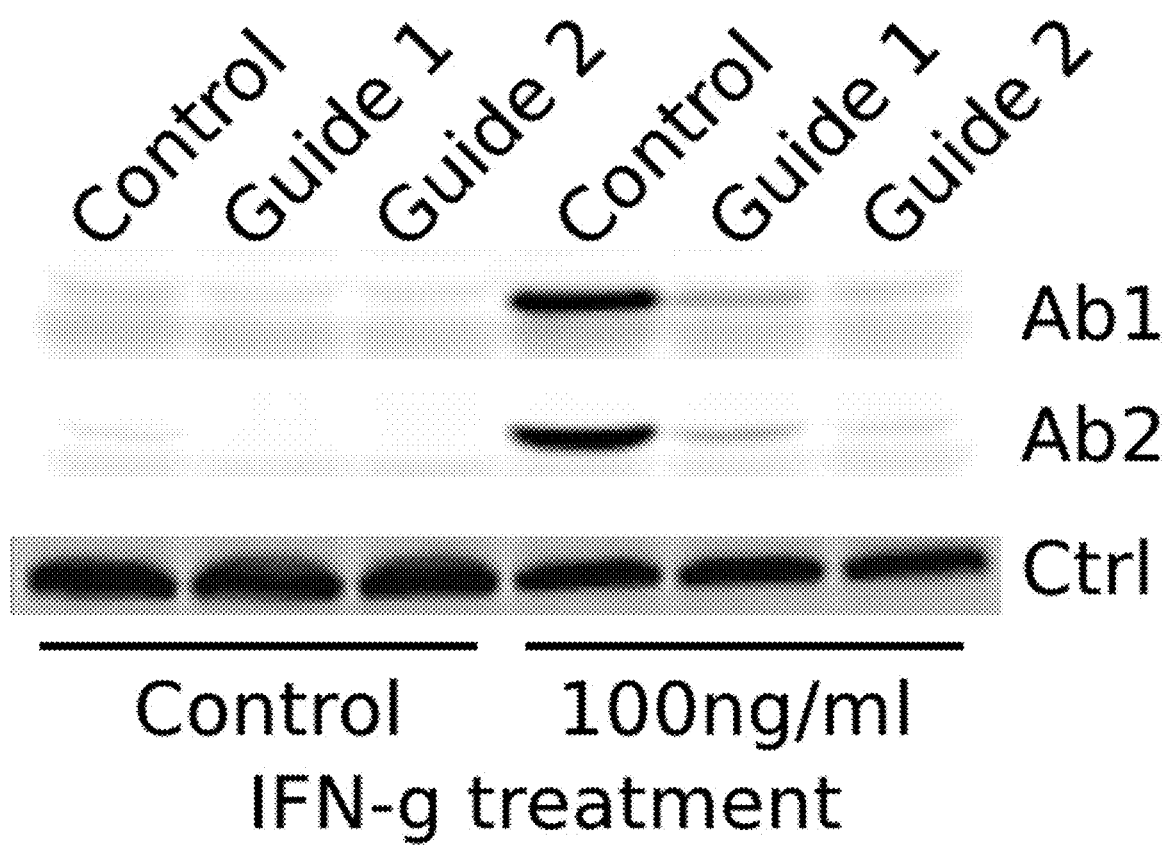
FIG. 16 is a photograph of a western blot of Serpinb9 protein levels after CRISPR knockout. There are two independent guides targeting Serpinb9 and a control non-targeting sequence. Cells were either untreated (left 3 lanes), or treated with 100 ng/mL IFNγ to induce Serpinb9 expression (right 3 lanes). Two different antibody clones (Ab1: F-6, Ab2: PI9-17) were used to detect Serpinb9 protein level. Detection of Vinculin is shown as a loading control (Ctrl).

To explore the Serpinb9 function in melanoma cancer cells, Serpinb9 knockout cells were generated by using CRIPSR/Cas9 in the B16F10 melanoma cell line, which is the parental line of the anti-CTLA4 resistant tumor model previously discussed (Twyman-Saint Victor et al., 2015 Nature, 520: 373-377). The protein level of Serpinb9 is significantly increased upon treatment of IFNγ, a cytokine produced by cytotoxic T cells upon antigen-specific activation (Schoenborn, J. R. & Wilson, C. B. 2007 Advances in Immunology, 96: 41-101) (FIG. 16). After knocking out Serpinb9 using two different CRISPR guide RNAs (gRNA), the Serpinb9 level became undetectable even after IFNγ treatment (FIG. 16). When co-cultured with Pmel-1 cytotoxic T cells, the Serpinb9 knockout B16 cells were more sensitive to T cell-mediated killing compared to control cells (FIG. 6D and FIG. 17). This result supports that high expression of Serpinb9 in cancer cells regulates resistance to T-cell mediated killing which is essential for an ICB response.

Example 7: Optimization of the Negative Predictive Value for Non-Responders Through Combination Metrics An essential measure of therapy response biomarkers is the negative predictive value (NPV), which is the fraction of predicted non-responders who truly will not benefit from the treatment. Any false negative prediction indicating that a patient would be non-responsive to therapy could cause potentially responding patients to "miss-out" on therapeutic benefits. Therefore, an optimized procedure was developed to predict patients that would not benefit from treatment. As described herein, a procedure combing both the TIDE value and the IFNγ expression level led to a more robust performance than either individual metric alone. In this procedure, a patient was predicted to be a non-responder if both TIDE and IFNγ values are lower than a threshold level (FIG. 18). For each clinical cohort in the collection, the NPV was evaluated at all threshold combinations. This resulted in consistently improved performance at cutoffs of TIDE and IFNG as −0.3 and 0, respectively. In this matter, non-responder ("no benefit") predictions are optimized.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference.

Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of determining whether inhibition of cytotoxic T-lymphocyte-associated protein 4 (CTLA4) in a subject with melanoma will result in clinical benefit in the subject comprising:
   obtaining a test sample from a subject having or at risk of developing melanoma;
   determining the expression level of tumor immune dysfunction and exclusion (TIDE)-associated genes in the test sample;
   wherein the TIDE-associated genes comprise serine proteinase inhibitor (serpin) Family B Member 9 (SerpinB9), transforming growth factor beta-1 (TGFβ-1), prolyl endopeptidase (FAP), vascular endothelial growth factor A (VEGFA), angiopoietin 2 (ANGPT2), cluster of differentiation 274 (CD274), interferon gamma (IFNγ), and alpha-mannosidase 2 (MAN2A1);
   comparing the expression level of the TIDE-associated genes in the test sample with the expression level of the corresponding genes in a reference sample; and
   determining that inhibition of CTLA4 in the subject with melanoma will result in clinical benefit in the subject when:
   i. the expression level of SerpinB9, TGFβ-1, FAP, VEGFA, ANGPT2, and MAN2A1 in the test sample is lower than the level of the corresponding gene in the reference sample, and
   ii. the expression level of CD274 and IFNγ in the test sample is higher than the level of the corresponding gene in the reference sample; and
   administering to the subject an effective amount of a CTLA4 inhibitor, wherein the CTLA4 inhibitor comprises a CTLA4 antibody, and wherein the CTLA4 antibody comprises ipilimumab or tremelimumab, thereby treating the melanoma.

2. The method of claim 1, wherein clinical benefit in the subject comprises complete or partial response as defined by response evaluation criteria in solid tumors (RECIST), stable disease as defined by RECIST, or long-term survival in spite of disease progression or response as defined by immune-related response criteria (irRC).

3. The method of claim 1, wherein the test sample is obtained from the melanoma tissue or from tumor microenvironment or from tumor-infiltrating immune cells.

4. The method of claim 1, wherein the sample comprises a biological sample, wherein the biological sample comprises a plasma sample or a blood sample.

5. The method of claim 1, wherein the sample comprises deoxyribonucleic acid (DNA) or ribonucleic acid (RNA).

6. The method of claim 1, wherein the reference sample is obtained from healthy normal tissue, a melanoma that received a clinical benefit from CTLA4 inhibition, or melanoma that did not receive a clinical benefit from CTLA4 inhibition.

7. The method of claim 1, wherein the expression level of the TIDE-associated genes is detected via an Affymetrix Gene Array hybridization, next generation sequencing, ribonucleic acid sequencing (RNA-seq), a real time reverse transcriptase polymerase chain reaction (real time RT-PCR) assay, immunohistochemistry (IHC), immunofluorescence.

8. The method of claim 1, wherein the expression level of the TIDE-associated genes is detected via RNA-seq and the reference sample is obtained from healthy normal tissue from the same individual as the test sample or one or more healthy normal tissues from different individuals.

9. The method of claim 1, wherein the expression level of the TIDE-associated genes is detected via RT-PCR and wherein the reference sample is obtained from the same tissue as the test sample.

10. The method of claim 1, wherein the subject is a human.

11. The method of claim 1, wherein the subject has not yet received treatment with a CTLA4 inhibitor, a PD1 inhibitor, or a PD-L1 inhibitor.

12. The method of claim 1, further comprising treating the subject with a chemotherapeutic agent, radiation therapy, cryotherapy, hormone therapy, or immunotherapy.

13. The method of claim 12, wherein the chemotherapeutic agent comprises dacarbazine, temozolomide, nab-paclitaxel, paclitaxel, cisplatin, or carboplatin.

14. The method of claim 1, further comprising administering an inhibitor of a TIDE-associated gene with a higher level of expression compared to the level of the TIDE-associated gene in the reference sample, wherein the TIDE-associated gene comprises CD247 or IFNγ, thereby treating the melanoma.

15. The method of claim 5, wherein the sample comprises ribonucleic acid (RNA).

* * * * *

SEQUENCE LISTING

```
Sequence total quantity: 20
SEQ ID NO: 1             moltype = AA  length = 376
FEATURE                  Location/Qualifiers
source                   1..376
                         mol_type = protein
                         organism = Homo sapiens
SEQUENCE: 1
METLSNASGT FAIRLLKILC QDNPSHNVFC SPVSISSALA MVLLGAKGNT ATQMAQALSL    60
NTEEDIHRAF QSLLTEVNKA GTQYLLRTAN RLFGEKTCQF LSTFKESCLQ FYHAELKELS   120
FIRAAEESRK HINTWVSKKT EGKIEELLPG SSIDAETRLV LVNAIYFKGK WNEPFDETYT   180
REMPFKINQE EQRPVQMMYQ EATFKLAHVG EVRAQLLELP YARKELSLLV LLPDDGVELS   240
TVEKSLTFEK LTAWTKPDCM KSTEVEVLLP KFKLQEDYDM ESVLRHLGIV DAFQQGKADL   300
SAMSAERDLC LSKFVHKSFV EVNEEGTEAA AASSCFVVAE CCMESGPRFC ADHPFLFFIR   360
HNRANSILFC GRFSSP                                                  376

SEQ ID NO: 2             moltype = DNA  length = 4167
FEATURE                  Location/Qualifiers
source                   1..4167
                         mol_type = genomic DNA
                         organism = Homo sapiens
SEQUENCE: 2
agcgggagtc cgcggcgagc gcagcagcag ggccgggtcc tgcgcctcgg gggtcggcgt    60
ccaggctcgg agcgcggcac ggagacggcg cagcgctgga actaggtggc aggccctgca   120
tcatggaaac tctttctaat gcaagtggta cttttgccat acgccttttt aagatactgt   180
gtcaagataa cccttcgcac aacgtgttct gttctcctgt gagcatctcc tctgccctgg   240
ccatggttct cctaggggca aagggaaaca ccgcaaccca gatggcccag gcactgtctt   300
taaacacaga ggaagacatt catcgggctt tccagtcgct tctcactgaa gtgaacaagg   360
ctggcacaca gtacctgctg agaacggcca acaggctctt tggagagaaa acttgtcagt   420
tcctctcaac gtttaaggaa tcctgtcttc aattctacca tgctgagctg aaggagcttt   480
cctttatcag agctgcagaa gagtccagga acacatcaa cacctgggtc tcaaaaaaga    540
ccgaaggtaa aattgaagag ttgttgccgg gtagctcaat tgatgcagaa accaggctgg   600
ttcttgtcaa tgccatctac ttcaaaggaa agtggaatga accgtttgac gaaacataca   660
caagggaaat gccctttaaa ataaaccagg aggagcaaag gccagtgcag atgatgtatc   720
aggaggccac gtttaagctc gcccacgtgg gcgaggtgcg cgcgcagctg ctggagctgc   780
cctacgccga gaaggagctg agcctgctgg tgctgctgcc tgacgacggc gtggagctca   840
gcacggtgga aaaaagtctc acttttgaga aactcacagc ctggaccaag ccagactgta   900
tgaagagtac tgaggttgaa gttctccttc caaaatttaa actacaagag gattatgaca   960
tggaatctgt gcttcggcat ttgggaattg ttgatgcctt ccaacagggc aaggctgact  1020
tgtcggcaat gtcagcggag agagacctgt gtctgtccaa gttcgtgcac aagagttttg  1080
tggaggtgaa tgaagaaggc accgaggcag cggcagcgtc gagctgcttt gtagttgcag  1140
agtgctgcat ggaatctggc ccaggttcc tgtgctgacca ccctttcctt ttcttcatca  1200
ggcacaacag agccaacagc attctgttct gtggcaggtt ctcatcgcca taagggtgc   1260
acttaccgtg cactcggcca tttccctctt cctgtgtccc cagatcccca ctacagctcc   1320
aagaggatgg gcctagaaag ccaagtgcaa agatgaggc agattcttta cctgtctgcc   1380
ctcatgattt gccagcatga attcatgatg ctccacactc gcttatgcta cttaatcaga  1440
atcttgagaa aatagaccat aatgattccc tgttgtatta aaattgcagt ccaaatccca  1500
taggatggca agcaaagttc ttctagaatt ccacatgcaa ttcactctgg cgaccctgtg  1560
ctttcctgac actgcgaata cattccttaa cccgctgcct cagtggtaat aaatggtgct  1620
agatattgct actattttat agatttcctg gtgcttagcc ttataaaaaa ggttgtaaaa  1680
tgtacattta tatttatct ttttttttttt tttttttctg agacgcagtc tggctctctg  1740
tcgcccagge tggagtgcag tggctcgatc tcggctcact gcaagctccg cctcccgggt  1800
tcacgccatt ctcctgcctc agcctcccga gtagctggga ctacaggcgc ccgccaccac  1860
gcccggctaa ttttttgtat ttttagtaga cacgggtttt caccgtgtta gccaggatgg  1920
tgtcgatctc ctgacctcgt gatccacccg cctcggcctc ccaaagtgct gggattacag  1980
gcttgagcca ccgcgcccgg ctatatttta tctttatct ttttcttga catttaccaa   2040
tcaccaagca tgcaccaaac actgctttag gcactgggga cacaaagggg acagagccat  2100
cctcctttga cacctggtct tcagttctgt gcccaacgta tatgttttg acaatgacca   2160
ggttggactg tttaatgtct ttcaacttac cacgtaatcc tcttgtaggg atcacatctt  2220
tctttatgat attgtatttc tctacctcta acagtaaaaa ttccattcaa cccttaaagc  2280
tcacttcaaa ttcttctttg agaagttttt cctttctccg caaccagatg tacatatttg  2340
aactctcttt gtacttggag ggcacttctt tcgtggtagt tcttttattt ttattaatct  2400
ctgtatcctt agatagtcct ccaacaacca aaggtgggga ctctgtctta catatctggg  2460
tgcccctcat agtgcagtaa taagtaagtt gattatatac gagctatgta acttatattt  2520
tttaatggtt ggatatcact gagttttttt tttaagaat ttttttattg aggtaaactt   2580
cacataacat aaaattaact atttttaaagt gagaagttca gtgccactta gtattgttaa  2640
caatgttgca taaccaccac ctttatttaa agttccaaaa aaaatgttct cctctaaaag  2700
gaaaccccat cccattaagc agatactctc cattccttcc ttcctccagc ccccagcaac  2760
caccaatctg ctttctgtct ctatggattt atctattctt gctattttat ataaattgaa  2820
ttgtatgaga ccttttgtgt ctggcttcct tcacttagta caagtttttg agatttattt  2880
acatagtagc atgtatcaac acttcatttt tatggccaaa taaaattgta ttatgtgttt  2940
atagcacaat ttatttatcc actcattcat tgatggactt tgggttgttt ctgacttttg  3000
gctattggga atagtgctgc tatgaatgtt tgtgtacctg tatttgtttg aatgccatt   3060
ttgcattctc ttgggtatat atctaggagt ggaactgttg ggtcatatgt taattcatt   3120
tttagctttt tgaggaacag acaaactgtt ttccacagca gttgaaccat tccacattcc  3180
caccagcaat gtatgagaat tccaattct gtccactcc tcaccaacac ttattatttt    3240
ccttttcctt ttttttaaaaa aaataagtta tggccatctt agtgggtgtg aagtggtatc  3300
tcattgtgtt ttttattggc atttcctatg taatgagcta gaaactaaag tacaaactag  3360
atgggacatc cagtcccttt gatagataat gctgagtaaa aaatgagatg aaagacattt  3420
```

```
gtttgttttt agaacacgag tgacagtttg ttaaaaagct ttagaggagg aatgaaaaca   3480
aagtgaagta cacttagaaa agggccaagt ggacatcttg gatgtcaagt gcctagttca   3540
gtatctttttt tttttttttt ttttttttg agacagtgcc tcactctgtc acccaggctg   3600
gagtgtagtg gcatgatctg ggctcactgc aacctcctcc tcctggattc aagcaattct   3660
cttgcttcag cctcccaagt agctgagact acaagcacac accatcacac ccagctaatt   3720
ttgtattttt cagtagagac ggggtttcgc cacattggcc gtgttggtct tgaactcctg   3780
gcctcaagcg atccgcctac ctcagcctcc caaagtgcta ggattacagg cataagccac   3840
tgagcccagc cctagttcag tatctttttat gtaaattaca aacatctgca acattatgta   3900
tcatatgcag atacttattg catttctttt attagtggtg aaagtgttct atgcatttat   3960
tggctcttga atttcctcat ctatgaattg tcattcatac acctactttt ctgcttcgtt   4020
tttacatatg tctttgccta ttaaagatat tatccctctg ttttatattt tctctcattc   4080
ttgtattgcc ttttaaattt tgttatgatg tttcattaat aaacagtgtt ttgttttcct   4140
ctataatcaa aaaaaaaaaa aaaaaaa                                       4167

SEQ ID NO: 3            moltype = AA  length = 390
FEATURE                 Location/Qualifiers
source                  1..390
                        mol_type = protein
                        organism = Homo sapiens
SEQUENCE: 3
MPPSGLRLLL LLLPLLWLLV LTPGRPAAGL STCKTIDMEL VKRKRIEAIR GQILSKLRLA   60
SPPSQGEVPP GPLPEAVLAL YNSTRDRVAG ESAEPEPEPE ADYYAKEVTR VLMVETHNEI   120
YDKFKQSTHS IYMFFNTSEL REAVPEPVLL SRAELRLLRL KLKVEQHVEL YQKYSNNSWR   180
YLSNRLLAPS DSPEWLSFDV TGVVRQWLSR GGEIEGFRLS AHCSCDSRDN TLQVDINGFT   240
TGRRGDLATI HGMNRPFLLL MATPLERAQH LQSSRHRRAL DTNYCFSSTE KNCCVRQLYI   300
DFRKDLGWKW IHEPKGYHAN FCLGPCPYIW SLDTQYSKVL ALYNQHNPGA SAAPCCVPQA   360
LEPLPIVYYV GRKPKVEQLS NMIVRSCKCS                                    390

SEQ ID NO: 4            moltype = DNA  length = 2741
FEATURE                 Location/Qualifiers
source                  1..2741
                        mol_type = genomic DNA
                        organism = Homo sapiens
SEQUENCE: 4
acctccctcc gcggagcagc cagacagcga gggccccggc cggggcaggg gggacgccc    60
cgtccgggc  accccccgg  ctctgagccg cccgcgggc  cggcctcggc ccggagcgga   120
ggaaggagtc gccgaggagc agcctgaggc cccagagtct gagacgagcc gccgccgccc   180
ccgccactgc ggggaggagg gggaggagga gcggaggag  ggacgagctg gtcgggagaa   240
gaggaaaaaa acttttgaga cttttccgtt gccgctgggg gccgagggcg cgggggacctc   300
ttggcgcgac gctgccccgc gaggaggcag gacttgggga cccagaccg  cctccctttg   360
ccgccgggga cgcttgctcc ctccctgccc cctacacggc gtccctcagg cgccccccatt  420
ccggaccagc cctcggagt  cgccgacccg gcctcccgca aagactttc  cccagacctc   480
gggcgcaccc cctgcacgcc gccttcatcc ccggcctgtc tcctgagccg cgcgcagtg    540
tagacccttt ctcctccagg agacggatct ctctccgacc tgccacagat ccctattca    600
agaccaccca ccttctggta ccagatcgcg cccatctagg ttatttccgt gggatactga   660
gacaccccg  gtccaagcct cccctccacc actgcgccct ctccctgag  gacctcagct   720
ttccctgcag gccctcctac cttttgccgg gagaccccca gctccgtgcag ggggggggcc   780
tccccaccac accagccctg ttcgcgctct cggcagtgcc gggggggcgcc gcctcccca   840
tgccgccctc cgggctgcgg ctgctgccgc tgctgctacc gctgctgtgg ctactggtgc   900
tgacgcctgc ccggccggcc gcgggactat ccacctgcaa gactatcgac atggagctgg   960
tgaagcggaa gcgcatcgag gccatcgcg  gccagatcct gtccaagctg cggctcgcca   1020
gcccccgag  ccaggggag  gtgccgcccg gccgctgcc  cgaggccgtg ctcgcccgt    1080
acaacagcac ccgcgaccgg gtgccgggg  agagtgcaga accggagccc gagcctgagg   1140
ccgactacta cgccaaggag gtcacccgcg tgctaatggt ggaaacccac aacgaaatct   1200
atgacaagtt caagcagagt acacacagca tatatatgtt cttcaacaca tcagagctcc   1260
gagaagcggt acctgaaccc gtgttgctct cccgggcaga gctcgtctg  ctgaggctca   1320
agttaaaagt ggagcagcac gtggagctgt accagaaata cagcaacaat tcctggcgat   1380
acctcagcaa ccggctgctg gcacccagcg actcgccaga gtggtatcgct tttgatgtca   1440
ccggagttgt gcggcagtgg ttgagccgtg gagggaaat  tgagggcttt cgccttagcg   1500
cccactgctc ctgtgacagc agggataaca cactgcaagt ggacatcaac gggttcacta   1560
ccggccgccg aggtgacctg gccaccattc atggcatgaa ccggcctttc ctgcttctca   1620
tggccacccc gctggagagg gccagcatc  tgcaaagctc ccggcaccgc cgagccctgg   1680
acaccaacta tgcttcagc  tccacggaga gaaactgctg cgtgcggcag ctgtacattg   1740
acttccgcaa ggactcggc  tggaagtgga tccacgaccg caagggctac catgccaact   1800
tctgcctcgg gccctgccc  tacatttgga gctggacaca gcagtacagc aaggtcctgg   1860
ccctgtacaa ccagcataac ccgggcgcct cggcggcgcc gtgctgcgtg ccgcaggcgc   1920
tggagccgct gcccatcgtg tactacgtgg gccgcaagcc caaggtggag cagctgtcca   1980
acatgatcgt gcgctcctgc aagtgcagct gaggtcccgc cccgccccgc ccgccccga   2040
caggcccggg ccaccccgc  gcccccccg  ctgccttgcc catggggggct gtatttaagg   2100
acacccgtgc cccaagccca cctgggggcc cattaaagat ggagagagga ctgcggatct   2160
ctgtgtcatt gggcgcctgc ctgggtctc  catccctgac gttccccac  tccactccc    2220
tctctctccc tctctgcctc ctcctgcctg tctgcactat tcctttgccc ggcatcaagg   2280
cacagggac  cagtggggaa cactactgta gttagatcta tttattgagc accttgggca   2340
ctgttgaagt gccttacatt aatgaactca ttcagtcaac atgcaacaat tctgagatgc   2400
agggactctg ataacaccca ttttaaaggt gaggaaacaa gcccagagag gttaaggag    2460
gagttcctgc ccaccaggaa cctgcttag  tgggggatag tgaagaagac aataaaagat   2520
agtagttcag gccaggcggg gtggctcacg cctgtaatcc tagcacttt  gggaggcaga   2580
gatgggagga ttacttgaat ccaggcattt gagaccagcc tgggtaacat agtgagaccc   2640
tatctctaca aacacttttt aaaaaatgta cacctgtggt cccagctact ctggaggcta   2700
```

```
aggtgggagg atcacttgat cctgggaggt caaggctgca g                  2741

SEQ ID NO: 5              moltype = AA  length = 760
FEATURE                   Location/Qualifiers
source                    1..760
                          mol_type = protein
                          organism = Homo sapiens
SEQUENCE: 5
MKTWVKIVFG VATSAVLALL VMCIVLRPSR VHNSEENTMR ALTLKDILNG TFSYKTFFPN    60
WISGQEYLHQ SADNNIVLYN IETGQSYTIL SNRTMKSVNA SNYGLSPDRQ FVYLESDYSK   120
LWRYSYTATY YIYDLSNGEF VRGNELPRPI QYLCWSPVGS KLAYVYQNNI YLKQRPGDPP   180
FQITFNGREN KIFNGIPDWV YEEEMLATKY ALWWSPNGKF LAYAEFNDTD IPVIAYSYYG   240
DEQYPRTINI PYPKAGAKNP VVRIFIIDTT YPAYVGPQEV PVPAMIASSD YYFSWLTWVT   300
DERVCLQWLK RVQNVSVLSI CDFREDWQTW DCPKTQEHIE ESRTGWAGGF FVSTPVFSYD   360
AISYYKIFSD KDGYKIHYI KDTVENAIQI TSGKWEAINI FRVTQDSLFY SSNEFEEYPG   420
RRNIYRISIG SYPPSKKCVT CHLRKERCQY YTASFSDYAK YYALVCYGPG IPISTLHDGR   480
TDQEIKILEE NKELENALKN IQLPKEEIKK LEVDEITLWY KMILPPQFDR SKKYPLLIQV   540
YGGPCSQSVR SVFAVNWISY LASKEGMVIA LVDGRGTAFQ GDKLLYAVYR KLGVYEVEDQ   600
ITAVRKFIEM GFIDEKRIAI WGWSYGGYVS SLALASGTGL FKCGIAVAPV SSWEYYASVY   660
TERFMGLPTK DDNLEHYKNS TVMARAEYFR NVDYLLIHGT ADDNVHFQNS AQIAKALVNA   720
QVDFQAMWYS DQNHGLSGLS TNHLYTHMTH FLKQCFSLSD                          760

SEQ ID NO: 6              moltype = DNA  length = 2837
FEATURE                   Location/Qualifiers
source                    1..2837
                          mol_type = genomic DNA
                          organism = Homo sapiens
SEQUENCE: 6
actcacagtt catttgaggg ccaagaacgc cccaaaatc tgtttctaat tttacagaaa     60
tcttttgaaa cttggcacgg tattcaaaag tccgtggaaa gaaaaaaacc ttgtcctggc   120
ttcagcttcc aactacaaag acagacttgg tccttttcaa cggttttcac agatccagtg   180
acccacgctc tgaagacaga attagctaac tttcaaaaac atctggaaaa atgaagactt   240
gggtaaaaat cgtatttgga gttgccacct ctgctgtgct tgccttattg gtgatgtgca   300
ttgtcttacg cccttcaaga gttcataact tgaagaaaca taacatgaga gcactcacac   360
tgaaggatat tttaaatgga acattttctt ataaaacatt ttttccaaac tggatttcag   420
gacaagaata tcttcatcaa tctgcagata acaatatagt actttataat attgaaacag   480
gacaatcata taccatttg agtaataga ccatgaaaag tgtgaatgct tcaaattacg   540
gcttatcacc tgatcggcaa tttgtatatc tagaaagtga ttattcaaag ctttggagat   600
actcttacac agcaacatat tacatctatg accttagcaa tggagaattt gtaagaggaa   660
atgagcttcc tcgtcaatt cagtatttat gctggtcgcc tgttgggagt aaattagcat   720
atgtctatca aaacaatatc tatttgaaac aaagaccagg agatccacct tttcaaataa   780
catttaatgg aagagaaaat aaaatattta tggaatcccc agactgggtt tatgaagagg   840
aaatgcttgc tacaaaatat gctctctgtt ggtctcctaa tggaaaattt ttggcatatg   900
cggaatttaa tgatacggat ataccagtta ttgcctattc ctattatggc gatgaacaat   960
atcctagaac aataaaatatt ccataccaa aggctggagc taagaatccc gttgttcgga  1020
tatttattat cgataccact taccctgcgt atgtaggtcc ccaggaagtg cctgttccag  1080
caatgatagc ctcaagtgat tattatttca gttggctcac gtggttact gatgaacgag  1140
tatgttttgca gtggctaaaa agagtccaga atgtttcggt cctgtctata tgtgacttca  1200
gggaagactg gcagacatgg gattgtccaa agacccagga gcatagaaa gaaagcagaa  1260
ctggatgggc tggtggattc tttgtttcaa caccagtttt cagctatgat gccatttcgt  1320
actacaaat atttagtgac aaggatggct acaaacatat tcactatatc aaagacactg  1380
tggaaaatgc tattcaaatt acaagtggca gtgggaggc cataaatata ttcagagtaa  1440
cacaggattc actgttttat tctagcaatg aatttgaaga ataccctgga agaagaaaca  1500
tctacagaat tagcattgga agctatcctc caagcaagaa gtgtgttact tgccatctaa  1560
ggaaagaaag gtgccaatat tacacaagcaa gtttcagcga ctacgccaag tactatgcac  1620
ttgtctgcta cggcccaggc atccccattt ccacccttca tgatggacgc actgatcaag  1680
aaattaaat cctggaagaa aacaaggaat tggaaaatgc tttgaaaaat atccagctgc  1740
ctaaagagga aattaagaaa cttgaagtag atgaaattac tttatggtac aagatgattc  1800
ttcctcctca atttgacaga tcaaagaagt atcccttgct aattcaagtg tatggtggtc  1860
cctgcagtca gagtgtaagg tctgtatttg ctgttaattg gatatcttat cttgcaagta  1920
aggaagggat ggtcattgcc ttggtggatg gtcgaggaac agcttccaa ggtgacaaac  1980
tcctctatgc agtgtatcga aagctgggtg tttatgaagt tgaagaccag attacagctg  2040
tcagaaaatt catagaaatg ggtttcattg atgaaaaaag aatagccata tggggctggt  2100
cctatggagg atacgtttca tcactgccc ttgcatctgg aactggtctt ttcaaatgtg  2160
gtatagcagt ggctccagtc tccagctggg aatattacgc gtctgtctac acagagagat  2220
tcatgggtct cccaacaaag gatgataatc ttgagcacta taagaattca actgtgatgg  2280
caagagcaga atatttcaga aatgtagact atcttctcat ccacggaaca gcagatgata  2340
atgtgcactt tcaaaactca gcacagattg ctaaagctct ggttaatgca caagtggatt  2400
tccaggcaat gtggtactct gaccagaacc acggcttatc cggcctgtcc acgaaccact  2460
tataccccca catgaccccac ttcctaaagc agtgttttc tttgtcagac taaaaacgat  2520
gcagatgcaa gcctgctatca gaatctgaaa acctatata aacccctcag acagtttgct  2580
tatttttattt tttatgttgt aaaatgctag tataaacaaa caattaatg ttgttctaaa  2640
ggctgttaaa aaaagatga ggactcagaa gttcaagcta aatattgttt acattttctg  2700
gtactctgtg aaagaagaga aaagggagtc atgcattttg ctttggacac agtgtttat  2760
cacctgttca tttgaagaaa aataataaag tcagaagttc aagtgctaaa aaaaaaaaaa  2820
aaaaaaaaaa aaaaaa                                                    2837

SEQ ID NO: 7              moltype = AA  length = 412
FEATURE                   Location/Qualifiers
```

```
source                      1..412
                            mol_type = protein
                            organism = Homo sapiens
SEQUENCE: 7
MTDRQTDTAP SPSYHLLPGR RRTVDAAASR GQGPEPAPGG GVEGVGARGV ALKLFVQLLG    60
CSRFGGAVVR AGEAEPSGAA RSASSGREEP QPEEGEEEEE KEEERGPQWR LGARKPGSWT   120
GEAAVCADSA PAARAPQALA RASGRGGRVA RRGAEESGPP HSPSRRGSAS RAGPGRASET   180
MNFLLSWVHW SLALLLYLHH AKWSQAAPMA EGGGQNHHEV VKFMDVYQRS YCHPIETLVD   240
IFQEYPDEIE YIFKPSCVPL MRCGGCCNDE GLECVPTEES NITMQIMRIK PHQGQHIGEM   300
SFLQHNKCEC RPKKDRARQE KKSVRGKGKG QKRKRKKSRY KSWSVYVGAR CCLMPWSLPG   360
PHPCGPCSER RKHLFVQDPQ TCKCSCKNTD SRCKARQLEL NERTCRCDKP RR           412

SEQ ID NO: 8                moltype = DNA  length = 3677
FEATURE                     Location/Qualifiers
source                      1..3677
                            mol_type = genomic DNA
                            organism = Homo sapiens
SEQUENCE: 8
tcgcggaggc ttggggcagc cgggtagctc ggaggtcgtg gcgctggggg ctagcaccag     60
cgctctgtcg ggaggcgcag cggttaggtg gaccggtcag cggactcacc ggccagggcg    120
ctcggtgctg gaatttgata ttcattgatc cgggttttat ccctcttctt ttttcttaaa    180
cattttttt taaaactgta ttgtttctcg ttttaattta tttttgcttg ccattcccca    240
cttgaatcgg gccgacggct tggggagatt gctctacttc cccaaatcac tgtggatttt    300
ggaaaccagc agaaagagga aagaggtagc aagagctcca gagagaagtc gaggaagaga    360
gagacgggt cagagagagc gcgcgggcgt gcgagcagcg aaagcgacag ggcaaagtg      420
agtgacctgc ttttgggggt gaccgccgga gcgcggcgtg agccctcccc ccttgggatcc    480
cgcagctgac cagtcgcgct gacgacagag cagacagaca ccgcccccag cccccagctac   540
cacctcctcc ccggccggcg gcggacagtg gacgcggcgg cgagccgcgg gcaggggccg    600
gagcccgcgc ccggaggcgg ggtggagggg gtcgggctcg gcggcgtcgc actgaaactt    660
ttcgtccaac ttctgggctg ttctcgcttc ggaggagccg tggtccgcgc ggggggaagcc  720
gagccgagcg gagccgcgag aagtgctagc tcgggccggg aggagccgca gccggaggag    780
ggggaggagg aagaagagaa ggaagaggag aggggggccgc agtggcgact cggcgctcgg   840
aagccgggct catggacggg tgaggcgcg gtgtgcgcag acagtgctcc agccgcgcgc     900
gctccccagg ccctggcccg ggcctcgggc cggggaggaa gagtagctcg ccgaggcgcc    960
gaggagagcg ggccgcccca cagcccgagc cggagaggga gcgcgagccg cgccggcccc   1020
ggtcgggcct ccgaaaccat gaactttctg ctgtctttgg gtgcattgga gccttgcttg   1080
ctgctctacc tccaccatgc caagtggtcc caggctgcac ccatggcaga aggaggaggg   1140
cagaatcatc acgaagtggt gaagttcatg gatgtctatc agcgcagcta ctgccatcca   1200
atcgagaccc tggtggacat cttccaggag taccctgatg agatcgagta catcttcaag   1260
ccatcctgtg tgcccctgat gcgatgcggg ggctgctgca atgacgaggg cctggagtgt   1320
gtgcccactg aggagtccaa catcaccatg cagattatgc ggatcaaacc tcaccaaggc   1380
cagcacatag agagatgag cttcctacag cacaacaaat gtgaatgcag accaaagaaa    1440
gatagagcaa gacaagaaaa aaaatcagtt cgaggaaagg gaaaggggca aaaacgaaag   1500
cgcaagaaat cccggtataa gtcctggagc gtgtacgttg gtgcccgctg ctgtctaatg   1560
ccctggagcc tccctggccc ccatccctgt gggccttgct cagagcggag aaagcatttg   1620
tttgtacaag atccgcagac gtgtaaatgt tcctgcaaaa acacagactc gcgttgcaag   1680
gcgagggcgc ttgagttaaa cgaacgtact tgcagatgtg acaagccgag gcggtgagcc   1740
gggcaggagg aaggagcctc cctcaggggt tcgggaacca gatctctcac caggaaagac   1800
tgatacagaa cgatcgatac agaaaccacg ctgccgccac cacaccatca ccatcgacag   1860
aacagtcctt aatccagaaa cctgaaatga aggaagagga gactctgcgc agagcacttt   1920
gggtccggag ggcgagactc cggcggaagc attcccggcc gggtgaccca gcacggtcca   1980
tcttggaatt ggattcgcca tttattttt cttgctgcta aatcaccgag cccgaaagat   2040
tagagagttt tatttctggg attcctgtag acacacccac ccacatacat acatttatat   2100
atatatatat tatatatata taaaaataaa tatctctatt ttatatatat aaaatatata   2160
tattcttttt ttaaattaac agtgctaatg ttattggtgt cttcactgga tgtatttgac   2220
tgctgtggac ttgagttggg aggggaatgt tcccactcag atcctgacag ggaagaggag   2280
gagatgagag actctggcat gatctttttt ttgtcccact tggtgggcc agggtcctct    2340
cccctgccca ggaatgtgca aggccagggc atggggcaa atatgaccca gttttgggaa   2400
caccgacaaa cccagccctg gcgctgagcc tctctacccc aggtcagacg gacagaaaga   2460
cagatcacag gtacagggat gaggacaccg gctctgacca ggagtttggg gagcttcagg   2520
acattgctgt gctttgggga ttccctccac atgctgcacg cgcatctcgc ccccaggggc   2580
actgcctgga agattcagga gcctgggcgg ccttcgctta ctctcacctg cttctgagtt   2640
gcccaggaga ccactggcag atgtcccggc gaagagaaga gacacattgt tggaagaagc   2700
agcccatgac agctcccctt cctgggactc gccctcatcc tcttcctgct ccccttcctg   2760
gggtgcagcc taaaaggacc tatgtcctca caccattgaa accactagtt ctgtcccccc   2820
aggagacctg gttgtgtgtg tgtgagtggt tgacttcct ccatccctg gtccttccct    2880
tcccttcccg aggcacagag agacagggca ggatccacgt gcccattgtg gaggcagaga   2940
aaagagaaag tgttttatat acggtactta tttaataccc ttttttaatt agaaattaaa   3000
acagttaatt taattaaaga gtaggtttt ttttcagtat tcttggttaa tatttatttt    3060
caactattta tgagatgtat cttttgctct ctcttgctct cttatttgta ccggttttg     3120
tatataaaat tcatgtttcc aatctctctc tccctgatcg gtgacagtca ctagcttatc   3180
ttgaacagat atttaatttt gctaacactc agctctgccc tccccgatcc cctggctccc   3240
cagcacacat tcctttgaaa taaggtttca atatacatct acatactata tatatatttg   3300
gcaacttgta tttgtgtgta tatatatata tatatgttta ttatctgtat tgattctgat   3360
aaaatagaca ttgctattct gttttttata tgtaaaaaca aaacaagaaa aaatagaaa    3420
ttctacatac taaatctctc tcctttttta atttttaatt ttgttatcat ttatttattg   3480
gtgctactgt ttatccgtaa taattgtggg gaaaagatat taacatcacg tcttttgtctc   3540
tagtgcagtt tttcgagata ttccgtagta catatttatt tttaaacaac gacaaagaaa   3600
tacagatata tcttaaaaaa aaaaaagcat tttgtattaa agaatttaat tctgatctca   3660
```

```
aaaaaaaaaa aaaaaaa                                                    3677

SEQ ID NO: 9            moltype = AA  length = 496
FEATURE                 Location/Qualifiers
source                  1..496
                        mol_type = protein
                        organism = Homo sapiens
SEQUENCE: 9
MWQIVFFTLS CDLVLAAAYN NFRKSMDSIG KKQYQVQHGS CSYTFLLPEM DNCRSSSSPY     60
VSNAVQRDAP LEYDDSVQRL QVLENIMENN TQWLMKLENY IQDNMKKEMV EIQQNAVQNQ    120
TAVMIEIGTN LLNQTAEQTR KLTDVEAQVL NQTTRLELQL LEHSLSTNKL EKQILDQTSE    180
INKLQDKNSF LEKKVLAMED KHIIQLQSIK EEKDQLQVLV SKQNSIIEEL EKKIVTATVN    240
NSVLQKQQHD LMETVNNLLT MMSTSNSAKD PTVAKEEQIS FRDCAEVFKS GHTTNGIYTL    300
TFPNSTEEIK AYCDMEAGGG GWTIIQRRED GSVDFQRTWK EYKVGFGNPS GEYWLGNEFV    360
SQLTNQQRYV LKIHLKDWEG NEAYSLYEHF YLSSEELNYR IHLKGLTGTA GKISSISQPG    420
NDFSTKDGDN DKCICKCSQM LTGGWWFDAC GPSNLNGMYY PQRQNTNKFN GIKWYYWKGS    480
GYSLKATTMM IRPADF                                                   496

SEQ ID NO: 10           moltype = DNA  length = 5270
FEATURE                 Location/Qualifiers
source                  1..5270
                        mol_type = genomic DNA
                        organism = Homo sapiens
SEQUENCE: 10
aaagtgattg attcggatac tgacactgta ggatctgggg agagaggaac aaaggaccgt     60
gaaagctgct ctgtaaaagc tgacacagcc ctcccaagtg agcaggactg ttcttcccac    120
tgcaatctga cagtttactg catgcctgga gagaacacag cagtaaaaac caggtttgct    180
actggaaaaa gaggaaagag aagactttca ttgacggacc cagccatggc agcgtagcag    240
ccctgcgttt tagacggcag cagctcggga ctctggacgt gtgtttgccc tcaagtttgc    300
taagctgctg gtttattact gaagaaagaa tgtggcagat tgttttcttt actctgagct    360
gtgatcttgt cttggccgca gcctataaca actttcggaa gagcatggac agcataggaa    420
agaagcaata tcaggtccag catgggtcct gcagctacac tttcctcctg ccagagatgg    480
acaactgccg ctcttcctcc agccctacg tgtccaatgc tgtgcagagg gacgcgccgc     540
tcgaatacga tgactcggtg cagaggctgc aagtgctgga gaacatcatg gaaaacaaca    600
ctcagtggct aatgaagctt gagaattata tccaggacaa catgaagaag gaaatggtag    660
agatacagca gaatgcagta cagaaccaga cggctgtgat gatagaaata gggacaaacc    720
tgttgaacca acagcggag caaacgcgga gttaactga tgtggaagcc caagtattaa      780
atcagaccac gagacttgaa cttcagctct ggaacactc cctctcgaca aacaaattgg     840
aaaaacagat tttggaccag accagtgaaa taaaaaatc gcaagataag aacagtttcc    900
tagaaaagaa ggtgctagct atggaagaca agcacatcat ccaactacag tcaataaag    960
aagagaaaga tcagctacag gtgttagtat ccaagcaaaa ttccatcatt gaagaactag   1020
aaaaaaaaat agtgactgcc acggtgaata attcagttct tcagaagcag caacatgatc   1080
tcatggagac agttaataac ttactgacta tgatgtccac atcaaactca gctaaggacc   1140
ccactgttgc taaagaagaa caaatcagct tcagagactg tgctgaagta ttcaaatcag   1200
gacacaccac gaatggcatc tacacgttaa cattccctaa ttctacagaa gagatcaagg   1260
cctactgtga catggaagct ggaggaggcg ggtggacaat tattcagcga cgtgaggatg   1320
gcagcgttga ttttcagagg acttggaaag aatataaagt ggatttggt aacccttcag    1380
gagaatattg gctgggaaat gagtttgttt cgcaactgac taatcagcaa cgctatgtgc   1440
ttaaaataca ccttaaagac tgggaaggga atgaggctta ctcattgtat gaacatttct   1500
atctctcaag tgaagaactc aattatagga ttcaccttaa aggacttaca gggacagccg   1560
gcaaaataag cagcatcagc caaccaggaa atgattttag cacaaaggat ggagacaacg   1620
acaaatgtat ttgcaaatgt tcacaaatgc taacaggagg ctggtggttt gatgcatgtg   1680
gtccttccaa cttgaacgga atgtactatc cacagaggca gaacacaaat aagttcaacg   1740
gcattaaatg gtactactgg aaaggctcag gctattcgct caaggccaca accatgatga   1800
tccgaccagc agatttctaa acatcccagt ccacctgagg aactgtctcg aactattttc   1860
aaagacttaa gcccagtgca ctgaaagtca cggctgcgca ctgtgtcctc ttccaccaca   1920
gagggcgtgt gctcggtgct gacgggaccc acatgctcca gattagagcc tgtaaacttt   1980
atcacttaaa cttgcatcac ttaacggacc aaagcaagac cctaaacatc cataattgtg   2040
attagacaga acacctatgc aaagatgaac ccgaggctga gaatcagact gacagtttac   2100
agacgctgct gtcacaacca agaatgttat gtgcaagttt atcagtaaat aactggaaaa   2160
cagaacactt atgttataca atacagatca tcttggaact gcattcttct gagcactgtt   2220
tatacactgt gtaaatacc atatgtcctg aattcaccat cactatcaca attaaaagga    2280
agaaaaaaac tctctaagcc ataaaagac atattcaggg atattctgag aaggggttac    2340
tagaagttta atatttggaa aaacagttag tgcattttta ttccatctct taggtgcttt   2400
aaattttttat ttcaaaaaca gcgtatttac atttatgttg acagcttagt tataagttaa   2460
tgctcaaata cgtatttcaa atttatatgg tagaaacttc cagaatctct gaaattatca   2520
acagaaacgt gccattttag tttatatgca gaccgtacta ttttttttctg cctgattgtt   2580
aaatatgaag gtattttag taattaaata taacttatta ggggatatgc ctatgtttaa    2640
ctttttatgat aatatttaca atttataat tgtttccaa aagacctaat tgtgccttgt    2700
gataaggaaa cttcttactt ttaatgatga ggaaaattat acatttcatt ctatgacaaa   2760
gaaactttac tatcttctca ctattctaaa acagaggtct gttttctttc ctagtaagat   2820
atattttttat agaactagac tacaatttaa tttctggttg agaaaagcct tctatttaag   2880
aaatttacaa agctatatgt ctcaagattc ccccttaaat ttacttaagg aaaaaaataa   2940
ttgacactga taagttttt tatgtcaatc agcaaactga aaaaaaaaaa aggtttcaa    3000
agtgcaaaaa caaaatctga tgttcataat atatttaaat atttaccaaa aatttgaaaa   3060
cacagggctg ggcgcagtgg ctcacaccta aatcccagt acattggtag gcaaggtggg   3120
cagatcacct gaggtcagga gttcaagacc agcctggaca acatggtgaa accctgtctc    3180
tactaaataa tacaaaaatt agccaggcgt gctggcgggc acctgtaatc ccagctactc   3240
gggaggctga ggcaggaga attgcttgca ccagggaggt agaggttgca gtgagccaag   3300
```

```
atcgcaccac tgcactccag ccggggcaac agagcaagac tccatctcaa aaaaaaaaaa  3360
aaaaaaagaa agaaaagaaa atttgagaac acagctttat actcgggact acaaaaccat  3420
aaactcctgg agtttaaact cctttttgaaa ttttcatagt acaattaata ctaatgaaca  3480
tttgtgtaaa gctttataat ttaaaggcaa tttctcatat attcttttct gaatcatttg  3540
caaggaagtt cagagtccag tctgtaacta gcatctacta tatgtctgtc ttcaccttac  3600
agtgttctac cattatttt tctttattcc atttcaaaat ctaatttatt ttaccccaac   3660
ttctccccac cacttgacgt agttttagaa cacacaggtg ttgctacata tttggagtca  3720
atgatggact ctggcaaagt caaggctctg ttttatttcc accaaggtgc acttttccaa  3780
caactattta actagttaag aacctcccta tcttagaact gtatctactt tatatttaag  3840
aaggttttat gaattcaaca acggtatcat ggccttgtat caagttgaaa aacaactgaa  3900
aataagaaaa tttcacagcc tcgaaagaca acaacaagtt tctaggatat ctcaatgaca  3960
agagtgatgg atacttaggt agggaaacgc taatgcagga aaaactggca acaacacaat  4020
ttatatcaat tctctttgta ggcaggtgat aaaaaattca aggacaaatc tcattatgtc  4080
attgtgcatc atatataatc tcttatgagc gagaatgggg ggaatttgtg tttttactttt  4140
acacttcaat tccttacacg gtatttcaaa caaacagttt tgctgagagg agcttttgtc  4200
tctccttaag aaaatgttta taagctgaaa aggaaatcaa acagtaatct taaaaatgaa  4260
aacaaaacaa cccaacaacc tagataacta cagtgatcag ggagcacagt tcaactcctt  4320
gttatgttt agtcatatgg cctactcaaa cagctaaata acaacaccag tggcagataa  4380
aaatcaccat ttatctttca gctattaatc ttttgaatga ataaactgtg acaaacaaat  4440
taacatttt gaacatgaaa ggcaacttct gcacaatcct gtatccaagc aaactttaaa  4500
ttatccactt aattattact taatcttaaa aaaaattaga acccagaact tttcaatgaa  4560
gcatttgaaa gttgaagtgg aatttaggaa agccataaaa atataaatac tgttatcaca  4620
gcaccagcaa gccataatct ttatacctat cagttctatt tctattaaca gtaaaaacat  4680
taagcaagat ataagactac ctgcccaaga attcagtctt ttttcatttt tgtttttctc  4740
agttctgagg atgttaatcg tcaaattttc tttggactgc attcctcact acttttttgca  4800
caatggtctc acgttctcac atttgttctc gcgaataaat tgataaaagg tgttaagttc  4860
tgtgaatgtc ttttaatta tgggcataat tgtgcttgac tggataaaaa cttaagtcca  4920
cccttatgtt tataataatt tcttgagaac agcaaactgc atttaccatc gtaaaacaac  4980
atctgactta cgggagctgc agggaagtgg tgagacagtt cgaacggctc ctcagaaatc  5040
cagtgaccca attctaaaga ccatagcacc tgcaagtgac aacaagca gatttattat  5100
acatttatta gccttagcag gcaataaacc aagaatcact ttgaagacac agcaaaaagt  5160
gatacactcc gcagatctga aatagatgtg ttctcagaca acaaagtccc ttcagaatct  5220
tcatgttgca taaatgttat gaatattaat aaaaagttga ttgagaaaaa              5270

SEQ ID NO: 11         moltype = AA   length = 290
FEATURE               Location/Qualifiers
source                1..290
                      mol_type = protein
                      organism = Homo sapiens
SEQUENCE: 11
MRIFAVFIFM TYWHLLNAFT VTVPKDLYVV EYGSNMTIEC KFPVEKQLDL AALIVYWEME   60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPELP LAHPPNERTH  240
LVILGAILLC LGVALTFIFR LRKGRMMDVK KCGIQDTNSK KQSDTHLEET            290

SEQ ID NO: 12         moltype = DNA   length = 3691
FEATURE               Location/Qualifiers
source                1..3691
                      mol_type = genomic DNA
                      organism = Homo sapiens
SEQUENCE: 12
ggcgcaacgc tgagcagctg gcgcgtcccg cgcggcccca gttctgcgca gcttcccgag    60
gctccgcacc agccgcgctt ctgtccgcct gcagggcatt ccagaaagat gaggatattt   120
gctgtcttta tattcatgac ctactggcat ttgctgaacg catttactgt cacggttgtc   180
aaggacctat atgtggtaga gtatggtagc aatatgacaa ttgaatgcaa attcccagta   240
gaaaaacaat tagacctggc tgcactaatt gtctattggg aaatggagga taagaacatt   300
attcaatttg tgcatggaga ggaagacctg aaggttcagc atagtagcta cagacagagg   360
gcccggctgt tgaaggacca gctctccctg ggaaatgctg cacttcagat cacagatgtg   420
aaattgcagg atgcagggt gtaccgctgc atgatcagct atggtggtgc cgactacaag   480
cgaattactg tgaaagtcaa tgccccatac aacaaaatca accaaagaat tttggttgtg   540
gatccagtca cctctgaaca tgaactgaca tgtcaggctg agggctaccc caaggccgaa   600
gtcatctgga agcagtgacc atcaagtc ctgagtggta agaccaccac caccaattcc   660
aagagagagg agaagctttt caatgtgacc agcacactga gaatcaacac aacaactaat   720
gagattttct actgcacttt taggagatta gatcctgagg aaaaccatac agctgaattg   780
gtcatcccag aactacctct ggcacatcct ccaaatgaaa ggactcactt ggtaattctg   840
ggagccatct tattatgcct tggtgtagca ctgacattca tcttccgttt aagaaaaggg   900
agaatgatgg atgtgaaaaa atgtggcatc caagatacaa actcaaagaa gcaagtgat   960
acacatttgg aggagacgta atccagcatt ggaacttctg atcttcaagc agggattctc  1020
aacctgtggt ttaggggttc atcggggctg agcgtgacaa gaggaaggaa tgggcccgtg  1080
ggatgcaggc aatgtgggac ttaaaaggcc caagcactga aaatgaacc tggcaaaagc  1140
agaggaggag aatgaagaaa gatggagtca acagggagc ctggagggag accttgatac  1200
tttcaaatgc ctgaggggct catcgacgcc tgtgacaggg agaaaggata cttctgaaca  1260
aggagccgca aagcaaatca tccattgctc atcctagga gacgggttga gaatccctaa  1320
tttgagggtc agttcctgca gaagtgccct ttgcctccac tcaatgcctc aatttgtttt  1380
ctgcatgact gagagtctca gtgttggaac gggacagtat ttatgtatga gttttcctta  1440
tttatttga gtctgtgagg tcttcttgtc atgtgagtgt ggttgtgaat gatttctttt   1500
gaagatatat tgtagtagat gttacaattt tgtcgccaaa ctaaacttgc tgcttaatga   1560
tttgctcaca tctagtaaaa catggagtat ttgtaaggtg cttggtctcc tctataacta   1620
```

```
caagtataca ttggaagcat aaagatcaaa ccgttggttg cataggatgt cacctttatt    1680
taacccatta atactctggt tgacctaatc ttattctcag acctcaagtg tctgtgcagt    1740
atctgttcca tttaaatatc agctttacaa ttatgtggta gcctacacac ataatctcat    1800
ttcatcgctg taaccaccct gttgtgataa ccactattat tttacccatc gtacagctga    1860
ggaagcaaac agattaagta acttgcccaa accagtaaga agcagacctc agactgccac    1920
ccactgtcct tttataatac aatttacagc tatattttac tttaagcaat tctttattc     1980
aaaaaccatt tattaagtgc ccttgcaata tcaatcgctg tgccaggcat tgaatctaca    2040
gatgtgagca agacaaagta cctgtcctca aggagctcat agtataatga ggagattaac    2100
aagaaaatgt attattacaa tttagtccag tgtcataaga taaggatgat gcgagggaa     2160
aaccccgagca gtgttgccaa gaggaggaaa taggccaatg tggtctggga cggttggata   2220
tacttaaaca tcttaataat cagagtaatt ttcatttaca aagagaggtc ggtacttaaa    2280
ataaccctga aaataacac tggaattcct tttctagcat tatatttatt cctgatttgc     2340
ctttgccata taatctaatg cttgtttata tagtgtctgg tattgtttaa cagttctgtc    2400
ttttctattt aaatgccact aaattttaaa ttcataccctt tccatgattc aaaattcaaa   2460
agatcccatg ggagatggtt ggaaaatctc cacttcatcc tccaagccat tcaagtttcc    2520
tttccagaag caactgctac tgcctttcat tcatatgttc ttctaaagat agtctacatt    2580
tggaaatgta tgttaaaagc acgtattttt aaaattttt tcctaaatag taacacattg     2640
tatgtctgct gtgtactttg ctattttat ttattttagt gtttcttata tagcagatgg     2700
aatgaatttg aagttcccag ggctgaggat ccatgccttc tttgtttcta agttatcttt    2760
cccatagctt tcattatct ttcatatgat ccagtatatg ttaaatatgt cctacatata     2820
catttagaca accaccattt gttaagtatt tgctctagga cagagtttgg atttgtttat    2880
gtttgctcaa aaggagaccc atgggctctc cagggtgcca tgagtcaatc tagtcctaaa    2940
aagcaatctt attattaact ctgtatgaca gaatcatgtc tggaactttt gttttctgct    3000
ttctgtcaag tataaacttc actttgatgc tgtacttgca aaatcacatt ttcttttctgg   3060
aaaattccggc agtgtaccctt gactgctagc taccctgtgc cagaaaagcc tcattcgttg   3120
tgcttgaacc cttgaatgcc accagctgtc atcactacac aggctctta atagggcttcc   3180
tggaggtttc gagattcaga tgccctggga gatcccagag tttcctttcc ctcttggcca    3240
tattctggtg tcaatgacaa ggagtaccttt ggctttgcca catgtcaagg ctgaagaaac   3300
agtgtctcca acagagctcc ttgtgttatc tgtttgtaca tgtgcatttg tacagtaatt    3360
ggtgtgacag tgttctttgt gtgaattaca ggcaagaatt gtggctgagc aaggcacata   3420
gtctactcag tctattccta agtcctaact cctccttgtg gtgttggatt tgtaaggcac    3480
tttatccctt ttgtctcatg tttcatcgta aatggcatag gcagagatga tacctaattc   3540
tgcatttgat tgtcactttt tgtacctgca ttaatttaat aaaatattct tatttatttt   3600
gttacttggt acaccagcat gtccatttc ttgtttattt tgtgtttaat aaaatgttca    3660
gtttaacatc ccagtggaga aagttaaaaa a                                   3691

SEQ ID NO: 13          moltype = AA   length = 249
FEATURE                Location/Qualifiers
source                 1..249
                       mol_type = protein
                       organism = Homo sapiens
SEQUENCE: 13
MAMLRVQPEA QAKVDVFRED LCTKTENLLG SYFPKKISEL DAFLKEPALN EANLSNLKAP    60
LDIPVPDPVK EKEKEERKKQ QEKEDKDEKK KGEDEDKGPP CGPVNCNEKI VVLLQRLKPE   120
IKDVIEQLNL VTTWLQLQIP RIEDGNNFGV AVQEKVFELM TSLHTKLEGF HTQISKYFSE   180
RGDAVTKAAK QPHVGDYRQL VHELDEAEYR DIRLMVMEIR NAYAVLYDII LKNFEKLKKP   240
RGETKGMIY                                                           249

SEQ ID NO: 14          moltype = DNA   length = 1240
FEATURE                Location/Qualifiers
source                 1..1240
                       mol_type = genomic DNA
                       organism = Homo sapiens
SEQUENCE: 14
cacattgttc tgatcatctg aagatcagct attagaagag aaagatcagt taagtccttt    60
ggacctgatc agcttgatac aagaactact gatttcaact tctttggctt aattctctcg   120
gaaacgatga aatatacaag ttatatcttg gcttttcagc tctgcatcgt tttgggttct   180
cttggctgtt actgccagga cccatatgta aagaagcag aaaaccttaa gaaatatttt    240
aatgcaggtc attcagatgt agcggataat ggaactcttt cttaggcat tttgaagaat   300
tggaaagagg agagtgacag aaaaataatg cagagccaaa ttgtctcctt ttacttcaaa   360
cttttttaaaa actttaaaga tgaccagagc atccaaaaga gtgtggagac catcaaggaa   420
gacatgaatg tcaagttttt caatagcaac aaaaagaaac gagatgactt cgaaaagctg   480
actaattatt cggtaactga cttgaatgtc caacgcaaag caatacatga actcatccaa   540
gtgatggctg aactgtcgcc agcagctaaa acagggaagc gaaaaaggag tcagatgctg   600
tttcgaggtc gaagagcatc ccagtaatgg ttgtcctgcc tgcaatattt gaattttaaa   660
tctaaatcta tttattaata tttaacatta tttatatggg gaatatattt ttagactcat   720
caatcaaata agtatttata atagcaactt tgtgtaatg aaaatgaata tctattaata    780
tatgtattat ttataattcc tatatcctgt gactgtctca cttaatcctt tgttttctga   840
ctaattaggc aaggctatgt gattacaagg ctttatctca ggggccaact aggcagccaa   900
cctaagcaag atcccatggg ttgtgtgttt atttcacttg atgatacaat gaacacttat   960
aagtgaagtg atactatcca gttactgccg gtttgaaaat atgcctgcaa tctgagccag  1020
tgctttaatg gcatgtcaga cagaacttga atgtgtcagg tgaccctgat gaaacatag    1080
catctcagga gatttcatgc ctggtgcttc caaatattgt tgacaactgt gactgtaccc   1140
aaatggaaag taactcattt gttaaaatta tcaatatcta atatatatga ataaagtgta   1200
agttcacaac aaaaaaaaaa aaaaaaaaaa aaaaaaaaa                          1240

SEQ ID NO: 15          moltype = AA   length = 1143
FEATURE                Location/Qualifiers
source                 1..1143
```

```
                        mol_type = protein
                        organism = Homo sapiens
SEQUENCE: 15
MKLSRQFTVF  GSAIFCVVIF  SLYLMLDRGH  LDYPRNPRRE  GSFPQGQLSM  LQEKIDHLER   60
LLAENNEIIS  NIRDSVINLS  ESVEDGPKSS  QSNFSQGAGS  HLLPSQLSLS  VDTADCLFAS  120
QSGSHNSDVQ  MLDVYSLISF  DNPDGGVWKQ  GFDITYESNE  WDTEPLQVFV  VPHSHNDPGW  180
LKTFNDYFRD  KTQYIFNNMV  LKLKEDSRRK  FIWSEISYLS  KWWDIIDIQK  KDAVKSLIEN  240
GQLEIVTGGW  VMPDEATPHY  FALIDQLIEG  HQWLENNIGV  KPRSGWAIDP  FGHSPTMAYL  300
LNRAGLSHML  IQRVHYAVKK  HFALHKTLEF  FWRQNWDLGS  VTDILCHMMP  FYSYDIPHTC  360
GPDPKICCQF  DFKRLPGGRF  GCPWGVPPET  IHPGNVQSRA  RMLLDQYRKK  SKLFRTKVLL  420
APLGDDFRYC  EYTEWDLQFK  NYQQLFDYMN  SQSKFKVKIQ  FGTLSDFFDA  LDKADETQRD  480
KGQSMFPVLS  GDFFTYADRD  DHYWSGYFTS  RPFYKRMDRI  MESHLRAAEI  LYYFALRQAH  540
KYKINKFLSS  SLYTALTEAR  RNLGLFQHHD  AITGTAKDWV  VVDYGTRPFH  SLMVLEKIIG  600
NSAFLLILKD  KLTYDSYSPD  TFLEMDLKQK  SQDSLPQKNI  IRLSAEPRYL  VVYNPLEQDR  660
ISLVSVYVSS  PTVQVFSASG  KPVEVQVSAV  WDTANTISET  AYEISFRAHI  PPLGLKVYKI  720
LESASSNSHL  ADYVLYKNKV  EDSGIFTIKN  MINTEEGITL  ENSFVLLRFD  QTGLMKQMMT  780
KEDGKHHEVN  VQFSWYGTTI  KRDKSGAYLF  LPDGNAKPYV  YTTPPFVRVT  HGRIYSEVTC  840
FFDHVTHRVR  LYHIQGIEGQ  SVEVSNIVDI  RKVYNREIAM  KISSDIKSQN  RFYTDLNGYQ  900
IQPRMTLSKL  PLQANVYPMT  TMAYIQDAKH  RLTLLSAQSL  GVSSLNSGQI  EVIMDRRLMQ  960
DDNRGLEQGI  QDNKITANLF  RILLEKRSAV  NTEEEKKSVS  YPSLLSHITS  SLMNHPVIPM 1020
ANKFSPTLEL  QGEFSPLQSS  LPCDIHLVNL  RTIQSKVGNG  HSNEAALILH  RKGFDCRFSS 1080
KGTGLFCSTT  QGKILVQKLL  NKFIVESLTP  SSLSLMHSPP  GTQNISEINL  SPMEISTFRI 1140
QLR                                                                   1143

SEQ ID NO: 16          moltype = DNA  length = 7114
FEATURE                Location/Qualifiers
source                 1..7114
                       mol_type = genomic DNA
                       organism = Homo sapiens
SEQUENCE: 16
ggcggggcca  gccgcccgct  cggctcaggc  gctgcgggcg  cctattgacc  cagcggctgc   60
tgcgccgccg  ctgtctcctc  ctgctcgtgg  cgggcggtgc  tggagcgcca  agtggcgctg  120
gagaaccggc  gcttcctttc  gccgcttccg  ccgccatctc  cgcgtttgtg  gggcgggaaa  180
gagggagggg  gctagcggcg  gcagctggag  cgggcttctc  tccggggacg  gtcctttcct  240
ccctgctctc  cttttccttc  tttcgcgctt  gccgccgccc  gccccctgcc  cctcccccgg  300
gagcctgggt  ccgggagggg  gaaggtaggg  gcggcggggg  gcggcgagag  ctggcgagcg  360
gacgctagct  ctgaggaaac  tcatcaatcc  gtgagcccg  gagtccgggg  tgcacatcgg  420
cccagccgca  gcgtcggcgg  cggcggcggc  agcagcacga  aggggctcag  tcggggtagg  480
cggggcgggt  gccggtgccg  cggggcgggg  cccgaccgtc  ccgcccagaa  gttgtagggc  540
ttggctcctc  gcgatcttgt  tccttttccc  tccgcttctc  tgacctagct  gcgcggcccc  600
ggcccgggag  ctgccgaacc  cgcgcctccc  ctgggtgagg  aggacacgcc  tgccctcgtc  660
gagaaaactt  ttcctgccga  ctcagttggg  gcggcggtgg  caggaagtgc  gggcagcgac  720
ctctcctccg  cctgccccgc  cgccctgcc  ggagtcgcg  ctgagcttg  cgatcaagtt  780
tgtgggggcc  cccccttccca  gttgccggcg  agtctcgcct  cgagagggc  gcccgacccc  840
ggggagggcg  gcaggccagg  gcgaaggcca  agggcgtgtg  gtggcgccgg  agactaggtg  900
cggagcaagg  cggggactcg  cacccgcatc  cgagagcgcg  gaggtcgcgc  agcccgggag  960
aagggagcct  ccggcagtgg  cttcctagag  tccacagtgg  gctgtctcct  ttggctgagg 1020
agagtgtcct  ggccccgagt  ctatcgagga  aaatgaagtt  aagccgccag  ttcaccgtgt 1080
tcggcagtgc  gatcttctgt  gtggtgattt  tctcgctcta  cctgatgctg  gaccggggtc 1140
acttagacta  ccccaggaac  ccgcgccgcg  agggctcctt  cctcagggc  cagctctcaa 1200
tgttgcaaga  aaaaatagac  catttggagc  gtttgctagc  tgagaataat  gagatcatct 1260
caaatattag  agactcagtc  atcaatttga  gtgagtctgt  ggaggatggt  ccgaaaagtt 1320
cacaaagcaa  tttcagccaa  ggtgctggct  cacatcttct  gccctcacaa  ttatccctct 1380
cagttgcac   tgcagactgt  ctgtttgctt  cacaaagtgg  aagtcacaat  tcagatgtgc 1440
agatgttgga  tgtttacagt  ctaatttctt  ttgacaatcc  agatggttga  gtttggaagc 1500
aaggatttga  cattacttat  gaatctaatg  aatgggacac  tgaacccctt  caagtctttg 1560
tggtgcctca  ttcccataac  gacccaggtt  ggttgaagac  tttcaatgac  tactttagag 1620
acaagactca  gtatattttt  aataacatgg  tcctaaagct  gaaagaagac  tcacggagga 1680
agtttatttg  gtctgagatc  tcttaccttt  caaagtggtg  ggatattata  gatattcaga 1740
agaaggatgc  tgttaaaagt  ttaatagaaa  atgggcagct  tgaaattgtg  acaggtggct 1800
gggttatgcc  tgatgaagct  actccacatt  attttgcctt  aattgatcaa  ctaattgaag 1860
gacatcagtg  gctggaaaat  aatataggag  tgaaacctcg  gtccggctgg  gctattgatc 1920
cctttggaca  ctcaccaaca  atggcttatc  ttctaaaccg  tgctggactt  tctcacatgc 1980
ttatccagag  agttcattat  gcagttaaaa  aacactttga  actgcataaa  acattggagt 2040
tttttttggag  acagaattgg  gatctgggat  ctgtcacaga  tattttatgc  cacatgatgc 2100
ccttctacag  ctatgacatc  cctcacactt  gtggacctga  tcctaaaata  tgctgccagt 2160
ttgattttaa  acgtcttcct  ggaggcagat  tggttgtcc   ctgggagtc   ccccagaaa  2220
caatacatcc  tggaaatgtc  caaagcaggg  ctcggatgct  actagatcag  taccgaaaga 2280
agtcaaagct  ttttcgtacc  aaagttctcc  tggctccact  aggagatgtt  ttccgctact 2340
gtgaatacac  ggaatgggat  ttacagttta  agaattatca  gcagcttttt  gattatatga 2400
attctcagtc  caagttttaaa gttaagatac  agtttggaac  tttatcagat  ttttttgatg 2460
cgctggataa  agcagatgaa  actcagagag  acaagggcca  atcgatgttc  cctgttttaa 2520
gtggagattt  tttcacttat  gccgatcgag  atgatcatta  ctggagtggc  tattttacat 2580
ccagaccctt  ttacaagcga  atggacagaa  tcatgaaact  ctttagggct  gctgaaa    2640
ttctttacta  tttcgccctg  agacaagctc  acaaatacaa  gataaataaa  tttctctcat 2700
catcacttta  cacggcactg  acagaagcca  aaggaatttt  gggactgttt  caacatcatg 2760
atgctatcac  aggaactgca  aaagactggg  tggttgtgga  ttatggtacc  agacttttc  2820
attcgttaat  ggttttggag  aagataattg  gaaattctgc  atttcttctt  attttgaagg 2880
acaaactcac  atacgactct  tactctcctg  ataccttcct  ggagatggat  ttgaaacaaa 2940
```

-continued

```
aatcacaaga ttctctgcca caaaaaaata taataaggct gagtgcggag ccaaggtacc 3000
ttgtggtcta taatccttta gaacaagacc gaatctcgtt ggtctcagtc tatgtgagtt 3060
ccccgacagt gcaagtgttc tctgcttcag gaaaacctgt ggaagttcaa gtcagcgcag 3120
tttgggatac agcaaatact atttcagaaa cagcctatga gatctctttt cgagcacata 3180
taccgccatt gggactgaaa gtgtataaga ttttggaatc agcaagttca aattcacatt 3240
tagctgatta tgtcttgtat aagaataaag tagaagatag cggaattttc accataaaga 3300
atatgataaa tactgaagaa ggtataacac tagagaactc ctttgtttta cttcggtttg 3360
atcaaactgg acttatgaag caaatgatga ctaaagaaga tggtaaacac catgaagtaa 3420
atgtgcaatt ttcatggtat ggaaccacaa ttaaaagaga caaaagtggt gcctacctct 3480
tcttacctga tggtaatgcc aagcctatg tttacacaac accgcccttt gtcagagtga 3540
cacatggaag gatttattcg gaagtgactt gcttttttga ccatgttact catagagtcc 3600
gactatacca catacaggga atagaaggac agtctgtgga agtttccaat attgtggaca 3660
tccgaaaagt atataaccgt gagattgcaa tgaaaatttc ttctgatata aaaagccaaa 3720
atagatttta tactgaccta aatggtacc agattcaacc tagaatgaca ctgagcaaat 3780
tgcctcttca agcaaatgtc tatcccatga ccacaatggc ctatatccag gatgccaaac 3840
atcgtttgac actgctctct gctcagtcat taggggtttc gagtttgaat agtggtcaga 3900
ttgaagttat catggatcga agactcatgc aagatgataa tcgtggcctt gagcaaggta 3960
tccaggataa caagattaca gctaatctat ttcgaatact actagaaaaa agaagtgctg 4020
ttaatacgga agaagaaaag aagtcggtca gttatccttc tctccttagc cacataactt 4080
cttctctcat gaatcatcca gtcattccaa tggcaaataa gttctcctca cctacccttg 4140
agctgcaagg tgaattctct ccattacagt catctttgcc ttgtgacatt catctggtta 4200
atttgagaac aatacagtca aaggtgggca atgggcactc gagtgaacc gccttgatcc 4260
tccacagaaa agggtttgat tgtcggttcc ctagcaaagg cacagggctg ttttgttcta 4320
ctactcaggg aaagatattg gtacagaaac ttttaaacaa gttattgtc gaaagtctca 4380
caccttcatc actatccttg atgcattcac ctcccggcac tcagaatata agtgagatca 4440
acttgagtcc aatggaaatc agcacattcc gaatccagtt gagtgaacc tgactttcca 4500
atttggattg agaatcattg gcttttatac ctttcttggt ttgacgtgca ataaagaagc 4560
acattatttt agcttctggc tactgtgaga acatgaattc tgtgattctg tgggtttttt 4620
cttttttctt ttaccagtac agtaagaaaa aaaaaaaaa aaaaaaagcc atgctatcaa 4680
tcaagattct tttttttaa actttctccc atgaactacc accatcagta tgaattgatg 4740
caacaaatga agaaatattt aaagacagcc tctcaacaga ttgtatctca ggttaaatgc 4800
taactaatta tgtctgtgtt gggggttgcg aagagattct taaagtatc tgtgtgttga 4860
tcatcagttt tacaaaaaca cctatttggc tgaaatggaa taaaatgttt gtgggtaaaa 4920
gctaatggcc aaaatggttg caatcattca tactagttag aaaaattatg tgttgaaata 4980
agtggaaaag tgcaatccat ccaccccttat gattaacgta gatgattttt atacctttt 5040
ctgatgtacc tcttgacctt ctccttcct tcctacccctt tctaagtatt tccagaaata 5100
cctgattttg aatcattcaa cagtagaaaa agaggcatat tttcattact tgacaatgtg 5160
ggatgggtgc aatttattcc atcttcacta aaatagaagc aattccatag gtaccataaa 5220
cctattttag gtaccacaag gtgtcttttt acacagctca tttgaataca ggtgttctga 5280
gaagggggttt ctattttaaa attaccatat caaaataaat gtgccttatt tttttataag 5340
tcttgttaaa tcagtgtcca tattactgtt tggggaaggg ggaatgttgt ggggtctggg 5400
agagggtggg tactttctat gacacataaa ttgtgtaatt tttgcctgac aatgctggcc 5460
acattctgat ctgttttcatt aaattttgtg tgatgttact ctaaacattt tgactatttg 5520
aatgtactga gatgtcagaa aacaaaaca ggaaggaaaa tattgttaat taaaatgtgc 5580
tgctgccaag gaaactgcaa cttgaagcaa ggattttgta aaatgcaaaa tccagctact 5640
gttttccattt cacagtagtt aactatatta aagagagaat gctttaaaat tgatcttgtt 5700
ttgaaaccca cttttatgta gctcatcatg gttttatctta ctaaggaata tgttttgttca 5760
ttcagttctc aacttttgta tgtgctaacc ttaaagtgaa gttctgagcc cgtgtgccat 5820
tacagtgctt ttaataaaat ttatttggga ttattgtttc cttaacatta aaataatagc 5880
gacatttaga ctatgcaatt ttagcataga aaggagtctt tgagtatgta cagttttgaa 5940
aattctcttt gagataattg atttcatatt ctgtggcatt caacctccat ttacctcttg 6000
tcattccaac atctttatag agaaataaaa acccaatttc tctttcacca tttagtttga 6060
ttatcatctg gattttcact caagatgcag ctcctaagat tattgttatg ttaaattcat 6120
aaactccttc acctttaata attaaggaaa caataccagt gttgataaag atattacaag 6180
gggtaatttc atgcaataaa catgtaccgt aagtttttct ccacatattt tgggaaaaaa 6240
ctaaaaaag aaaaaggact tccttttttgt ggacatctac agatgttagg gttgccagaa 6300
gcaaatccca ggaatgagat cagtattttc attgcatctt aaatgtataa ccttcctgtg 6360
ggagttcagt ttgtctgtgg ttaagtgggt gtgcttaatc attctcgaaa ttgtgatcag 6420
atgaaataaa aaaaaaatct tgatgcaata acagtgtttt tgccacttct ggttgtttgc 6480
gatggatctg tcccatgtca gtctggggtt ttattcagct tgtgttgcta ccagcagttc 6540
acaggtaaag cagaaattct ctttaaccag caagtttctg cttttttaagg ttacttttag 6600
aataaatcat cagggaaaca gagaggatgc tttgctttgg gttgtagtca aaaactgatt 6660
aaataattta atgtctctgg cacacactaa aaaccataca cttcagttgt gatctcagtg 6720
gcatatttat ttggttaggt ttcgttacat ttattattac agattgttcag ttgaccaagt 6780
agttcagtgt tttctttcct ttttttggaa attttagttt gagttttgtga ctgcagtgtt 6840
caagaactca gcatccttgt tttctacaaa tactgattaa aataaaatgc tgtaaaatgt 6900
gatgtaaaac attatcatga tcttcccatg cctttgttgt acttgtgccg aagtgttttg 6960
atattccttt gtctggaaga aaatgtttgc tttcattttg atcattttgt tcaccttgga 7020
atcaacaggt tttgatattt tctcttggaa gatttttat ctttttggga atatgtaata 7080
taagatctct aataaaagat aatcttatca tgta        7114
```

SEQ ID NO: 17        moltype = AA  length = 288
FEATURE              Location/Qualifiers
source               1..288
                     mol_type = protein
                     organism = Homo sapiens
SEQUENCE: 17
MQIPQAPWPV VWAVLQLGWR PGWFLDSPDR PWNPPTFSPA LLVVTEGDNA TFTCSFSNTS   60
ESFVLNWYRM SPSNQTDKLA AFPEDRSQPG QDCRFRVTQL PNGRDFHMSV VRARRNDSGT  120

```
YLCGAISLAP KAQIKESLRA ELRVTERRAE VPTAHPSPSP RPAGQFQTLV VGVVGGLLGS    180
LVLLVWVLAV ICSRAARGTI GARRTGQPLK EDPSAVPVFS VDYGELDFQW REKTPEPPVP    240
CVPEQTEYAT IVFPSGMGTS SPARRGSADG PRSAQPLRPE DGHCSWPL                288

SEQ ID NO: 18           moltype = DNA   length = 2115
FEATURE                 Location/Qualifiers
source                  1..2115
                        mol_type = genomic DNA
                        organism = Homo sapiens
SEQUENCE: 18
agtttccctt ccgctcacct ccgcctgagc agtggagaag gcggcactct ggtggggctg    60
ctccaggcat gcagatccca caggcgccct ggccagtcgt ctgggcggtg ctacaactgg   120
gctggcggcc aggatggttc ttagactccc agacaggcc ctggaacccc ccaccttct    180
cccagccct gctcgtggtg accgaagggg acaaacgcac cttcacctgc agcttctcca   240
acacatcgga gagcttcgtg ctaaactggt accgcatgag ccccagcaac cagacggaca   300
agctggccgc cttccccgag accgcagcc agcccggcca ggactgccgc ttccgtgtca   360
cacaactgcc caacgggcgt gacttccaca tgagcgtggt cagggcccgg cgcaatgaca   420
gcggcaccta cctctgtggg gccatctccc tggccccaa ggcgcagatc aaagagagcc   480
tgcgggcaga gctcagggtg acagagagaa gggcagaagt gcccacagcc cacccccagc   540
cctcacccag gccagccggc cagttccaaa ccctggtggt tggtgtcgtg ggcggcctgc   600
tgggcagcct ggtgctgcta gtctgggtcc tggccgtcat ctgctcccgg gccgcacgag   660
ggacaatagg agccaggcgc accggccagc ccctgaagga gaccccctca gccgtgcctg   720
tgttctctgt ggactatggg gagctggatt tccagtggcg agagaagacc ccggagcccc   780
ccgtgccctg tgtccctgag cagacggagt atgccaccat tgtctttcct agcggaatgg   840
gcacctcatc cccgcccgc aggggctcag ctgacggccc tcggagtgcc cagccactga   900
ggctgaggga tggacactgc tcttggcccc tctgacccggc ttccttggcc accagtgttc   960
tgcagaccct ccaccatgag cccgggtcag cgcattcct caggagaagc aggcagggtg   1020
caggccattg caggccgtcc aggggctgag ctgcctgggg gcgacggggg ctccagcctg   1080
cacctgcacc aggcacagcc ccaccacagg actcatgtct caatgccac agtgagccca   1140
ggcacaggt gtcaccgtcc cctacaggga gggcagatg cagtcactgc ttcaggtcct   1200
gccagcacag agctgcctgc gtccagctcc ctgaatctct gctgctgctg ctgctgctgc   1260
tgctgctgcc tgcggcccgg ggctgaaggc gccgtggccc tgcctgacgc cccggagcct   1320
cctgcctgaa cttgggggct ggttggagat ggccttggag cagccaaggt gcccctggca   1380
gtggcatccc gaaacgccct ggacgcaggg cccaagactg gcacaggag tgggaggtac   1440
atggggctgg ggactcccca ggagttatct gctccctgca ggctagaga agtttcaggg   1500
aaggtcagaa gagctcctgg ctgtggtggg cagggcagga aaccccctcca cctttacaca   1560
tgcccaggca gcacctcagg ccctttgtgg ggcaggaag ctgaggcagt aagcgggcag   1620
gcagagctgg aggcctttca ggcccagcca gcactctggc ctcctgccgc cgcattccac   1680
cccagccct cacaccactc gggagaggga catcctacgg tcccaaggtc aggagggcag   1740
ggctggggtt gactcaggcc cctcccagct gtggccacct gggtgttggg agggcagaag   1800
tgcaggcacc tagggccccc catgtgccca ccctgggagc tctccttgga acccattcct   1860
gaaattattt aaaggggttg gccgggctcc caccagggcc tgggtgggaa ggtacaggcg   1920
ttcccccggg gcctagtacc cccgccgtgg cctatccact cctcacatcc acacactgca   1980
cccccactcc tggggcaggg ccaccagcat ccaggcggcc agcaggcacc tgagtggctg   2040
ggacaaggga tccccttcc ctgtggttct attatattat aattataatt aaatatgaga    2100
gcatgctaag gaaaa                                                   2115

SEQ ID NO: 19           moltype = AA    length = 223
FEATURE                 Location/Qualifiers
source                  1..223
                        mol_type = protein
                        organism = Homo sapiens
SEQUENCE: 19
MACLGFQRHK AQLNLATRTW PCTLLFFLLF IPVFCKAMHV AQPAVVLASS RGIASFVCEY    60
ASPGKATEVR VTVLRQADSQ VTEVCAATYM MGNELTFLDD SICTGTSSGN QVNLTIQGSLR  120
AMDTGLYICK VELMPPPYY LGIGNGTQIY VIDPEPCPDS DFLLWILAAV SSGLFFYSFL   180
LTAVSLSKML KKRSPLTTGV YVKMPPTEPE CEKQFQPYFI PIN                    223

SEQ ID NO: 20           moltype = DNA   length = 2025
FEATURE                 Location/Qualifiers
source                  1..2025
                        mol_type = genomic DNA
                        organism = Homo sapiens
SEQUENCE: 20
cttctgtgtg tgcacatgtg taatacatat ctgggatcaa agctatctat ataaagtcct    60
tgattctgtg tgggttcaaa cacatttcaa agcttcagga tcctgaaagg ttttgctcta   120
cttcctgaag acctgaacac cgctcccata agccatggc ttgccttgga tttcagcggc   180
acaaggctca gctgaacctg gctaccagga cctggccctg cactctctg ttttttcttc   240
tcttcatccc tgtcttctgc aaagcaatgc acgtggccca gcctgctgtg gtactggcca   300
gcagccgagg catcgccagc tttgtgtgtg agtatgcatc tccaggcaaa gccactgagg   360
tccgggtgac agtgctcgg caggctgaca gccaggtgac tgaagtctgt gcggcaacct   420
acatgatggg gaatgagttg accttcctag atgattccat ctgcacgggc acctccagtg   480
gaaatcaagt gaacctcact atccaaggac tgagggcat ggacacggga ctctacatct   540
gcaaggtgga tcatgtac ccaccgccat actacctggg cataggcaac ggaacccaga   600
tttatgtaat tgatccagaa ccgtgcccag attctgactt cctcctctgg atccttgcag   660
cagttagttc gggggttgttt ttttatagct ttctcctcac agctgtttct ttgagcaaaa   720
tgctaaagaa aagaagccct cttacaacag gggtctatgt gaaaatgccc ccaacagagc   780
cagaatgtga aaagcaattt cagccttatt ttattcccat caattgagaa accattatga   840
agaagagagt ccatatttca atttccaaga gctgaggcaa ttctaacttt tttgctatcc   900
```

-continued

```
agctattttt atttgtttgt gcatttgggg ggaattcatc tctctttaat ataaagttgg  960
atgcggaacc caaattacgt gtactacaat ttaaagcaaa ggagtagaaa gacagagctg 1020
ggatgtttct gtcacatcag ctccactttc agtgaaagca tcacttggga ttaatatggg 1080
gatgcagcat tatgatgtgg gtcaaggaat taagttaggg aatggcacag cccaaagaag 1140
gaaaaggcag ggagcgaggg agaagactat attgtacaca cctatattt acgtatgaga 1200
cgtttatagc cgaaatgatc ttttcaagtt aaattttatg ccttttattt cttaaacaaa 1260
tgtatgatta catcaaggct tcaaaaatac tcacatggct atgttttagc cagtgatgct 1320
aaaggttgta ttgcatatat acatatatat atatatatat atatatatat atatatatat 1380
atatatatat tttaatttga tagtattgtg catagagcca cgtatgtttt tgtgtatttg 1440
ttaatggttt gaatataaac actatatggc agtgtctttc caccttgggt cccagggaag 1500
ttttgtggag gagctcagga cactaataca ccaggtagaa cacaaggtca tttgctaact 1560
agcttggaaa ctgatgagg tcatagcagt gcttgattgc gtggaattgt gctgagttgg 1620
tgttgacatg tgctttgggg cttttacacc agttcctttc aatggtttgc aaggaagcca 1680
cagctggtgg tatctgagtt gacttgacag aacactgtct tgaagacaat ggcttactcc 1740
aggagaccca caggtatgac cttctaggaa gctccagttc gatgggccca attcttacaa 1800
acatgtggtt aatgccatgg acagaagaag gcagcaggtg gcagaatggg gtgcatgaag 1860
gtttctgaaa attaacactg cttgtgtttt taactcaata ttttccatga aaatgcaaca 1920
acatgtataa tattttaat taaataaaaa tctgtggtgg tcgtttaaa aaaaaaaaaa 1980
aaaaaaaaaa aaaaaaaaaa aaaaaaaaaa aaaaaaaaaa aaaaa             2025
```